US009845319B2

(12) United States Patent
Goldberg et al.

(10) Patent No.: US 9,845,319 B2
(45) Date of Patent: Dec. 19, 2017

(54) AMIDE SUBSTITUTED THIAZOLES AS MODULATORS OF RORYT

(71) Applicant: Janssen Pharmaceutica NV, Beerse (BE)

(72) Inventors: Steven Goldberg, Carlsbad, CA (US); Hariharan Venkatesan, San Diego, CA (US); Virginia Tanis, Vista, CA (US); Maud Urbanski, Flemington, NJ (US); Aihua Wang, Jamison, PA (US); David Kummer, San Diego, CA (US); Christoph Steeneck, Heidelberg (DE); Christian Gege, Ehingen (DE); Olaf Kinzel, Heidelberg (DE); Gerald Kleymann, Bad Salzuflen (DE); Thomas Hoffmann, Speyer (DE); Anne M. Fourie, San Diego, CA (US); Xiaohua Xue, San Diego, CA (US)

(73) Assignee: Janssen Pharmaceutiuca NV, Beerse (BE)

( * ) Notice: Subject to any disclaimer, the term of this patent is extended or adjusted under 35 U.S.C. 154(b) by 0 days.

(21) Appl. No.: 14/927,502

(22) Filed: Oct. 30, 2015

(65) Prior Publication Data
US 2016/0122335 A1 May 5, 2016

Related U.S. Application Data

(60) Provisional application No. 62/072,599, filed on Oct. 30, 2014.

(51) Int. Cl.
| C07D 417/04 | (2006.01) |
| C07D 417/06 | (2006.01) |
| C07D 417/14 | (2006.01) |
| A61K 31/427 | (2006.01) |
| A61K 45/06 | (2006.01) |
| A61K 31/454 | (2006.01) |
| A61K 31/4439 | (2006.01) |
| A61K 31/4545 | (2006.01) |

(52) U.S. Cl.
CPC .......... *C07D 417/04* (2013.01); *A61K 31/427* (2013.01); *A61K 31/4439* (2013.01); *A61K 31/454* (2013.01); *A61K 31/4545* (2013.01); *A61K 45/06* (2013.01); *C07D 417/06* (2013.01); *C07D 417/14* (2013.01)

(58) Field of Classification Search
CPC ... C07D 417/04; C07D 417/06; C07D 417/14
See application file for complete search history.

(56) References Cited

U.S. PATENT DOCUMENTS

| 5,342,835 A | 8/1994 | Pepin et al. |
| 2015/0038350 A1 | 2/2015 | Nishinaga et al. |
| 2015/0072890 A1 | 3/2015 | James |

FOREIGN PATENT DOCUMENTS

| EP | 360701 A1 | 3/1990 |
| EP | 2738170 | 6/2014 |
| WO | WO 9603392 A1 | 2/1996 |
| WO | WO 0283111 A2 | 10/2002 |
| WO | WO 03015776 A1 | 2/2003 |
| WO | WO 2006124687 A1 | 11/2006 |
| WO | WO 2007087427 A2 | 8/2007 |
| WO | WO 2008064317 A1 | 5/2008 |
| WO | WO 2008064318 A2 | 5/2008 |
| WO | WO 2009011850 | 1/2009 |
| WO | WO 2010006713 | 1/2010 |
| WO | WO 2011053948 A1 | 5/2011 |
| WO | WO 2011112263 A1 | 9/2011 |
| WO | WO 2011112264 A1 | 9/2011 |
| WO | WO 2011115892 A1 | 9/2011 |
| WO | WO 2012027965 | 3/2012 |

(Continued)

OTHER PUBLICATIONS

U.S. Appl. No. 14/927,499.
U.S. Appl. No. 14/927,501.
PCT/US2015/058193, Dated Jan. 26, 2016.
PCT/US2015/058198, Dated Jan. 21, 2016.
PCT/US2015/058200, Dated Jan. 27, 2016.
U.S. Appl. No. 14/927,499, Office Action Dated Feb. 24, 2016.
Liegault, et al., "Establishment of Broadly Applicable reaction condisions for the Palladium-Catalyzed Direct Arylation of Heteroatom-Containing Aromatic Compounds", The Journal of Organic Chemistry, (2009), vol. 74, No. 5, 6, pp. 1826-1834.
Kumar N, "The Benzenesulfoamide T0901317 [$N$-(2,2,2-Trifluoroethyl)-$N$-[4-[2,2,2-trifluoro-1-hydroxy-1-(trifluoromethyl)ethyl]phenyl]-benzenesulfonamide] Is a Novel Retinoic Acid Receptor-Related Orphan Receptor-α/γInverse Agonist", Molecular Pharmacology (2010), 77(2), 228-236.

(Continued)

*Primary Examiner* — Rebecca Anderson
(74) *Attorney, Agent, or Firm* — Yuriy P. Stercho

(57) ABSTRACT

The present invention comprises compounds of Formula I.

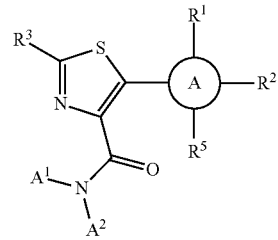

Formula I wherein:
$R^1$, $R^2$, $R^3$, $R^5$, $A^1$, $A^2$, and

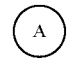

are defined in the specification.
The invention also comprises a method of treating or ameliorating a syndrome, disorder or disease, wherein the syndrome, disorder or disease is rheumatoid arthritis or psoriasis. The invention also comprises a method of modulating RORγt activity in a mammal by administration of a therapeutically effective amount of at least one compound of Formula I.

24 Claims, No Drawings

(56) References Cited

FOREIGN PATENT DOCUMENTS

| | | |
|---|---|---|
| WO | WO 2012074547 A2 | 6/2012 |
| WO | WO 2012129491 | 9/2012 |
| WO | WO 2012158784 A2 | 11/2012 |
| WO | WO 2013036912 A2 | 3/2013 |
| WO | WO 2013079223 A | 6/2013 |
| WO | WO 2013092939 A1 | 6/2013 |
| WO | WO 2013178362 A1 | 12/2013 |
| WO | WO 2015035278 A1 | 3/2015 |
| WO | WO 2015042212 A1 | 3/2015 |
| WO | WO 2015082533 A1 | 6/2015 |
| WO | WO 2015103507 A1 | 7/2015 |
| WO | WO 2015103508 A1 | 7/2015 |
| WO | WO 2015103509 A1 | 7/2015 |
| WO | WO 2015103510 A1 | 7/2015 |
| WO | WO 2015145371 A1 | 10/2015 |

OTHER PUBLICATIONS

Chang M, "Pharmacologic Repression of Retinoic Acid Receptor—Related Orphan Nuclear Receptor γ Is Therapeutic in the Collagen-Induced Arthritis Experimental Model", Arthritis & Rheumatology (2014), 66(3), 579-588.

Yao, et al, "Preparation Method of N-butyl-5-phenylthiazole-4-Formamide Derivative Via Coupling Reaction Under Catalysis of Copper Catalyst", Database accession No. 2014:924023, 2014.

Zhang, et al., "Decarboxylative Cross-Coupling of Azoyl Carboxylic Acids with Aryl Halides", Organic Letters, (2010) vol. 12, No. 21, pp. 4745-47457.

PCT/US2015/058193, Written Opinion dated Jan. 26, 2016.

PCT/US2015/058198, Written Opinion dated Jan. 21, 2016.

PCT/US2015/058200, Written Opinion dated Jan. 27, 2016.

Fauber et al., J. Med. Chem. 2014, 57, 5871-5892.

Yang et al., Trends in Pharmacological Sciences, Oct. 2014, vol. 35, No. 10, 493-500.

Steven Goldberg et al., U.S. Appl. No. 15/497,565.

Barczyk, A., W. Pierzchala, et al. (2003). "Interleukin-17 in sputum correlates with airway hyperresponsiveness to methacholine." Respir Med 97(6): 726-33.

Beurel, E., Harrington, L. E., Jope, R. S. (2013) "Inflammatory T helper 17 cells promote depression-like behavior in mice." Biol Psychiatry 73(7): 622-30.

Bowes, J. and A. Barton "The genetics of psoriatic arthritis: lessons from genome-wide association studies." Discov Med 10(52): 177-83 (2010).

Chang, M. R. et al. (2015) "Antiobesity Effect of a Small Molecule Repressor of RORγ." Mol Pharmacol. 88(1): 48-56.

Chen, Y., et al. (2011). "Emerging tendency towards autoimmune process in major depressive patients: A novel insight from Th17 cells." Psychiatry Research 188(2): 224-230.

Cua, D. J., J. Sherlock, et al. (2003). "Interleukin-23 rather than interleukin-12 is the critical cytokine for autoimmune inflammation of the brain." Nature 421(6924): 744-8.

Dong, C. (2006). "Diversification of T-helper-cell lineages: finding the family root of IL-17-producing cells." Nat Rev Immunol 6(4): 329-33.

Fujino, S., A. Andoh, et al. (2003). "Increased expression of interleukin 17 in inflammatory bowel disease." Gut 52(1): 65-70.

Garber K. (2011). "Psoriasis: from bed to bench and back" Nat Biotech 29, 563-566.

Gazouli, M., I. Pachoula, et al. "NOD2/CARD15, ATG16L1 and IL23R gene polymorphisms and childhood-onset of Crohn's disease." World J Gastroenterol 16(14): 1753-8 (2010).

Hueber, W., Patel, D.D., Dryja, T., Wright, A.M., Koroleva, I., Bruin, G., Antoni, C., Draelos, Z., Gold, M.H., Durez, P., Tak, P.P., Gomez-Reino, J.J., Foster, C.S., Kim, R.Y., Samson, C.M., Falk, N.S., Chu, D.S., Callanan, D., Nguyen, Q.D., Rose, K., Haider, A., Di Padova, F. (2010) Effects of AIN457, a fully human antibody to interleukin-17A, on psoriasis, rheumatoid arthritis, and uveitis. Sci Transl Med 2, 5272.

Ivanov, II, B. S. McKenzie, et al. (2006). "The orphan nuclear receptor RORgammat directs the differentiation program of proinflammatory IL-17+T helper cells." Cell 126(6): 1121-33.

Kochi, Y., Y. Okada, et al. (2010) "A regulatory variant in CCR6 is associated with rheumatoid arthritis susceptibility." Nat Genet 42(6): 515-9.

Kolls, J. K. and A. Linden (2004). "Interleukin-17 family members and inflammation." Immunity 21(4): 467-76.

Korn, T., E. Bettelli, et al. (2009). "IL-17 and Th17 Cells." Annu Rev Immunol 27: 485-517.

Krueger, J. G., S. Fretzin, et al. "IL-17A is essential for cell activation and inflammatory gene circuits in subjects with psoriasis." J Allergy Clin Immunol 130(1): 145-154 e9 (2012).

Langrish, C. L., Y. Chen, et al. (2005). "IL-23 drives a pathogenic T cell population that induces autoimmune inflammation." J Exp Med 201(2): 23340.

Leonardi, C., R. Matheson, et al. "Anti-interleukin-17 monoclonal antibody ixekizumab in chronic plaque psoriasis." N Engl J Med 366(13): 1190-9 (2012).

Lock, C., G. Hermans, et al. (2002). "Gene-microarray analysis of multiple sclerosis lesions yields new targets validated in autoimmune encephalomyelitis." Nat Med 8(5): 500-8.

Matulis, D., Kranz, J. K., Salemme, F. R., and Todd, M. J. (2005) Thermodynamic stability of carbonic anhydrase: measurements of binding affinity and stoichiometry using ThermoFluor. *Biochemistry* 44, 5258-66.

McKenzie, B. S., R. A. Kastelein, et al. (2006). "Understanding the IL-23-IL-17 immune pathway." Trends Immunol 27(1): 17-23.

Meissburger, B. et al. (2011) "Adipogenesis and insulin sensitivity in obesity are regulated by retinoid-related orphan receptor gamma." EMBO Mol Med. 3(11): 637-651.

Nunez, C., B. Dema, et al. (2008). "IL23R: a susceptibility locus for celiac disease and multiple sclerosis?" Genes Immun 9(4): 289-93.

Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) High-density miniaturized thermal shift assays as a general strategy for drug discovery. *J Biomol Screen 6*, 429-40.

Papp, K. A., "Brodalumab, an anti-interleukin-17-receptor antibody for psoriasis." N Engl J Med 2012 366(13): 1181-9.

Stamp, L. K., M. J. James, et al. (2004). "Interleukin-17: the missing link between T-cell accumulation and effector cell actions in rheumatoid arthritis" Immunol Cell Biol 82(1): 1-9.

Tonel, G., C. Conrad, et al. "Cutting edge: A critical functional role for IL-23 in psoriasis." J Immunol 185(10): 5688-91 (2010).

Yen, D., J. Cheung, et al. (2006). "IL-23 is essential for T cell-mediated colitis and promotes inflammation via IL-17 and IL-6." J Clin Invest 116(5): 1310-6.

AMIDE SUBSTITUTED THIAZOLES AS MODULATORS OF RORγt

CROSS-REFERENCE TO RELATED APPLICATIONS

This application claims priority from U.S. Application No. 62/072,599, filed on Oct. 30, 2014, which is incorporated herein by reference.

FIELD OF THE INVENTION

The invention is directed to substituted thiazole compounds, which are modulators of the nuclear receptor RORγt, pharmaceutical compositions, and methods for use thereof. More particularly, the RORγt modulators are useful for preventing, treating or ameliorating an RORγt mediated inflammatory syndrome, disorder or disease.

BACKGROUND OF THE INVENTION

Retinoic acid-related nuclear receptor gamma t (RORγt) is a nuclear receptor, exclusively expressed in cells of the immune system, and a key transcription factor driving Th17 cell differentiation. Th17 cells are a subset of $CD4^+$ T cells, expressing CCR6 on their surface to mediate their migration to sites of inflammation, and dependent on IL-23 stimulation, through the IL-23 receptor, for their maintenance and expansion. Th17 cells produce several proinflammatory cytokines including IL-17A, IL-17F, IL-21, and IL-22 (Korn, T., E. Bettelli, et al. (2009). "IL-17 and Th17 Cells." Annu Rev Immunol 27: 485-517), which stimulate tissue cells to produce a panel of inflammatory chemokines, cytokines and metalloproteases, and promote recruitment of granulocytes (Kolls, J. K. and A. Linden (2004). "Interleukin-17 family members and inflammation." Immunity 21(4): 467-76; Stamp, L. K., M. J. James, et al. (2004). "Interleukin-17: the missing link between T-cell accumulation and effector cell actions in rheumatoid arthritis" Immunol Cell Biol 82(1): 1-9). Th17 cells have been shown to be the major pathogenic population in several models of autoimmune inflammation, including collagen-induced arthritis (CIA) and experimental autoimmune encephalomyelitis (EAE) (Dong, C. (2006). "Diversification of T-helper-cell lineages: finding the family root of IL-17-producing cells." Nat Rev Immunol 6(4): 329-33; McKenzie, B. S., R. A. Kastelein, et al. (2006). "Understanding the IL-23-IL-17 immune pathway." Trends Immunol 27(1): 17-23). RORγt-deficient mice are healthy and reproduce normally, but have shown impaired Th17 cell differentiation in vitro, a significantly reduced Th17 cell population in vivo, and decreased susceptibility to EAE (Ivanov, II, B. S. McKenzie, et al. (2006). "The orphan nuclear receptor RORgammat directs the differentiation program of proinflammatory IL-17+ T helper cells." Cell 126(6): 1121-33). Mice deficient for IL-23, a cytokine required for Th17 cell survival, fail to produce Th17 cells and are resistant to EAE, CIA, and inflammatory bowel disease (IBD) (Cua, D. J., J. Sherlock, et al. (2003). "Interleukin-23 rather than interleukin-12 is the critical cytokine for autoimmune inflammation of the brain." Nature 421(6924): 744-8; Langrish, C. L., Y. Chen, et al. (2005). "IL-23 drives a pathogenic T cell population that induces autoimmune inflammation." J Exp Med 201(2): 233-40; Yen, D., J. Cheung, et al. (2006). "IL-23 is essential for T cell-mediated colitis and promotes inflammation via IL-17 and IL-6." J Clin Invest 116(5): 1310-6). Consistent with these findings, an anti-IL23-specific monoclonal antibody blocks development of psoriasis-like inflammation in a murine disease model (Tonel, G., C. Conrad, et al. "Cutting edge: A critical functional role for IL-23 in psoriasis." J Immunol 185(10): 5688-91).

In humans, a number of observations support the role of the IL-23/Th17 pathway in the pathogenesis of inflammatory diseases. IL-17, the key cytokine produced by Th17 cells, is expressed at elevated levels in a variety of allergic and autoimmune diseases (Barczyk, A., W. Pierzchala, et al. (2003). "Interleukin-17 in sputum correlates with airway hyperresponsiveness to methacholine." Respir Med 97(6): 726-33; Fujino, S., A. Andoh, et al. (2003). "Increased expression of interleukin 17 in inflammatory bowel disease." Gut 52(1): 65-70; Lock, C., G. Hermans, et al. (2002). "Gene-microarray analysis of multiple sclerosis lesions yields new targets validated in autoimmune encephalomyelitis." Nat Med 8(5): 500-8; Krueger, J. G., S. Fretzin, et al. "IL-17A is essential for cell activation and inflammatory gene circuits in subjects with psoriasis." J Allergy Clin Immunol 130(1): 145-154 e9). Furthermore, human genetic studies have shown association of polymorphisms in the genes for Th17 cell-surface receptors, IL-23R and CCR6, with susceptibility to IBD, multiple sclerosis (MS), rheumatoid arthritis (RA) and psoriasis (Gazouli, M., I. Pachoula, et al. "NOD2/CARD15, ATG16L1 and IL23R gene polymorphisms and childhood-onset of Crohn's disease." World J Gastroenterol 16(14): 1753-8., Nunez, C., B. Dema, et al. (2008). "IL23R: a susceptibility locus for celiac disease and multiple sclerosis?" Genes Immun 9(4): 289-93; Bowes, J. and A. Barton "The genetics of psoriatic arthritis: lessons from genome-wide association studies." Discov Med 10(52): 177-83; Kochi, Y., Y. Okada, et al. "A regulatory variant in CCR6 is associated with rheumatoid arthritis susceptibility." Nat Genet 42(6): 515-9).

Ustekinumab (Stelara®), an anti-p40 monoclonal antibody blocking both IL-12 and IL-23, is approved for the treatment of adult patients (18 years or older), with moderate to severe plaque psoriasis, who are candidates for phototherapy or systemic therapy. Currently, monoclonal antibodies specifically targeting only IL-23, to more selectively inhibit the Th17 subset, are also in clinical development for psoriasis (Garber K. (2011). "Psoriasis: from bed to bench and back" Nat Biotech 29, 563-566), further implicating the important role of the IL-23- and RORγt-driven Th17 pathway in this disease. Results from recent phase II clinical studies strongly support this hypothesis, as anti-IL-17 receptor and anti-IL-17 therapeutic antibodies both demonstrated high levels of efficacy in patients with chronic psoriasis (Papp, K. $A_4$., "Brodalumab, an anti-interleukin-17-receptor antibody for psoriasis." N Engl J Med 2012 366(13): 1181-9; Leonardi, C., R. Matheson, et al. "Anti-interleukin-17 monoclonal antibody ixekizumab in chronic plaque psoriasis." N Engl J Med 366(13): 1190-9). Anti-IL-17 antibodies have also demonstrated clinically relevant responses in early trials in RA and uveitis (Hueber, W., Patel, D. D., Dryja, T., Wright, A. M., Koroleva, I., Bruin, G., Antoni, C., Draelos, Z., Gold, M. H., Durez, P., Tak, P. P., Gomez-Reino, J. J., Foster, C. S., Kim, R. Y., Samson, C. M., Falk, N. S., Chu, D. S., Callanan, D., Nguyen, Q. D., Rose, K., Haider, $A_4$., Di Padova, F. (2010) Effects of AIN457, a fully human antibody to interleukin-17A, on psoriasis, rheumatoid arthritis, and uveitis. Sci Transl Med 2, 5272).

All the above evidence supports inhibition of the Th17 pathway by modulating RORγt activity as an effective strategy for the treatment of immune-mediated inflammatory diseases.

SUMMARY OF THE INVENTION

The present invention comprises compounds of Formula I.

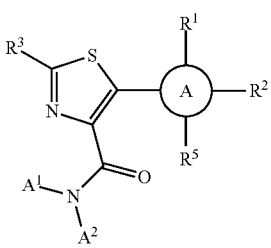

Formula I wherein:

is phenyl, pyridyl, pyrimidyl, pyrazinyl, or pyridazyl;
$R^1$ is Cl, —CN, H, F, $OC_{(1-4)}$alkyl,

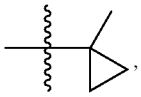

$OCHF_2$, $OCF_3$, $C_{(1-4)}$alkyl (including $C_{(1-2)}$alkyl), Br, I, or cyclopropyl; wherein said $C_{(1-4)}$alkyl is optionally substituted with up to six fluorine atoms;
$R^2$ is F, Cl, —CN, H, $OC_{(1-4)}$alkyl, $OCHF_2$, $OCF_3$, cyclopropyl, or $C_{(1-4)}$alkyl; wherein said $C_{(1-4)}$alkyl is optionally substituted with up to five fluorine atoms, and said cyclopropyl is optionally substituted with OH, $CH_3$, $CF_3$, and up to five fluorine atoms; or $R^1$ and $R^2$ may be taken together with their attached ring A to form a fused ring system selected from the group consisting of naphthalenyl, tetrahydronaphthalenyl, isoquinolinyl, quinolinyl, 2,3-dihydro-1H-indenyl, chromanyl, isochromanyl, and naphthyridinyl; wherein said naphthalenyl, tetrahydronaphthalenyl, isoquinolinyl, quinolinyl, 2,3-dihydro-1H-indenyl, chromanyl, isochromanyl, and naphthyridinyl may optionally be substituted with up to three substituents independently selected from the group consisting of F, $OC_{(1-3)}$alkyl or $C_{(1-3)}$alkyl wherein said $OC_{(1-3)}$alkyl and $C_{(1-3)}$alkyl is optionally substituted with up to five fluorine atoms (including $CHF_2$, $CH_2F$, $CF_3$, and $CH_3$; provided that $R^2$ may not be H if $R^1$ is H;
$R^3$ is thiadiazolyl, oxadiazolyl, isoxadiazolyl, oxazolyl, isoxazolyl, triazolyl, tetrazolyl, 1,2,4-oxadiazol-5(4H)-on-3-yl, pyridyl, thiazolyl, pyrimidyl, pyridazyl, pyrazyl, imidazolyl, pyrrolyl, furanyl, or phenyl; wherein said thiadiazolyl, oxadiazolyl, isoxadiazolyl, oxazolyl, isoxazolyl, triazolyl, pyridyl, thiazolyl, pyrimidyl, pyridazyl, pyrazyl, imidazolyl, pyrrolyl, furanyl, or phenyl is optionally substituted with $R^4$, and further optionally substituted with one substituent selected from the group consisting of F, $CH_3$, $CF_3$, and cyclopropyl;
$R^4$ is H, $C_{(1-6)}$alkylSO$_2$C$_{(1-6)}$alkyl, C(O)NH$_2$, $C_{(1-6)}$alkyl (including $C_{(1-4)}$alkyl), —CN, $C_{(3-6)}$cycloalkyl, NH$_2$, NH(C$_{(1-6)}$alkyl), N(C$_{(1-6)}$alkyl)$_2$, NHCO(C$_{(1-6)}$alkyl), N(C$_{(1-6)}$alkyl)CO(C$_{(1-6)}$alkyl), NHSO$_2$(C$_{(1-6)}$alkyl), N(C$_{(1-6)}$alkyl)SO$_2$(C$_{(1-6)}$alkyl), O(C$_{(1-6)}$alkyl), C(O)NH$_2$, CONH(C$_{(1-6)}$alkyl), CON(C$_{(1-6)}$alkyl)$_2$, SO$_2$NH$_2$, SO$_2$NH(C$_{(1-6)}$alkyl), SO$_2$NH(COC$_{(1-6)}$alkyl), or SO$_2$N(C$_{(1-6)}$alkyl)$_2$; wherein said $C_{(1-6)}$alkyl or $C_{(3-6)}$cycloalkyl is optionally substituted independently with up to six fluorine atoms, $CF_3$, $CO_2H$, OH, —CN, C(O)NH$_2$, NH$_2$, $OCH_3$, $OCHF_2$, $OCF_3$, —(CX$_2$)$_m$—, or N(CH$_3$)$_2$;
m is 2, 3, 4, or 5;
X is H, or F; wherein each occurrence of X in a single molecule is independently defined;
$A^1$ is H, or $C_{(1-4)}$alkyl; wherein said $C_{(1-4)}$alkyl is optionally substituted with up to six fluorine atoms, Cl, —CN, $OCH_3$, $OCHF_2$, or $OCF_3$;
$A^2$ is $C_{(1-6)}$alkyl (including $C_{(1-4)}$alkyl), $C_{(0-2)}$alkyl-$C_{(3-6)}$cycloalkyl,

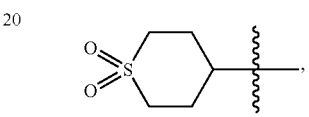

$CH_2$—$C_6H_4$—C(O)NH$_2$, —$C_6H_4$—F, $CH_2$—CCH, or $CH_2$—CC—$CH_3$; wherein said $C_{(1-6)}$alkyl, and said $C_{(0-2)}$alkyl-$C_{(3-6)}$cycloalkyl are optionally substituted with up to six fluorine atoms, Cl, —CN, $OCH_3$, $OCHF_2$, or $OCF_3$;
or $A^1$ and $A^2$ may be taken together with their attached nitrogen to form a ring selected from the group consisting of: thiomorpholinyl, piperidinyl, pyrrolidinyl, piperazinyl, morpholinyl, azetidinyl, and aziridinyl; wherein said piperidinyl, pyrrolidinyl, piperazinyl, morpholinyl, azetidinyl, and aziridinyl are optionally substituted with $CF_3$, $CH_2CH_2F$, $C_{(1-2)}$alkyl, $C_{(3-6)}$cycloalkyl, —CN, OH, $CH_2OH$, $CH_2F$, F, Cl, $OCH_3$, $OCHF_2$, $OCF_3$, —(CX$_2$)$_n$O(CX$_2$)$_n$—, or —(CX$_2$)$_n$— and up to three additional substituents selected from the group consisting of $CH_3$ and F (including

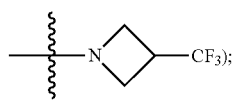

n is independently 0, 1, 2, 3, or 4;
X is H, or F; wherein each occurrence of X in a single molecule is independently defined;
$R^5$ is SO$_2$NA$^3$A$^4$, CONA$^3$A$^4$, NA$^3$A$^4$, OCH$_2$C(CF$_3$)$_2$OH, $C_{(3-6)}$cycloalkyl, or $C_{(1-6)}$alkyl; wherein said $C_{(3-6)}$cycloalkyl and said $C_{(1-6)}$alkyl are optionally substituted with OH, Cl, —CN, H, $OCH_3$, $OCHF_2$, $OCF_3$, or NA$^3$A$^4$, further optionally substituted with —CH$_2$CH$_2$— attached to the same carbon atom, and up to seven fluorine atoms;
$A^3$ is H, or $C_{(1-4)}$alkyl; wherein said $C_{(1-4)}$alkyl is optionally substituted with OH, Cl, —CN, $OCH_3$, $OCHF_2$, or $OCF_3$; and up to six fluorine atoms;
$A^4$ is H, $C_{(1-6)}$alkyl, $C_{(3-6)}$cycloalkyl (including cyclopropyl, and cyclobutyl), or $C_{(3-6)}$heterocycloalkyl (including oxetanyl and tetrahydrofuranyl); wherein said $C_{(1-6)}$alkyl is optionally substituted with cyclopropyl, morpholinyl, OH, $OCH_3$, C(O)NH$_2$, Cl, —CN, $OCHF_2$, $OCF_3$ and additionally substituted with up to three fluorine atoms; and wherein said $C_{(3-6)}$cycloalkyl, and $C_{(3-6)}$heterocycloalkyl are optionally substituted with $CF_3$, $CH_3$, —CN, C(O)NH$_2$, and up to three fluorine atoms;

or A³ and A⁴ can be taken together with their attached nitrogen to form a ring selected from the group consisting of piperidinyl, morpholinyl, piperazinyl, pyrrolidinyl, aziridinyl, and azetidinyl wherein said piperidinyl, morpholinyl, piperazinyl, pyrrolidinyl, aziridinyl, and azetidinyl are optionally substituted with up to four groups selected from the group consisting of $CF_3$, OH, $CH_3$, $CH_2F$, and $CHF_2$; and further optionally substituted with up to four groups selected from the group consisting of $CF_3$, OH, $CH_3$, $CH_2F$, and $CHF_2$; and further optionally substituted with up to six fluorine atoms;

and pharmaceutically acceptable salts thereof.

DETAILED DESCRIPTION OF THE INVENTION

The present invention comprises compounds of Formula I.

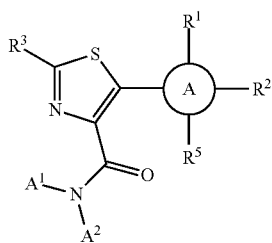

Formula I wherein:

is phenyl, pyridyl, pyrimidyl, pyrazinyl, or pyridazyl;

$R^1$ is Cl, —CN, H, F, $OC_{(1-4)}$alkyl,

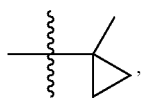 [SMILES: *C1(C)CC1]

$OCHF_2$, $OCF_3$, $C_{(1-4)}$alkyl (including $C_{(1-2)}$alkyl), Br, I, or cyclopropyl; wherein said $C_{(1-4)}$alkyl is optionally substituted with up to six fluorine atoms;

$R^2$ is F, Cl, —CN, H, $OC_{(1-4)}$alkyl, $OCHF_2$, $OCF_3$, cyclopropyl, or $C_{(1-4)}$alkyl; wherein said $C_{(1-4)}$alkyl is optionally substituted with up to five fluorine atoms, and said cyclopropyl is optionally substituted with OH, $CH_3$, $CF_3$, and up to five fluorine atoms; or $R^1$ and $R^2$ may be taken together with their attached ring A to form a fused ring system selected from the group consisting of naphthalenyl, tetrahydronaphthalenyl, isoquinolinyl, quinolinyl, 2,3-dihydro-1H-indenyl, chromanyl, isochromanyl, and naphthyridinyl; wherein said naphthalenyl, tetrahydronaphthalenyl, isoquinolinyl, quinolinyl, 2,3-dihydro-1H-indenyl, chromanyl, isochromanyl, and naphthyridinyl may optionally be substituted with up to three substituents independently selected from the group consisting of F, $OC_{(1-3)}$alkyl or $C_{(1-3)}$alkyl wherein said $OC_{(1-3)}$alkyl and $C_{(1-3)}$ alkyl is optionally substituted with up to five fluorine atoms (including $CHF_2$, $CH_2F$, $CF_3$, and $CH_3$; provided that $R^2$ may not be H if $R^1$ is H;

$R^3$ is thiadiazolyl, oxadiazolyl, isoxadiazolyl, oxazolyl, isoxazolyl, triazolyl, tetrazolyl, 1,2,4-oxadiazol-5(4H)-on-3-yl, pyridyl, thiazolyl, pyrimidyl, pyridazyl, pyrazyl, imidazolyl, pyrrolyl, furanyl, or phenyl; wherein said thiadiazolyl, oxadiazolyl, isoxadiazolyl, oxazolyl, isoxazolyl, triazolyl, pyridyl, thiazolyl, pyrimidyl, pyridazyl, pyrazyl, imidazolyl, pyrrolyl, furanyl, or phenyl is optionally substituted with $R^4$, and further optionally substituted with one substituent selected from the group consisting of F, $CH_3$, $CF_3$, and cyclopropyl;

$R^4$ is H, $C_{(1-6)}$alkyl$SO_2C_{(1-6)}$alkyl (including $CH_2SO_2CH_3$), $C(O)NH_2$, $C_{(1-6)}$alkyl (including $C_{(1-4)}$alkyl), —CN, $C_{(3-6)}$cycloalkyl, $NH_2$, $NH(C_{(1-6)}$alkyl), $N(C_{(1-6)}$alkyl)$_2$, $NHCO(C_{(1-6)}$alkyl), $N(C_{(1-6)}$alkyl)CO $(C_{(1-6)}$alkyl), $NHSO_2(C_{(1-6)}$alkyl), $N(C_{(1-6)}$alkyl)$SO_2$ $(C_{(1-6)}$alkyl), $O(C_{(1-6)}$alkyl), $C(O)NH_2$, $CONH(C_{(1-6)}$alkyl), $CON(C_{(1-6)}$alkyl)$_2$, $SO_2NH_2$, $SO_2NH(C_{(1-6)}$alkyl), $SO_2NH(COC_{(1-6)}$alkyl), or $SO_2N(C_{(1-6)}$alkyl)$_2$; wherein said $C_{(1-6)}$alkyl or $C_{(3-6)}$cycloalkyl is optionally substituted independently with up to six fluorine atoms, $CF_3$, $CO_2H$, OH, —CN, $C(O)NH_2$, $NH_2$, $OCH_3$, $OCHF_2$, $OCF_3$, —$(CX_2)_m$—, or $N(CH_3)_2$;

m is 2, 3, 4, or 5;

X is H, or F; wherein each occurrence of X in a single molecule is independently defined;

$A^1$ is H, or $C_{(1-4)}$alkyl; wherein said $C_{(1-4)}$alkyl is optionally substituted with up to six fluorine atoms, Cl, —CN, $OCH_3$, $OCHF_2$, or $OCF_3$;

$A^2$ is $C_{(1-6)}$alkyl (including $C_{(1-4)}$alkyl), $C_{(0-2)}$alkyl-$C_{(3-6)}$ cycloalkyl,

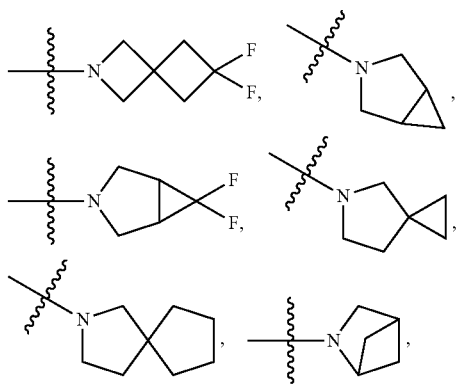

$CH_2$—$C_6H_4$—$C(O)NH_2$, —$C_6H_4$—F, $CH_2$—CCH, or $CH_2$—CC—$CH_3$; wherein said $C_{(1-6)}$alkyl, and said $C_{(0-2)}$ alkyl-$C_{(3-6)}$cycloalkyl are optionally substituted with up to six fluorine atoms, Cl, —CN, $OCH_3$, $OCHF_2$, or $OCF_3$;

or $A^1$ and $A^2$ may be taken together with their attached nitrogen to form a ring selected from the group consisting of: thiomorpholinyl, piperidinyl, pyrrolidinyl, piperazinyl, morpholinyl, azetidinyl, and aziridinyl; wherein said piperidinyl, pyrrolidinyl, piperazinyl, morpholinyl, azetidinyl, and aziridinyl are optionally substituted with $CF_3$, $CH_2CH_2F$, $C_{(1-2)}$alkyl, $C_{(3-6)}$cycloalkyl, —CN, OH, $CH_2OH$, $CH_2F$, F, Cl, $OCH_3$, $OCHF_2$, $OCF_3$, —$(CX_2)_nO(CX_2)_n$—, or —$(CX_2)_n$— (including

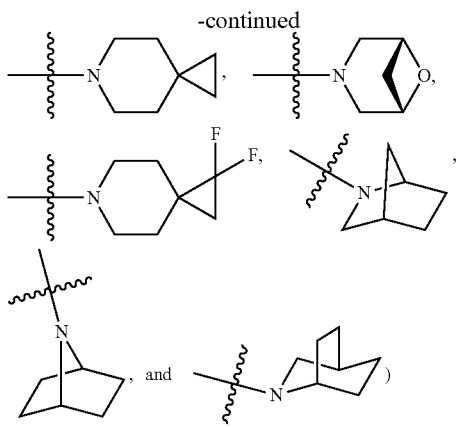

and up to three additional substituents selected from the group consisting of CH$_3$ and F (including

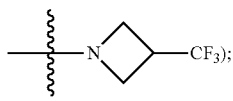

n is independently 0, 1, 2, 3, or 4;

X is H, or F; wherein each occurrence of X in a single molecule is independently defined;

R$^5$ is SO$_2$NA$^3$A$^4$, CONA$^3$A$^4$, NA$^3$A$^4$, OCH$_2$C(CF$_3$)$_2$OH, C$_{(3-6)}$cycloalkyl, or C$_{(1-6)}$alkyl; wherein said C$_{(3-6)}$cycloalkyl and said C$_{(1-6)}$alkyl are optionally substituted with OH, Cl, —CN, H, OCH$_3$, OCHF$_2$, OCF$_3$, or NA$^3$A$^4$, further optionally substituted with —CH$_2$CH$_2$— attached to the same carbon atom, and up to seven fluorine atoms; (including

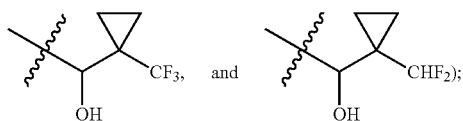

A$^3$ is H, or C$_{(1-4)}$alkyl; wherein said C$_{(1-4)}$alkyl is optionally substituted with OH, Cl, —CN, OCH$_3$, OCHF$_2$, or OCF$_3$; and up to six fluorine atoms;

A$^4$ is H, C$_{(1-6)}$alkyl, C$_{(3-6)}$cycloalkyl (including cyclopropyl, and cyclobutyl), or C$_{(3-6)}$heterocycloalkyl (including oxetanyl and tetrahydrofuranyl); wherein said C$_{(1-6)}$alkyl is optionally substituted with cyclopropyl, morpholinyl, OH, OCH$_3$, C(O)NH$_2$, Cl, —CN, OCHF$_2$, OCF$_3$ and additionally substituted with up to three fluorine atoms; and wherein said C$_{(3-6)}$cycloalkyl, and C$_{(3-6)}$heterocycloalkyl are optionally substituted with CF$_3$, CH$_3$, —CN, C(O)NH$_2$, and up to three fluorine atoms;

or A$^3$ and A$^4$ can be taken together with their attached nitrogen to form a ring selected from the group consisting of piperidinyl, morpholinyl, piperazinyl, pyrrolidinyl, aziridinyl, and azetidinyl wherein said piperidinyl, morpholinyl, piperazinyl, pyrrolidinyl, aziridinyl, and azetidinyl are optionally substituted with up to four groups selected from the group consisting of CF$_3$, OH, CH$_3$, CH$_2$F, and CHF$_2$; and further optionally substituted with up to four groups selected from the group consisting of CF$_3$, OH, CH$_3$, CH$_2$F, and CHF$_2$; and further optionally substituted with up to six fluorine atoms;

and pharmaceutically acceptable salts thereof.

In another embodiment of the invention:

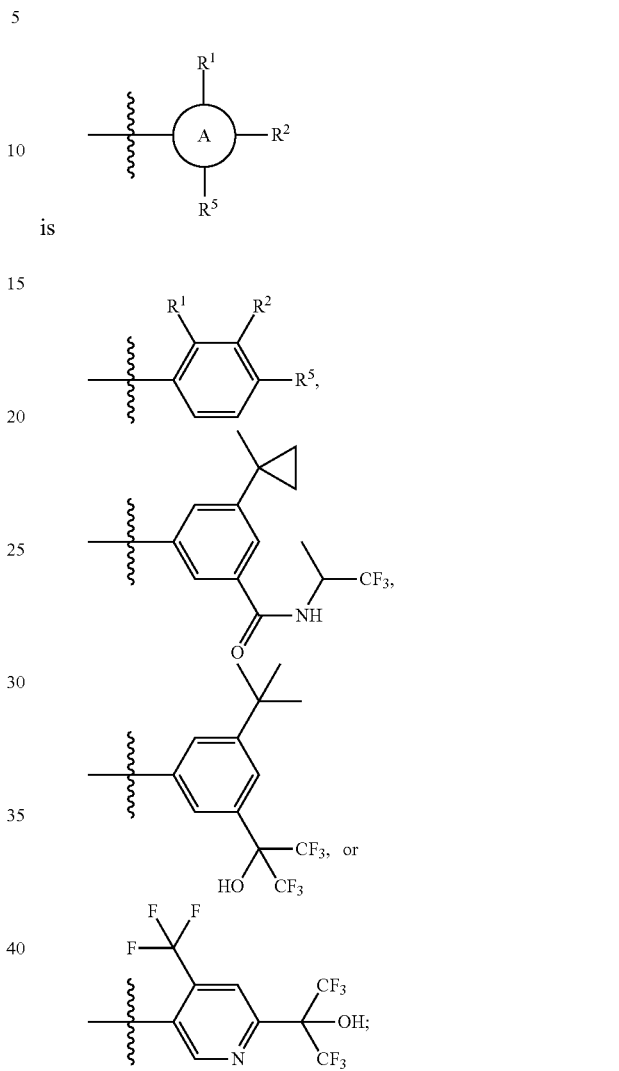

R$^1$ is Cl, —CN, H, F, OCH$_3$,

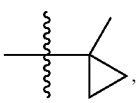 [SMILES: *C1(C)CC1]

OCHF$_2$, OCF$_3$, C$_{(1-2)}$alkyl, Br, or I; wherein said C$_{(1-2)}$alkyl is optionally substituted with up to five fluorine atoms;

R$^2$ is F, Cl, —CN, H, OCH$_3$, OCHF$_2$, OCF$_3$, cyclopropyl or C$_{(1-2)}$alkyl; wherein said C$_{(1-2)}$alkyl is optionally substituted with up to five fluorine atoms (including CH$_3$, CHF$_2$, and CF$_3$), and said cyclopropyl is optionally substituted with OH, CH$_3$, CF$_3$, and up to five fluorine atoms; or R$^1$ and R$^2$ may be taken together with their attached phenyl to form a fused ring system selected from the group consisting of naphthalenyl, tetrahydronaphthalenyl, isoqinolinyl, quinolinyl, and chromanyl; provided that R$^2$ may not be H if R$^1$ is H;

R$^3$ is oxadiazolyl, isoxadiazolyl, oxazolyl, isoxazolyl, triazolyl, tetrazolyl, 1,2,4-oxadiazol-5(4H)-on-3-yl, pyridyl, thiazolyl, pyrimidyl, pyridazyl, pyrazyl, imidazolyl, or pyrrolyl; wherein said oxadiazolyl, isoxadiazolyl, oxazolyl, isoxazolyl, triazolyl, pyridyl, thiazolyl, pyrimidyl, pyridazyl, pyrazyl, imidazolyl, or pyrrolyl is optionally substituted with $R^4$, and said triazolyl may be additionally substituted with one substituent selected from the group consisting of $CH_3$ and cyclopropyl;

$R^4$ is H, $CH_2SO_2CH_3$, $C(O)NH_2$, $C_{(1-4)}$alkyl (including $C_{(1-2)}$alkyl),

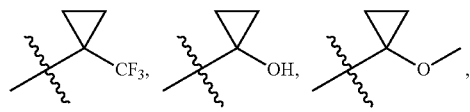

or —CN; wherein said $C_{(1-4)}$alkyl is optionally substituted with up to six fluorine atoms, $CO_2H$, OH, or —CN (including $CH_2C(CH_3)_2CO_2H$, $CH_2C(CH_3)_2CN$, and $C_{(0-1)}$alkylC$(CH_3)_2OH$);

$A^1$ is H, or $C_{(1-3)}$alkyl; wherein said $C_{(1-3)}$alkyl is optionally substituted with up to five fluorine atoms, Cl, —CN, $OCH_3$, $OCHF_2$, or $OCF_3$;

$A^2$ is $C_{(1-4)}$alkyl, $C_{(0-2)}$alkyl-$C_{(3-6)}$cycloalkyl, $CH_2$—$C_6H_4$—$C(O)NH_2$, —$C_6H_4$—F, $CH_2$—CCH, $CH_2$—CC—$CH_3$, or $CH_2CH_2OCH_3$; wherein said $C_{(1-4)}$alkyl, and said $C_{(0-2)}$alkyl-$C_{(3-6)}$cycloalkyl are optionally substituted with up to three fluorine atoms, Cl, —CN, $OCH_3$, $OCHF_2$, or $OCF_3$ (including $CH_2CH_2$—CN);

or $A^1$ and $A^2$ may be taken together with their attached nitrogen to form a ring selected from the group consisting of:

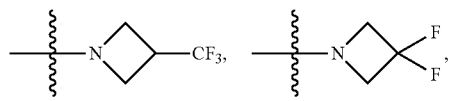
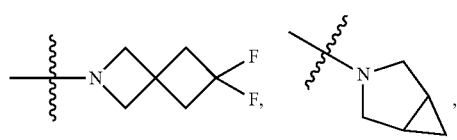
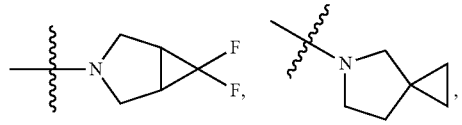
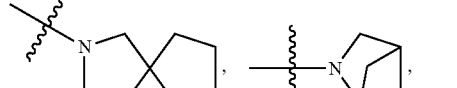
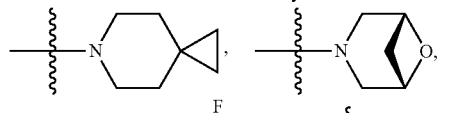
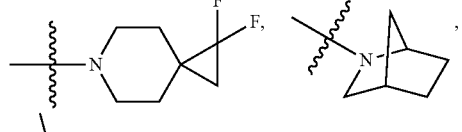
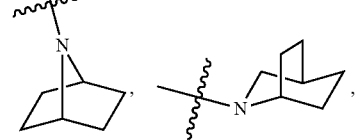

thiomorpholinyl, piperidinyl, pyrrolidinyl, piperazinyl, and morpholinyl; wherein said piperidinyl, pyrrolidinyl, piperazinyl, and morpholinyl are optionally substituted with $CF_3$, $CH_2CH_2F$, $C_{(1-2)}$alkyl, —CN, OH, $CH_2OH$, $CH_2F$, F, Cl, $OCH_3$, $OCHF_2$, or $OCF_3$, and up to three additional substituents selected from the group consisting of $CH_3$ and F;

$R^5$ is $SO_2NA^3A^4$,

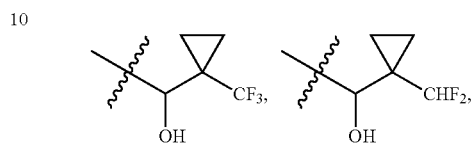

$OCH_2C(CF_3)_2OH$, or $C_{(1-6)}$alkyl; wherein said $C_{(1-6)}$alkyl is optionally substituted with OH, Cl, —CN, H, $OCH_3$, $OCHF_2$, or $OCF_3$; and up to six fluorine atoms;

$A^3$ is H, or $C_{(1-4)}$alkyl; wherein said $C_{(1-4)}$alkyl is optionally substituted with OH, Cl, —CN, $OCH_3$, $OCHF_2$, or $OCF_3$; and up to six fluorine atoms;

$A^4$ is $C_{(1-6)}$alkyl, $C_{(3-6)}$cycloalkyl (including cyclopropyl, and cyclobutyl), oxetanyl, or tetrahydrofuranyl; wherein said $C_{(1-6)}$ alkyl is optionally substituted with cyclopropyl, morpholinyl, OH, $OCH_3$, or $C(O)NH_2$, and additionally substituted with up to three fluorine atoms; and wherein said $C_{(3-6)}$cycloalkyl, oxetanyl, and tetrahydrofuranyl are optionally substituted with $CF_3$, $CH_3$, —CN, or $C(O)NH_2$;

or $A^3$ and $A^4$ can be taken together with their attached nitrogen to form a ring selected from the group consisting of piperidinyl, morpholinyl, piperazinyl, and pyrrolidinyl, wherein said piperidinyl, morpholinyl, and piperazinyl are optionally substituted with up to four methyl groups and up to six fluorine atoms;

and pharmaceutically acceptable salts thereof.

In another embodiment of the invention:

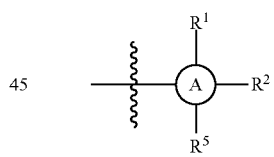

is

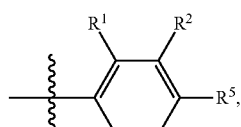

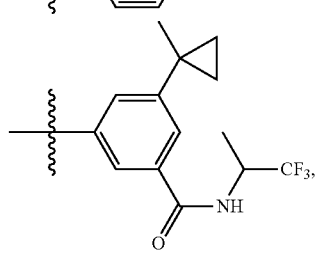

-continued

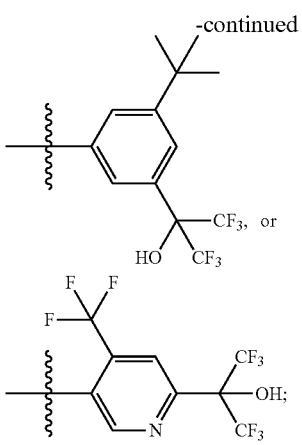

$R^1$ is Cl, —CN, H, F, OCH$_3$,

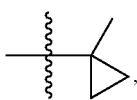

OCHF$_2$, OCF$_3$, or C$_{(1-2)}$alkyl; wherein said C$_{(1-2)}$alkyl is optionally substituted with up to five fluorine atoms (including CHF$_2$, CF$_3$, CH$_3$, and CH$_2$CH$_3$);

$R^2$ is F, Cl, —CN, CHF$_2$, CF$_3$, CH$_3$, or H; or $R^1$ and $R^2$ may be taken together with their attached phenyl to form a fused ring system selected from the group consisting of naphthalenyl, tetrahydronaphthalenyl, isoqinolinyl, quinolinyl, and chromanyl; provided that $R^2$ may not be H if $R^1$ is H;

$R^3$ is oxadiazolyl, isoxadiazolyl, oxazolyl, isoxazolyl, triazolyl, tetrazolyl, 1,2,4-oxadiazol-5(4H)-on-3-yl, pyridyl, thiazolyl, pyrimidyl, pyridazyl, or pyrazyl; wherein said oxadiazolyl, isoxadiazolyl, oxazolyl, isoxazolyl, triazolyl, pyridyl, thiazolyl, pyrimidyl, pyridazyl, or pyrazyl is optionally substituted with $R^4$, and said triazolyl may be additionally substituted with one substituent selected from the group consisting of CH$_3$ and cyclopropyl;

$R^4$ is H, CH$_2$SO$_2$CH$_3$, C(O)NH$_2$, CH$_2$C(CH$_3$)$_2$CO$_2$H, CH$_2$C(CH$_3$)$_2$CN, C$_{(0-1)}$alkylC(CH$_3$)$_2$OH,

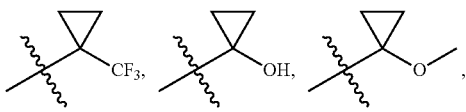

—CN, or C$_{(1-2)}$alkyl (including CH$_3$);
wherein said C$_{(1-2)}$alkyl is optionally substituted with up to five fluorine atoms;

$A^1$ is H, or C$_{(1-3)}$alkyl; wherein said C$_{(1-3)}$alkyl is optionally substituted with up to five fluorine atoms (including CH$_2$CH$_2$F);

$A^2$ is C$_{(1-4)}$alkyl (including C$_{(2-4)}$alkyl), C$_{(0-2)}$alkyl-C$_{(3-6)}$cycloalkyl (including CH$_2$-cyclopentyl, CH$_2$CH$_2$-cyclopropyl, C$_{(3-4)}$cycloalkyl, and

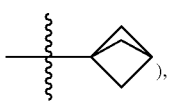 [SMILES: *C12CC(C1)C2]),

CH$_2$—C$_6$H$_4$—C(O)NH$_2$, —C$_6$H$_4$—F, CH$_2$—CCH, CH$_2$—CC—CH$_3$, or CH$_2$CH$_2$—CN; wherein C$_{(1-4)}$alkyl, and said C$_{(0-2)}$alkyl-C$_{(3-6)}$cycloalkyl are optionally substituted with up to three fluorine atoms;

or $A^1$ and $A^2$ may be taken together with their attached nitrogen to form a ring selected from the group consisting of:

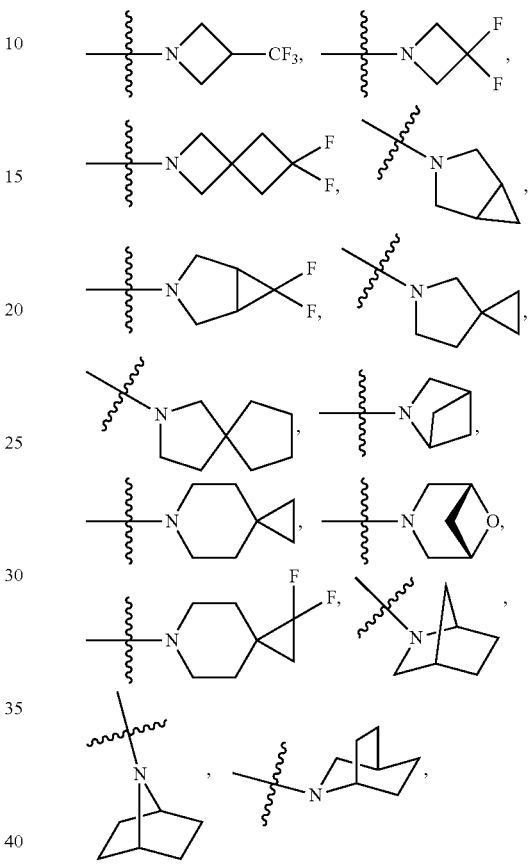

thiomorpholinyl, piperidinyl, pyrrolidinyl, piperazinyl, and morpholinyl; wherein said piperidinyl, pyrrolidinyl, piperazinyl, and morpholinyl are optionally substituted with CF$_3$, CH$_2$CH$_2$F, C$_{(1-2)}$alkyl, —CN, OH, CH$_2$OH, CH$_2$F, or F, and up to three additional substituents selected from the group consisting of CH$_3$ and F;

$R^5$ is SO$_2$NA$^3$A$^4$,

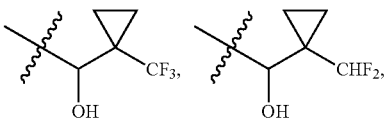

OCH$_2$C(CF$_3$)$_2$OH, or C$_{(1-6)}$alkyl; wherein said C$_{(1-6)}$alkyl is optionally substituted with one OH group and up to six fluorine atoms (including C(CF$_3$)$_2$OH, and CH$_2$C(CF$_3$)$_2$OH);

$A^3$ is H, or C$_{(1-4)}$alkyl;

$A^4$ is C$_{(1-6)}$alkyl (including CH(CH$_3$)$_2$, C(CH$_3$)$_3$, C(CH$_3$)$_2$CH$_2$CH$_3$, and CH$_2$C(CH$_3$)$_3$), cyclopropyl, cyclobutyl, oxetanyl, or tetrahydrofuranyl; wherein said C$_{(1-6)}$ alkyl is optionally substituted with cyclopropyl, morpholinyl, OH, OCH$_3$, or C(O)NH$_2$, and additionally substituted with up to three fluorine atoms (including C(CH$_3$)$_2$CH$_2$OCH$_3$, C(CH$_3$)$_2$ CH$_2$OH, C(CH$_3$)$_2$CH$_2$-morpholinyl, C(CH$_3$)$_2$CH$_2$CH$_2$OH, C(CH$_3$)$_2$CH$_2$C(O)NH$_2$, and CH$_2$C(CH$_3$)$_2$OH); and wherein said cyclopropyl cyclobutyl, oxetanyl, and tetrahydrofuranyl are optionally substituted with CF$_3$, CH$_3$, —CN, or C(O)NH$_2$;

or A$^3$ and A$^4$ can be taken together with their attached nitrogen to form a ring selected from the group consisting of piperidinyl, morpholinyl, piperazinyl, and pyrrolidinyl, wherein said piperidinyl, morpholinyl, and piperazinyl are optionally substituted with one or two methyl groups and up to three fluorine atoms;

and pharmaceutically acceptable salts thereof.

In another embodiment of the invention:

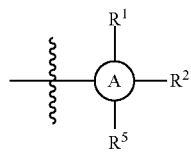

is

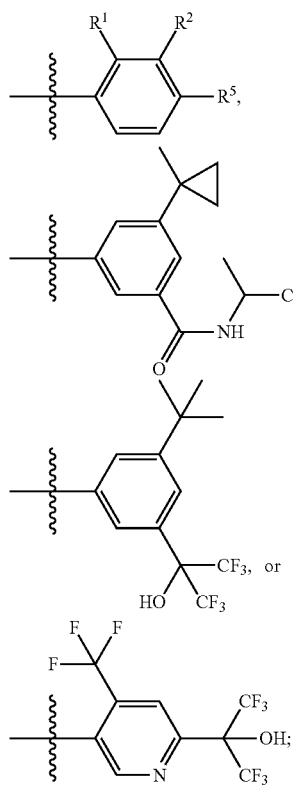

R$^1$ is Cl, CHF$_2$, CF$_3$, CH$_3$, CH$_2$CH$_3$, —CN, H, F, OCH$_3$, OCHF$_2$, or OCF$_3$;

R$^2$ is F, Cl, CHF$_2$, CF$_3$, CH$_3$, or H; or R$^1$ and R$^2$ may be taken together with their attached phenyl to form a fused ring system selected from the group consisting of naphthalenyl, tetrahydronaphthalenyl, isoqinolinyl, and chromanyl; provided that R$^2$ may not be H if R$^1$ is H;

R$^3$ is oxadiazolyl, isoxadiazolyl, oxazolyl, isoxazolyl, triazolyl, tetrazolyl, 1,2,4-oxadiazol-5(4H)-on-3-yl, pyridyl, or thiazolyl, wherein said oxadiazolyl, isoxadiazolyl, oxazolyl, isoxazolyl, triazolyl, pyridyl, or thiazolyl is optionally substituted with R$^4$, and said triazolyl may be additionally substituted with one substituent selected from the group consisting of CH$_3$ and cyclopropyl;

R$^4$ is H, CH$_2$SO$_2$CH$_3$, C(O)NH$_2$, CH$_3$, CH$_2$C(CH$_3$)$_2$CO$_2$H, CH$_2$C(CH$_3$)$_2$CN, C$_{(0-1)}$alkylC(CH$_3$)$_2$OH,

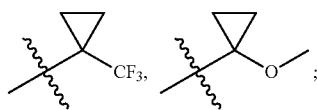

A$^1$ is H, C$_{(1-3)}$alkyl (including CH$_2$CH$_3$), or CH$_2$CH$_2$F;
A$^2$ is C$_{(2-4)}$alkyl (including CH$_2$CH$_3$), CH$_2$-cyclopentyl, CH$_2$CH$_2$-cyclopropyl, C$_{(3-4)}$cycloalkyl,

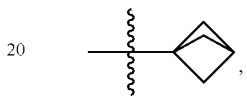

CH$_2$—C$_6$H$_4$—C(O)NH$_2$, —C$_6$H$_4$—F, CH$_2$—CCH, CH$_2$—CC—CH$_3$, or CH$_2$CH$_2$—CN; wherein said C$_{(3-4)}$cycloalkyl is optionally substituted with one fluorine atom and said C$_{(2-4)}$alkyl is optionally substituted with up to three fluorine atoms (including CH$_2$CF$_3$);

or A$^1$ and A$^2$ may be taken together with their attached nitrogen to form a ring selected from the group consisting of:

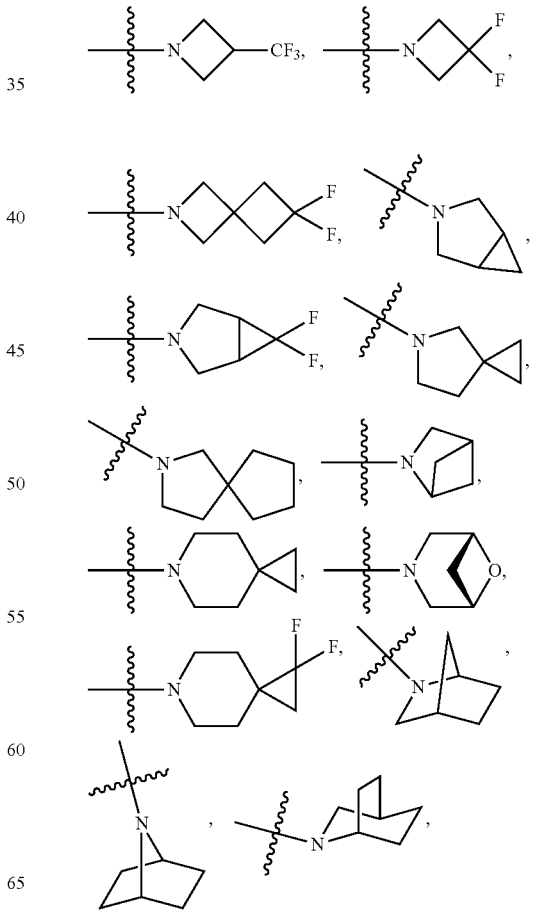

thiomorpholinyl, piperidinyl, pyrrolidinyl, and morpholinyl; wherein said piperidinyl, pyrrolidinyl, and morpholinyl are optionally substituted with CF₃, CH₂CH₂F, C₍₁₋₂₎alkyl, —CN, OH, CH₂OH, or CH₂F and up to three additional substituents selected from the group consisting of CH₃ and F;

$R^5$ is SO₂NA³A⁴,

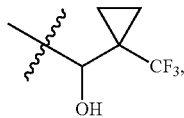

CH₂C(CF₃)₂OH, OCH₂C(CF₃)₂OH, or C(CF₃)₂OH;
$A^3$ is H, or C₍₁₋₄₎alkyl;
$A^4$ is C₍₁₋₆₎alkyl,

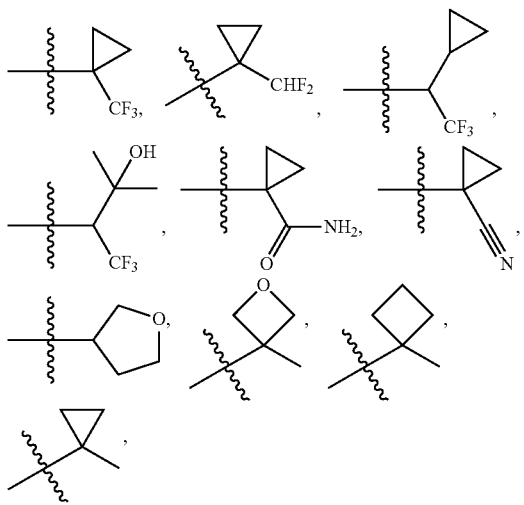

C(CH₃)₂CH₂OCH₃, C(CH₃)₂CH₂OH, C(CH₃)₂CH₂-morpholinyl, C(CH₃)₂CH₂CH₂OH, C(CH₃)₂CH₂C(O)NH₂, or CH₂C(CH₃)₂OH; wherein said C₍₁₋₆₎alkyl is optionally substituted with up to three fluorine atoms;

or $A^3$ and $A^4$ can be taken together with their attached nitrogen to form a ring selected from the group consisting of

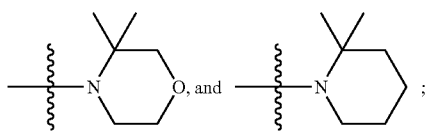

and pharmaceutically acceptable salts thereof.

In another embodiment of the invention:

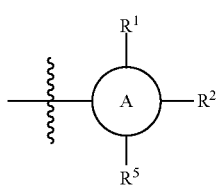

is

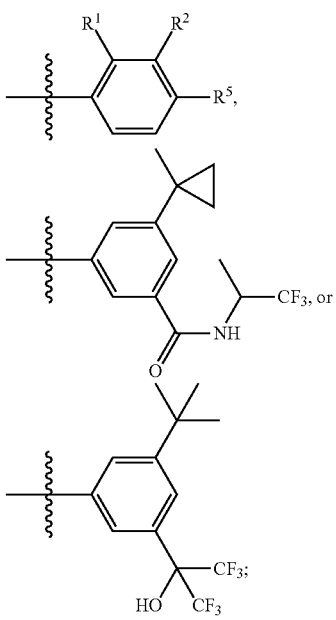

$R^1$ is H, Cl, CHF₂, CF₃, CH₃, F, OCHF₂, or OCF₃;
$R^2$ is F, Cl, CHF₂, CF₃, CH₃, or H; or $R^1$ and $R^2$ may be taken together with their attached phenyl to form a fused ring system selected from the group consisting of naphthalenyl, and chromanyl; provided that $R^2$ may not be H if $R^1$ is H;

$R^3$ is

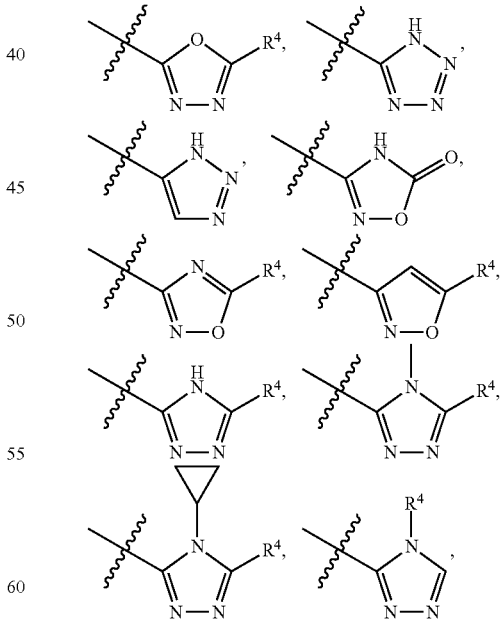

pyridyl, or pyrimidyl, wherein said pyridyl or pyrimidyl is optionally substituted with $R^4$;

$R^4$ is H, CH₂SO₂CH₃, C(O)NH₂, CH₃, CH₂C(CH₃)₂CO₂H, CH₂C(CH₃)₂CN, C₍₀₋₁₎alkylC(CH₃)₂OH,

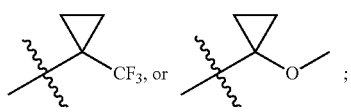

$A^1$ is $CH_3$, $CH_2CH_3$;
$A^2$ is $CH_2CH_2CH_3$, $CH(CH_3)_2$, $CH_2CH_3$, or $CH_2CF_3$;
or $A^1$ and $A^2$ may be taken together with their attached nitrogen to form a ring selected from the group consisting of:

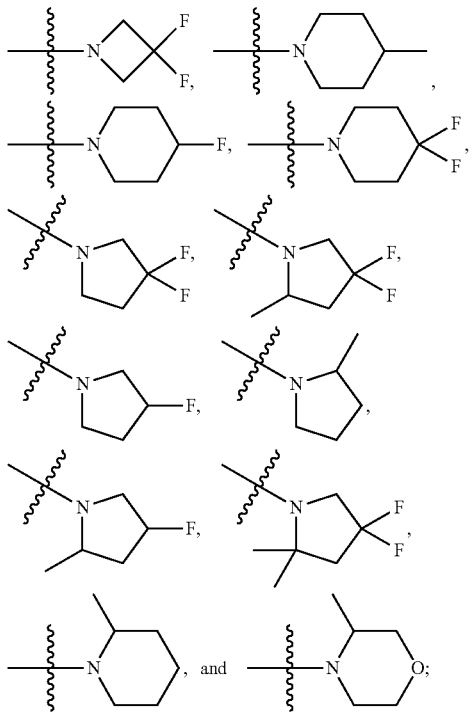

$R^5$ is $SO_2NA^3A^4$,

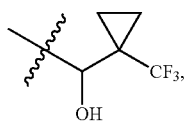

$CH_2C(CF_3)_2OH$, $OCH_2C(CF_3)_2OH$, or $C(CF_3)_2OH$;
$A^3$ is H, or $CH_3$;
$A^4$ is

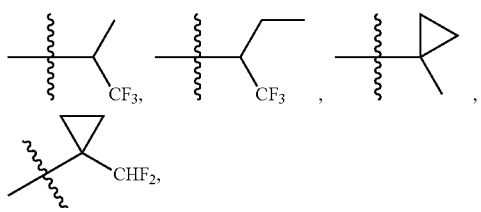

$CH_2CF_3$, or $C(CH_3)_2CF_3$;
and pharmaceutically acceptable salts thereof.
Another embodiment of the invention is a compound selected from the group consisting of:

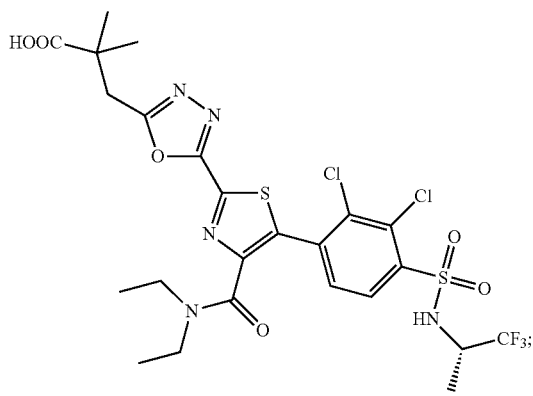

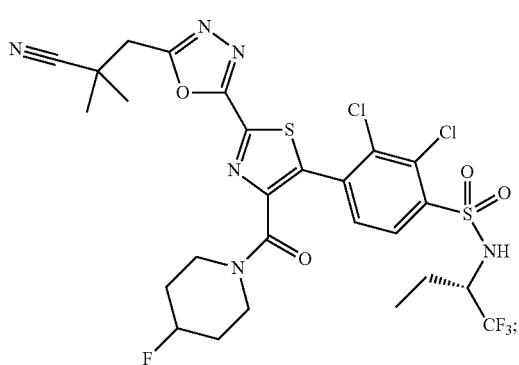

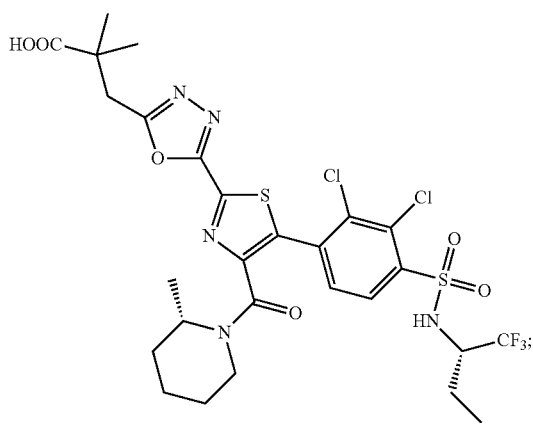

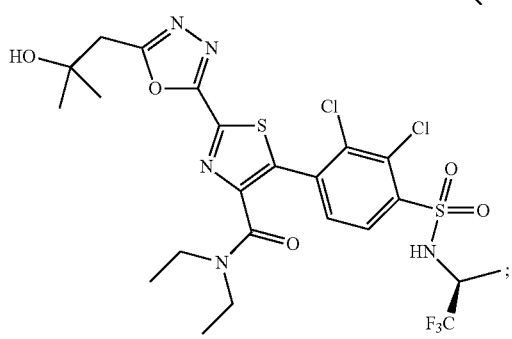

-continued
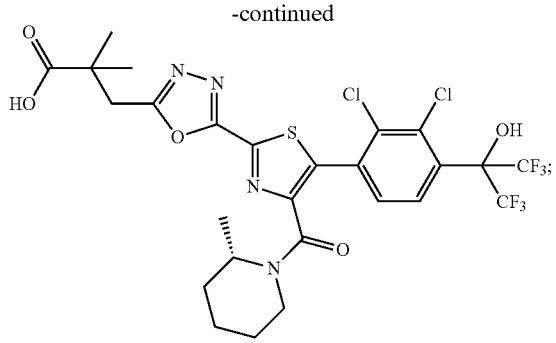
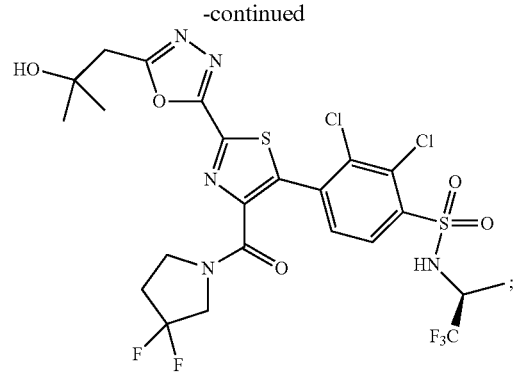
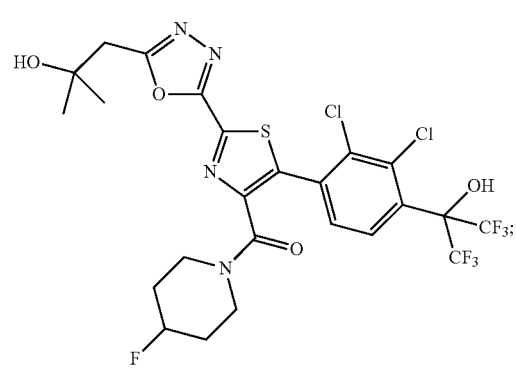 [SMILES: CC(C)(O)Cc1nnc(-c2nc(C(=O)N3CCC(F)CC3)c(-c3ccc(C(O)(C(F)(F)F)C(F)(F)F)c(Cl)c3Cl)s2)o1]
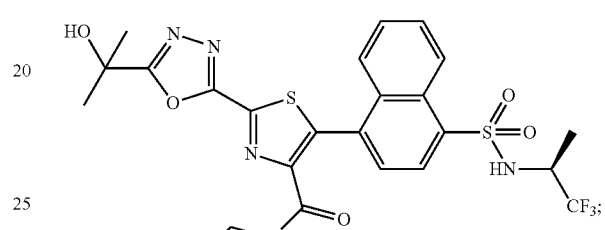
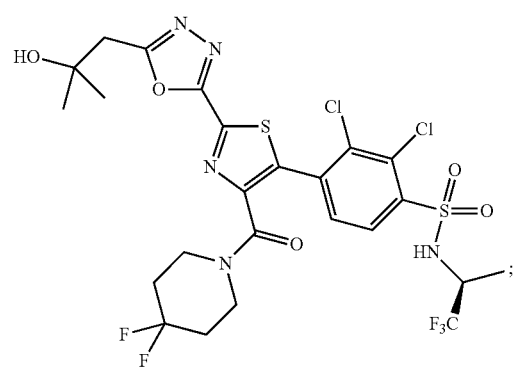
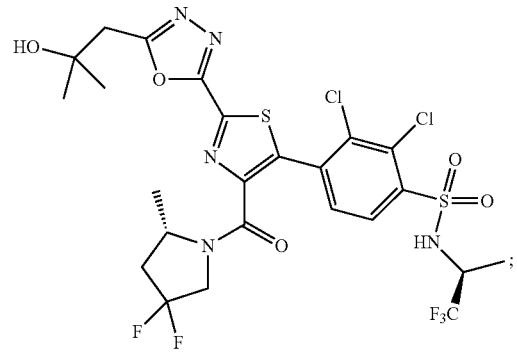
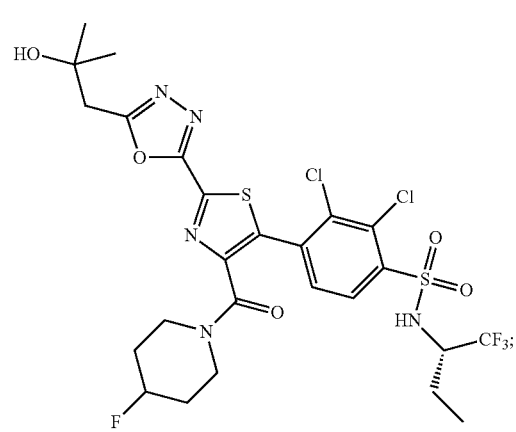
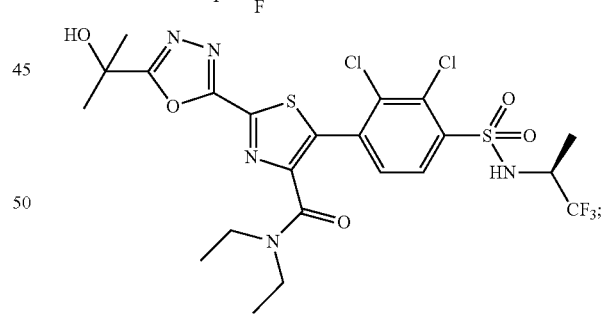
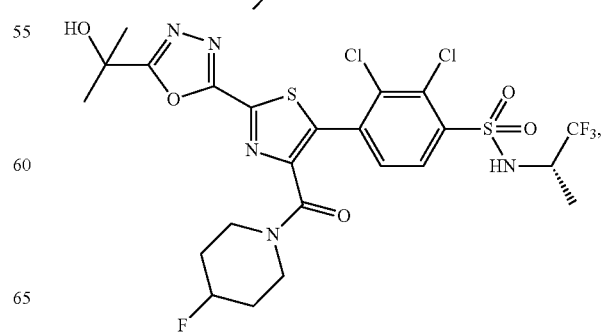

-continued
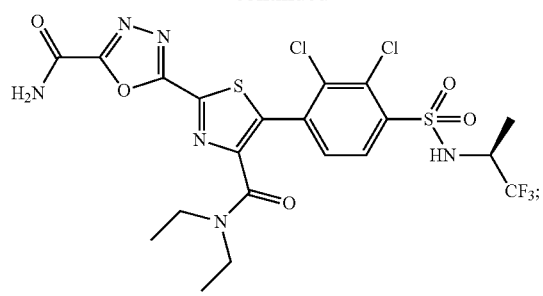
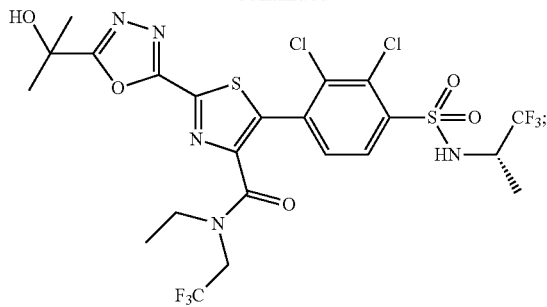
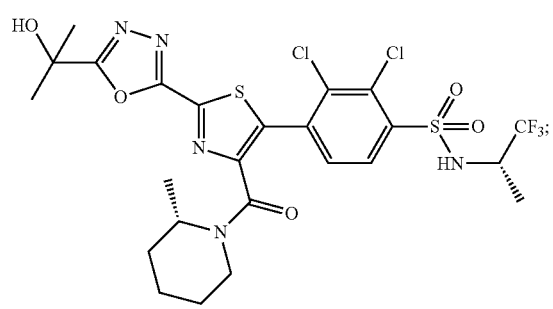
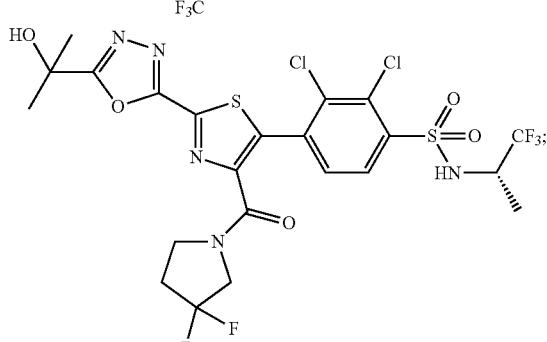
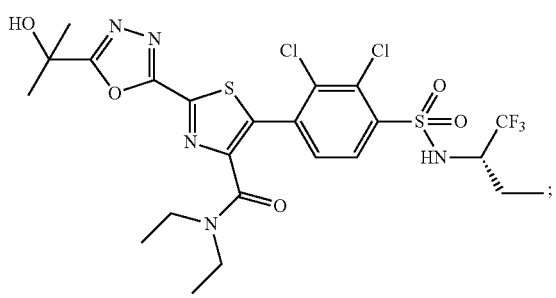
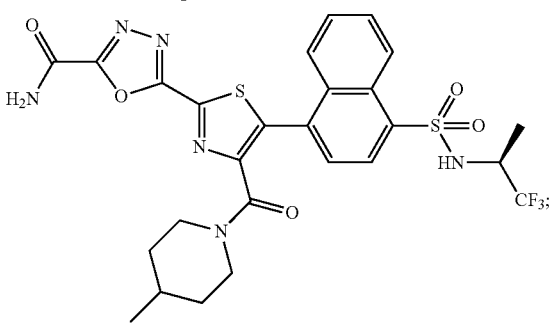
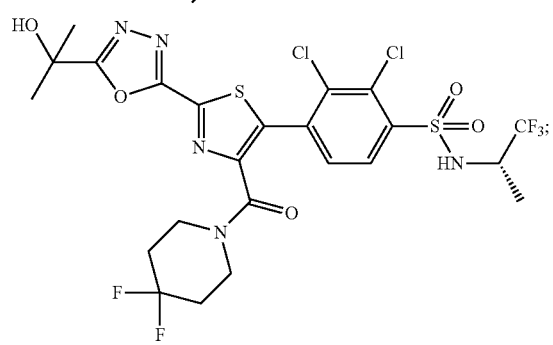
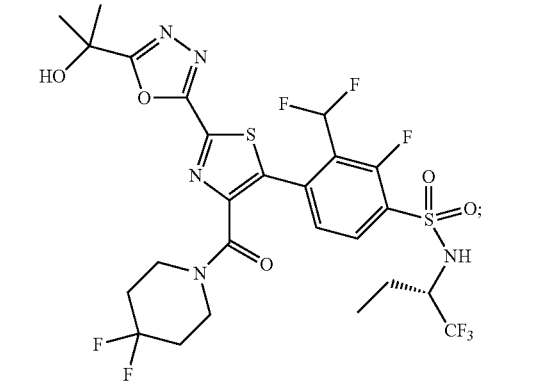
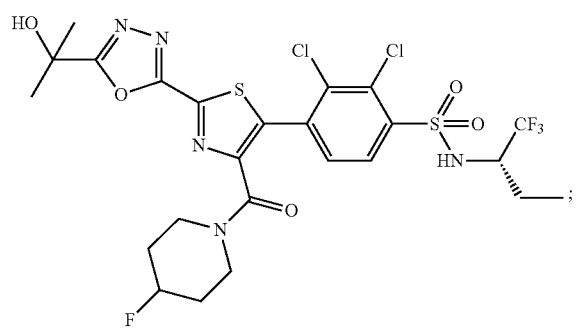
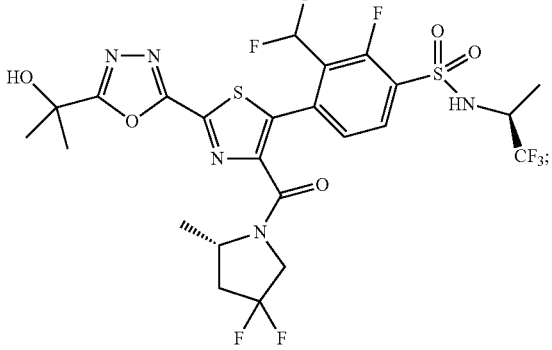

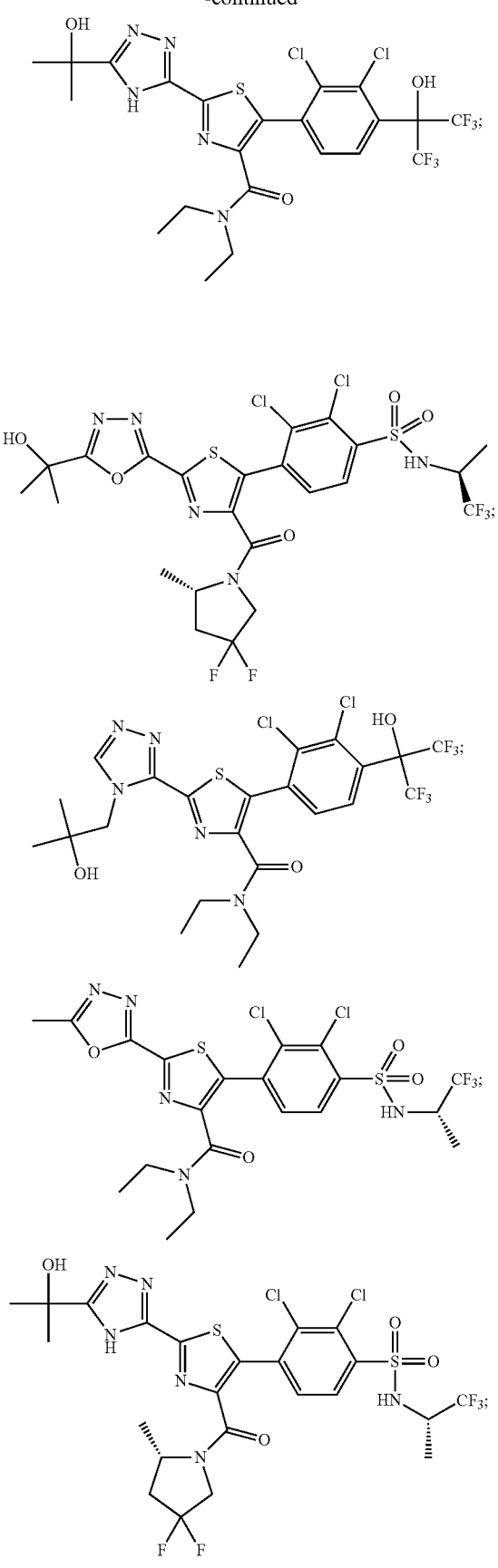
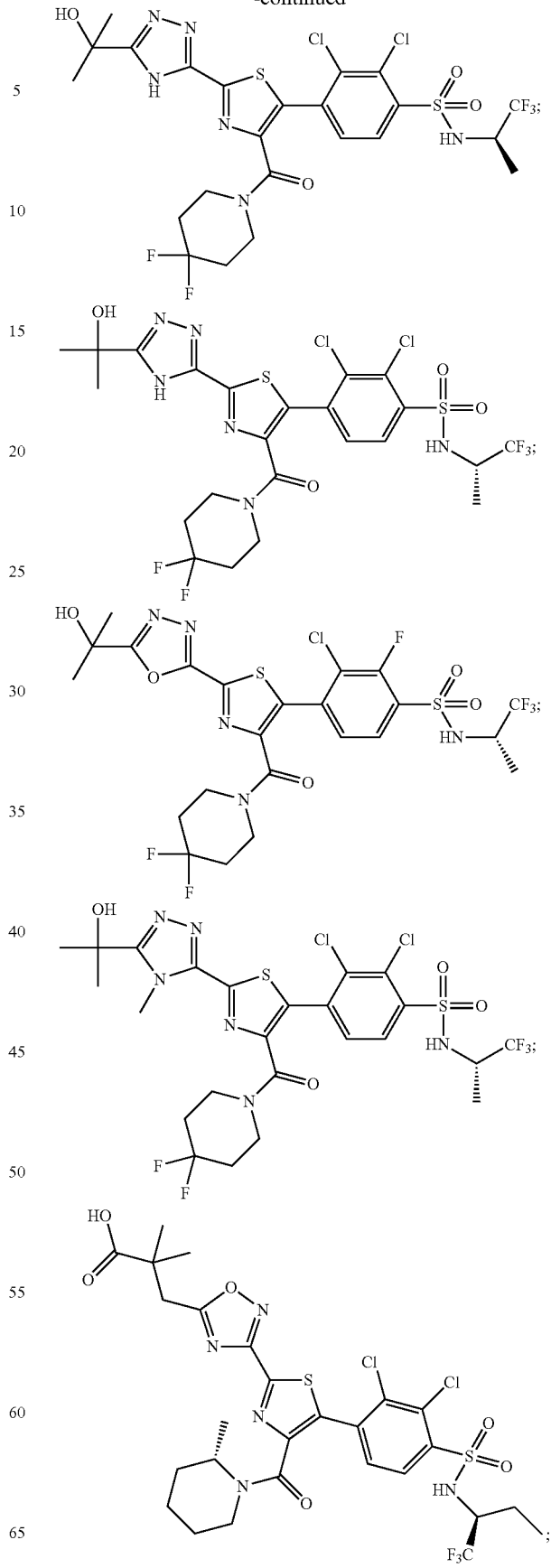

-continued
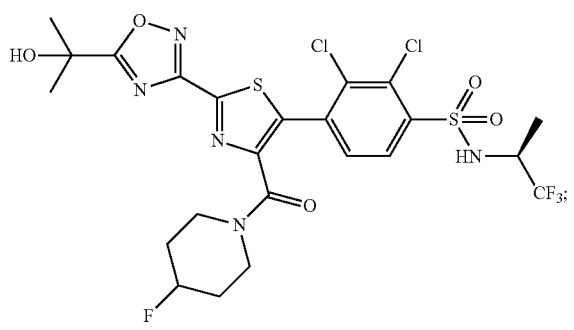
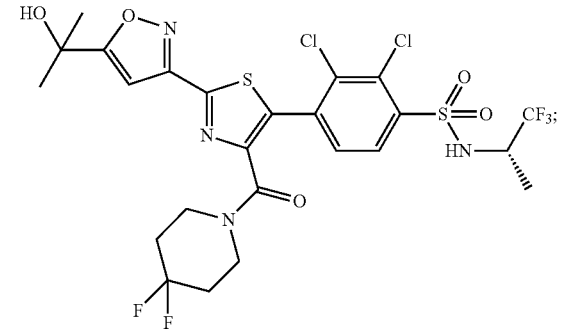
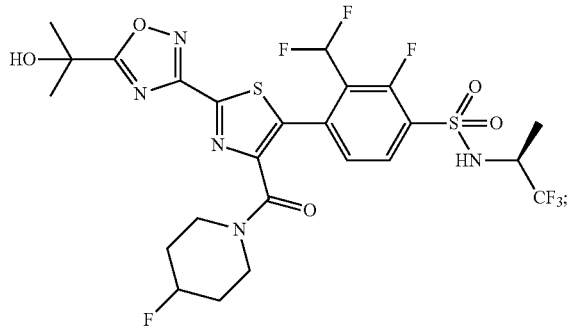
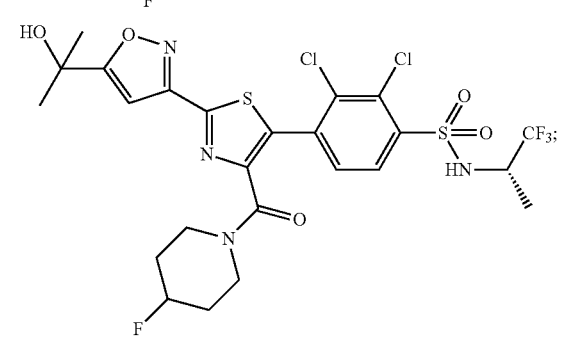
-continued
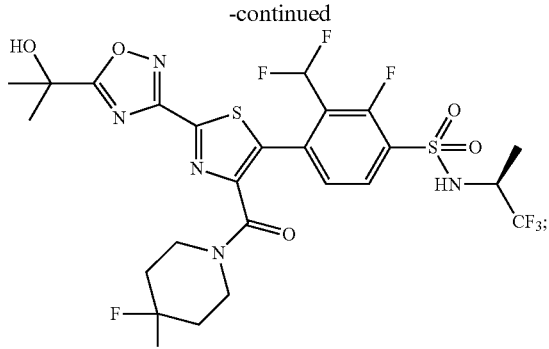
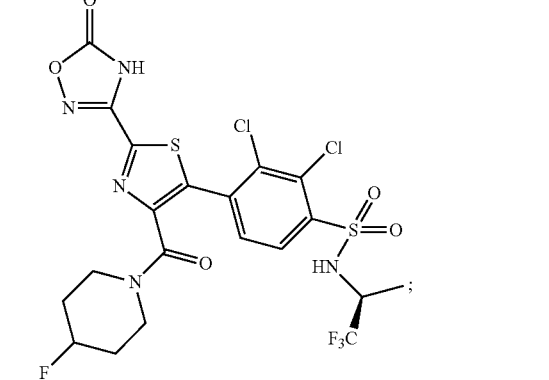
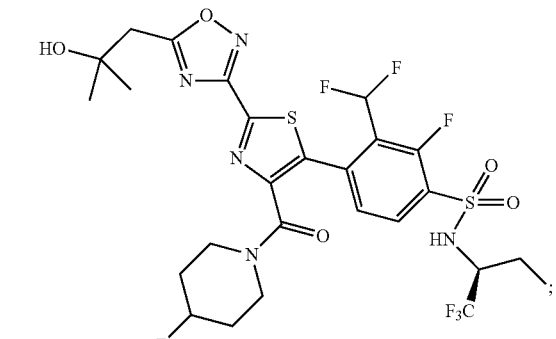
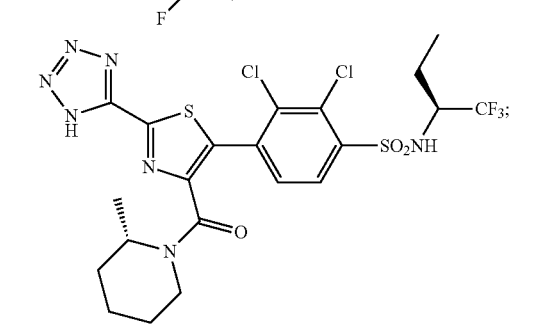
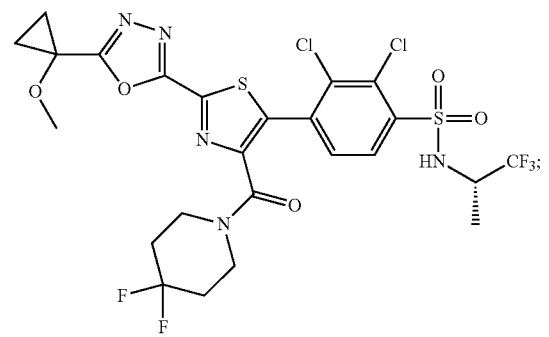

27
-continued
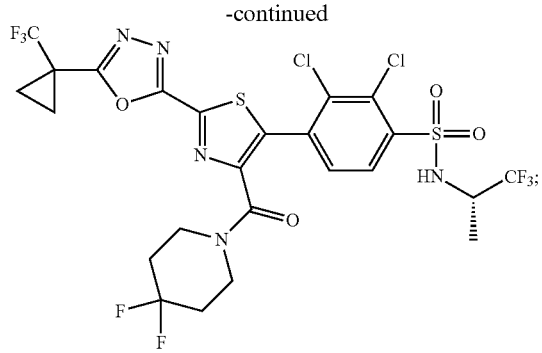
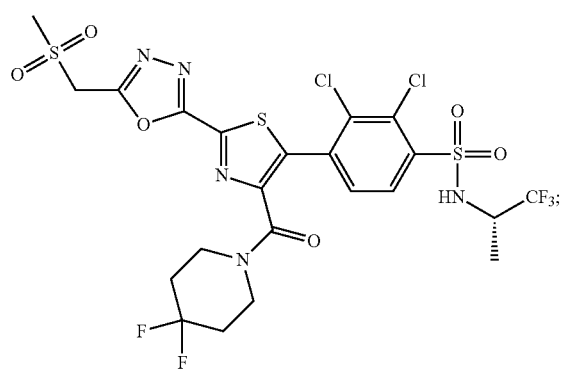
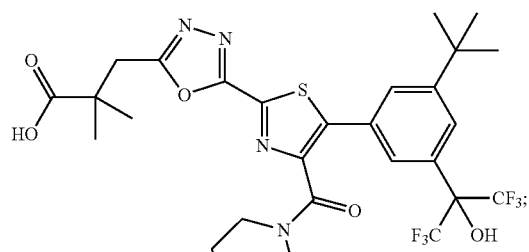
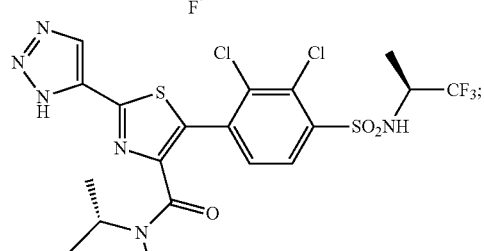
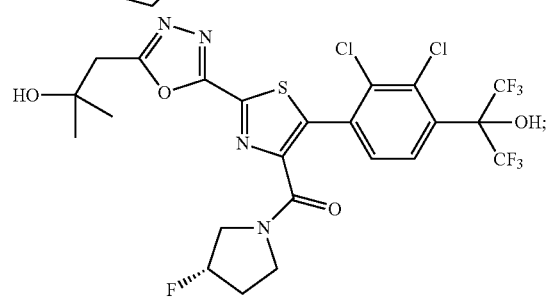
28
-continued
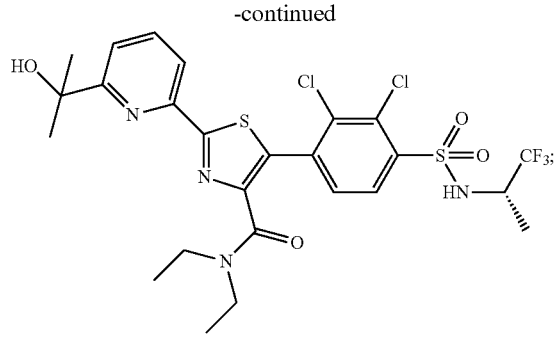
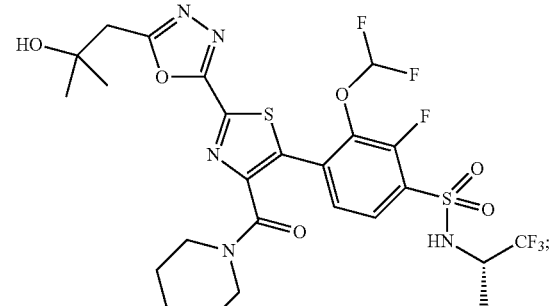
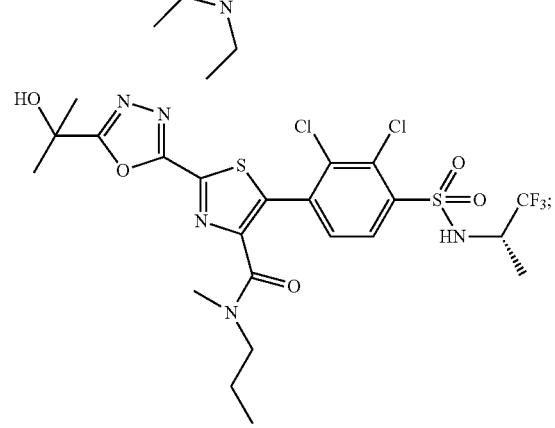
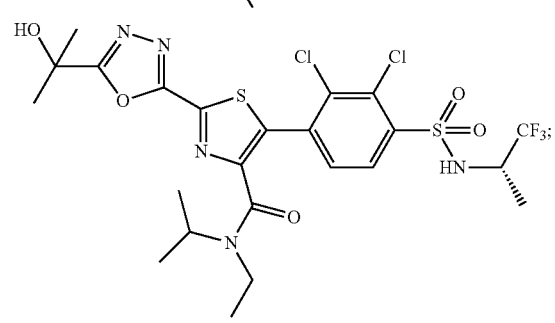

-continued
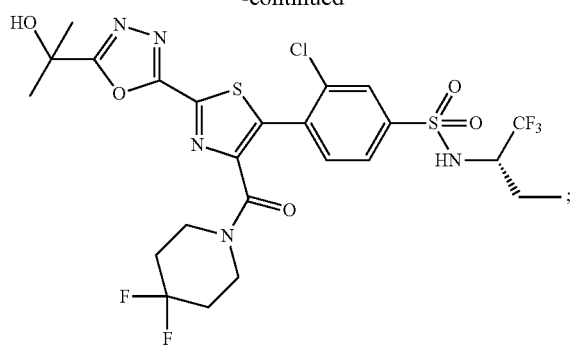
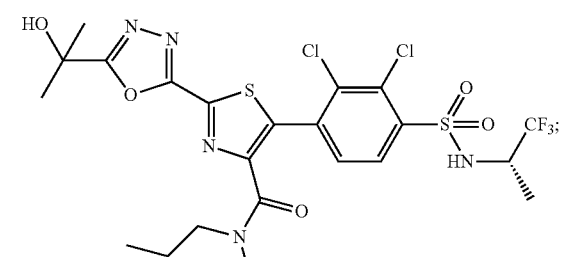
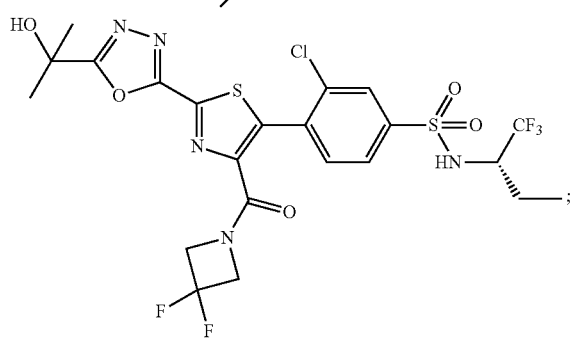
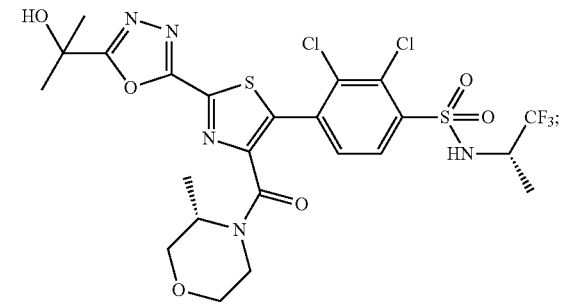
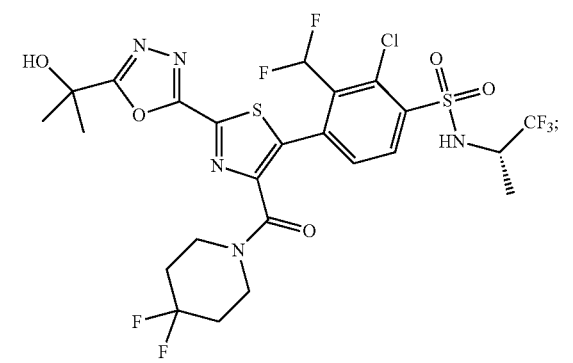
-continued
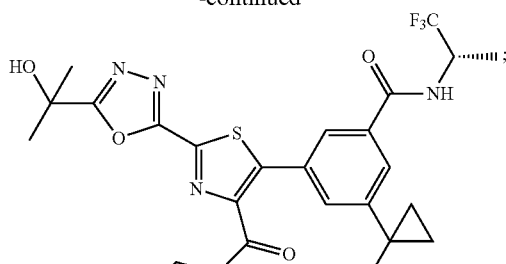
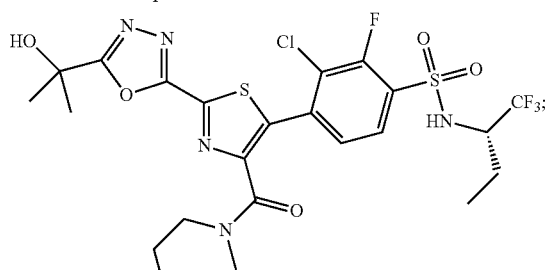
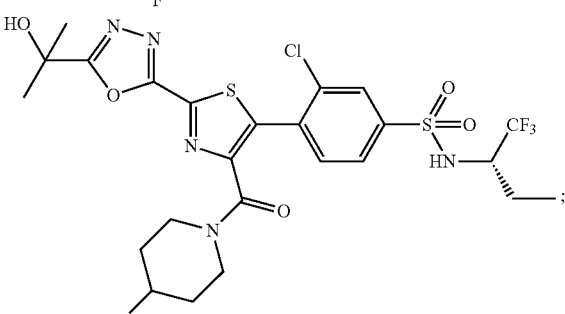
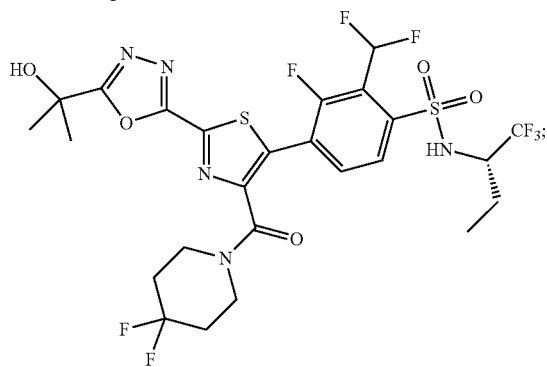
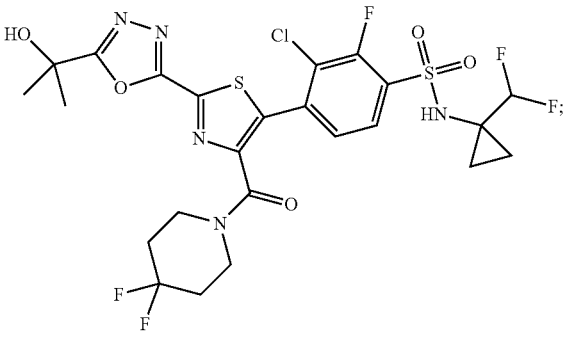

-continued
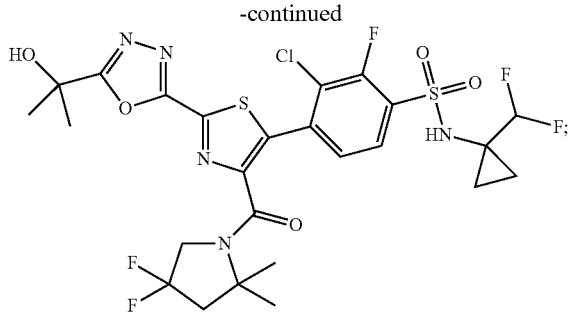
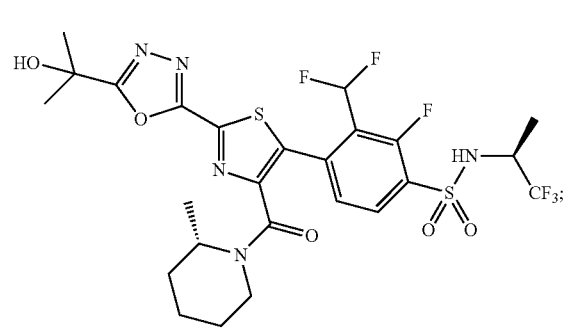
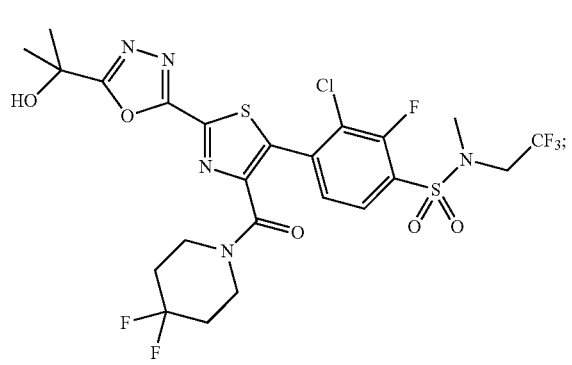
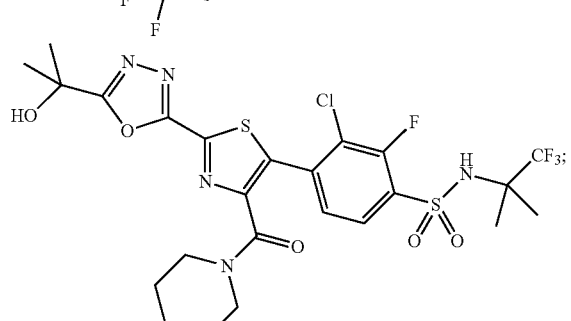
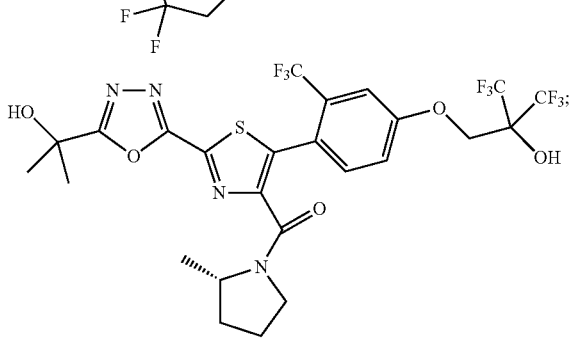
-continued
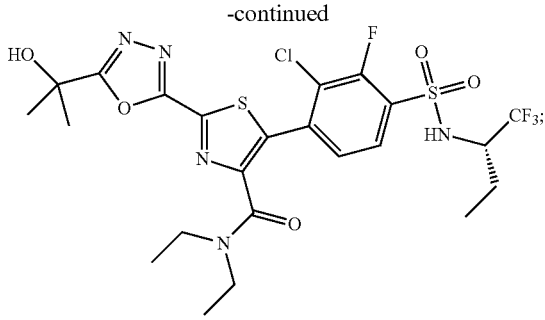
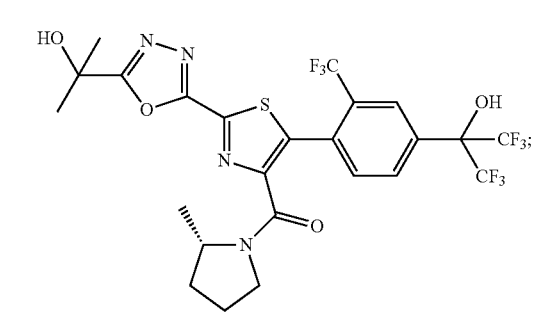
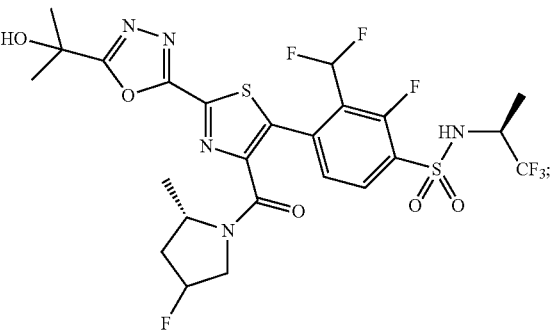
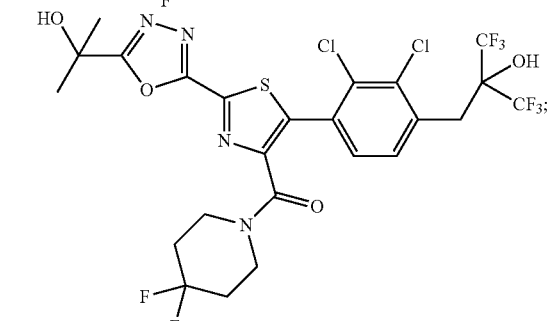
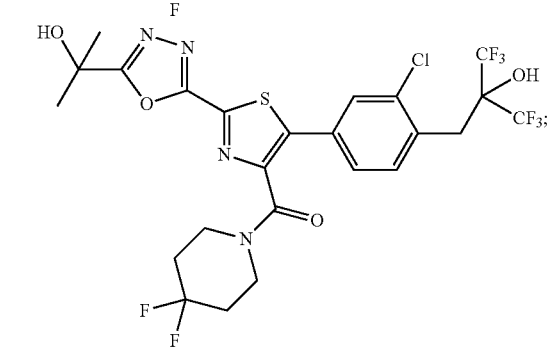

33
-continued
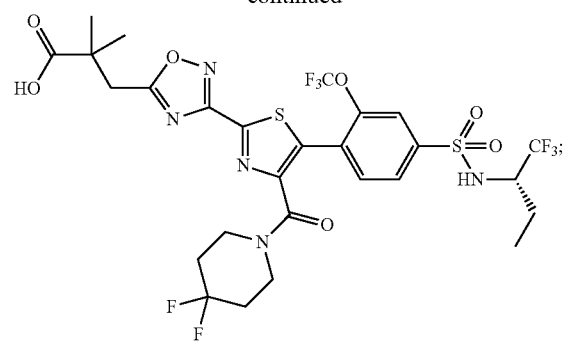
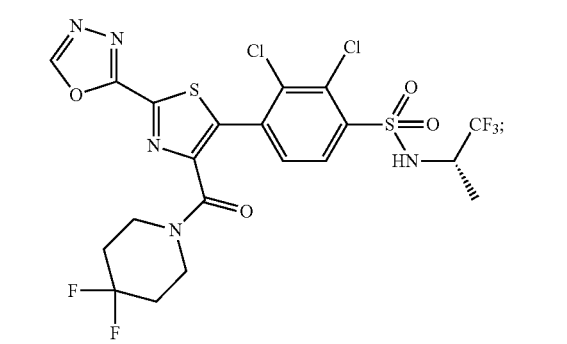
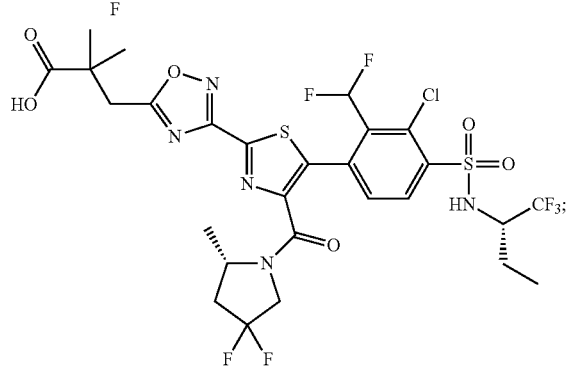
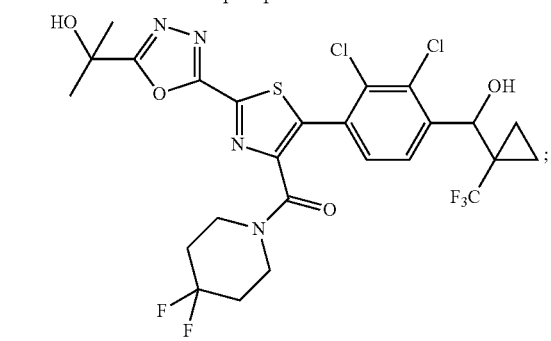
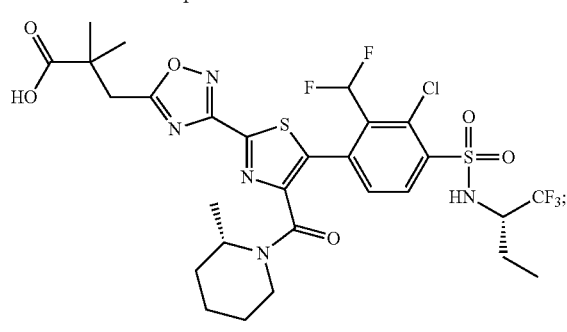
34
-continued
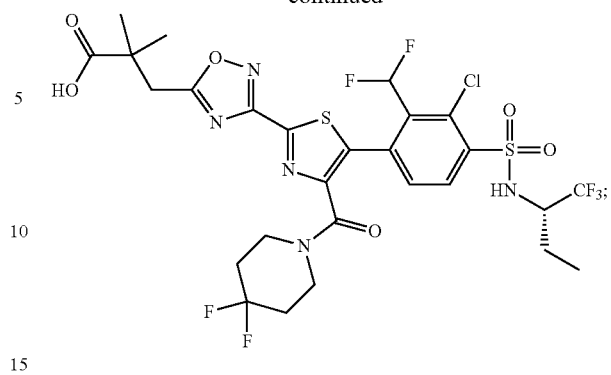
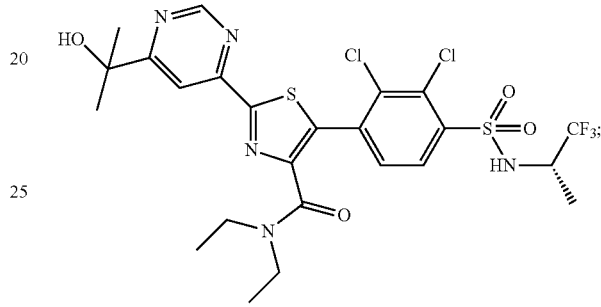
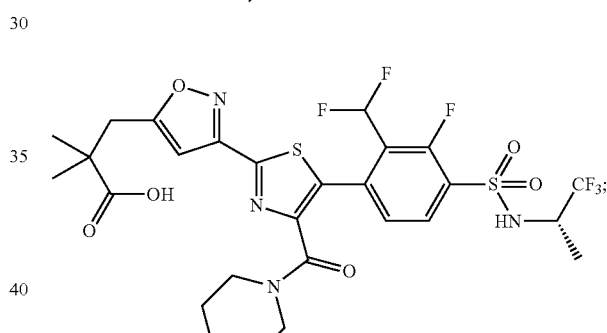
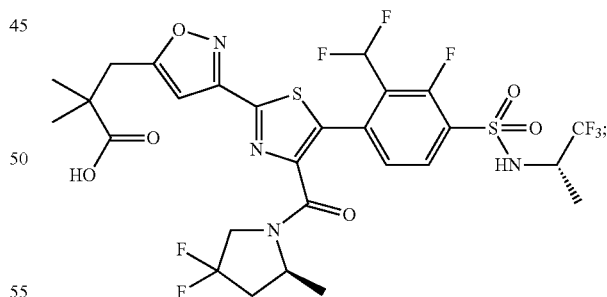
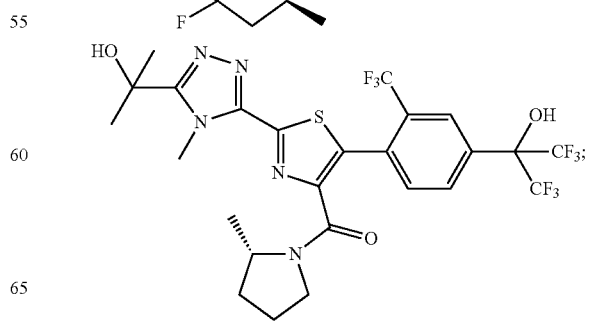

35
-continued
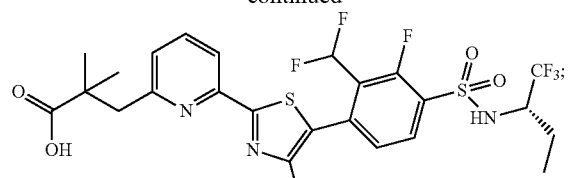
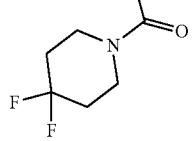
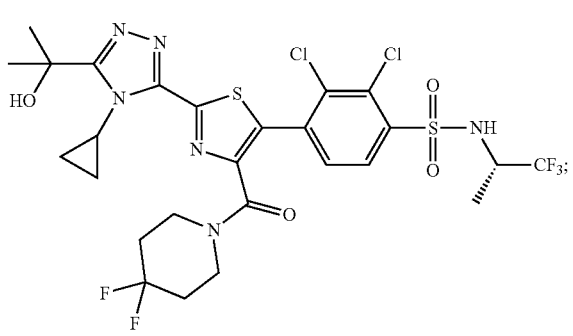
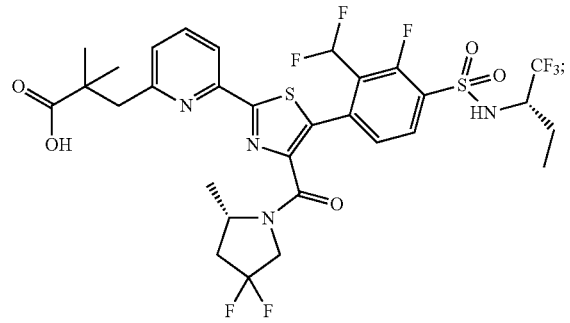
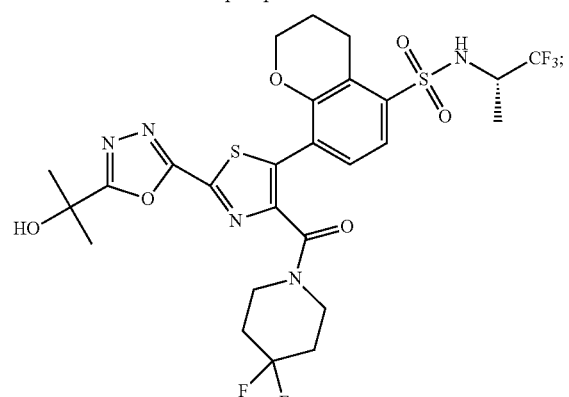
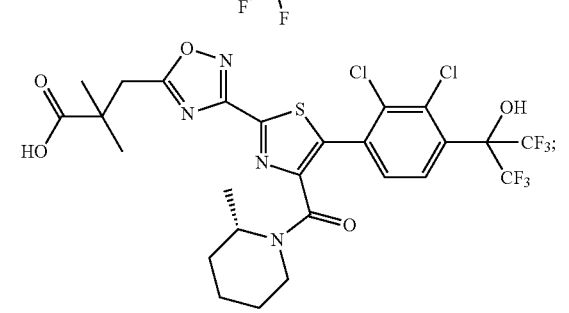
36
-continued
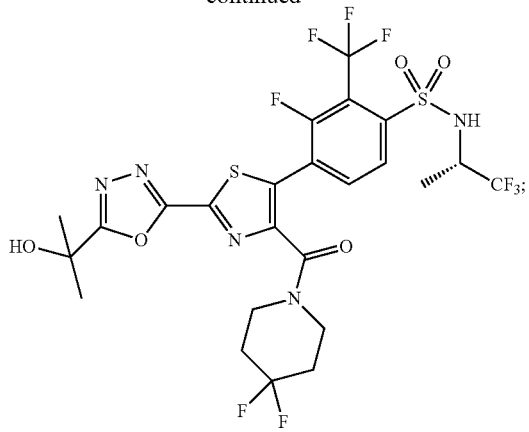
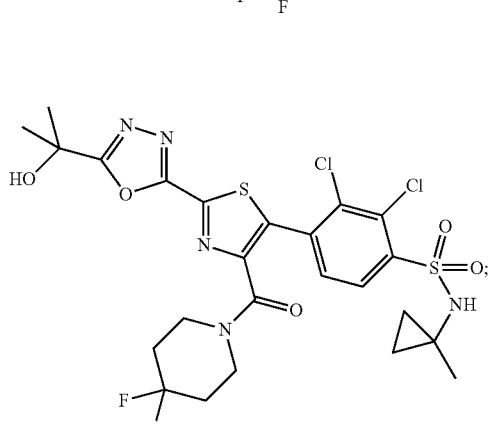
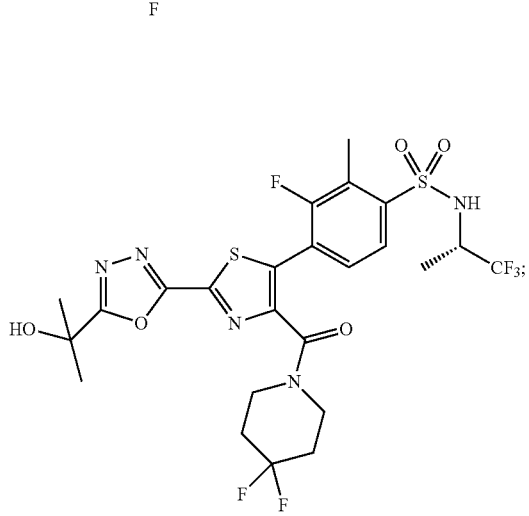
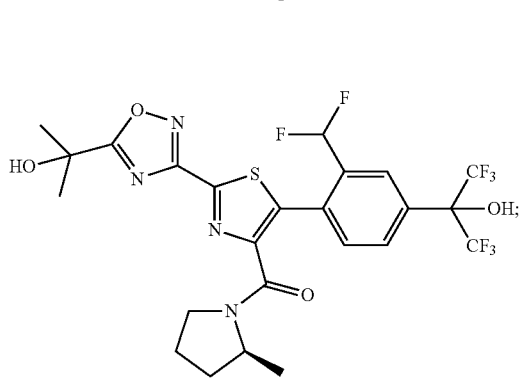

-continued
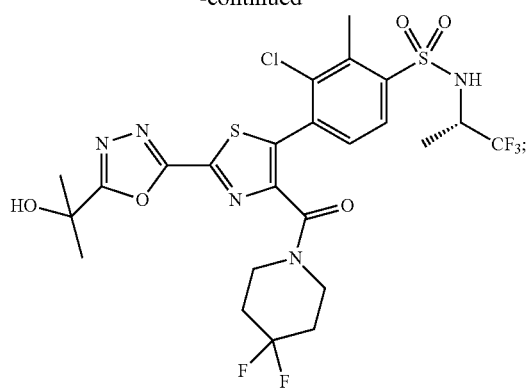
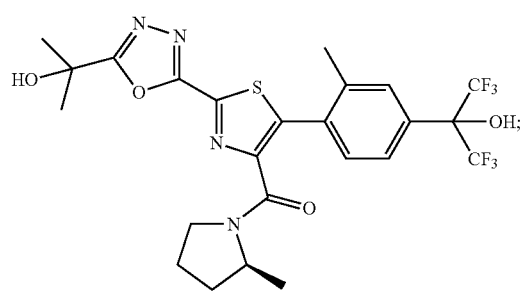
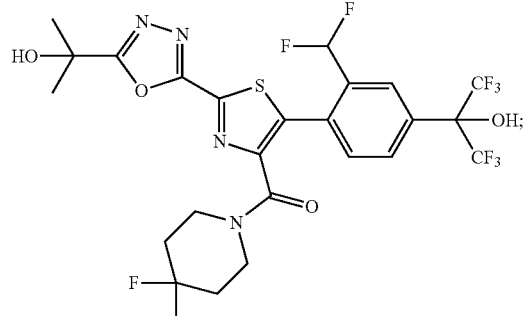
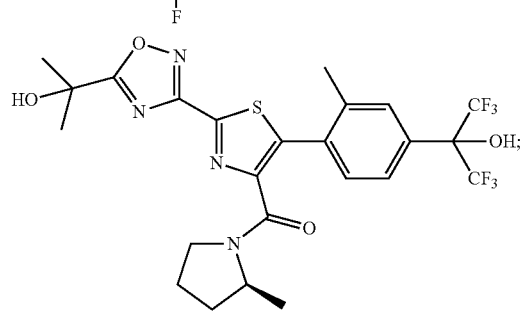
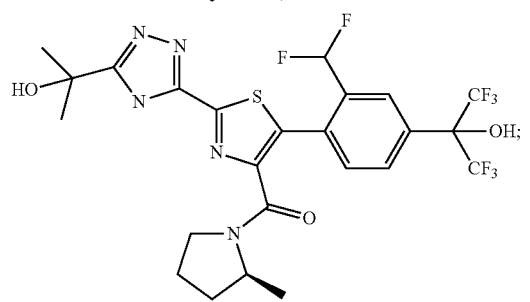
and pharmaceutically acceptable salts thereof.
Another embodiment of the invention is a compound selected from the group consisting of:
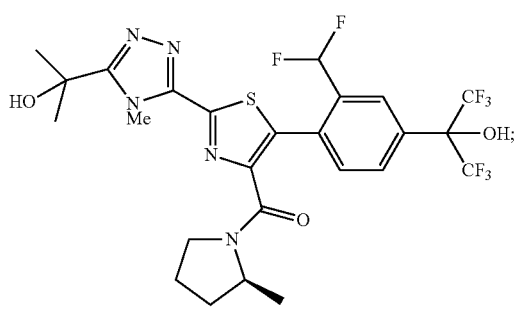
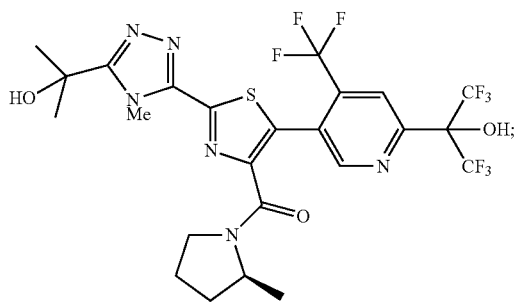
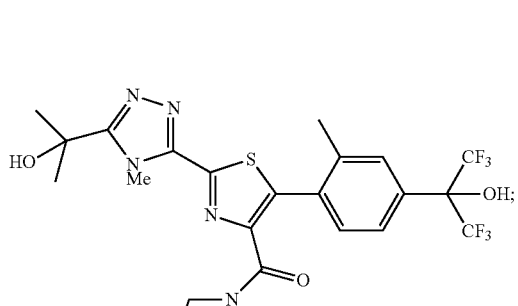
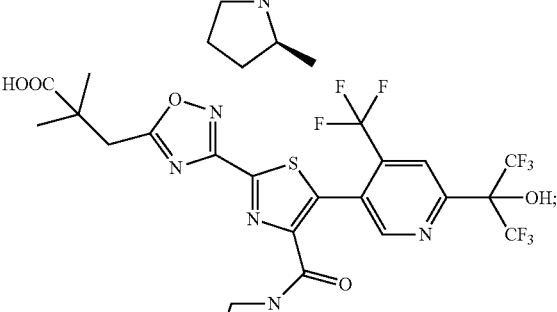
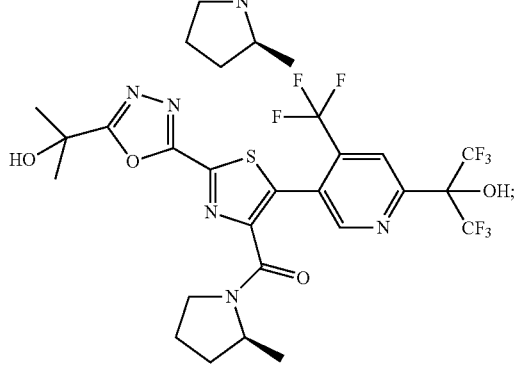

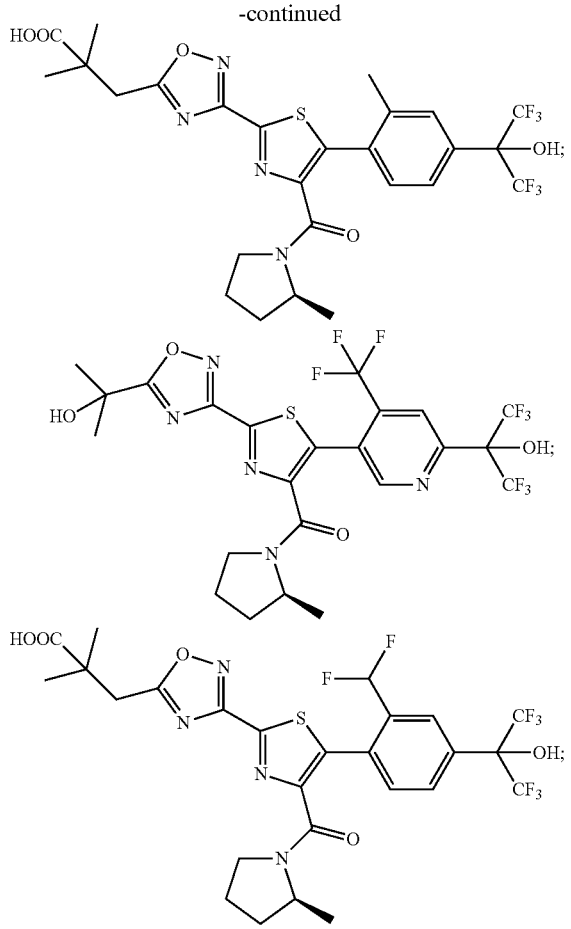

and pharmaceutically acceptable salts thereof.

Another embodiment of the invention comprises a compound of Formula I and a pharmaceutically acceptable carrier.

The present invention also provides a method for preventing, treating or ameliorating an RORγt mediated inflammatory syndrome, disorder or disease comprising administering to a subject in need thereof an effective amount of a compound of Formula I or a form, composition or medicament thereof.

The present invention provides a method of preventing, treating or ameliorating a syndrome, disorder or disease, wherein said syndrome, disorder or disease is selected from the group consisting of: ophthalmic disorders, uveitis, atherosclerosis, rheumatoid arthritis, psoriasis, psoriatic arthritis, atopic dermatitis, multiple sclerosis, Crohn's Disease, ulcerative colitis, ankylosing spondylitis, nephritis, organ allograft rejection, fibroid lung, systic fibrosis, renal insufficiency, diabetes and diabetic complications, diabetic nephropathy, diabetic retinopathy, diabetic retinitis, diabetic microangiopathy, tuberculosis, chronic obstructive pulmonary disease, sarcoidosis, invasive *staphylococcia*, inflammation after cataract surgery, allergic rhinitis, allergic conjunctivitis, chronic urticaria, systemic lupus erythematosus, asthma, allergic asthma, steroid resistant asthma, neutrophilic asthma, periodontal diseases, periodontis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis comprising administering to a subject in need thereof an effective amount of a compound of Formula i or a form, composition or medicament thereof.

The present invention provides a method of treating or ameliorating a syndrome, disorder or disease, wherein said syndrome, disorder or disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, and psoriasis comprising administering to a subject in need thereof an effective amount of a compound of Formula I or a form, composition or medicament thereof.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: rheumatoid arthritis, and psoriasis.

The present invention provides a method of treating or ameliorating a syndrome, disorder or disease, wherein said syndrome, disorder or disease is rheumatoid arthritis, comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is chronic obstructive pulmonary disorder comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriatic arthritis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is ankylosing spondylitis comprising administering to a subject in need thereof an effective amount of a compound of Formula I or a form, composition or medicament thereof.

The present invention provides a method of treating or ameliorating an inflammatory bowel disease, wherein said inflammatory bowel disease is Crohn's disease comprising administering to a subject in need thereof an effective amount of a compound of Formula I or a form, composition or medicament thereof.

The present invention provides a method of treating or ameliorating an inflammatory bowel disease, wherein said inflammatory bowel disease is ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is neutrophilic asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is steroid resistant asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is multiple sclerosis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is systemic lupus erythematosus comprising administering to a subject in need thereof an effective amount of a compound of Formula I or a form, composition or medicament thereof.

The invention also relates to methods of modulating RORγt activity in a mammal by administration of an effective amount of at least one compound of Formula I.

DEFINITIONS

The term "administering" with respect to the methods of the invention, means a method for therapeutically or prophylactically preventing, treating or ameliorating a syndrome, disorder or disease as described herein by using a compound of Formula I or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be an animal, typically a mammal, typically a human, which has been the object of treatment, observation or experiment and is at risk of (or susceptible to) developing a syndrome, disorder or disease that is associated with abberant RORγt expression or RORγt overexpression, or a patient with an inflammatory condition that accompanies syndromes, disorders or diseases associated with abberant RORγt expression or RORγt overexpression.

The term "effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

As used herein, the term "composition" is intended to encompass a product comprising the specified ingredients in the specified amounts, as well as any product which results, directly or indirectly, from combinations of the specified ingredients in the specified amounts.

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl. Any alkyl group may be optionally substituted with one $OCH_3$, one OH, or up to two fluorine atoms.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

The term "cycloalkyl" refers to a saturated or partially unsaturated monocyclic or bicyclic hydrocarbon ring radical derived by the removal of one hydrogen atom from a single ring carbon atom. Typical cycloalkyl radicals include cyclopropyl, cyclobutyl, cyclopentyl, cyclopentenyl, cyclohexyl, cyclohexenyl, cycloheptyl and cyclooctyl. Additional examples include $C_{(3-6)}$cycloalkyl, $C_{(5-8)}$cycloalkyl, decahydronaphthalenyl, and 2,3,4,5,6,7-hexahydro-1H-indenyl. Any cycloalkyl group may be optionally substituted with one $OCH_3$, one OH, or up to two fluorine atoms.

The term "heterocycloalkyl" refers to a saturated or partially unsaturated monocyclic or bicyclic hydrocarbon ring radical containing at least one ring atom selected from the group consisting O, N, or S, derived by the removal of one hydrogen atom from a single ring carbon atom or nitrogen atom. Typical heterocycloalkyl radicals include azetidinyl, pyrrolidinyl, piperazinyl, morpholinyl, thiomorpholinyl, oxetanyl and tetrahydrofuranyl. Sulfur atoms in the ring of the heterocycloalkyl group may be in any oxidation state.

As used herein, the term "thiophenyl" is intended to describe the radical formed by removing a hydrogen atom from the molecule with the structure:

Whenever a variable, such as "n" in —$(CX_2)_nO(CX_2)_n$—, appears more than one time in a chemical formula, each definition is considered to be independent.

Where an alkyl substituent, such as but not limited to $C_{(1-6)}$alkyl, appears more than once in a compound of Formula I, each substitution on said alkyl group is independently selected.

An alkyl group may be substituted as described in the specification. When an alkyl group is substituted with the diradical —(CX$_2$)$_m$— both termini of the diradical may be attached to either the same or different carbon atoms. For example, both

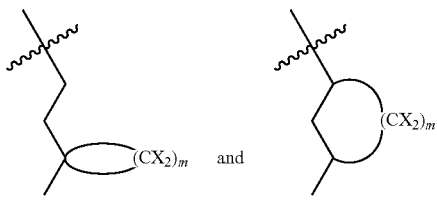

are examples of —(CX$_2$)$_m$— substitution on a butyl group. Examples of —(CX$_2$)$_m$— substitution include without limitation

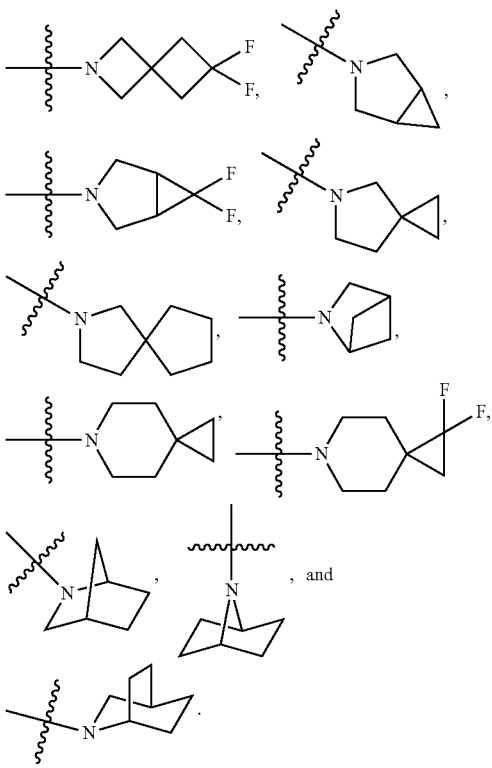

Similarly, —(CX$_2$)$_n$—, or —(CX$_2$)$_n$O(CX$_2$)$_n$— diradical substitution may occur on either the same or different ring carbons. Examples of —(CX$_2$)$_n$— substitution include without limitation

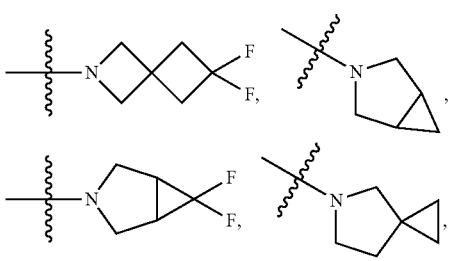

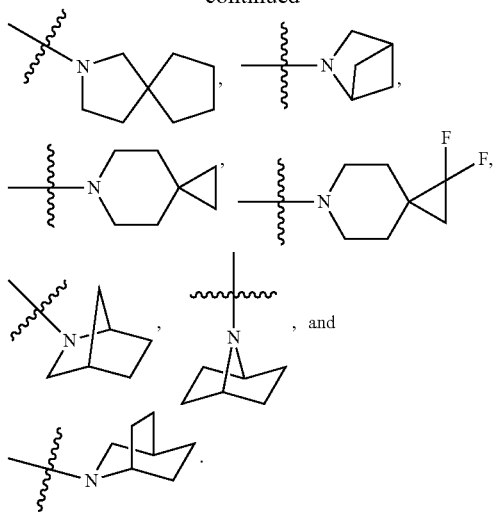

Examples of —(CX$_2$)$_n$O(CX$_2$)$_n$— substitution include without limitation

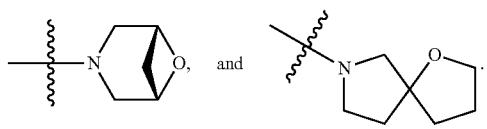 [SMILES: *N1C[C@H]2C[C@@H](C1)O2 ; "and" ; *N1CCC2(CCCO2)C1 ; "."]

Pharmaceutically Acceptable Salts

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethylpropane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, NH$_3$, NH$_4$OH, N-methyl-D-glucamine, piperidine, potassium, potassium-t-butoxide, potassium hydroxide (aqueous), procaine, quinine, sodium, sodium carbonate, sodium-2-ethylhexanoate, sodium hydroxide, triethanolamine, or zinc.

Methods of Use

The present invention is directed to a method for preventing, treating or ameliorating a RORγt mediated inflammatory syndrome, disorder or disease comprising administering to a subject in need thereof an effective amount of a compound of Formula I or a form, composition or medicament thereof.

Since RORγt is an N-terminal isoform of RORγ, it is recognized that compounds of the present invention which are modulators of RORγt are likely to be modulators of RORγ as well. Therefore the mechanistic description "RORγt modulators" is intended to encompass RORγ modulators as well.

When employed as RORγt modulators, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in Formula I for use as a medicament.

In another embodiment, the invention relates to the use of a compound as described in Formula I for the preparation of a medicament for the treatment of a disease associated with an elevated or aberrant RORγt activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Furthermore, it is intended that within the scope of the present invention, any element, in particular when mentioned in relation to a compound of Formula I, shall comprise all isotopes and isotopic mixtures of said element, either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. Radiolabelled compounds of Formula I may comprise a radioactive isotope selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$.

Preferably, the radioactive isotope is selected from the group of $^3$H, $^{11}$C and $^{18}$F.

Some compounds of the present invention may exist as atropisomers. Atropisomers are stereoisomers resulting from hindered rotation about single bonds where the steric strain barrier to rotation is high enough to allow for the isolation of the conformers. It is to be understood that all such conformers and mixtures thereof are encompassed within the scope of the present invention.

Where the compounds according to this invention have at least one stereo center, they may accordingly exist as enantiomers or diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

ABBREVIATIONS

Herein and throughout the application, the following abbreviations may be used.
Ac acetyl
ACN acetonitrile
aq aqueous
Bu butyl
br broad
Bn benzyl
conc. concentrated
Cy cyclohexyl
° C. celcius (in degrees)
d doublet
DABCO 1,4-diazabicyclo[2.2.2]octane
DAST diethylaminosulfur trifluoride
dba dibenzylideneacetone
DCM dichloromethane
Dess-Martin Periodinane 1,1,1-tris(acetyloxy)-1,1-dihydro-1,2-benziodoxol-3-(1H)-one
DIPEA N,N-diisopropylethylamine (Hünig's base)
DMA N,N-dimethylacetamide
DMAP 4-dimethylaminopyridine
DME 1,2-dimethoxyethane
DMF N,N-dimethylformamide
DMP 1,1,1-tris(acetyloxy)-1,1-dihydro-1,2-benziodoxol-3-(1H)-one (Dess-Martin periodinane)
DMSO dimethyl sulfoxide
ESI electrospray ionization
Et ethyl
EtOAc ethyl acetate
FCC flash column chromatography
g gram
h hour
HATU O-(7-azabenzotriazol-1-yl)-N,N,N',N'-tetramethyluronium hexafluorophosphate
HOBt 1-hydroxybenzotriazole
HPLC high performance liquid chromatography
Hz Hertz
IBX 2-iodoxybenzoic acid
i-Pr iso-propyl
$K_2CO_3$ potassium carbonate
MS mass spectrometry
LAH lithium aluminum hydride
m multiplet
M molar (moles/liter)
Me methyl
mg milligram
min minutes
mmol millimole
mL milliliter
N normality
NBS N-bromosuccinimide
NMR nuclear magnetic resonance
n-BuLi n-butyllithium
PE petroleum ether
Ph phenyl
Piv pivaloyl (Me$_3$CO)
PMB 4-methoxybenzyl
ppm parts per million
prep-HPLC preparative high performance liquid chromatography
prep-TLC preparative thin layer chromatography
Psi pounds per square inch
q quartet
rt room temperature
RuPhos 2-dicyclohexylphosphino-2',6'-diisopropoxybiphenyl
s singlet
sat. saturated
SEM 2-(trimethylsilyl)ethoxymethyl
SFC Supercritical Fluid Chromatography
t triplet
tert tertiary
TBAI tetrabutylammonium iodide
TBAF tetrabutylammonium fluoride
TEA triethylamine
TEMPO (2,2,6,6-tetramethylpiperidin-1-yl)oxidanyl
Tf triflate
TFAA trifluoroacetic acid anhydride
THF tetrahydrofuran
TLC thin layer chromatography
TMS trimethylsilyl
Ts tosyl
wt % weight, by percent General Schemes The compounds of the present invention can be prepared by a combination of methods known in the art including the procedures described in Schemes I to XI below. The following reaction schemes are only meant to represent examples of the invention and are in no way meant to be a limit of the invention.

Scheme I describes the preparation of [1,3,4]-oxadiazoles of the present invention. 1-Bromo-3-hydroxypropan-2-one can be cyclized with ethyl 2-amino-2-thioxoacetate to give the thiazole intermediate A-I. Protection using SEMCl is followed by acyl hydrazide formation, R⁴COOH coupling and cyclization with, e.g., TsCl, to afford the intermediate A-II. Deprotection using HCl is followed by Pd catalyzed coupling with an appropriate aryl halide and oxidation with, e.g., TEMPO/PhI(OAc)₂, to give a carboxylic acid intermediate A-III. Amide coupling leads to compounds of structure A-IV. Alternatively, A-I can first be converted to A-V by a sequence of Pd catalyzed coupling, oxidation, and amide coupling. Applying the same three step ester to oxadiazole transformation as described for A-II, compounds of structure A-IV can be obtained from A-V. Another alternative route starts with 2-(ethoxycarbonyl)thiazole-4-carboxylic acid A-VI, prepared by the cyclization of ethyl 2-amino-2-thioxoacetate and 3-bromo-2-oxopropanoic acid, which is subjected to a sequence of amide coupling, hydrazide formation, R⁴COOH coupling, and cyclization to afford A-VII. Pd catalyzed coupling leads to compounds of structure A-IV. Intermediate A-VII can be made by an alternative route involving deprotection of A-II using HCl, oxidation with TEMPO/PhI(OAc)₂, and amide coupling.

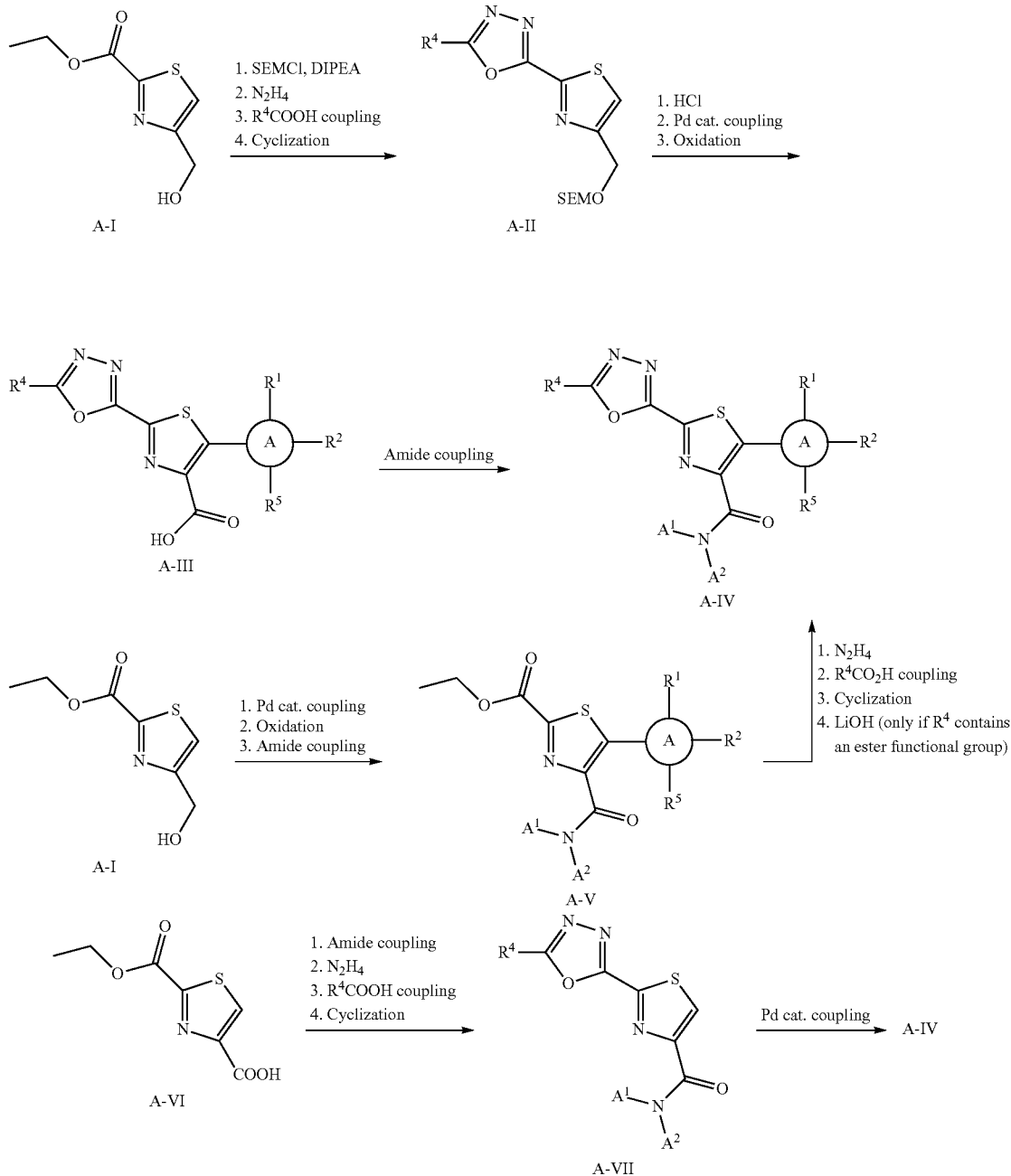

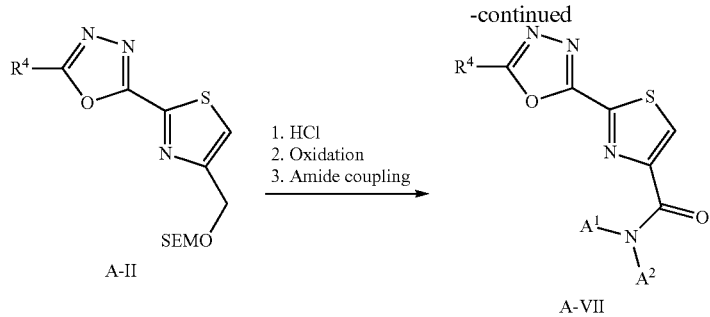

Scheme II shows the preparation of [1,2,4]-oxadiazoles of the present invention. A-I is protected by using, e.g., SEMCl, followed by ammonolysis, and dehydration with TFAA to give the nitrile intermediate B-I. Amidoxime formation using hydroxylamine, followed by acylation with $R^6$COOH and cyclization affords the intermediate B-II. A sequence of deprotection, Pd catalyzed coupling and oxidation gives the carboxylic acid intermediate of structure B-III. Amide coupling leads to compounds of structure B-IV. Alternatively, B-II can first be converted to B-V by a sequence of deprotection, oxidation and amide coupling. Compounds of structure B-IV can be obtained from B-V by Pd catalyzed coupling. Alternatively compounds of the structure B-V can be obtained from 4-tert-butyl 2-ethyl thiazole-2,4-dicarboxylate by a sequence of ammonolysis and dehydration with TFAA to give compounds of the structure B-VI. Amidoxime formation using hydroxylamine, followed by acylation with $R^6$COCl and cyclization affords compounds of the structure B-VII. Deprotection and amide coupling leads to compounds of the structure B-V.

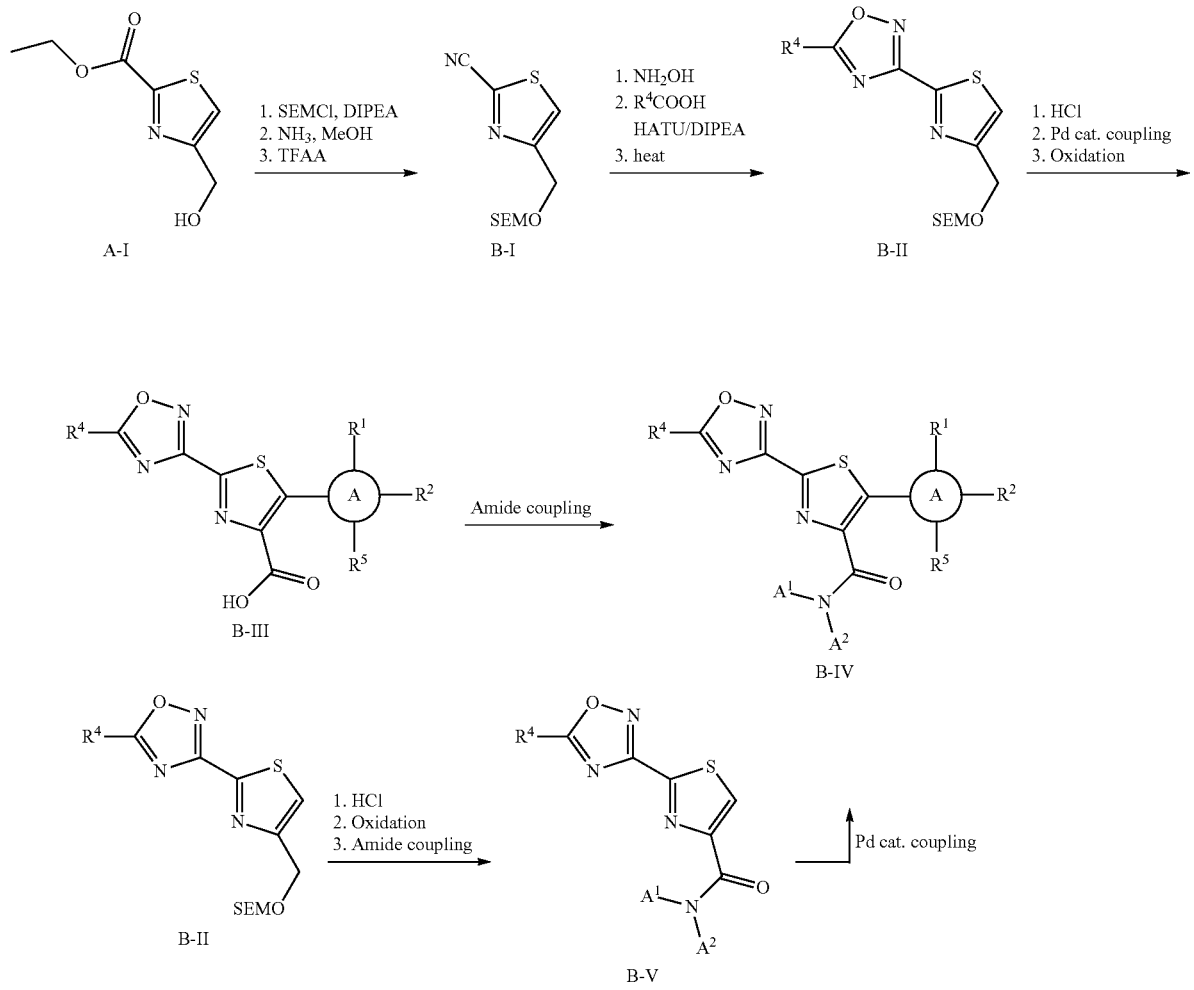

-continued

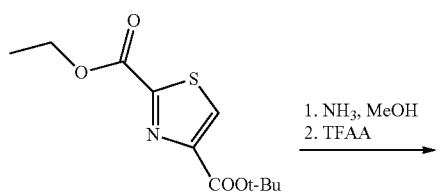

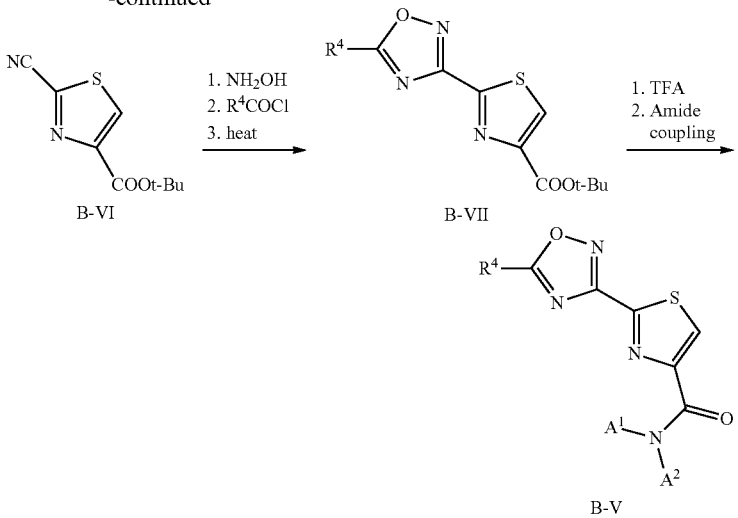

Scheme III shows the preparation of oxadiazolones and tetrazoles of the present invention. A-V can be converted into the nitrile intermediate C-I by a sequence of ester saponification, formation of the primary carboxamide with NH₃ and HOBt, and dehydration using TFAA. Treatment of C-I with hydroxylamine followed by reaction with triphosgene furnishes compounds of structure C-II. For the synthesis of tetrazoles the intermediate C-I can be treated with sodium azide to afford compounds of structure C-III.

Scheme III

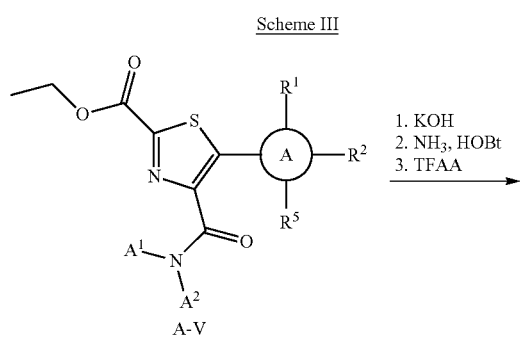

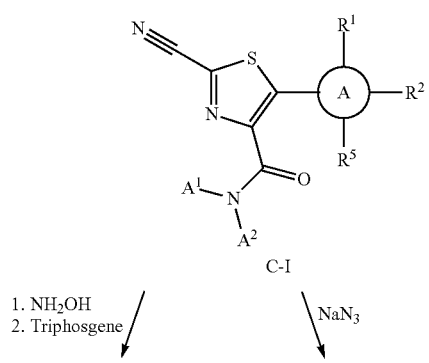

The preparation of triazoles of the present invention is described in Scheme IV. A-V is converted to intermediate D-I by a sequence of NaBH₄ reduction, IBX oxidation, and treatment with dimethyl(1-diazo-2-oxopropyl)phosphonate. Treatment of D-I with sodium azide at elevated temperature can afford [1,2,3]-triazole compounds of structure D-II. [1,2,4]-Triazoles can be prepared starting from A-II, which is deprotected with HCl followed by treatment with a primary amine RxNH₂ at elevated temperature to afford intermediate D-III. Alternatively A-II is first treated with a primary amine RxNH₂ at elevated temperature followed by deprotection with HCl to afford compounds of the structure D-III A sequence of Pd catalyzed coupling, oxidation, and amide coupling affords compounds of structure D-IV. In case of [1,2,4]triazoles that are unsubstituted at the 4-position a deprotection step follows. Alternatively D-III is first oxidized then amide bond formation and Pd catalyzed coupling gives D-IV. In addition A-IV can be heated in the presence of amines to afford compounds of the structure D-IV.

Scheme IV

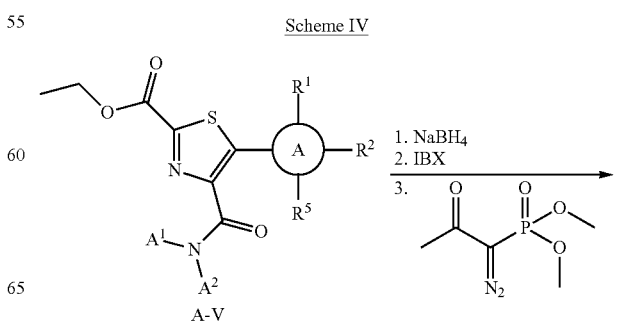

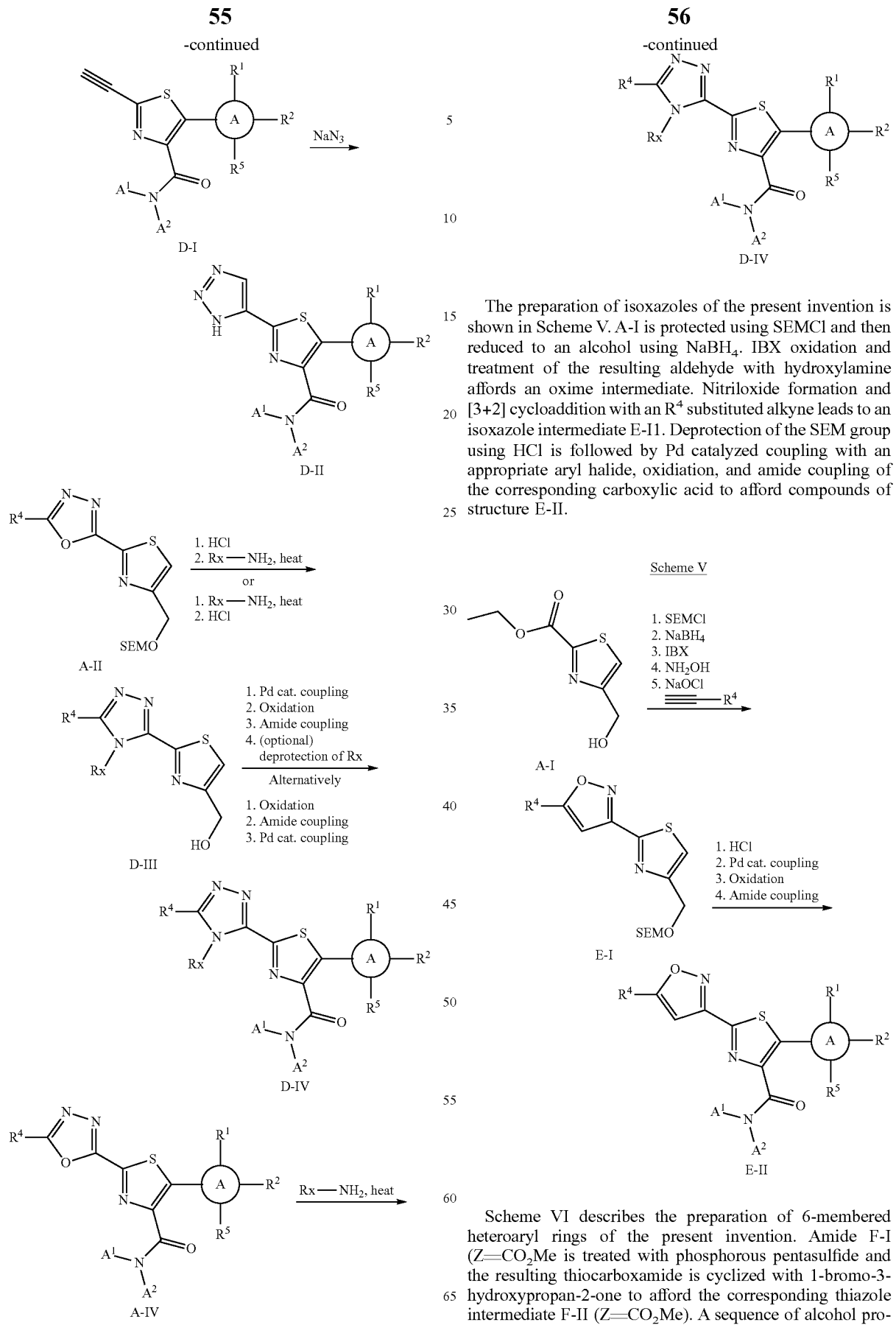

The preparation of isoxazoles of the present invention is shown in Scheme V. A-I is protected using SEMCl and then reduced to an alcohol using NaBH$_4$. IBX oxidation and treatment of the resulting aldehyde with hydroxylamine affords an oxime intermediate. Nitriloxide formation and [3+2] cycloaddition with an R$^4$ substituted alkyne leads to an isoxazole intermediate E-I1. Deprotection of the SEM group using HCl is followed by Pd catalyzed coupling with an appropriate aryl halide, oxidiation, and amide coupling of the corresponding carboxylic acid to afford compounds of structure E-II.

Scheme VI describes the preparation of 6-membered heteroaryl rings of the present invention. Amide F-I (Z═CO$_2$Me is treated with phosphorous pentasulfide and the resulting thiocarboxamide is cyclized with 1-bromo-3-hydroxypropan-2-one to afford the corresponding thiazole intermediate F-II (Z═CO$_2$Me). A sequence of alcohol protection, methyl addition, alcohol deprotection, Pd catalyzed coupling, oxidation and amide coupling affords compounds of structure F-III. Thioamide F-IV is cyclized with 1-bromo-3-hydroxypropan-2-one to afford the corresponding thiazole intermediate F-II (Z=Br). A sequence of alcohol protection, palladium-catalyzed coupling, alcohol deprotection, Pd catalyzed coupling, oxidation, amide coupling, and hydrolysis affords compounds of structure F-V.

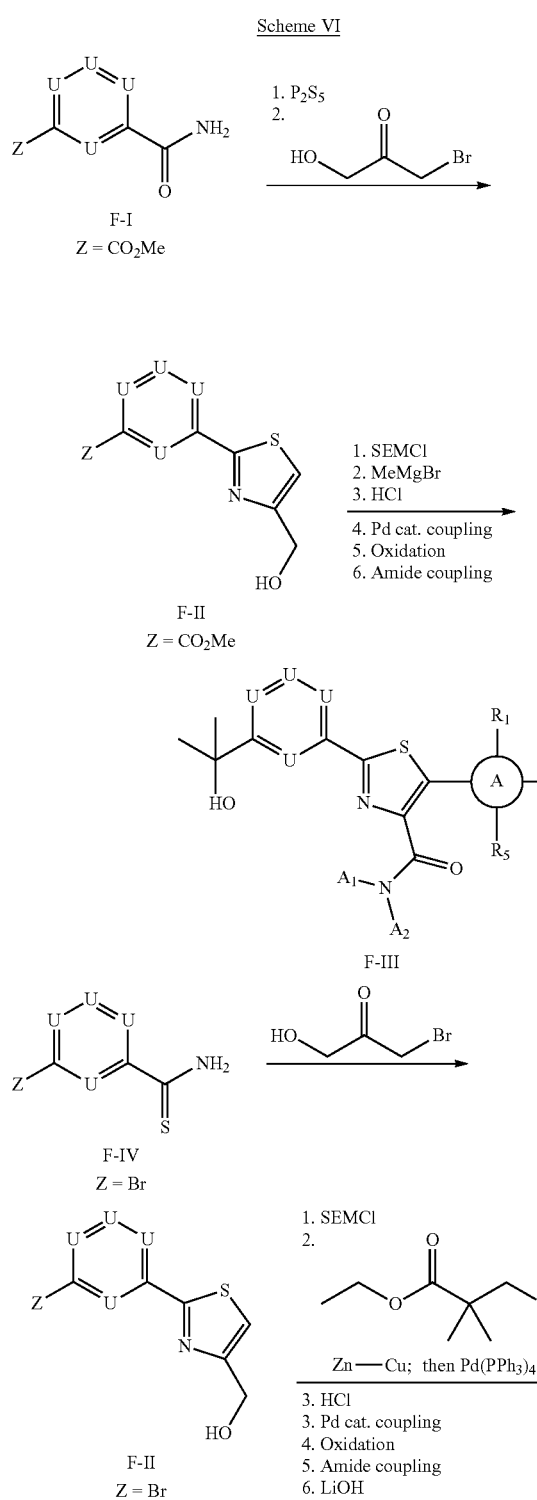

Scheme VI

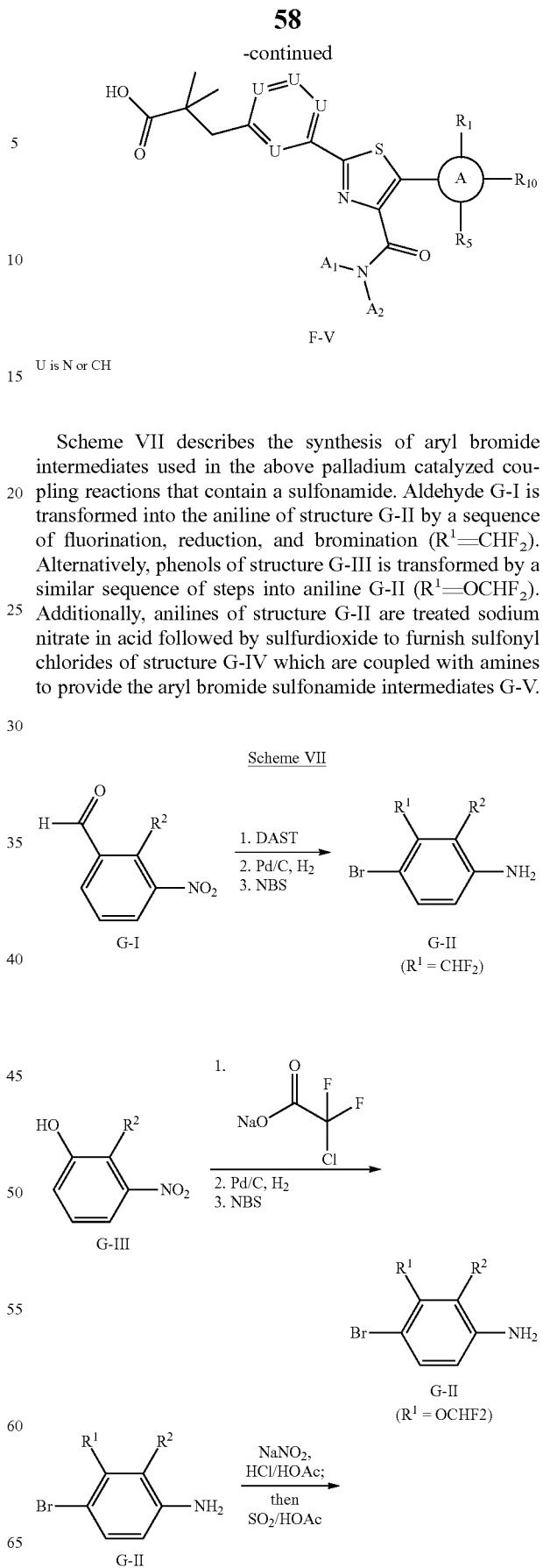

U is N or CH

Scheme VII describes the synthesis of aryl bromide intermediates used in the above palladium catalyzed coupling reactions that contain a sulfonamide. Aldehyde G-I is transformed into the aniline of structure G-II by a sequence of fluorination, reduction, and bromination ($R^1$=$CHF_2$). Alternatively, phenols of structure G-III is transformed by a similar sequence of steps into aniline G-II ($R^1$=$OCHF_2$). Additionally, anilines of structure G-II are treated sodium nitrate in acid followed by sulfurdioxide to furnish sulfonyl chlorides of structure G-IV which are coupled with amines to provide the aryl bromide sulfonamide intermediates G-V.

Scheme VII

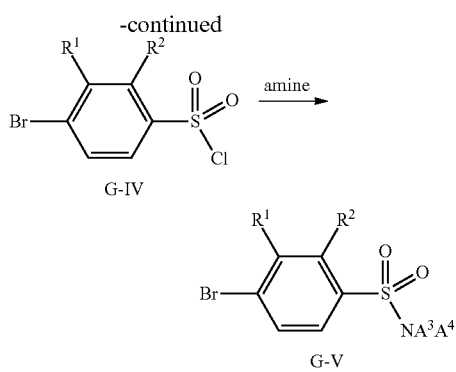

Preparation of the bromo-aryl/heteroaryl compounds H-I and H-X used in palladium catalyzed coupling reactions above are shown in Scheme VIII. 1,4-Dibromo- or 1-bromo-4-iodo-aromatics H-II can be metalated by aryllithium formation with n-butyl lithium or Grignard formation using isopropyl magnesium chloride. The 1,4-dibromo aromatics should have identical substituents $R^1$ and $R^2$. The metallated species can be coupled with 2,2,2-trifluoro-N-methoxy-N-methylacetamide to form 1-bromo-4-trifluoroacetyl derivates H-III. The trifluoromethyl alcohols H-I can be formed by reaction of H-III with $TMSCF_3$ in the presence of a fluoride source. Alternatively, the metallated species can react with hexafluoroacetone to directly form trifluoroacetone alcohols H-I. The intermediates H-III can also be formed by starting with methyl 4-bromobenzoates of structure H-IV and using a reaction sequence of reduction, oxidation, trifluoromethyl addition, and oxidation or alternatively by treatment with $TMSCF_3/TBAF$. 5-Bromo-2-iodobenzene/pyridines (H-VI, U=C or N) can be used as reactants for a metallation reaction, e.g. a lithiation with n-butyl-lithium, and the metallated species can react with the ethyl trifluoroacetate to form compounds of structure H-VII. Trifluoromethyl addition affords compounds of structure H-I (U=C or N). Additionally, trifluoromethyl alcohols H-X can be formed by reaction of H-IX with $TMSCF_3$ in the presence of a fluoride source. 1,3-Dibromoaryl derivatives H-VIII can be metallated, e.g. a lithiation with n-butyl-lithium, and coupled with 2,2,2-trifluoro-N-methoxy-N-methylacetamide will form the 1-bromo-3-trifluoroacetyl derivates H-IX.

Scheme VIII

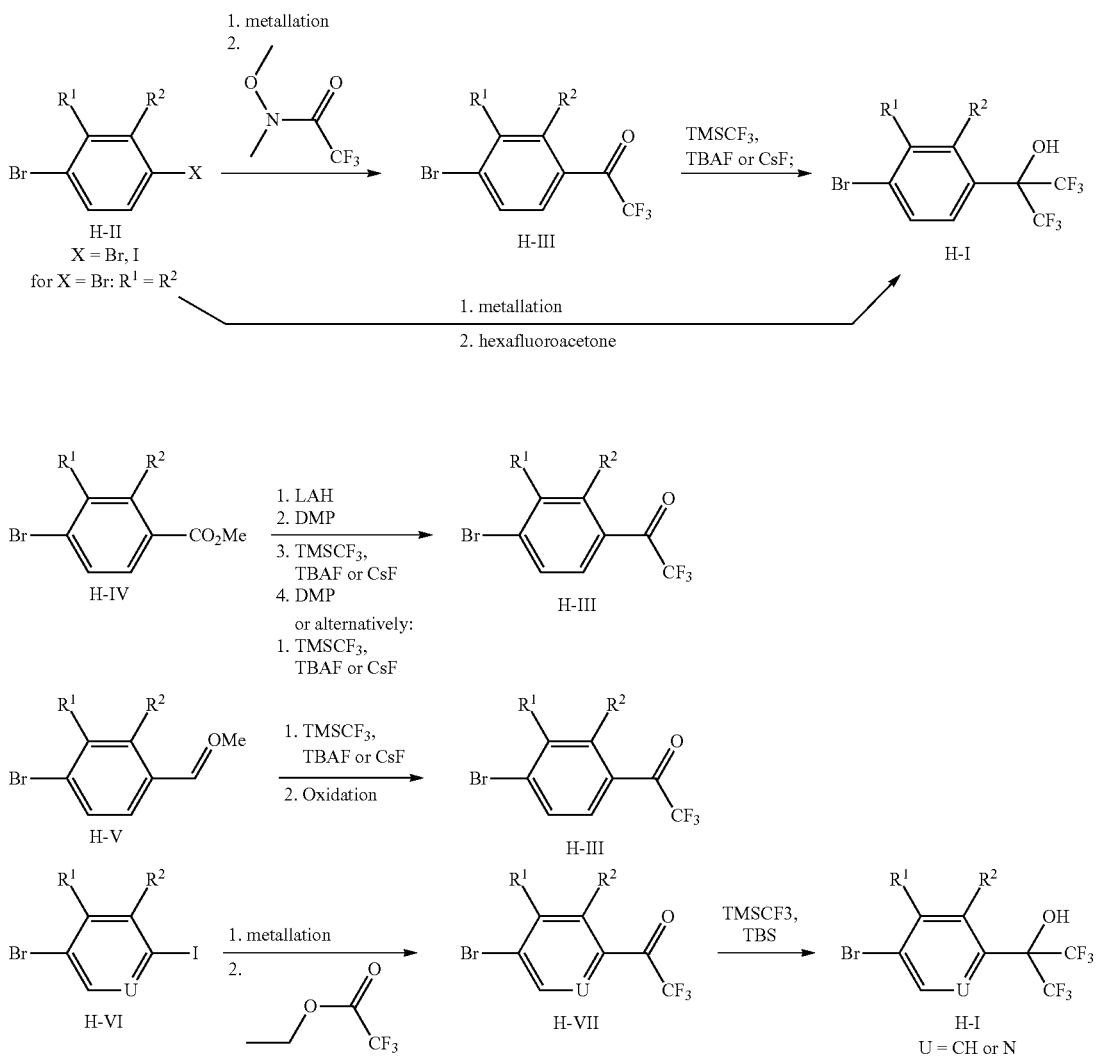

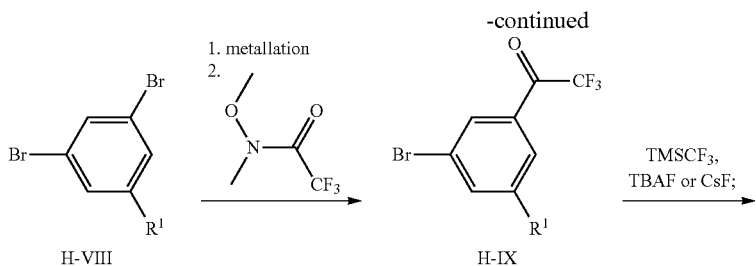
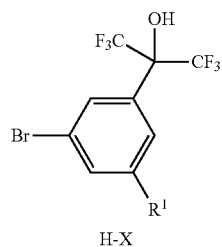

Scheme IX describes the synthesis amine intermediates used above in amide coupling reactions. Compounds I-I and I-III are treated with DAST and the tert-butoxycarbonyl group removed with HCl to provide the fluorinated amines I-II and I-IV as hydrochloride salts.

Scheme IX

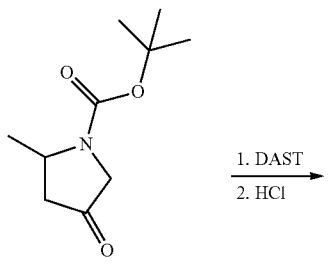

Scheme X

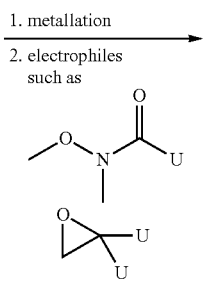

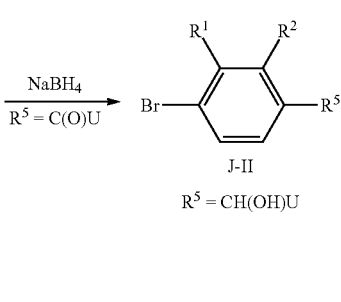

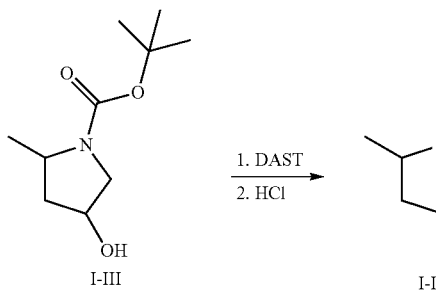

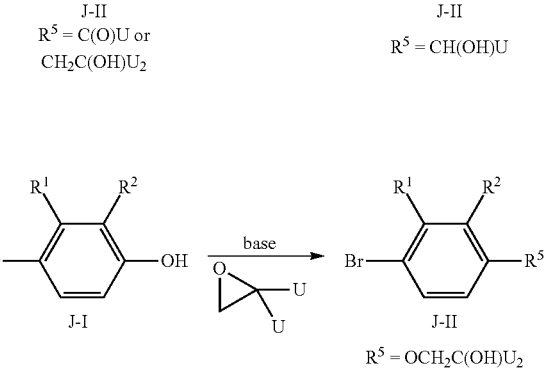

Preparation of the arylbromide derivatives J-II and J-V used in palladium catalyzed coupling reactions above are shown in Scheme X. H-II can be metalated with n-butyllithium or isopropyl magnesium chloride. The 1,4-dibromo aromatics should have identical substituents $R^1$ and $R^2$. The metalated species can react with electrophiles to form derivatives J-II. In the case of ketone derivatives J-II, reduction of the ketone functional group with a reductant such as sodium borohydride provides alcohols of the general structure J-II. Phenols J-1 can be treated with base and an electrophile to afford aryl ethers of the general structure J-II. Alternatively, aryl bromides of structure H-VIII can undergo a sequence consisting of metalation, trapping with methyl chloroformate to give compounds of the general structure J-III. Subsequent saponification, and amide coupling then gives compounds of the structure J-IV.

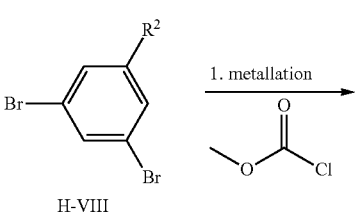

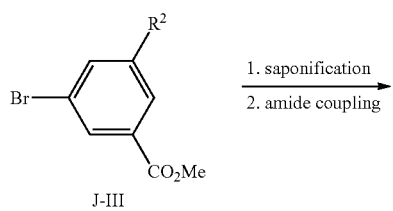

-continued

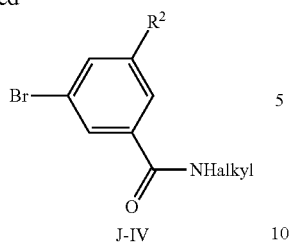

Preparation of sulfonamides of structure K-III is described in Scheme XI. Intermediate K-I is transformed into K-II by a sequence of palladium-catalyzed coupling, oxidation, and amide coupling reactions. K-II is converted into a sulfonyl chloride derivative with sulfuryl dichloride which is coupled with an amine to furnish compounds of the structure K-III.

Scheme XI

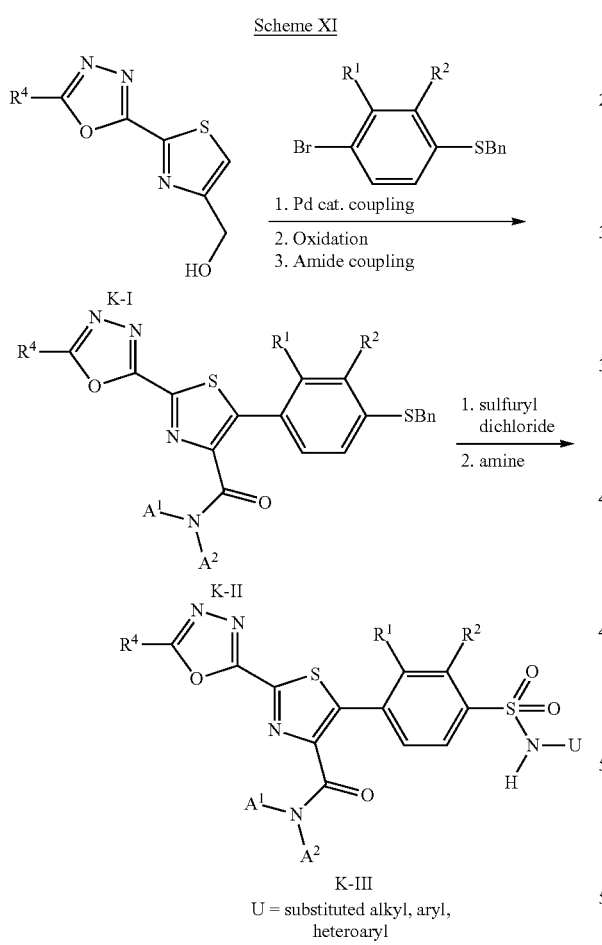

U = substituted alkyl, aryl, heteroaryl

EXAMPLES

Compounds of the present invention can be prepared by methods known to those who are skilled in the art. The following examples are only meant to represent examples of the invention and are in no way meant to be a limit of the invention.

Intermediate 1

Step a

Ethyl 4-(hydroxymethyl)thiazole-2-carboxylate

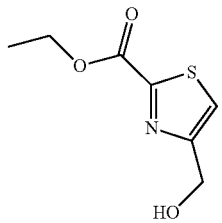

A mixture of 1-bromo-3-hydroxypropan-2-one (3.0 g, 20 mmol) in anhydrous dioxane (100 mL) was treated with ethyl 2-amino-2-thioxoacetate (2.7 g, 20 mmol) for 2 h at 50° C., and then concentrated to dryness at 50° C. to yield a dry yellow solid. The crude product was dissolved in saturated $Na_2CO_3$ (150 mL) and water (150 mL). The aqueous layer was extracted with EtOAc (50 mL×6). The aqueous layer was acidified to pH=2 with concentrated aqueous HCl, resulting in the formation of a precipitate. This suspension was extracted with EtOAc (50 mL×3). The combined organic layers were dried over anhydrous $Na_2SO_4$, filtered, and concentrated to dryness to give the title compound as a red-brown solid.

Intermediate 1

Step b

Ethyl 4-(((2-(trimethylsilyl)ethoxy)methoxy)methyl)thiazole-2-carboxylate

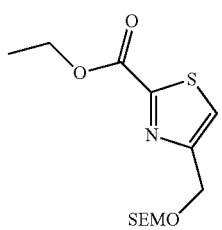

To a solution of ethyl 4-(hydroxymethyl)thiazole-2-carboxylate (375 mg, 2.0 mmol, Intermediate 1, step a) in DCM (20 mL) was added DIPEA (516 mg, 4.00 mmol) at 0° C. SEMCl (670 mg, 4.0 mmol) was added dropwise over a period of 10 min and the mixture was stirred at rt overnight. The mixture was quenched with water and extracted with EtOAc (50 mL×3). The combined organic layers were washed with brine, dried over anhydrous $Na_2SO_4$ and concentrated to dryness. The residue was purified by FCC on silica gel (PE/EtOAc=20:1) to obtain the title compound.

Intermediate 1

Step c 4-(((2-(Trimethylsilyl)ethoxy)methoxy)methyl)thiazole-2-carbohydrazide

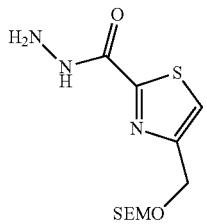

Ethyl 4-(((2-(trimethylsilyl)ethoxy)methoxy)methyl)thiazole-2-carboxylate (3.17 g, 10.0 mmol, Intermediate 1, step b) and hydrazine monohydrate (2 mL, 64 mmol) in ethanol (30 mL) was stirred at 50° C. for 4 h. The mixture was concentrated to dryness and the residue was purified by FCC on silica gel (EtOAc) to give the title compound as a colorless oil.

Intermediate 1

Step d

Methyl 2,2-dimethyl-4-oxo-4-(2-(4-(((2-(trimethylsilyl)ethoxy)methoxy)methyl)thiazole-2-carbonyl)hydrazinyl)butanoate

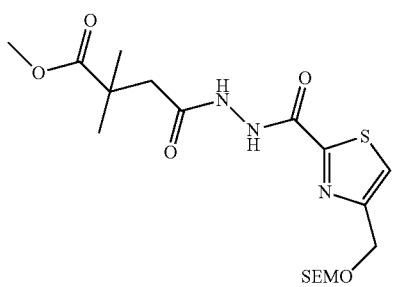

A solution of 4-(((2-(trimethylsilyl)ethoxy)methoxy)methyl)thiazole-2-carbohydrazide (2.7 g, 8.9 mmol, Intermediate 1, step c), 4-methoxy-3,3-dimethyl-4-oxobutanoic acid (1.76 g, 11.0 mmol), HATU (4.2 g, 11 mmol) and TEA (1.82 g, 18.0 mmol) in acetonitrile (40 mL) was stirred at rt for 2 h. The mixture was poured into $H_2O$ (40 mL) and extracted with EtOAc (5 mL×4). The combined organic layers were washed with brine, dried over anhydrous $Na_2SO_4$, and concentrated to dryness. The residue was purified by FCC on silica gel (DCM/MeOH=10:1) to afford the title compound as a colorless oil.

Intermediate 1

Step e

Methyl 2,2-dimethyl-3-(5-(4-(((2-(trimethylsilyl)ethoxy)methoxy)methyl)thiazol-2-yl)-1,3,4-oxadiazol-2-yl)propanoate

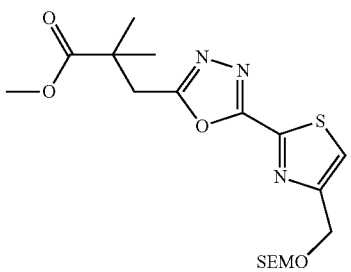

A mixture of methyl 2,2-dimethyl-4-oxo-4-(2-(4-(((2-(trimethylsilyl)ethoxy)methoxy)methyl)thiazole-2-carbonyl)hydrazinyl)butanoate (1.6 g, 3.6 mmol, Intermediate 1, step d), 4-methylbenzene-1-sulfonyl chloride (1.4 g, 7.2 mmol), and TEA (720 mg, 7.2 mmol) in DCM (30 mL) was stirred at rt overnight. The mixture was poured into $H_2O$ (10 mL) and extracted with EtOAc (8 mL×3). The combined organic layers were washed with brine, dried over anhydrous $Na_2SO_4$, filtered, and the filtrate was concentrated to dryness. The residue was purified by FCC on silica gel (EtOAc/PE=1:5) to give the title compound as a colorless oil.

Intermediate 1

Step f

Methyl 3-(5-(4-(hydroxymethyl)thiazol-2-yl)-1,3,4-oxadiazol-2-yl)-2,2-dimethylpropanoate

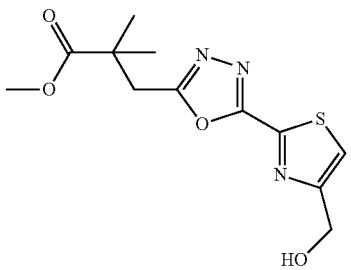 [SMILES: COC(=O)C(C)(C)Cc1nnc(-c2nc(CO)cs2)o1]

A mixture of methyl 2,2-dimethyl-3-(5-(4-(((2-(trimethylsilyl)ethoxy)methoxy)methyl)thiazol-2-yl)-1,3,4-oxadiazol-2-yl)propanoate (1.38 g, 3.24 mmol, Intermediate 1, step e) in HCl/dioxane (4 M, 40 mL) was stirred at rt for 4 h. The mixture was concentrated to dryness to afford the title compound, which was used in the next step without further purification.

Intermediate 2

Step a 2-(Ethoxycarbonyl)thiazole-4-carboxylic acid

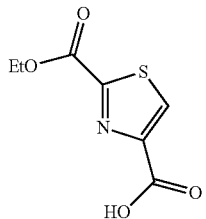

A mixture of ethyl 2-amino-2-thioxoacetate (60.0 g, 428 mmol) and 3-bromo-2-oxopropanoic acid (147 g, 856 mmol) in dioxane (229 mL) was stirred at 50° C. for 70 min. The reaction mixture was cooled to rt and poured into 450 mL of water and stirred for 2 h. The precipitated solid was isolated by filtration, washed with water and dried under high vacuum at 60° C. for 2 days to provide the title compound as an off-white solid.

Intermediate 2

Step b

Ethyl 4-(4-fluoropiperidine-1-carbonyl)thiazole-2-carboxylate

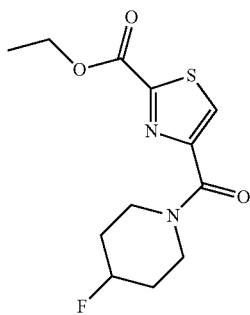 [SMILES: CCOC(=O)c1nc(C(=O)N2CCC(F)CC2)cs1]

To a solution of 2-(ethoxycarbonyl)thiazole-4-carboxylic acid (5.0 g, 36 mmol, Intermediate 2, step a) in DMF (100 mL) was added HATU (20.3 g, 53.4 mmol) and DIPEA (18.4 g, 140 mmol) and the mixture was stirred at rt for 0.5 h. Then, 4-fluoropiperidine (3.7 g, 35.8 mmol) was added and the mixture was stirred for an additional 4 h, diluted with water, and extracted with EtOAc. The combined organic layers were washed with water, brine, dried over anhydrous $Na_2SO_4$, filtered, concentrated to dryness, and purified by FCC on silica gel (PE/EtOAc=1/1) to give the title compound as a yellow oil.

Intermediate 2

Step c 4-(4-Fluoropiperidine-1-carbonyl)thiazole-2-carbohydrazide

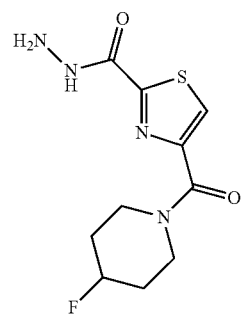 [SMILES: NNC(=O)c1nc(C(=O)N2CCC(F)CC2)cs1]

To a solution of ethyl 4-(4-fluoropiperidine-1-carbonyl)thiazole-2-carboxylate (5.88 g, 20.5 mmol, Intermediate 2, step b) in EtOH (53 mL) was added $N_2H_4$ (11.8 mL). The solution was stirred at rt for 2 h, quenched with water, and extracted with DCM. The organic layer was washed with brine, dried over anhydrous $Na_2SO_4$, filtered, and concentrated to dryness to give the title compound as an off-white solid.

Intermediate 2

Step d

Methyl 4-(2-(4-(4-fluoropiperidine-1-carbonyl)thiazole-2-carbonyl)hydrazinyl)-2,2-dimethyl-4-oxobutanoate

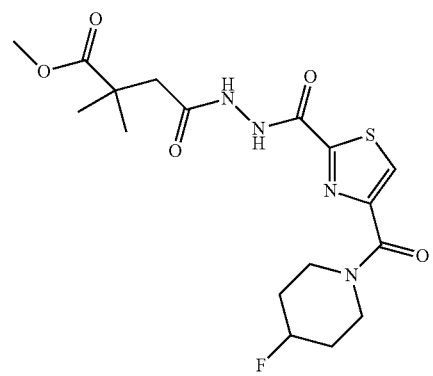 [SMILES: COC(=O)C(C)(C)CC(=O)NNC(=O)c1nc(C(=O)N2CCC(F)CC2)cs1]

To a solution of 4-methoxy-3,3-dimethyl-4-oxobutanoic acid (2.6 g, 16 mmol) in DCM (200 mL) was added DIPEA (5.7 g, 44 mmol) and HATU (6.7 g, 18 mmol). The mixture was stirred at rt for 30 min, then 4-(4-fluoropiperidine-1-carbonyl)thiazole-2-carbohydrazide (4.0 g, 14.7 mmol, Intermediate 2, step c) was added. The mixture was stirred at rt for 3 h and diluted with DCM. The organic layer was washed with water, brine, dried over anhydrous $Na_2SO_4$, filtered, concentrated to dryness, and purified by FCC on silica gel (PE/EtOAc=1/3) to give the title compound as a white solid.

Intermediate 2

Step e

Methyl 3-(5-(4-(4-fluoropiperidine-1-carbonyl)thiazol-2-yl)-1,3,4-oxadiazol-2-yl)-2,2-dimethylpropanoate

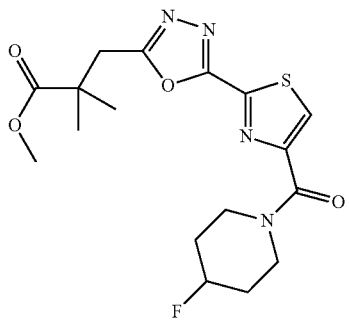 [SMILES: COC(=O)C(C)(C)Cc1nnc(-c2nc(C(=O)N3CCC(F)CC3)cs2)o1]

To a solution of methyl 4-(2-(4-(4-fluoropiperidine-1-carbonyl)thiazole-2-carbonyl)hydrazinyl)-2,2-dimethyl-4-oxobutanoate (1.7 g, 4.1 mmol, Intermediate 2, step d) in anhydrous DCM (170 mL) was added pyridine (1.02 mL, 12.7 mmol). The reaction was cooled to −10° C. and Tf$_2$O (5.1 mL, 30 mmol) was added dropwise. The reaction mixture was warmed to rt and stirred overnight. The reaction mixture was diluted with DCM, and the organic layer was washed with saturated NaHCO$_3$, brine, dried over anhydrous Na$_2$SO$_4$, filtered, concentrated to dryness, and purified by prep-TLC (PE/EtOAc=1/5) to give the title compound as an off-white oil.

Intermediate 3

Step a

N'-(2-Hydroxy-2-methylpropanoyl)-4-(((2-(trimethylsilyl)ethoxy)methoxy)methyl)thiazole-2-carbohydrazide

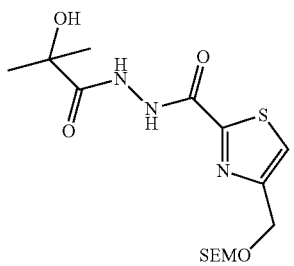

A solution of 4-(((2-(trimethylsilyl)ethoxy)methoxy)methyl)thiazole-2-carbohydrazide (1.41 g, 4.65 mmol, Intermediate 1, step c), 2-hydroxy-2-methylpropanoic acid (729 g, 7.00 mmol), HATU (2.66 g, 7.00 mmol), TEA (1.0 mL, 7.2 mmol), and acetonitrile (50 mL) was stirred at rt for 2 h.

The mixture was poured into H$_2$O (30 mL) and extracted with EtOAc (30 mL×4). The combined organic layers were washed with brine, dried over anhydrous Na$_2$SO$_4$, and concentrated to dryness. The residue was purified by FCC on silica gel (PE/EtOAc=1:2) to afford the title compound as a yellow solid.

Intermediate 3

Step b 2-(5-(4-(((2-(Trimethylsilyl)ethoxy)methoxy)methyl)thiazol-2-yl)-1,3,4-oxadiazol-2-yl)propan-2-ol

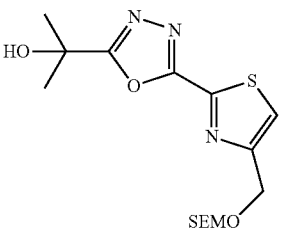

A solution of N-(2-hydroxy-2-methylpropanoyl)-4-(((2-(trimethylsilyl)ethoxy)methoxy)methyl)thiazole-2-carbohydrazide (759 mg, 1.95 mmol, Intermediate 3, step a), 4-methylbenzene-1-sulfonyl chloride (1.90 g, 10.0 mmol), TEA (2 mL), and DCM (20 mL) was stirred at rt overnight. The mixture was poured into H$_2$O (20 mL) and extracted with EtOAc (25 mL×3). The combined organic layers were washed with brine, dried over anhydrous Na$_2$SO$_4$, filtered, and concentrated to dryness. The residue was purified by FCC on silica gel (PE/EtOAc=2:1) to give the title compound as a yellow oil.

Intermediate 3

Step c 2-(5-(4-(Hydroxymethyl)thiazol-2-yl)-1,3,4-oxadiazol-2-yl)propan-2-ol

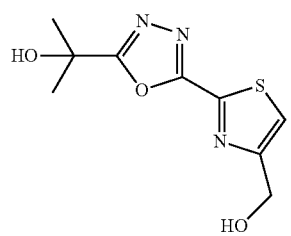 [SMILES: CC(C)(O)c1nnc(-c2nc(CO)cs2)o1]

2-(5-(4-(((2-(Trimethylsilyl)ethoxy)methoxy)methyl)thiazol-2-yl)-1,3,4-oxadiazol-2-yl)propan-2-ol (434 mg, 1.17 mmol, Intermediate 3, step b) was treated with HCl/dioxane (11 mL, 4 M) for 1 h. The mixture was quenched with NH$_3$/MeOH (7 mL, 7 M) and extracted with EtOAc (50 mL×3). The combined organic layers were concentrated to dryness to give the title compound.

Intermediate 3/1

1-(5-(4-(Hydroxymethyl)thiazol-2-yl)-1,3,4-oxadiazol-2-yl)-2-methylpropan-2-ol

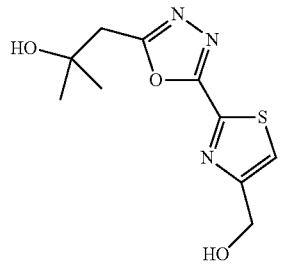 [SMILES: CC(C)(O)Cc1nnc(-c2nc(CO)cs2)o1]

The title compound was prepared as described for the synthesis of Intermediate 3, step c, using in step a 3-hydroxy-3-methylbutanoic acid in place of 2-hydroxy-2-methylpropanoic acid.

Intermediate 4

Step a

Ethyl 4-(4,4-difluoropiperidine-1-carbonyl)thiazole-2-carboxylate

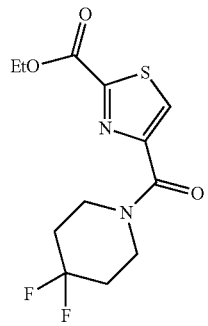 [SMILES: CCOC(=O)c1nc(C(=O)N2CCC(F)(F)CC2)cs1]

4,4-Difluoropiperidine hydrochloride (30.9 g, 192 mmol) was added to a mixture of 2-(ethoxycarbonyl)thiazole-4-carboxylic acid (38.7 g, 192 mmol, Intermediate 2, step a) in 2-methyl tetrahydrofuran (484 mL). Then, 2,4,6-tripropyl-1,3,5,2,4,6-trioxatriphosphinane 2,4,6-trioxide (174 mL, 292 mmol) was added followed by addition of DIPEA (66.7 mL, 387.4 mmol) via syringe at rt. After 1.5 h of stirring, the mixture was poured into 300 mL of aqueous saturated sodium carbonate solution. The layers were separated and the aqueous layer was extracted with EtOAc. The combined organic layers were washed with brine, dried over anhydrous MgSO$_4$ and concentrated to provide the title compound as a brownish yellow solid.

Intermediate 4

Step b 4-(4,4-Difluoropiperidine-1-carbonyl)thiazole-2-carbohydrazide

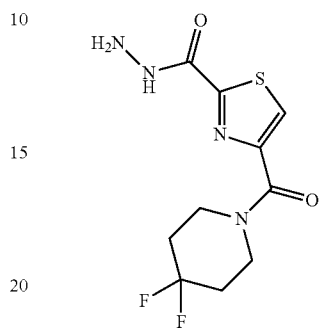

Anhydrous hydrazine (11.4 mL, 364 mmol) was added to a suspension of ethyl 4-(4,4-difluoropiperidine-1-carbonyl)thiazole-2-carboxylate (55.3 g, 182 mmol, Intermediate 4, step a) in EtOH (360 mL) at rt and the reaction mixture was stirred for 3 h. The mixture was partially concentrated, and the solids were isolated by filtration, washed with small amounts of cold EtOH and dried under high vacuum to provide the title compound as a light yellow solid.

Intermediate 4

Step c 4-(4,4-Difluoropiperidine-1-carbonyl)-N'-(2-hydroxy-2-methylpropanoyl)thiazole-2-carbohydrazide

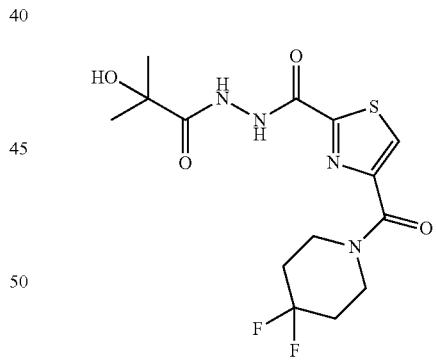

Carbonyl diimidazole (5.5 g, 34 mmol) was added to a solution of 2-hydroxy-2-methylpropanoic acid (3.7 g, 35 mmol) in THF (86 mL) at rt and stirred for 20 min. Then, 4-(4,4-difluoropiperidine-1-carbonyl)thiazole-2-carbohydrazide (4.99 g, 17.2 mmol, Intermediate 4, step b) was added at rt and the reaction mixture was stirred for 30 min. The mixture was cooled to 0° C., and 4 M HCl in dioxane (18 mL, 72 mmol) was added over 10 min. The ice bath was removed and the mixture stirred at rt for 15 min, and at 60° C. for 1 h. The hot mixture was filtered and washed with hot THF (60 mL). The filtrate was concentrated and toluene (40 mL) was added to the flask and the resulting mixture was heated to 70° C. for 1 h. After cooling to rt, the solids were isolated by filtration and dried under vacuum at 60° C. to provide the title compound as a white solid.

Intermediate 4

Step d (4,4-Difluoropiperidin-1-yl)(2-(5-(2-hydroxypropan-2-yl)-1,3,4-oxadiazol-2-yl)thiazol-4-yl)methanone

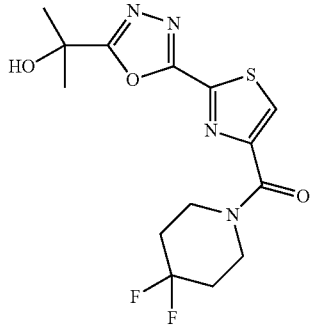 [SMILES: CC(C)(O)c1nnc(-c2nc(C(=O)N3CCC(F)(F)CC3)cs2)o1]

p-Toluene sulfonyl chloride (10.7 g, 56.1 mmol) was added to a suspension of 4-(4,4-difluoropiperidine-1-carbonyl)-N-(2-hydroxy-2-methylpropanoyl)thiazole-2-carbohydrazide (20.2 g, 53.6 mmol, Intermediate 4, step c) in DCM (130 mL) at 0° C., followed by TEA (16 mL, 115 mmol). The reaction mixture was stirred and allowed to warm to rt over 18 h. An additional amount of p-toluene sulfonyl chloride (1.07 g, 5.61 mmol) was added followed by TEA (1.6 mL, 11.5 mmol) and the mixture was stirred for 6 h. The mixture was diluted with DCM, washed with 1 M aqueous HCl (×2), aqueous saturated NaHCO$_3$ solution, brine, dried over anhydrous MgSO$_4$, filtered and concentrated. After addition of diethyl ether, the crude mixture was sonicated for 15 min and stirred for 15 h at rt. The resulting solids were isolated by filtration and dried under high vacuum to provide the title compound as a white solid.

Intermediate 4/1

Step a 2-(5-(2-Hydroxypropan-2-yl)-1,3,4-oxadiazol-2-yl)thiazole-4-carboxylic acid

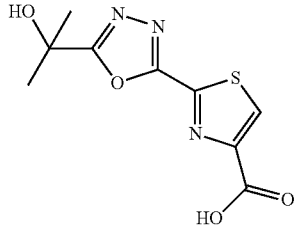 [SMILES: CC(C)(O)c1nnc(-c2nc(C(=O)O)cs2)o1]

To a solution of 2-(5-(4-(hydroxymethyl)thiazol-2-yl)-1,3,4-oxadiazol-2-yl)propan-2-ol (8.30 g, 34.4 mmol, Intermediate 3, step c) in acetonitrile/H$_2$O (160 mL, 5:1) was added TEMPO (5.38 g, 34.4 mmol) and iodobenzene diacetate (39.6 g, 124 mmol). The mixture was stirred at rt for 2 h. The resulting solution was basified with saturated aqueous Na$_2$CO$_3$ to pH=11 and extracted with EtOAc. The aqueous layer was acidified with 6 M aqueous HCl to pH=3 and extracted with EtOAc. The combined organic layers were washed with brine, dried over anhydrous Na$_2$SO$_4$, filtered, and concentrated to dryness to give the title compound as a yellow solid.

Intermediate 4/1

Step b (S)-(2-(5-(2-Hydroxypropan-2-yl)-1,3,4-oxadiazol-2-yl)thiazol-4-yl)(2-methylpyrrolidin-1-yl)methanone

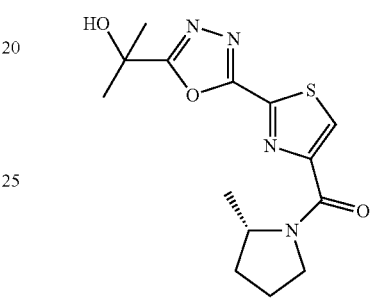

To a solution of 2-(5-(2-hydroxypropan-2-yl)-1,3,4-oxadiazol-2-yl)thiazole-4-carboxylic acid (3.40 g, 13.3 mmol, Intermediate 4/1, step a) in anhydrous DMF (50 mL) was added (S)-2-methylpyrrolidine hydrochloride (1.6 g, 13.4 mmol) and DIEA (5.2 g, 40 mmol). The mixture was stirred for 30 min, then HATU (5.10 g, 13.4 mmol) was added. The mixture was stirred for 3 h at rt. The solution was quenched with H$_2$O and extracted with EtOAc. The combined organic layers were washed with brine, dried over anhydrous Na$_2$SO$_4$, filtered and concentrated to dryness. The residue was purified by FCC on silica gel (EtOAc) to give the title compound as a yellow oil.

Intermediate 5

2-(5-(4-(Hydroxymethyl)thiazol-2-yl)-4-(4-methoxybenzyl)-4H-1,2,4-triazol-3-yl)propan-2-ol

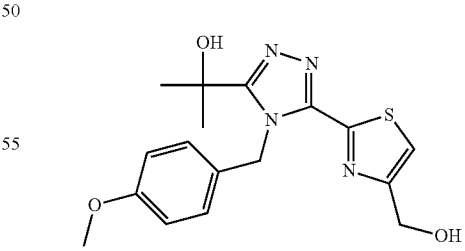

To a solution of 2-(5-(4-(hydroxymethyl)thiazol-2-yl)-1,3,4-oxadiazol-2-yl)propan-2-ol (420 mg, 1.74 mmol, Intermediate 3, step c) in toluene (5 mL) was added PMBNH$_2$ (716 mg, 5.22 mmol). The mixture was stirred at 120° C. for 12 h. The reaction mixture was concentrated to dryness and the residue was purified by prep-TLC (PE/EtOAc=4:1) to give the title compound.

Intermediate 6

2-(5-(4-(Hydroxymethyl)thiazol-2-yl)-4-methyl-4H-1,2,4-triazol-3-yl)propan-2-ol

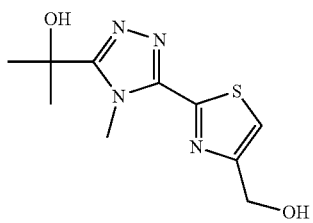 [SMILES: Cn1c(-c2nc(CO)cs2)nnc1C(C)(C)O]

To a solution of 2-(5-(4-(hydroxymethyl)thiazol-2-yl)-1,3,4-oxadiazol-2-yl)propan-2-ol (420 mg, 1.74 mmol, Intermediate 3, step c) in CH$_3$NH$_2$/MeOH (5 mL, 2 M) was added TsOH (135 mg, 0.71 mmol). The mixture was stirred at 60° C. for 12 h. The reaction mixture was concentrated to dryness and the residue was purified by prep-TLC (PE/EtOAc=4:1) to give the title compound.

Intermediate 7

Step a 2-(4-(((2-(Trimethylsilyl)ethoxy)methoxy)methyl)thiazol-2-yl)-1,3,4-oxadiazole

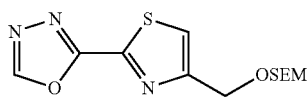

A mixture of 4-(((2-(trimethylsilyl)ethoxy)methoxy)methyl)thiazole-2-carbohydrazide (1.4 g, 4.6 mmol, Intermediate 1, step c) and triethylorthoformate (6 mL, 36 mmol) was vigorously stirred at 120° C. overnight. The excess triethylorthoformate was removed under reduced pressure. The resulting oil was purified by FCC on silica gel (n-hexane/EtOAc=70:30) to afford the title compound.

Intermediate 7

Step b

2-Methyl-1-(3-(4-(((2-(trimethylsilyl)ethoxy)methoxy)methyl)thiazol-2-yl)-4H-1,2,4-triazol-4-yl)propan-2-ol

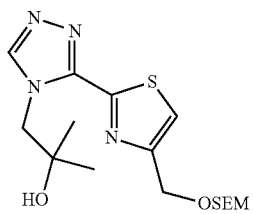

To a solution of 2-(4-(((2-(trimethylsilyl)ethoxy)methoxy)methyl)thiazol-2-yl)-1,3,4-oxadiazole (500 mg, 1.6 mmol, Intermediate 7, step a) in toluene (5 mL) was added 1-amino-2-methylpropan-2-ol (284 mg, 3.19 mmol). The mixture was stirred at 120° C. for 12 h, cooled to rt, concentrated to dryness and the residue was purified by prep-TLC (PE:EtOAc=1:1) to give the title compound.

Intermediate 7

Step c 1-(3-(4-(Hydroxymethyl)thiazol-2-yl)-4H-1,2,4-triazol-4-yl)-2-methylpropan-2-ol

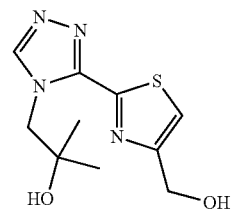 [SMILES: CC(C)(O)Cn1cnnc1-c1nc(CO)cs1]

A solution of 2-methyl-1-(3-(4-(((2-(trimethylsilyl)ethoxy)methoxy)methyl)thiazol-2-yl)-4H-1,2,4-triazol-4-yl)propan-2-ol (400 mg, 1.04 mmol, Intermediate 7, step b) in HCl/dioxane (5 mL, 4 M) was stirred for 1 h. The solution was quenched with NH$_3$/MeOH (7 mL, 7 M) and extracted with EtOAc (3×50 mL). The combined organic phases were dried over anhydrous Na$_2$SO$_4$, filtered, and concentrated to dryness to give the title compound.

Intermediate 8

Step a 4-(((2-(Trimethylsilyl)ethoxy)methoxy)methyl)thiazole-2-carboxamide

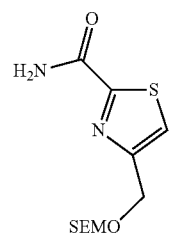

A solution of ethyl 4-(((2-(trimethylsilyl)ethoxy)methoxy)methyl)thiazole-2-carboxylate (3.17 g, 10.0 mmol, Intermediate 1, step b) in ammonia (7 N in MeOH, 50 mL) was stirred at 60° C. for 12 h and concentrated to dryness to give the title compound as a white solid.

Intermediate 8

Step b 4-(((2-(Trimethylsilyl)ethoxy)methoxy)methyl)thiaz-ole-2-carbonitrile

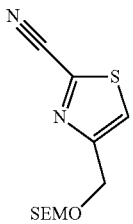

To a solution of 4-(((2-(trimethylsilyl)ethoxy)methoxy)methyl)thiazole-2-carboxamide (2.88 g, 10.0 mmol, Intermediate 8, step a) in DCM (100 mL) was added pyridine (1.46 g, 18.5 mmol) at 0° C. and then add TFAA (4.19 g, 20 mmol) dropwise over 10 min. The mixture was stirred for 1 h at this temperature, quenched with H$_2$O and extracted with EtOAc (50 mL×3). The combined organic layers were washed with brine, dried over anhydrous Na$_2$SO$_4$, and concentrated to dryness to give the title compound.

Intermediate 8

Step c

N'-Hydroxy-4-(((2-(trimethylsilyl)ethoxy)methoxy)methyl)thiazole-2-carboximidamide

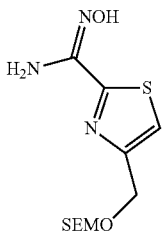

A suspension of 4-(((2-(trimethylsilyl)ethoxy)methoxy)methyl)thiazole-2-carbonitrile (986 mg, 3.65 mmol, Intermediate 8, step b), NH$_2$OH.HCl (504 mg, 7.25 mmol), Na$_2$CO$_3$ (2.32 g, 21.9 mmol) in EtOH-H$_2$O (20 mL, 5:1) was refluxed for 3 h, concentrated to dryness, redissolved in H$_2$O, and extracted with EtOAc. The organic layer was washed with saturated aqueous NaCl, dried over anhydrous Na$_2$SO$_4$, filtered and concentrated to dryness to afford the title compound.

Intermediate 8

Step d

Methyl 4-(((amino(4-(((2-(trimethylsilyl)ethoxy)methoxy)methyl)thiazol-2-yl)methylene)amino)oxy)-2,2-dimethyl-4-oxobutanoate

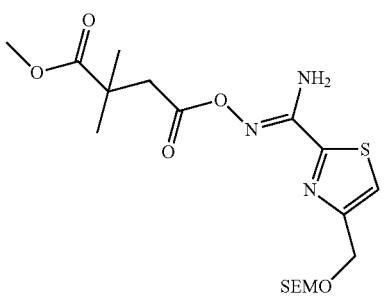

A mixture of N'-hydroxy-4-(((2-(trimethylsilyl)ethoxy)methoxy)methyl)thiazole-2-carboximidamide (1.0 g, 3.3 mmol, Intermediate 8, step c), 4-methoxy-3,3-dimethyl-4-oxobutanoic acid (528 mg, 3.30 mmol), HATU (1.25 g, 3.29 mmol), DIPEA (1.65 mL, 9.47 mmol), and DMF (20 mL) was stirred at rt for 2 h, poured into H$_2$O (120 mL) and extracted with EtOAc (100 mL×3). The combined organic layers were washed with brine, dried over anhydrous Na$_2$SO$_4$, filtered, concentrated to dryness, and purified by FCC on silica gel (PE/EtOAc=1:1) to afford the title compound as a yellow oil.

Intermediate 8

Step e

Methyl 2,2-dimethyl-3-(3-(4-(((2-(trimethylsilyl)ethoxy)methoxy)methyl)thiazol-2-yl)-1,2,4-oxadiazol-5-yl)propanoate

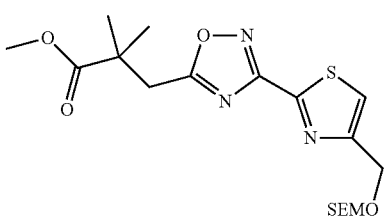

A solution of methyl 4-(((amino(4-(((2-(trimethylsilyl)ethoxy)methoxy)methyl)thiazol-2-yl)methylene)amino)oxy)-2,2-dimethyl-4-oxobutanoate (1.0 g, 2.2 mmol, Intermediate 8, step d) in DMF (10 mL) was stirred at 120° C. for 12 h, poured into H$_2$O (120 mL) and extracted with EtOAc (100 ml, ×3). The combined organic layers were washed with brine, dried over anhydrous Na$_2$SO$_4$, filtered, concentrated to dryness, and purified by FCC on silica gel (PE/EtOAc=1:1) to afford the title compound.

Intermediate 8

Step f

Methyl 3-(3-(4-(hydroxymethyl)thiazol-2-yl)-1,2,4-oxadiazol-5-yl)-2,2-dimethylpropanoate

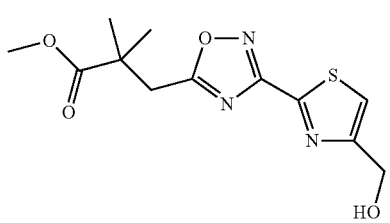 [SMILES: COC(=O)C(C)(C)Cc1nc(-c2nc(CO)cs2)no1]

Methyl 2,2-dimethyl-3-(3-(4-(((2-(trimethylsilyl)ethoxy)methyl)thiazol-2-yl)-1,2,4-oxadiazol-5-yl)propanoate (350 mg, 0.82 mmol, Intermediate 8, step e) was treated with HCl/dioxane (11 mL, 4 M) for 1 h, quenched with NH$_3$/MeOH (7 mL, 7 M), poured into H$_2$O (20 mL), and extracted with EtOAc (50 mL×3). The combined organic layers were concentrated to dryness to give the title compound.

Intermediate 9

Step a 2-(3-(4-(((2-(Trimethylsilyl)ethoxy)methoxy)methyl)thiazol-2-yl)-1,2,4-oxadiazol-5-yl)propan-2-ol

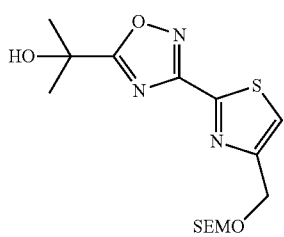

To a solution of N'-hydroxy-4-(((2-(trimethylsilyl)ethoxy)methoxy)methyl)thiazole-2-carboximidamide (360 mg, 1.18 mmol, Intermediate 8, step c) in DMF (10 mL) were added HATU (450 mg, 1.18 mmol), DIEA (456 mg, 3.54 mmol), and 2-hydroxy-2-methylpropanoic acid (122 mg, 1.18 mmol) and the mixture was stirred for 1 h at rt. The mixture was diluted with EtOAc and washed with water followed by brine, dried over anhydrous Na$_2$SO$_4$, filtered and concentrated to dryness. The residue was dissolved in DMF and heated at 120° C. overnight. The mixture was quenched with water and extracted with EtOAc (50 mL×3). The combined organic layers were washed with brine, dried over anhydrous Na$_2$SO$_4$, filtered and concentrated to dryness. The residue was purified by FCC on silica gel to provide the title compound.

Intermediate 9

Step b 2-(3-(4-(Hydroxymethyl)thiazol-2-yl)-1,2,4-oxadiazol-5-yl)propan-2-ol

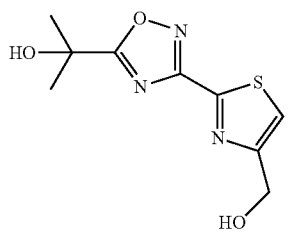 [SMILES: CC(C)(O)c1nc(-c2nc(CO)cs2)no1]

The title compound was prepared as described for the synthesis of Intermediate 3, using in step c 2-(3-(4-(((2-(trimethylsilyl)ethoxy)methoxy)methyl)thiazol-2-yl)-1,2,4-oxadiazol-5-yl)propan-2-ol (Intermediate 9, step a) in place of 2-(5-(4-(((2-(trimethylsilyl)ethoxy)methoxy)methyl)thiazol-2-yl)-1,3,4-oxadiazol-2-yl)propan-2-ol.

Intermediate 9/1

1-(3-(4-(Hydroxymethyl)thiazol-2-yl)-1,2,4-oxadiazol-5-yl)-2-methylpropan-2-ol

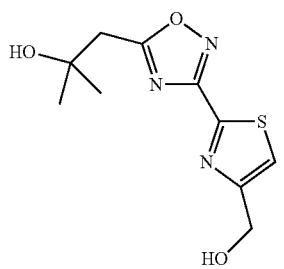 [SMILES: CC(C)(O)Cc1nc(-c2nc(CO)cs2)no1]

The title compound was prepared as described for the synthesis of Intermediate 9, using in step a 3-hydroxy-3-methylbutanoic acid in place of 2-hydroxy-2-methylpropanoic acid.

Intermediate 10

Step a (4-(((2-(Trimethylsilyl)ethoxy)methoxy)methyl)thiazol-2-yl)methanol

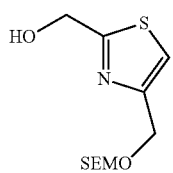

To a solution of ethyl 4-(((2-(trimethylsilyl)ethoxy)methoxy)methyl)thiazole-2-carboxylate (1.9 g, 6.0 mmol, Intermediate 1, step b) in MeOH (10 mL) was slowly added sodium tetrahydridoborate (456 mg, 12.0 mmol) at 0° C. and the mixture was stirred at 0° C. for 6 h. Water was added and the mixture was extracted with EtOAc (3×). The combined organic layers were washed with brine, dried over anhydrous $Na_2SO_4$, filtered and concentrated to dryness to give the title compound as brown oil.

Intermediate 10

Step b 4-(((2-(Trimethylsilyl)ethoxy)methoxy)methyl)thiazole-2-carbaldehyde

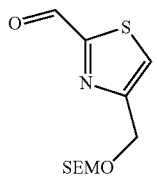

A solution of (4-(((2-(trimethylsilyl)ethoxy)methoxy)methyl)thiazol-2-yl)methanol (1.1 g, 4.1 mmol, Intermediate 10, step a), IBX (2.27 g, 8.12 mmol), and acetone (20 mL) was refluxed overnight. After filtration, the filtrate was concentrated to dryness to give the title compound as a brown oil.

Intermediate 10

Step c 4-(((2-(Trimethylsilyl)ethoxy)methoxy)methyl)thiazole-2-carbaldehyde oxime

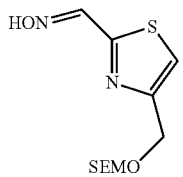

A suspension of 4-(((2-(trimethylsilyl)ethoxy)methoxy)methyl)thiazole-2-carbaldehyde (955 mg, 3.49 mmol, Intermediate 10, step b), $NH_2OH \cdot HCl$ (483 mg, 6.97 mmol), $Na_2CO_3$ (742 mg, 7.00 mmol) in ethanol-water (20 ml, 5:1) was stirred at rt for 1 h. The mixture was concentrated to dryness and the residue was treated with water, followed by extraction with EtOAc. The organic layer was washed with brine, dried over anhydrous $Na_2SO_4$, filtered and concentrated to dryness to afford the title compound.

Intermediate 10

Step d 2-(3-(4-(((2-(Trimethylsilyl)ethoxy)methoxy)methyl)thiazol-2-yl)isoxazol-5-yl)propan-2-ol

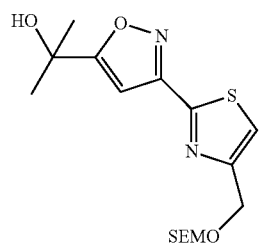

4-(((2-(Trimethylsilyl)ethoxy)methoxy)methyl)thiazole-2-carbaldehyde oxime (1.1 g, 3.8 mmol, Intermediate 10, step c) and 2-methylbut-3-yn-2-ol (317 mg, 3.8 mmol) were mixed in DCM (5 mL). The mixture was cooled to 0° C. and a sodium hypochlorite solution (5% chlorine, 15 mL, 11 mmol) was added dropwise to the solution. The mixture was stirred overnight at rt and DCM (20 mL) was added. The organic layer was washed with water, 1 M aqueous HCl, saturated aqueous $NaHCO_3$, brine, dried over anhydrous $MgSO_4$, filtered and concentrated to dryness. The residue was purified by FCC on silica gel (PE/EtOAc=8:1) to give the title compound as a white solid.

Intermediate 10

Step e 2-(3-(4-(Hydroxymethyl)thiazol-2-yl)isoxazol-5-yl)propan-2-ol

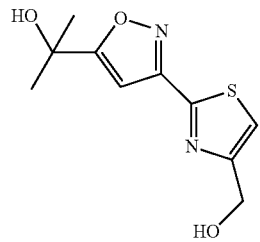 [SMILES: CC(C)(O)c1cc(-c2nc(CO)cs2)no1]

The title compound was prepared as described for the synthesis of Intermediate 3 using in step c 2-(3-(4-(((2-(trimethylsilyl)ethoxy)methoxy)methyl)thiazol-2-yl)isoxazol-5-yl)propan-2-ol (Intermediate 10, step d) in place of 2-(5-(4-(((2-(trimethylsilyl)ethoxy)methoxy)methyl)thiazol-2-yl)-1,3,4-oxadiazol-2-yl)propan-2-ol.

Intermediate 10/1

Methyl 3-(3-(4-(hydroxymethyl)thiazol-2-yl)isoxazol-5-yl)-2,2-dimethylpropanoate

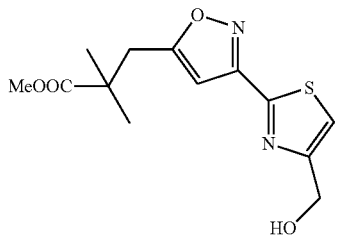 [SMILES: COC(=O)C(C)(C)Cc1cc(-c2nc(CO)cs2)no1]

The title compound was prepared as described for the synthesis of Intermediate 10, using in step d methyl 2,2-dimethylpent-4-ynoate in place of 2-methylbut-3-yn-2-ol.

Intermediate 11

Step a

Methyl 6-carbamoylpicolinate

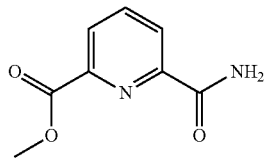

To a solution of 6-(methoxycarbonyl)picolinic acid (225 mg, 1.24 mmol) in DCM (5 mL) was added 1-chloro-N,N,2-trimethylpropenylamine (247 mg, 1.86 mmol) at 0° C. and the mixture was stirred for 1 h. The mixture was slowly added to a stirred solution of $NH_3$ in MeOH (7 M, 0.5 mL, 3.5 mmol) at 0° C., and stirred for 1 h. The solvent was removed and the yellow residue was purified by FCC on silica gel (PE/EtOAc=2:1) to afford the title compound as a yellow oil.

Intermediate 11

Step b

Methyl 6-carbamothioylpicolinate

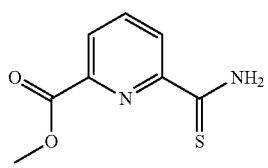

To a solution of methyl 6-carbamoylpicolinate (148 mg, 0.822 mmol, Intermediate 11, step a) in THF (5 mL) was added $P_2S_5$ (273 mg, 1.23 mmol) and the mixture was stirred at rt overnight. The solvent was removed and the residue was purified by FCC on silica gel (PE/EtOAc=3:1) to give the title compound as a yellow solid.

Intermediate 11

Step c

Methyl 6-(4-(hydroxymethyl)thiazol-2-yl)picolinate

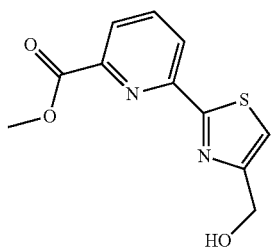 [SMILES: COC(=O)c1cccc(-c2nc(CO)cs2)n1]

A solution of methyl 6-carbamothioylpicolinate (141 mg, 0.719 mmol, Intermediate 11, step b), 1-bromo-3-hydroxypropan-2-one (142 mg, 0.94 mmol), and EtOH (8 mL) was stirred at 75° C. overnight. Water was added and the mixture was extracted with EtOAc (3×). The combined organic layers were washed with brine, dried over anhydrous $Na_2SO_4$, and filtered. The filtrate was concentrated to dryness and the yellow residue was purified by FCC on silica gel (PE/EtOAc=5:1) to give the title compound as a yellow solid.

Intermediate 11

Step d

Methyl 6-(4-(((2-(trimethylsilyl)ethoxy)methoxy)methyl)thiazol-2-yl)picolinate

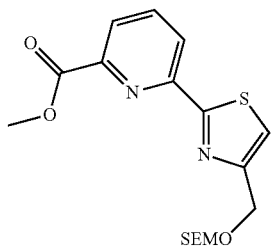

To a solution of methyl 6-(4-(hydroxymethyl)thiazol-2-yl)picolinate (144 mg, 0.575 mmol, Intermediate 11, step c), DIPEA (147 mg, 1.14 mmol), and DCM (5 mL) was added SEMCl (189 mg, 1.14 mmol) at 0° C. and the solution was stirred at rt overnight. The mixture was partitioned between EtOAc and water, and the layers were separated. The organic layer was washed with water and brine, dried over anhydrous $Na_2SO_4$, filtered, and concentrated to dryness. The yellow residue was purified by FCC on silica gel (PE/EtOAc=8:1) to give the title compound as a yellow oil.

Intermediate 11

Step e 2-(6-(4-(((2-(Trimethylsilyl)ethoxy)methoxy)methyl)thiazol-2-yl)pyridin-2-yl)propan-2-ol

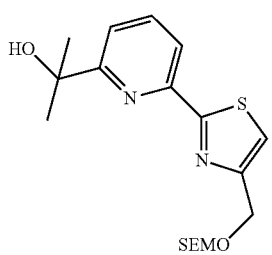

To a solution of methyl 6-(4-(((2-(trimethylsilyl)ethoxy)methoxy)methyl)thiazol-2-yl)picolinate (153 mg, 0.402 mmol, Intermediate 11, step d) in anhydrous THF (5 mL) was added MeMgBr (2.5 M in diethylether, 0.3 mL, 0.75 mmol) and the mixture was stirred at rt for 1 h. Water was added and the mixture was extracted with EtOAc (3×). The combined organic layers were washed with brine, dried over anhydrous Na$_2$SO$_4$, and filtered. The filtrate was concentrated to dryness to give the title compound as a yellow oil.

Intermediate 11

Step f 2-(6-(4-(Hydroxymethyl)thiazol-2-yl)pyridin-2-yl)propan-2-ol

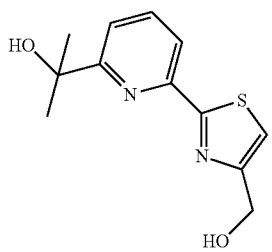 [SMILES: CC(C)(O)c1cccc(-c2nc(CO)cs2)n1]

To a solution of 2-(6-(4-(((2-(trimethylsilyl)ethoxy)methoxy)methyl)thiazol-2-yl)pyridin-2-yl)propan-2-ol (128 mg, 0.336 mmol, Intermediate 11, step e) and 1,4-dioxane (4 mL) was added HCl in 1,4-dioxane (4 M, 1 mL, 4 mmol), and the mixture was stirred at rt for 1 h. The solvent was removed under reduced pressure and the yellow residue was purified by FCC on silica gel (PE/EtOAc=2:1) to give the title compound as a white solid.

Intermediate 11/1

Step a

Methyl 2-carbamoylisonicotinate

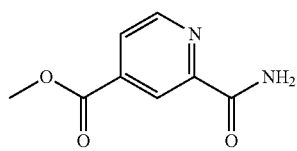

To a solution of methyl isonicotinate (918 mg, 6.70 mmol) in formamide (20 mL) was added ferrous sulfate heptahydrate (2.78 g, 10.1 mmol) and H$_2$SO$_4$ (985 mg, 10.1 mmol) under cooling to keep the temperature between 8-10° C. Hydrogen peroxide (30% solution, 1.14 mL, 13.6 mmol) was added over a period of 25 min. The resulting mixture was stirred at rt for 2 h. The mixture was poured into a solution of sodium citrate dihydrate (4.01 g, 14.0 mmol) in water (30 mL), the pH was adjusted to pH>8 with NaHCO$_3$ and filtered. The residue and filtrate were extracted with DCM. The combined organic layers were evaporated and washed with PE/Et$_2$O (30:1) twice to give the title compound as a white solid.

Intermediate 11/1

Step b 2-(2-(4-(Hydroxymethyl)thiazol-2-yl)pyridin-4-yl)propan-2-ol

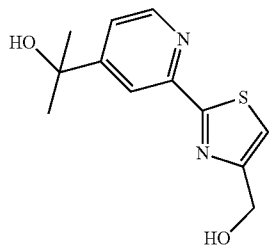 [SMILES: CC(C)(O)c1ccnc(-c2nc(CO)cs2)c1]

The title compound was prepared as described for the synthesis of Intermediate 11 using in step b methyl 2-carbamoylisonicotinate (Intermediate 11/1, step a) in place of methyl 6-carbamoylpicolinate.

Intermediate 11/2

Step a 6-(Methoxycarbonyl)pyrimidine-4-carboxylic acid

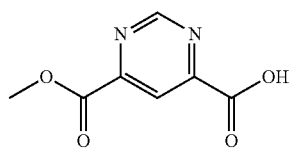

To a solution of dimethyl pyrimidine-4,6-dicarboxylate (300 mg, 1.56 mmol) in MeOH (10 mL) and DCM (5 mL) was added NaOH (63 mg, 1.6 mmol). The resulting mixture was stirred at rt overnight. The mixture was concentrated and the pH adjusted to pH<2 with 2 M aqueous HCl. The mixture was extracted with EtOAc. The combined organic layers were washed with brine, dried over anhydrous $Na_2SO_4$, filtered and concentrated to dryness to afford the title compound as a white solid.

Intermediate 11/2

Step b 2-(6-(4-(Hydroxymethyl)thiazol-2-yl)pyrimidin-4-yl)propan-2-ol

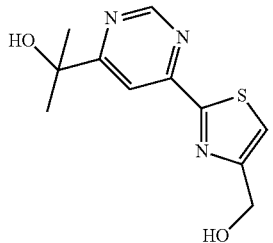 [SMILES: CC(C)(O)c1cc(-c2nc(CO)cs2)ncn1]

The title compound was prepared as described for the synthesis of Intermediate 11, using in step a 6-(methoxycarbonyl)pyrimidine-4-carboxylic acid (Intermediate 11/2, step a) in place of 6-(methoxycarbonyl)picolinic acid.

Intermediate 12/1

Step a 1-(Difluoromethyl)-2-fluoro-3-nitrobenzene

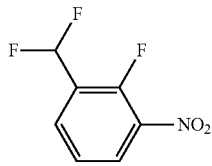 [SMILES: O=[N+]([O-])c1cccc(C(F)F)c1F]

A solution of 2-fluoro-3-nitrobenzaldehyde (564 mg, 3.34 mmol) in DCM (20 mL) was cooled to −78° C. DAST (645 mg, 4.01 mmol) was added dropwise and the mixture was stirred at rt for 1 h. The mixture was poured into ice water, extracted with EtOAc (3×30 mL) and the combined organic layers were washed with brine and concentrated to dryness. The residue was purified by prep-TLC (PE/EtOAc=5:1) to give the title compound as a yellow solid.

Alternatively Intermediate 12/1, step a was prepared by the following route:
2-Fluoro-3-nitrobenzaldehyde (1.0 g, 5.92 mmol) and anhydrous DCM (10 mL) were added to a flask and the flask was cooled to −78° C. Diethylaminosulfur trifluoride (1.14 g, 7.07 mmol) was then added dropwise while the reaction temperature was kept below −65° C. After addition, the reaction mixture was warmed slowly to 15-20° C. and stirred at this temperature for 4 h. The reaction mixture was then poured into ice water (10 mL), and the aqueous layer was extracted with DCM (2×6 mL). The organic layer was washed with saturated aqueous $NaHCO_3$ (2×10 mL) and the aqueous layer was extracted with DCM (2×5 mL). The combined organic layers were washed with brine, dried over $Na_2SO_4$, filtered and concentrated to dryness. The residue was purified by FCC on silica gel (PE/EA=10/1) to afford the title compound.

Intermediate 12/1

Step b 3-(Difluoromethyl)-2-fluoroaniline

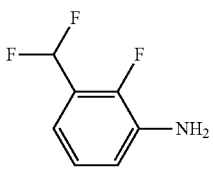

1-(Difluoromethyl)-2-fluoro-3-nitrobenzene (387 mg, 2.03 mmol, Intermediate 12/1, step a) in methanol (20 mL) was added to a flask and Pd/C (10%, 80 mg) was added. The mixture was stirred under a hydrogen atmosphere at rt overnight. The mixture was filtered through a pad of Celite® and the filtrate was concentrated to dryness to give the title compound, which was used in the next step directly.

Alternatively Intermediate 12/1, step b was prepared by the following route:
1-(Difluoromethyl)-2-fluoro-3-nitrobenzene (1 g, 5.92 mmol, Intermediate 12/1, step a) and anhydrous MeOH (10 mL) were added to a high pressure reaction bottle. The reaction vessel was treated with 10 wt % Pd/C (200 mg) in one portion under Ar. The resultant mixture was stirred at 10-20° C. under 30 Psi of $H_2$ for 4 days. The reaction mixture was then filtered through Celite® and washed with MeOH (3×7.2 mL). The filtrate was dried over $Na_2SO_4$, filtered and concentrated under reduced pressure to afford the title compound as a brown oil.

Intermediate 12/1

Step c

4-Bromo-3-(difluoromethyl)-2-fluoroaniline

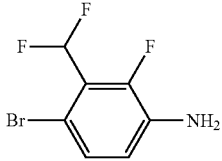 [SMILES: Nc1ccc(Br)c(C(F)F)c1F]

A solution of 3-(difluoromethyl)-2-fluoroaniline (319 mg, 1.98 mmol, Intermediate 12/1, step b) in DMF (10 mL) was cooled to 0° C. NBS (480 mg, 2.38 mmol) was added portion wise and the mixture was stirred at rt for 3 h. The mixture was poured into ice water and extracted with EtOAc (3×30 mL). The combined organic layers were washed with brine and filtered. The filtrate was concentrated to dryness and the residue was purified by FCC on silica gel (PE/EtOAc=5:1) to give the title compound as a white solid.

Alternatively Intermediate 12/1, step c was prepared by the following route:

3-(Difluoromethyl)-2-fluoroaniline (5 g, 31.0 mmol, Intermediate 12/1, step b) and anhydrous DMF (50 mL) were added to a flask. The reaction vessel was cooled to −5° C. and treated with N-bromosuccinimide (5.8 g, 32.6 mmol) in portions under $N_2$. The resultant mixture was stirred for 1.5 h at −5~5° C. The reaction mixture was then poured into ice water, and the aqueous layer was extracted with EtOAc. The combined organic layers were washed with water and brine, dried over $Na_2SO_4$, filtered and concentrated to dryness. The residue was purified by FCC on silica gel (1/100-1/5 EtOAc/PE) to afford the title compound.

Intermediate 12/1

Step d

4-Bromo-3-(difluoromethyl)-2-fluorobenzene-1-sulfonyl chloride

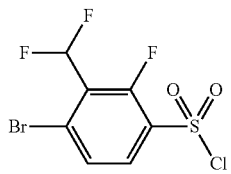

To a suspension of 4-bromo-3-(difluoromethyl)-2-fluoroaniline (331 mg, 1.38 mmol, Intermediate 12/1, step c) in HCl/HOAc (10/5, 15 mL), $NaNO_2$ (143 mg, 2.07 mmol) dissolved in $H_2O$ (5 mL) was added dropwise at −10° C. The mixture was stirred at −10° C. for 1 h and then poured into a complex of HOAc and $SO_2$ (saturated) at 0° C., warmed to rt and stirred for an additional 2 h. The mixture was poured into ice water, and the precipitate was collected and dried to give the title compound as a white solid.

Alternatively Intermediate 12/1, step d was prepared by the following route:

4-Bromo-3-(difluoromethyl)-2-fluoroaniline (1.0 g, 4.17 mmol, Intermediate 12/1 step c) and acetic acid (7.5 mL) were added to a flask. The reaction vessel was treated with concentrated HCl (5 mL, 60 mmol) in portions at 10-15° C. and cooled to −5° C. A solution of $NaNO_2$ (0.345 g, 5 mmol) in water (7.5 mL) was added dropwise into the reaction vessel at −5-0° C. and stirred at −5-0° C. for 1 h. The reaction mixture was added to a pre-cooled mixture of saturated solution of $SO_2$ in acetic acid (~16 mL) and $CuCl_2 \cdot H_2O$ (0.76 g, 5 mmol) in water (~3 mL) at −5-0° C. The resultant mixture was warmed slowly to 0-15° C. and stirred for 1 h. The mixture was poured into ice water (30 mL). The precipitate was filtered, the filtrate was extracted with DCM (2×20 mL), and the precipitate was dissolved with DCM (37.5 mL). The combined organic layers were washed with saturated aqueous $Na_2CO_3$ to pH=7~8, washed with brine, dried over $Na_2SO_4$, filtered and concentrated to dryness. The residue was purified by FCC on silica gel (PE/DCM=10/1-5/1) to afford the title compound.

Intermediate 12/1

Step e (S)-4-Bromo-3-(difluoromethyl)-2-fluoro-N-(1,1,1-trifluorobutan-2-yl)benzenesulfonamide

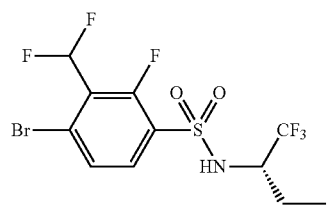 [SMILES: CC[C@H](NS(=O)(=O)c1ccc(Br)c(C(F)F)c1F)C(F)(F)F]

A solution of 4-bromo-3-(difluoromethyl)-2-fluorobenzene-1-sulfonyl chloride (246 mg, 0.761 mmol, Intermediate 12/1, step d), (S)-1,1,1-trifluorobutan-2-amine (106 mg, 0.835 mmol) and DMAP (0.1 g, 0.8 mmol) in pyridine (20 mL) was stirred at 90° C. for 2 h. The mixture was concentrated, $H_2O$ (20 mL) was added and the mixture was extracted with EtOAc (4×20 mL).

The combined organic layers were washed with brine, dried over anhydrous $Na_2SO_4$, filtered and concentrated to dryness. The residue was purified by FCC on silica gel (PE/EtOAc=10:1) to afford the title compound as a white solid.

Alternatively Intermediate 12/1, step e was prepared by the following route:

(S)-1,1,1-Trifluorobutan-2-amine (0.19 g, 1.5 mmol) and pyridine (1.5 mL) were added to a flask. The reaction vessel was cooled to −5° C. and treated with 4-bromo-3-(difluoromethyl)-2-fluorobenzene-1-sulfonyl chloride (0.5 g, 1.5 mmol, Intermediate 12/1, step d) in one portion under $N_2$. The resultant mixture was stirred for 1 h at −5° C., and then stirred at about 10° C. for 20 h. 1 M Aqueous HCl (10 mL) was added into the reaction mixture. The mixture was extracted with EtOAc (2×10 mL). The combined organic layers were washed with 1 M aqueous HCl, and concentrated to dryness. The residue was purified by FCC on silica gel (PE/EA=10/1) to give the title compound.

Intermediate 12/2

(S)-4-Bromo-3-(difluoromethyl)-2-fluoro-N-(1,1,1-trifluoropropan-2-yl)benzenesulfonamide

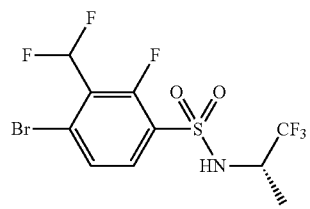 [SMILES: C[C@H](NS(=O)(=O)c1ccc(Br)c(C(F)F)c1F)C(F)(F)F]

The title compound was prepared as described for the synthesis of Intermediate 12/1 using in step e (S)-1,1,1-trifluoropropan-2-amine in place of (S)-1,1,1-trifluorobutan-2-amine.

Intermediate 12/3

(S)-4-Bromo-2,3-dichloro-N-(1,1,1-trifluoropropan-2-yl)benzenesulfonamide

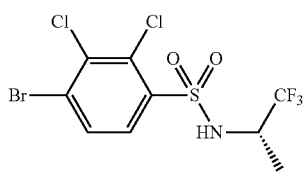 [SMILES: C[C@H](NS(=O)(=O)c1ccc(Br)c(Cl)c1Cl)C(F)(F)F]

The title compound was prepared as described for the synthesis of Intermediate 12/2, using in Intermediate 12/1, step d 4-bromo-2,3-dichloroaniline in place of 4-bromo-3-(difluoromethyl)-2-fluoroaniline.

Intermediate 12/4

(S)-4-Bromo-2,3-dichloro-N-(1,1,1-trifluorobutan-2-yl)benzenesulfonamide

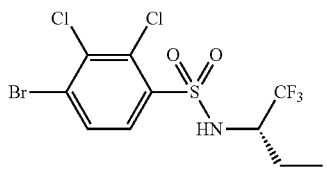 [SMILES: CC[C@H](NS(=O)(=O)c1ccc(Br)c(Cl)c1Cl)C(F)(F)F]

The title compound was prepared as described for the synthesis of Intermediate 12/3, using in Intermediate 12/1, step e (S)-1,1,1-trifluorobutan-2-amine in place of (S)-1,1,1-trifluoropropan-2-amine.

Intermediate 12/5

(R)-4-Bromo-2,3-dichloro-N-(1,1,1-trifluoropropan-2-yl)benzenesulfonamide

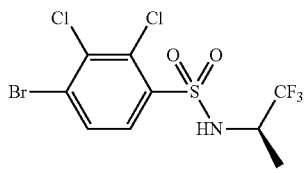 [SMILES: C[C@@H](NS(=O)(=O)c1ccc(Br)c(Cl)c1Cl)C(F)(F)F]

The title compound was prepared as described for the synthesis of Intermediate 12/3, using in Intermediate 12/1, step e (R)-1,1,1-trifluoropropan-2-amine in place of (S)-1,1,1-trifluoropropan-2-amine.

Intermediate 12/6

(S)-4-Bromo-3-chloro-2-fluoro-N-(1,1,1-trifluoropropan-2-yl)benzenesulfonamide

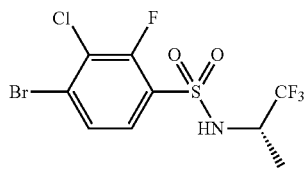 [SMILES: C[C@H](NS(=O)(=O)c1ccc(Br)c(Cl)c1F)C(F)(F)F]

The title compound was prepared as described for the synthesis of Intermediate 12/1, using in step d 4-bromo-3-chloro-2-fluoroaniline in place of 4-bromo-3-(difluoromethyl)-2-fluoroaniline and in step e (S)-1,1,1-trifluoropropan-2-amine in place of (S)-1,1,1-trifluorobutan-2-amine.

Intermediate 12/7

(S)-4-Bromo-N-(1,1,1-trifluoropropan-2-yl)naphthalene-1-sulfonamide

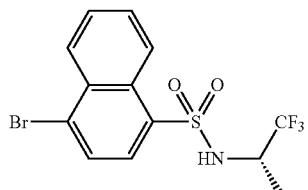

The title compound was prepared as described for the synthesis of Intermediate 12/1, using in step e 4-bromonaphthalene-1-sulfonyl chloride in place of 4-bromo-3-(difluoromethyl)-2-fluorobenzene-1-sulfonyl chloride and (S)-1,1,1-trifluoropropan-2-amine in place of (S)-1,1,1-trifluorobutan-2-amine.

Intermediate 12/8

Step a 1-(Difluoromethoxy)-2-fluoro-3-nitrobenzene

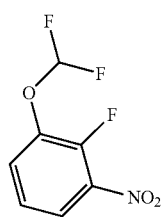 [SMILES: O=[N+]([O-])c1cccc(OC(F)F)c1F]

A mixture of 2-fluoro-3-nitrophenol (4.7 g, 30 mmol), sodium 2-chloro-2,2-difluoroacetate (6.8 g, 45 mmol) and $K_2CO_3$ (8.3 g, 60 mmol) in dry DMF (50 mL) was stirred at 110° C. overnight, poured into ice and extracted with EtOAc (50 mL×3). The combined organic layers were concentrated to dryness and purified by FCC on silica gel (PE/EtOAc=25:1) to give the title compound as a yellow solid.

Intermediate 12/8

Step b (S)-4-Bromo-3-(difluoromethoxy)-2-fluoro-N-(1,1,1-trifluoropropan-2-yl)benzenesulfonamide

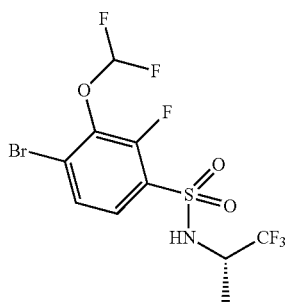 [SMILES: C[C@H](NS(=O)(=O)c1ccc(Br)c(OC(F)F)c1F)C(F)(F)F]

The title compound was prepared as described for the synthesis of Intermediate 12/1, using in step b 1-(difluoromethoxy)-2-fluoro-3-nitrobenzene (Intermediate 12/8, step a) in place of 1-(difluoromethyl)-2-fluoro-3-nitrobenzene and in step e (S)-1,1,1-trifluoropropan-2-amine in place of (S)-1,1,1-trifluorobutan-2-amine.

Intermediate 12/9

(S)-4-Bromo-3-chloro-N-(1,1,1-trifluorobutan-2-yl)benzenesulfonamide

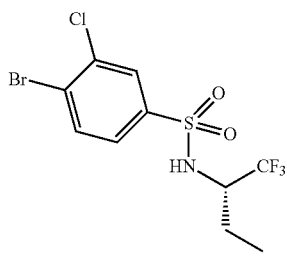 [SMILES: CC[C@H](NS(=O)(=O)c1ccc(Br)c(Cl)c1)C(F)(F)F]

The title compound was prepared as described for the synthesis of Intermediate 12/1, using in step e 4-bromo-3-chlorobenzene-1-sulfonyl chloride in place of 4-bromo-3-(difluoromethyl)-2-fluorobenzene-1-sulfonyl chloride.

Intermediate 12/10

(S)-4-Bromo-2-chloro-3-(difluoromethyl)-N-(1,1,1-trifluoropropan-2-yl)benzenesulfonamide

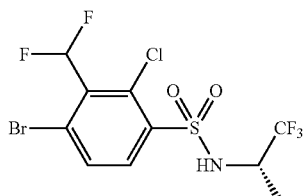

The title compound was prepared as described for the synthesis of Intermediate 12/1, using in step a 2-chloro-3-nitrobenzaldehyde in place of 2-fluoro-3-nitrobenzaldehyde and using in step e (S)-1,1,1-trifluoropropan-2-amine in place of (S)-1,1,1-trifluorobutan-2-amine.

Intermediate 12/11

(S)-4-Bromo-3-chloro-2-fluoro-N-(1,1,1-trifluorobutan-2-yl)benzenesulfonamide

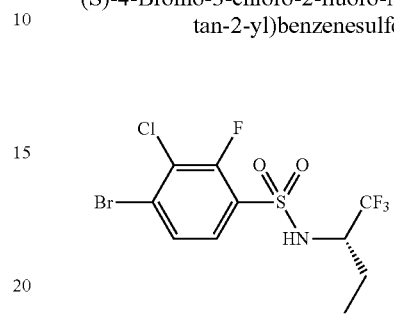

The title compound was prepared as described for the synthesis of Intermediate 12/6, using (S)-1,1,1-trifluorobutan-2-amine in place of (S)-1,1,1-trifluoropropan-2-amine.

Intermediate 12/12

(S)-4-Bromo-2-(difluoromethyl)-3-fluoro-N-(1,1,1-trifluorobutan-2-yl)benzenesulfonamide

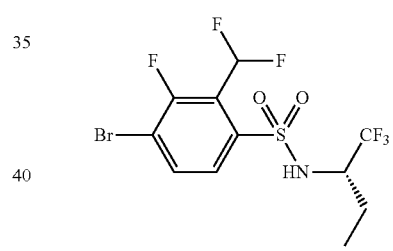

The title compound was prepared as described for the synthesis of Intermediate 12/1, using in step a 2-fluoro-6-nitrobenzaldehyde in place of 2-fluoro-3-nitrobenzaldehyde.

Intermediate 12/13

4-Bromo-3-chloro-N-(1-(difluoromethyl)cyclopropyl)-2-fluorobenzenesulfonamide

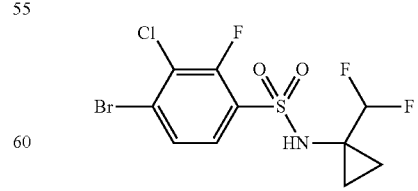

The title compound was prepared as described for the synthesis of Intermediate 12/6, using 1-(difluoromethyl)cyclopropanamine in place of (S)-1,1,1-trifluoropropan-2-amine.

Intermediate 12/14

(S)-4-Bromo-2-chloro-3-(difluoromethyl)-N-(1,1,1-trifluorobutan-2-yl)benzenesulfonamide

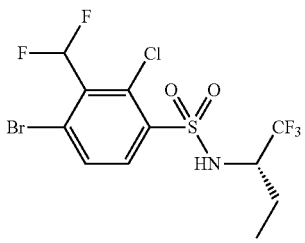 [SMILES: CC[C@H](NS(=O)(=O)c1ccc(Br)c(C(F)F)c1Cl)C(F)(F)F]

The title compound was prepared as described for the synthesis of Intermediate 12/1, using in step a 2-chloro-3-nitrobenzaldehyde in place of 2-fluoro-3-nitrobenzaldehyde.

Intermediate 12/15

(S)-4-Bromo-N-(1,1,1-trifluorobutan-2-yl)-3-(trifluoromethoxy)benzenesulfonamide

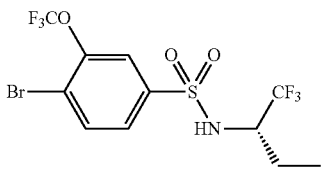 [SMILES: CC[C@H](NS(=O)(=O)c1ccc(Br)c(OC(F)(F)F)c1)C(F)(F)F]

The title compound was prepared as described for the synthesis of Intermediate 12/1, steps c to e, using in step c 3-(trifluoromethoxy)aniline in place of 3-(difluoromethyl)-2-fluoroaniline.

Intermediate 12/16

4-Bromo-3-chloro-2-fluoro-N-(1,1,1-trifluoro-2-methylpropan-2-yl)benzenesulfonamide

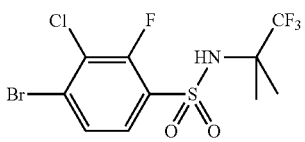 [SMILES: CC(C)(NS(=O)(=O)c1ccc(Br)c(Cl)c1F)C(F)(F)F]

The title compound was prepared as described for the synthesis of Intermediate 12/6, using 1,1,1-trifluoro-2-methylpropan-2-amine in place of (S)-1,1,1-trifluoropropan-2-amine.

Intermediate 12/17

4-Bromo-3-chloro-2-fluoro-N-methyl-N-(2,2,2-trifluoroethyl)benzenesulfonamide

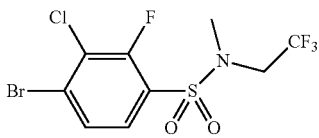 [SMILES: CN(CC(F)(F)F)S(=O)(=O)c1ccc(Br)c(Cl)c1F]

The title compound was prepared as described for the synthesis of Intermediate 12/6, using 2,2,2-trifluoro-N-methylethanamine in place of (S)-1,1,1-trifluoropropan-2-amine.

Intermediate 13

Step a 1-(4-Bromo-2,3-dichlorophenyl)-2,2,2-trifluoroethanone

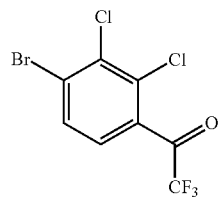 [SMILES: O=C(c1ccc(Br)c(Cl)c1Cl)C(F)(F)F]

To a solution of 1-bromo-2,3-dichloro-4-iodobenzene (3.52 g, 10.0 mmol) in anhydrous THF (20 mL) was added n-BuLi (2.5 M in hexane, 4.4 mL, 11.0 mmol) at −78° C. under nitrogen, and the solution was stirred at this temperature for 30 min. The resulting solution was slowly added to a solution of 2,2,2-trifluoro-N-methoxy-N-methyl-acetamide (2.35 g, 14.8 mmol) in anhydrous THF (25.0 mL) at −78° C., and the solution was stirred for an additional 2 h. The solution was quenched with saturated aqueous NH$_4$Cl and extracted with EtOAc twice. The combined organic layers were washed with water and brine, dried over anhydrous Na$_2$SO$_4$, filtered, and concentrated to dryness. The residue was purified by FCC on silica gel (PE/EtOAc=100/1) to give the title compound as a pale yellow oil.

Alternate Synthesis of Intermediate 13

Step a

To a flask was added 1-bromo-2,3-dichloro-4-iodobenzene (30.0 g, 85.3 mmol) and THF (240 mL). This mixture was cooled to −85-−78° C., and i-PrMgCl.LiCl (78.7 mL, 1.3 M in THF, 102 mmol) was added dropwise. Then 2,2,2-trifluoro-N-methoxy-N-methylacetamide (20.1 g, 128 mmol) was added one portion. The mixture was warmed to 20-25° C. and stirred for 4 h. The reaction was quenched with saturated aqueous NH$_4$Cl (120 mL), diluted with EtOAc (150 mL). The aqueous phase was further extracted with EtOAc (90 mL) and the combined organic phases were washed with water (60 mL) and brine (60 mL) successively, and concentrated under vacuum to give the title compound as brown solid, which was used in the next step without further purification.

Intermediate 13

Step b 2-(4-Bromo-2,3-dichlorophenyl)-1,1,1,3,3,3-hexafluoropropan-2-ol

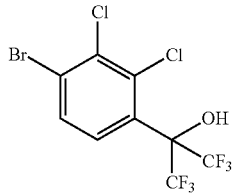 [SMILES: OC(c1ccc(Br)c(Cl)c1Cl)(C(F)(F)F)C(F)(F)F]

To a solution of 1-(4-bromo-2,3-dichlorophenyl)-2,2,2-trifluoroethanone (1.99 g, 6.18 mmol, Intermediate 13, step a) and TMSCF$_3$ (4.38 g, 30.9 mmol) in anhydrous THF (30 mL) was added a solution of TBAF (2.45 g, 9.27 mmol) in anhydrous THF (25 mL) at 0° C., and the solution was stirred at rt overnight. The resulting solution was quenched with 1 N aqueous HCl, diluted with EtOAc and the two layers were separated. The organic layer was washed with water and brine, dried over anhydrous Na$_2$SO$_4$, filtered, concentrated to dryness, and purified by FCC on silica gel (PE/EtOAc=5/1) to give the title compound as a yellow oil.

Alternate Synthesis of Intermediate 13

Step b

To a flask was added 1-(4-bromo-2,3-dichlorophenyl)-2,2,2-trifluoroethanone (10.0 g, 31.1 mmol), THF (10 mL) and TMSCF$_3$ (22.1 g, 155 mmol). This mixture stirred and was cooled to −15--10° C., and TBAF (14.3 g, 46.6 mmol) in THF (40 mL) was added dropwise. Then the reaction was quenched with 2 N aqueous HCl (78 mL), diluted with EtOAc (50 mL), and separated. The organic phase was washed with water (40 mL) and brine (40 mL) successively, and concentrated under vacuum. The residue was dissolved with heptane (50 mL), and DABCO (1.7 g, 15.2 mmol) was added one portion. The mixture was stirred overnight, filtered, and the cake was washed with heptane (10 mL×2). The cake was dissolved with EtOAc (100 mL), washed with 1 N aqueous HCl (30 mL×3), and concentrated under vacuum to give the title compound as a brown liquid.

Intermediate 14

Step a (S)-tert-Butyl 4,4-difluoro-2-methylpyrrolidine-1-carboxylate

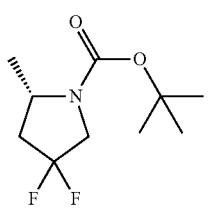

Under a nitrogen atmosphere, DAST (0.60 mL, 4.4 mmol) was added to a solution of (S)-tert-butyl 2-methyl-4-oxopyrrolidine-1-carboxylate (420 mg, 2.10 mmol) in DCM (5.0 mL) under ice cooling and the resultant mixture was stirred for 16 h at rt and quenched with saturated aqueous NaHCO$_3$. The organic layer was dried over anhydrous Na$_2$SO$_4$, filtered, concentrated to dryness, and purified by FCC on silica gel (PE/EtOAc=70/1) to give the title compound as a yellow oil.

Intermediate 14

Step b (S)-4,4-Difluoro-2-methylpyrrolidine hydrochloride

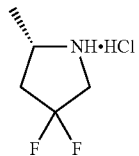

To a solution of (S)-tert-butyl 4,4-difluoro-2-methylpyrrolidine-1-carboxylate (250 mg, 1.13 mmol, Intermediate 14, step a) in 1,4-dioxane (2 mL) was added a solution of HCl in 1,4-dioxane (4 M, 5.0 mL) at 0° C. and the mixture was stirred at rt for 1 h and concentrated to dryness to give the title compound as a red solid.

Intermediate 14/1

(2S)-4-Fluoro-2-methylpyrrolidine hydrochloride

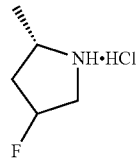

The title compound was prepared as described for the synthesis of Intermediate 14, using in step a (2S)-tert-butyl 4-hydroxy-2-methylpyrrolidine-1-carboxylate in place of (S)-tert-butyl 2-methyl-4-oxopyrrolidine-1-carboxylate.

Intermediate 15

Step a 1-(3-Bromo-5-(tert-butyl)phenyl)-2,2,2-trifluoroethanone

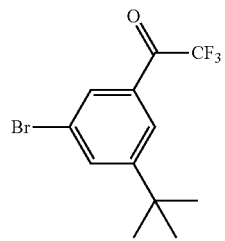 [SMILES: CC(C)(C)c1cc(Br)cc(C(=O)C(F)(F)F)c1]

To a solution of 1,3-dibromo-5-(tert-butyl)benzene (5.84 g, 20.0 mmol) in anhydrous THF (60 mL) was added n-BuLi (2.5 M in THF, 10 mL, 25 mmol) at −78° C. under nitrogen, and the resulting solution was stirred for 40 min. Then 2,2,2-trifluoro-N-methoxy-N-methyl-acetamide (3.93 g, 25.0 mmol) was added slowly at this temperature, and the solution was warmed to rt and stirred overnight, quenched with saturated aqueous NH$_4$Cl, and extracted with EtOAc (×2). The combined organic layers were washed with water and brine, dried over anhydrous Na$_2$SO$_4$, filtered and concentrated to dryness. The residue was purified by FCC on silica gel (PE) followed by prep-HPLC to give the title compound as a yellow oil.

Intermediate 15

Step b 2-(3-Bromo-5-(tert-butyl)phenyl)-1,1,1,3,3,3-hexafluoropropan-2-ol

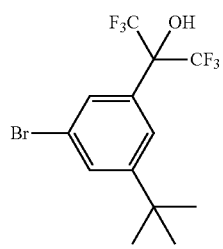 [SMILES: CC(C)(C)c1cc(Br)cc(C(O)(C(F)(F)F)C(F)(F)F)c1]

To a solution of 1-(3-bromo-5-(tert-butyl)phenyl)-2,2,2-trifluoroethanone (3.77 g, 12.2 mmol, Intermediate 15, step a) and (trifluoromethyl)trimethylsilane (2.33 mL, 15.0 mmol) in dry DME (50 mL) was added anhydrous CsF (60.8 mg, 0.40 mmol) at rt under nitrogen and the mixture was stirred for 3 h at rt. An additional portion of (trifluoromethyl)trimethylsilane (1.00 mL, 6.44 mmol) was added and the mixture stirred for 2 h, diluted with 2 N aqueous HCl, stirred for 18 h at rt, and extracted with EtOAc twice. The combined organic layers were washed with water and brine, dried over anhydrous Na$_2$SO$_4$, filtered and concentrated to dryness. The residue was purified by FCC on silica gel (PE/EtOAc=10/1) and then prep-HPLC to give the title compound as a colorless oil.

Intermediate 16

(S)-3-Bromo-5-(1-methylcyclopropyl)-N-(1,1,1-trifluoropropan-2-yl)benzamide

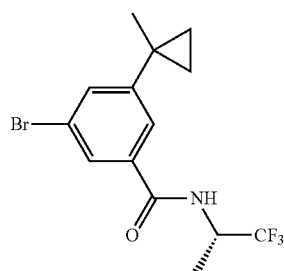

The title compound was prepared as described for the synthesis of Preparative Example P33d in WO2013/079223, using in step 5 (S)-1,1,1-trifluoropropan-2-amine in place of N,2-dimethylpropan-2-amine.

Intermediate 17

Step a (2-(6-Bromopyridin-2-yl)thiazol-4-yl)methanol

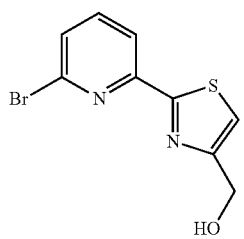 [SMILES: OCc1csc(-c2cccc(Br)n2)n1]

A solution of 6-bromopyridine-2-carbothioamide (1.6 g, 7.4 mmol) and 1-bromo-3-hydroxypropan-2-one (1.4 g, 8.8 mmol) in EtOH (30 mL) was stirred at 75° C. overnight. Water was added and the mixture was extracted with EtOAc three times. The combined organic layers were washed with brine and dried over anhydrous Na$_2$SO$_4$. The organic layer was filtered and concentrated to dryness. The residue was purified by FCC on silica gel (PE/EtOAc=5:1) to afford the title compound as a yellow solid.

Intermediate 17

Step b 2-(6-Bromopyridin-2-yl)-4-(((2-(trimethylsilyl)ethoxy)methoxy)methyl)thiazole

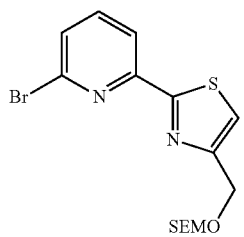

To a solution of (2-(6-bromopyridin-2-yl)thiazol-4-yl)methanol (1.5 g, 5.5 mmol, Intermediate 17, step a) in DCM (50 mL) was added DIPEA (1.8 g, 13.8 mmol) and SEMCl (1.4 g, 8.3 mmol). The solution was stirred at rt for 3 h. The mixture was concentrated to dryness and the residue was purified by FCC on silica gel (PE/EtOAc=20:1) to afford the title compound as a yellow oil.

Intermediate 17

Step c

Ethyl 2,2-dimethyl-3-(6-(4-(((2-(trimethylsilyl)ethoxy)methoxy)methyl)thiazol-2-yl)pyridin-2-yl)propanoate

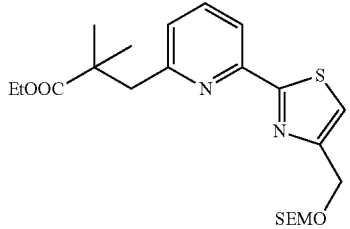

A suspension of Zn—Cu couple (2.6 g, 40 mmol) in toluene-DMA (11:1, 60 mL) was purged with Ar for 15 min. Ethyl 3-iodo-2,2-dimethylpropanoate (1.5 g, 6.0 mmol) was added and the resulting mixture was heated at 110° C. for 2 h. 2-(6-Bromopyridin-2-yl)-4-(((2-(trimethylsilyl)ethoxy)methoxy)methyl)thiazole (2.0 g, 5.0 mmol, Intermediate 17, step b) and Pd(PPh$_3$)$_4$ (187 mg, 0.162 mmol) were added and the mixture was stirred at 110° C. for 16 h. The mixture was cooled, quenched with aqueous NH$_4$Cl and extracted with EtOAc (3×50 mL). The combined organic layers were washed with brine, dried over anhydrous Na$_2$SO$_4$, filtered and concentrated to dryness. The residue was purified by FCC on silica gel (PE/EtOAc=15:1) to give the title compound as a colorless oil.

Intermediate 17

Step d

Ethyl 3-(6-(4-(hydroxymethyl)thiazol-2-yl)pyridin-2-yl)-2,2-dimethylpropanoate

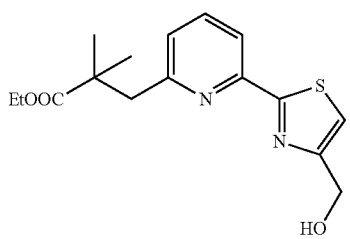 [SMILES: CCOC(=O)C(C)(C)Cc1cccc(-c2nc(CO)cs2)n1]

To a solution of ethyl 2,2-dimethyl-3-(6-(4-(((2-(trimethylsilyl)ethoxy)methoxy)methyl)thiazol-2-yl)pyridin-2-yl)propanoate (1.0 g, 2.2 mmol, Intermediate 17, step c) in DCM (5 mL) was added HCl in 1,4-dioxane (4 N, 1 mL), and the mixture was stirred at rt for 1 h. Aqueous NaOH was added until neutral pH. The mixture was extracted with EtOAc (3×30 mL). The combined organic layers were dried over anhydrous Na$_2$SO$_4$, filtered and concentrated to dryness. The residue was purified by FCC on silica gel (PE/EtOAc=3:1) to afford the title compound as a colorless oil.

Intermediate 18

Step a (4-Bromo-3-(trifluoromethyl)phenyl)methanol

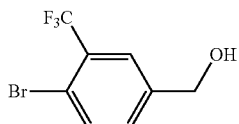

To a solution of methyl 4-bromo-3-(trifluoromethyl)benzoate (2.0 g, 7.1 mmol) in THF (20 mL) was added LiAlH$_4$ (403 mg, 10.6 mmol) at 0° C. under N$_2$. The mixture was stirred at rt for 2 h. The mixture was quenched with water (0.4 mL), 15% NaOH (0.4 mL) and water (1.2 mL) at 0° C. The mixture was filtered and concentrated to dryness to afford the crude title compound which was used in the next step without further purification.

Intermediate 18

Step b

4-Bromo-3-(trifluoromethyl)benzaldehyde

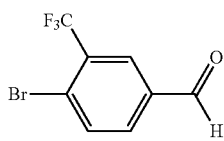

To a solution of (4-bromo-3-(trifluoromethyl)phenyl)methanol (1.5 g, crude, Intermediate 18, step a) in DCM (10 mL) was added Dess-Martin-periodinane (3.7 g, 8.8 mmol) at 0° C. The mixture was stirred at rt for 3 h, diluted with saturated aqueous NaHCO$_3$ (50 mL) and extracted with DCM (10 mL×3). The combined organic layers were dried over anhydrous Na$_2$SO$_4$ and concentrated to dryness to afford the crude title compound which was used in the next step without further purification.

Intermediate 18

Step c 1-(4-Bromo-3-(trifluoromethyl)phenyl)-2,2,2-trifluoroethanol

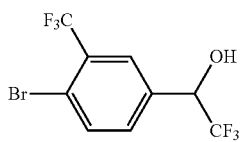

To a solution of 4-bromo-3-(trifluoromethyl)benzaldehyde (1.5 g, crude, Intermediate 18, step b) in THF (15 mL) was added TMSCF$_3$ (1.30 g, 9.15 mmol) and CsF (90 mg, 0.59 mmol) at 0° C. After addition, the reaction was stirred Intermediate 18

Step d 1-(4-Bromo-3-(trifluoromethyl)phenyl)-2,2,2-trifluoroethanone

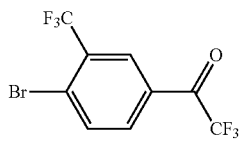

To a solution of 1-(4-bromo-3-(trifluoromethyl)phenyl)-2,2,2-trifluoroethanol (900 mg, 2.78 mmol, Intermediate 18, step c) in DCM (20 mL) was added Dess-Martin periodinane (1.8 g, 4.2 mmol) at 0° C. and the mixture was stirred at rt for 2 h. The mixture was diluted with saturated aqueous NaHCO$_3$ (50 mL) and extracted with DCM (15 mL×3). The combined organic layers were dried over anhydrous Na$_2$SO$_4$ and concentrated to dryness. The residue was purified by FCC on silica gel (PE/EtOAc=50/1) to afford the title compound as a yellow oil.

Intermediate 18

Step e 2-(4-Bromo-3-(trifluoromethyl)phenyl)-1,1,1,3,3,3-hexafluoropropan-2-ol

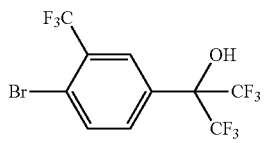 [SMILES: OC(c1ccc(Br)c(C(F)(F)F)c1)(C(F)(F)F)C(F)(F)F]

To a solution of 1-(4-bromo-3-(trifluoromethyl)phenyl)-2,2,2-trifluoroethanone (800 mg, 2.49 mmol, Intermediate 18, step d) in THF (6 mL) were added TMSCF$_3$ (723 mg, 4.98 mmol) and CsF (38 mg, 0.25 mmol) at 0° C. The mixture was stirred at rt overnight. 1 M Aqueous HCl (10 mL) was added and the mixture was stirred for 30 min, poured into water (30 mL) and extracted with EtOAc (10 mL×3). The combined organic layers were washed with brine, dried over anhydrous Na$_2$SO$_4$ and concentrated to dryness to afford the title compound as a yellow oil.

Intermediate 19

2-((4-Bromo-3-(trifluoromethyl)phenoxy)methyl)-1,1,1,3,3,3-hexafluoropropan-2-ol

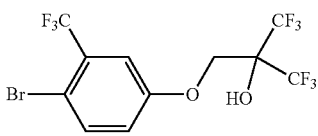 [SMILES: OC(COc1ccc(Br)c(C(F)(F)F)c1)(C(F)(F)F)C(F)(F)F]

To a solution of 4-bromo-3-(trifluoromethyl)phenol (1.0 g, 4.17 mmol) and tetrabutylammonium hydrogensulfate (282 mg, 0.83 mmol) in anhydrous THF (10 mL) at 0° C. was slowly added NaH (200 mg, 8.24 mmol). The mixture was stirred for 30 min at 0° C. 2,2-Bis(trifluoromethyl)oxirane (750 mg, 4.17 mmol) was added dropwise and the mixture was stirred at rt overnight. Then it was quenched with water and extracted with EtOAc. The organic layer was washed with brine, dried over anhydrous Na$_2$SO$_4$, filtered and concentrated to dryness. The residue was purified by FCC on silica gel (PE/EtOAc=20:1) to give the title compound.

Intermediate 20

2-(4-Bromo-2,3-dichlorobenzyl)-1,1,1,3,3,3-hexafluoropropan-2-ol

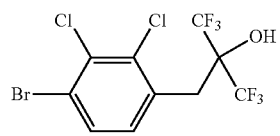 [SMILES: OC(Cc1ccc(Br)c(Cl)c1Cl)(C(F)(F)F)C(F)(F)F]

To a solution of 1-bromo-2,3-dichloro-4-iodobenzene (500 mg, 1.42 mmol) in dry THF (6 mL) at −78° C. was added n-BuLi in THF (1.6 M, 0.93 mL, 1.5 mmol). After stirring for 12 min, neat 2,2 bis(trifluoromethyl)oxirane (300 mg, 1.67 mmol) was added. The mixture was stirred at −78° C. and allowed to warm to rt overnight. A saturated aqueous NH$_4$Cl solution was added, the organic layer separated and the aqueous layer extracted with DCM. The combined organic layers were dried over anhydrous Na$_2$SO$_4$, filtered, and concentrated to give an oil. This crude mixture was purified by FCC on silica gel (0-50% EtOAc in heptanes) to give the title compound as a yellow oil.

Intermediate 21

Step a

N-Methoxy-N-methyl-1-(trifluoromethyl)cyclopropanecarboxamide

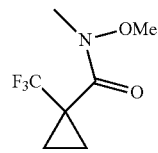

To a mixture of 1-(trifluoromethyl)cyclopropanecarboxylic acid (1.60 g, 10.4 mmol) and DMF (0.081 mL, 1.0 mmol) in DCM (10 mL) at 4° C. was added oxalyl chloride (1.0 mL, 12 mmol). After stirring for 30 min at 4° C., and 2 h at room temperature, the mixture was concentrated to a semi-solid. This material was dissolved in DCM (10 mL), and added to a mixture of N,O-dimethylhydroxylamine.HCl (1.33 g, 13.6 mmol) and Et₃N (4.7 mL, 34 mmol) in DCM (20 mL) at room temperature. After stirring overnight, the precipitated white solid was filtered off and washed with diethyl ether. The filtrate was concentrated, dissolved in DCM, and washed with 1 N aqueous HCl. The aqueous layer was back extracted with DCM. The combined organic layers were washed with saturated aqueous NaHCO₃, and the aqueous layer was back extracted with DCM. The combined organic layers were dried, filtered, and concentrated to dryness to give the title compound as a yellow oil.

Intermediate 21

Step b (4-Bromo-2,3-dichlorophenyl)(1-(trifluoromethyl)cyclopropyl)methanone

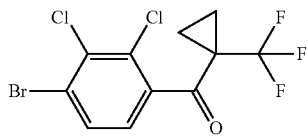 [SMILES: O=C(c1ccc(Br)c(Cl)c1Cl)C1(C(F)(F)F)CC1]

To a solution of 1-bromo-2,3-dichloro-4-iodobenzene (1.65 g, 4.70 mmol) and N-methoxy-N-methyl-1-(trifluoromethyl)cyclopropanecarboxamide (960 mg, 4.87 mmol, Intermediate 21, step a) in dry THF (18 mL) at −78° C. was added n-BuLi in THF (1.6 M, 4.0 mL, 6.4 mmol). After stirring at −78 to 0° C. for ~2 h, the mixture was quenched with saturated aqueous NH₄Cl. The organic layer was separated and the aqueous layer was extracted with DCM. The combined organic phases were dried, filtered, concentrated, and purified by FCC on silica gel (0-50% EtOAc in heptanes) to give the title compound as a yellow oil.

Intermediate 21

Step c (4-Bromo-2,3-dichlorophenyl)(1-(trifluoromethyl)cyclopropyl)methanol

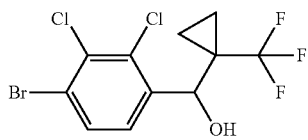 [SMILES: OC(c1ccc(Br)c(Cl)c1Cl)C1(C(F)(F)F)CC1]

To a mixture of (4-bromo-2,3-dichlorophenyl)(1-(trifluoromethyl)cyclopropyl)methanone (160 mg, 0.440 mmol, Intermediate 21, step b) in MeOH (2 mL) and THF (1 mL) was added NaBH₄ (40 mg, 1.1 mmol) at room temperature. After stirring for 1.5 h, the mixture was concentrated and the residue was partitioned between EtOAc and water. The organic layer was dried, filtered, and concentrated to give the title compound as a yellow oil.

Intermediate 22

Step a 1-(4-Bromo-3-methylphenyl)-2,2,2-trifluoroethanone

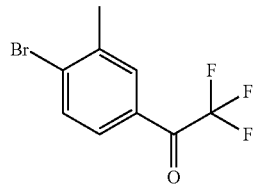

A solution of methyl 4-bromo-3-methylbenzoate (10 g, 43.7 mmol) in THF (200 mL) was cooled to −10° C., then TMSCF₃ (31.04 g, 218.3 mmol) was added followed by TBAF (34.24 g, 130.97 mmol) in THF (130 mL) dropwise. Immediately after addition, 1 M aqueous HCl (200 mL) was added and the resulting mixture stirred at rt for 10 minutes. The mixture was extracted with petroleum ether (2×200 mL). The organic layers were combined, washed with brine (2×200 mL), dried over anhydrous Na₂SO₄, filtered and concentrated to dryness. The residue was purified by FCC on silica gel (PE) to provide the title compound as a yellow oil.

Intermediate 22

2-(4-Bromo-3-methylphenyl)-1,1,1,3,3,3-hexafluoropropan-2-ol

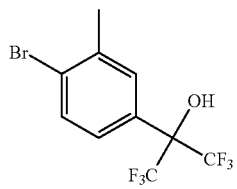

A solution of 1-(4-bromo-3-methylphenyl)-2,2,2-trifluoroethanone (5.8 g, 21.72 mmol, Intermediate 22, step a) in THF (80 mL) was cooled to −10° C., then TMSCF₃ (15.44 mg, 108.6 mmol) was added followed by TBAF (15 mL, 15 mmol, 1 M in THF) dropwise. Immediately after addition, 1 M aqueous HCl (100 mL) was added and the resulting mixture was stirred at rt for 10 minutes. The mixture was extracted with petroleum ether (2×100 mL). The organic layers were combined, washed with brine (2×100 mL), dried over anhydrous Na₂SO₄, filtered and concentrated to dryness. The residue was purified by FCC on silica gel (PE/DCM) to provide the title compound as a white solid.

Intermediate 23

Step a

1-Bromo-2-(difluoromethyl)-4-iodobenzene

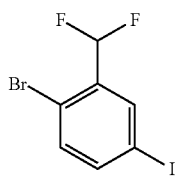 [SMILES: FC(F)c1cc(I)ccc1Br]

Diethylaminosulfur trifluoride (77.8 g, 482 mmol) was added to a solution of 2-bromo-5-iodobenzaldehyde (100 g, 322 mmol) and DCM (1 L) at 0° C. The resultant mixture was stirred at room temperature for 2 h before quenching with ice/water (1 L) and extracting with DCM (800 mL×3). The combined organic extracts were washed with brine, dried over anhydrous Na$_2$SO$_4$, filtered and concentrated to dryness to give the crude product, which was purified by FCC on silica gel (PE: EtOAc=50:1) to afford the title compound.

Intermediate 23

Step b 1-(4-Bromo-3-(difluoromethyl)phenyl)-2,2,2-trifluoroethanone

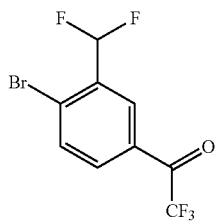

Isopropylmagnesium chloride lithium chloride complex (194 mL, 1.3 M in THF, 252 mmol) was added dropwise to a solution of 1-bromo-2-(difluoromethyl)-4-iodobenzene (70.0 g, 210 mmol, Intermediate 23, step a) and anhydrous THF (200 mL) at −78° C. The resultant mixture was stirred at −78° C. for 30 minutes and then treated with 2,2,2-trifluoro-N-methoxy-N-methylacetamide (49.5 g, 315 mmol). The resultant mixture was stirred at −78° C. under N$_2$ for 1 h before it was quenched with saturated aqueous NH$_4$Cl (600 mL) solution and extracted with EtOAc (800 ml, ×3). The combined organic extracts were dried over anhydrous Na$_2$SO$_4$, filtered, and concentrated to dryness to give the crude product, which was purified by FCC on silica gel (PE: EtOAc=10:1 to 4:1) to afford the title compound.

Intermediate 23

2-(4-Bromo-3-(difluoromethyl)phenyl)-1,1,1,3,3,3-hexafluoropropan-2-ol

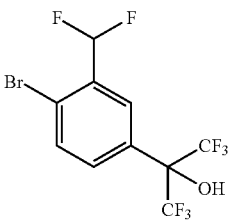

Tetrabutylammonium fluoride (470 mL, 1 M in THF, 470 mmol) was added dropwise to a solution of 1-(4-bromo-3-(difluoromethyl)phenyl)-2,2,2-trifluoroethanone (95.0 g, 313 mmol, Intermediate 23, step b), TMSCF$_3$ (223 g, 1.6 mol), and anhydrous THF (100 mL) at −15° C. The resultant mixture was stirred at −15-10° C. for 30 minutes and then was allowed to warm to rt over 2 h before it was quenched with 2 N aqueous HCl (400 mL) and extracted with EtOAc (800 mL×3). The combined organic extracts were dried over anhydrous Na$_2$SO$_4$, filtered, and concentrated to dryness to give the crude product, which was purified by FCC on silica gel (PE:EtOAc=100:1 to 20:1) to afford the title compound.

Intermediate 24

Step a

2-Hydroxy-2-methylpropanoyl chloride

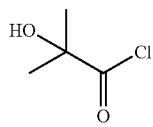

Oxalyl chloride (52.0 mL, 614 mmol) was added to a solution of 2-hydroxy-2-methylpropanoic acid (13.0 g, 125 mmol), DMF (0.01 mL) and dichloromethane (200 mL). The resultant mixture was stirred at room temperature for 4 hours before concentrating to dryness under reduced pressure to afford the title compound, which was used in the next step without further purification.

Intermediate 24

Step b tert-Butyl 2-carbamoylthiazole-4-carboxylate

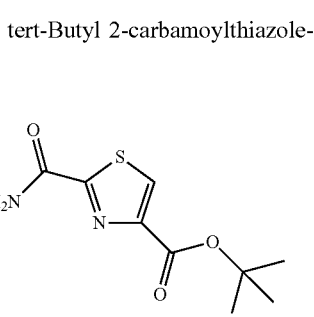

4-tert-Butyl 2-ethyl thiazole-2,4-dicarboxylate (100 g, 389 mmol) and saturated ammonia methanol solution (500 mL) were added to a 1 L round-bottomed flask. The resultant mixture was stirred at room temperature for 6 hours before concentrating to dryness to afford the title compound, which was used in the next step without further purification.

Intermediate 24

Step c tert-Butyl 2-cyanothiazole-4-carboxylate

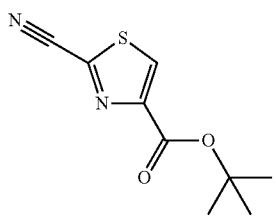

Trifluoroacetic anhydride (19.0 mL, 137 mmol) was added drop wise to a 0° C. mixture of tert-butyl 2-carbamoylthiazole-4-carboxylate (16 g, 70 mmol, Intermediate 24, step b), $Et_3N$ (44.0 mL, 316 mmol), and dichloromethane (200 mL). The reaction mixture was stirred at 0° C. for 4 hours before pouring it into brine (500 mL) and extracting with dichloromethane (100 mL×3). The combined organic extracts were dried over anhydrous $Na_2SO_4$, filtered, and concentrated to dryness. The residue was purified by FCC on silica gel (PE:EtOAc=5:1 to 1:1) to afford the title compound.

Intermediate 24

Step d (Z)-tert-Butyl 2-(N'-hydroxycarbamimidoyl)thiazole-4-carboxylate

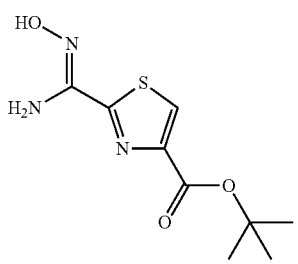 [SMILES: CC(C)(C)OC(=O)c1csc(/C(N)=N/O)n1]

Hydroxylamine hydrochloride (33.0 g, 475 mmol) was added to a solution of tert-butyl 2-cyanothiazole-4-carboxylate (20 g, 95 mmol, Intermediate 24, step c), potassium carbonate (65.7 g, 475 mmol), ethanol (200 mL), and water (200 mL). The resultant mixture was stirred at room temperature for 2 hours before pouring it into brine (500 mL) and extracting with ethyl acetate (200 ml, ×3). The combined organic extracts were dried over anhydrous $Na_2SO_4$, filtered, and concentrated to dryness. The residue was purified by FCC on silica gel (PE:EtOAc=5:1 to 1:1) to afford the title compound as a white solid.

Intermediate 24

Step e tert-Butyl 2-(5-(2-hydroxypropan-2-yl)-1,2,4-oxadiazol-3-yl)thiazole-4-carboxylate

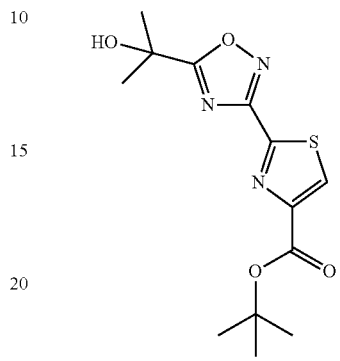

A solution of 2-hydroxy-2-methylpropanoyl chloride (18.0 g, 147 mmol, Intermediate 24, step a) in 1,4-dioxane (30 mL) was added to a 0° C. solution of (Z)-tert-butyl 2-(N-hydroxycarbamimidoyl)thiazole-4-carboxylate (30.0 g, 123 mmol, Intermediate 24, step d) in pyridine (200 mL). The resultant mixture was stirred at 120° C. for 16 hours before concentrating to dryness. The residue was dissolved in dichloromethane (300 mL) and the resultant mixture washed with water (100 mL), dried over anhydrous $Na_2SO_4$, filtered, and concentrated to dryness. The residue was purified by FCC on silica gel (DCM:methanol=100:1 to 50:1) to afford the title compound, which was used in the next step without further purification.

Intermediate 24

Step f 2-(5-(2-Hydroxypropan-2-yl)-1,2,4-oxadiazol-3-yl)thiazole-4-carboxylic acid

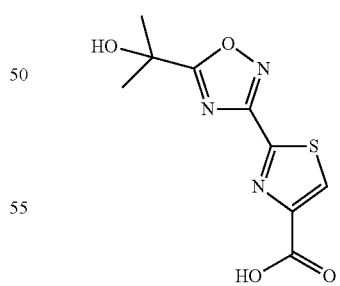

Trifluoroacetic acid (30 mL) was added to a solution of tert-butyl 2-(5-(2-hydroxypropan-2-yl)-1,2,4-oxadiazol-3-yl)thiazole-4-carboxylate (25 g, 38 mmol, Intermediate 24, step e) in dichloromethane (60 mL). The resultant mixture was stirred at room temperature for 16 hours before concentrating to dryness. The residue was triturated with petroleum ether (100 mL) and ethyl acetate (10 mL) and the solid was isolated via filtration. The filter cake was washed with petroleum ether (20 mL) before drying under reduced pressure to afford the title compound, which was used in the next step without further purification.

Intermediate 24

(S)-(2-(5-(2-Hydroxypropan-2-yl)-1,2,4-oxadiazol-3-yl)thiazol-4-yl)(2-methylpyrrolidin-1-yl)methanone

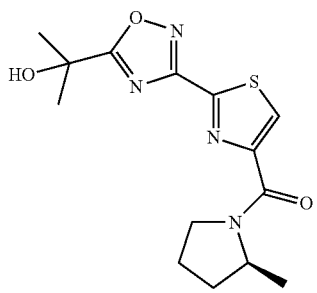 [SMILES: C[C@H]1CCCN1C(=O)c1csc(-c2noc(C(C)(C)O)n2)n1]

HATU (22 g, 59 mmol) was added to a 0° C. solution of 2-(5-(2-hydroxypropan-2-yl)-1,2,4-oxadiazol-3-yl)thiazole-4-carboxylic acid (10 g, 39 mmol, Intermediate 24, step f), (S)-2-methylpyrrolidine hydrochloride (4.8 g, 39 mmol), DIPEA (25.3 g, 196 mmol), and THF (200 mL). The resultant mixture was stirred at room temperature for 16 hours before pouring it into aqueous HCl (1 M, 300 mL) and extracting with ethyl acetate (100 mL×3). The combined organic extracts were washed with saturated aqueous NaHCO₃ (700 mL) solution, dried over anhydrous Na₂SO₄, filtered, and concentrated to dryness. The residue was purified by FCC on silica gel (PE:EtOAc=10:1 to 3:1) to afford the title compound.

Example 1

Step a (S)-Ethyl 5-(2,3-dichloro-4-(N-(1,1,1-trifluoropropan-2-yl)sulfamoyl)phenyl)-4-(hydroxymethyl)thiazole-2-carboxylate

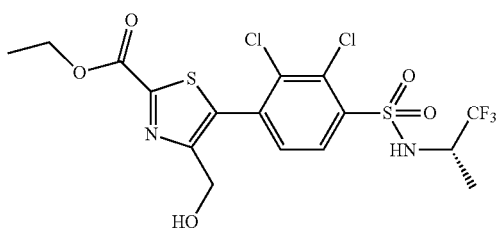 [SMILES: CCOC(=O)c1nc(CO)c(-c2ccc(S(=O)(=O)N[C@@H](C)C(F)(F)F)c(Cl)c2Cl)s1]

A mixture of ethyl 4-(hydroxymethyl)thiazole-2-carboxylate (470 mg, Intermediate 1, step a), (S)-4-bromo-2,3-dichloro-N-(1,1,1-trifluoropropan-2-yl)benzenesulfonamide (1.0 g, 2.5 mmol, Intermediate 12/3), Pd(OAc)₂ (200 mg, 0.89 mmol), P(Cy)₃·HBF₄ (200 mg, 0.54 mmol), pivalic acid (200 mg, 2.0 mmol), and Na₂CO₃ (530 mg, 5.0 mmol) in DMA (20 mL) was stirred at 90° C. overnight. The mixture was poured into water (100 mL), and extracted with EtOAc (50 mL×3). The combined organic layers were washed with brine, dried over anhydrous Na₂SO₄, and concentrated to dryness. The residue was purified by FCC on silica gel (PE/EtOAc=2:1) to give the title compound as a brown solid.

Example 1

Step b (S)-5-(2,3-Dichloro-4-(N-(1,1,1-trifluoropropan-2-yl)sulfamoyl)phenyl)-2-(ethoxycarbonyl)thiazole-4-carboxylic acid

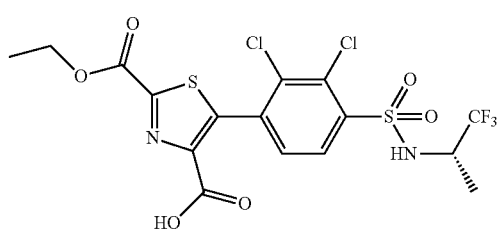 [SMILES: CCOC(=O)c1nc(C(=O)O)c(-c2ccc(S(=O)(=O)N[C@@H](C)C(F)(F)F)c(Cl)c2Cl)s1]

A mixture of (S)-ethyl 5-(2,3-dichloro-4-(N-(1,1,1-trifluoropropan-2-yl)sulfamoyl)phenyl)-4-(hydroxymethyl)thiazole-2-carboxylate (520 mg, 1.0 mmol, Example 1, step a), TEMPO (187 mg, 1.2 mmol), iodobenzene diacetate (1.3 g, 4.0 mmol) in H₂O (10 mL), and acetonitrile (20 mL) was stirred at rt overnight. H₂O (50 mL) and EtOAc (30 mL) were added and the aqueous layer was extracted with EtOAc (30 mL×2). The combined organic layers were washed with brine, dried over anhydrous MgSO₄, filtered, and concentrated to dryness to give the title compound as a brown solid.

Example 1

Step c (S)-Ethyl 5-(2,3-dichloro-4-(N-(1,1,1-trifluoropropan-2-yl)sulfamoyl)phenyl)-4-(diethylcarbamoyl)thiazole-2-carboxylate

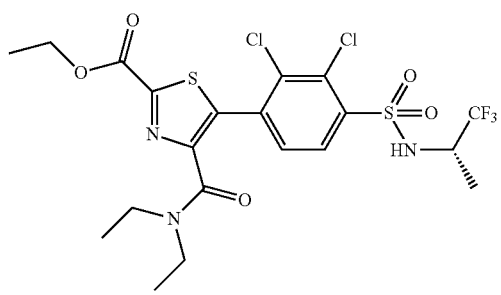 [SMILES: CCOC(=O)c1nc(C(=O)N(CC)CC)c(-c2ccc(S(=O)(=O)N[C@@H](C)C(F)(F)F)c(Cl)c2Cl)s1]

A mixture of (S)-5-(2,3-dichloro-4-(N-(1,1,1-trifluoropropan-2-yl)sulfamoyl)phenyl)-2-(ethoxycarbonyl)thiazole-4-carboxylic acid (520 mg, 1.00 mmol, Example 1, step b), diethylamine (370 mg, 5.1 mmol), HATU (570 mg, 1.5 mmol) and TEA (510 mg, 5.0 mmol) in acetonitrile (20 mL) was stirred at rt for 2 h. The mixture was poured into H₂O (50 mL), extracted with EtOAc (30 mL×3) and the combined organic layers were washed with brine, dried over anhydrous Na₂SO₄, and concentrated to dryness. The residue was purified by prep-TLC (PE/EtOAc=1:1) to afford the title compound as a colorless solid.

Example 1

Step d (S)-5-(2,3-Dichloro-4-(N-(1,1,1-trifluoropropan-2-yl)sulfamoyl)phenyl)-N,N-diethyl-2(hydrazinecarbonyl)thiazole-4-carboxamide

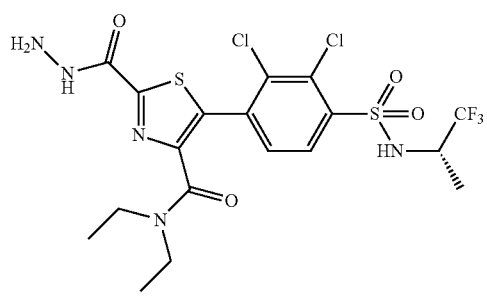 [SMILES: CCN(CC)C(=O)c1nc(C(=O)NN)sc1-c1ccc(S(=O)(=O)N[C@@H](C)C(F)(F)F)c(Cl)c1Cl]

A solution of (S)-ethyl 5-(2,3-dichloro-4-(N-(1,1,1-trifluoropropan-2-yl)sulfamoyl)phenyl)-4-(diethylcarbamoyl)thiazole-2-carboxylate (370 mg, 0.64 mmol, Example 1, step c) and hydrazine hydrate (0.3 mL) in ethanol (10 mL) was stirred at 50° C. for 4 h. The mixture was concentrated to dryness and the residue was purified by prep-TLC (EtOAc) to give the title compound as a brown solid.

Example 1

Step e (S)-Methyl 4-(2-(5-(2,3-dichloro-4-(N-(1,1,1-trifluoropropan-2-yl)sulfamoyl)phenyl)-4-(diethylcarbamoyl)thiazole-2-carbonyl)hydrazinyl)-2,2-dimethyl-4-oxobutanoate

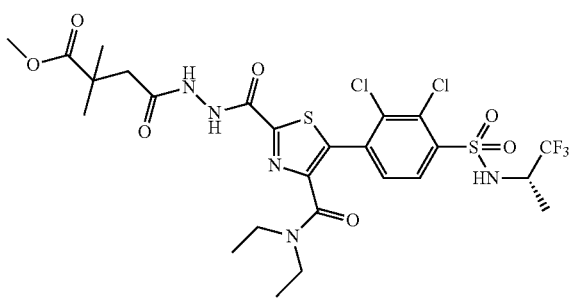 [SMILES: CCN(CC)C(=O)c1nc(C(=O)NNC(=O)CC(C)(C)C(=O)OC)sc1-c1ccc(S(=O)(=O)N[C@@H](C)C(F)(F)F)c(Cl)c1Cl]

A mixture of (S)-5-(2,3-dichloro-4-(N-(1,1,1-trifluoropropan-2-yl)sulfamoyl)phenyl)-N,N-diethyl-2 (hydrazinecarbonyl)thiazole-4-carboxamide (280 mg, 0.50 mmol, Example 1, step d), 4-methoxy-3,3-dimethyl-4-oxobutanoic acid (160 mg, 1.0 mmol), HATU (230 mg, 0.60 mmol) and TEA (0.2 mL) in acetonitrile (10 mL) was stirred at rt for 2 h. The mixture was poured into H$_2$O (30 mL) and extracted with EtOAc (30 mL×4). The combined organic layers were washed with brine, dried over anhydrous Na$_2$SO$_4$, and concentrated to dryness. The residue was purified by prep-TLC (DCM/MeOH=10:1) to afford the title compound as a colorless solid.

Example 1

Step f (S)-Methyl 3-(5-(5-(2,3-dichloro-4-(N-(1,1,1-trifluoropropan-2-yl)sulfamoyl)phenyl)-4-(diethylcarbamoyl)thiazol-2-yl)-1,3,4-oxadiazol-2-yl)-2,2-dimethyl-propanoate

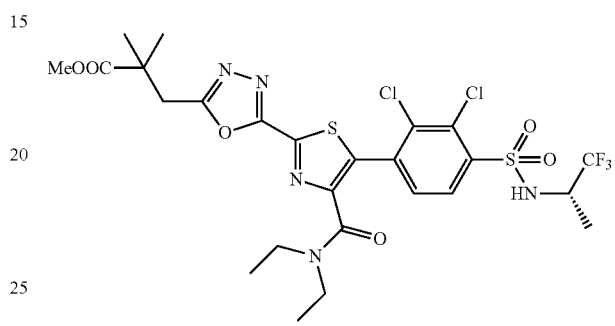

(S)-Methyl 4-(2-(5-(2,3-dichloro-4-(N-(1,1,1-trifluoropropan-2-yl)sulfamoyl)phenyl)-4-(diethylcarbamoyl)thiazole-2-carbonyl)hydrazinyl)-2,2-dimethyl-4-oxobutanoate (150 mg, 0.21 mmol, Example 1, step e), 4-methylbenzene-1-sulfonyl chloride (210 mg, 1.1 mmol) and TEA (0.1 mL, 0.72 mmol) in DCM was stirred at rt overnight. The mixture was poured into H$_2$O (20 mL) and extracted with EtOAc (15 mL×3). The combined organic layers were washed with brine, dried over anhydrous Na$_2$SO$_4$, filtered, and concentrated to dryness. The residue was purified by prep-TLC (EtOAc/PE=5:1) to give the title compound as a yellow solid.

Example 1

(S)-3-(5-(5-(2,3-Dichloro-4-(N-(1,1,1-trifluoropropan-2-yl)sulfamoyl)phenyl)-4-(diethylcarbamoyl)thiazol-2-yl)-1,3,4-oxadiazol-2-yl)-2,2-dimethylpropanoic acid

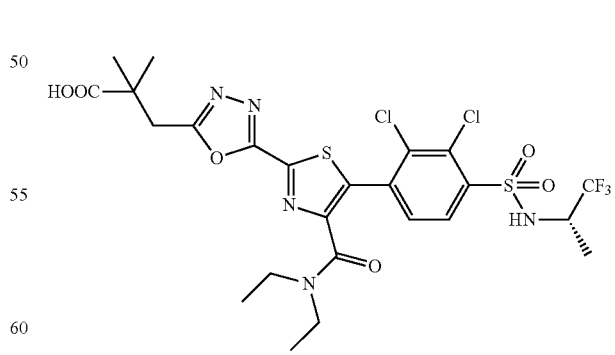

A mixture of (S)-methyl 3-(5-(5-(2,3-dichloro-4-(N-(1,1,1-trifluoropropan-2-yl)sulfamoyl)phenyl)-4-(diethylcarbamoyl)thiazol-2-yl)-1,3,4-oxadiazol-2-yl)-2,2-dimethyl-propanoate (100 mg, 0.15 mmol, Example 1, step f), LiOH.H$_2$O (25 mg, 0.57 mmol), H$_2$O (15 mL) and methanol (15 mL) was stirred at rt for 1 h. The mixture was concentrated to dryness and the residue was purified by prep-HPLC to give the title compound as a colorless solid. $^1$H NMR (400 MHz, CDCl$_3$): δ ppm 8.08 (d, J=8.4 Hz, 1H), 7.71 (d, J=8.4 Hz, 1H), 4.08-4.04 (m, 1H), 3.48-3.39 (m, 2H), 3.29-3.24 (m, 4H), 1.42 (s, 3H), 1.40 (s, 6H), 1.12-1.08 (m, 6H). MS (ESI): m/z 672.1 [M+H]$^+$.

Example 1/1

Step a (S)-3-(5-(5-(2,3-Dichloro-4-(N-(1,1,1-trifluorobutan-2-yl)sulfamoyl)phenyl)-4-(4-fluoropiperidine-1-carbonyl)thiazol-2-yl)-1,3,4-oxadiazol-2-yl)-2,2-dimethylpropanoic acid

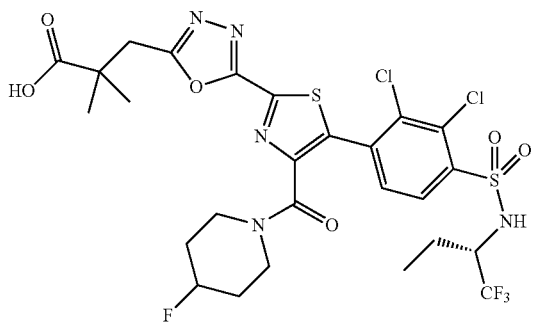 [SMILES: CC[C@H](NS(=O)(=O)c1ccc(-c2sc(-c3nnc(CC(C)(C)C(=O)O)o3)nc2C(=O)N2CCC(F)CC2)c(Cl)c1Cl)C(F)(F)F]

The title compound was prepared as described for the synthesis of Example 1, using in step a (S)-4-bromo-2,3-dichloro-N-(1,1,1-trifluorobutan-2-yl)benzenesulfonamide (Intermediate 12/4) in place of (S)-4-bromo-2,3-dichloro-N-(1,1,1-trifluoropropan-2-yl)benzenesulfonamide and in step c 4-fluoropiperidine in place of diethylamine.

Example 1/1

Step b (S)-3-(5-(5-(2,3-Dichloro-4-(N-(1,1,1-trifluorobutan-2-yl)sulfamoyl)phenyl)-4-(4-fluoropiperidine-1-carbonyl)thiazol-2-yl)-1,3,4-oxadiazol-2-yl)-2,2-dimethylpropanamide

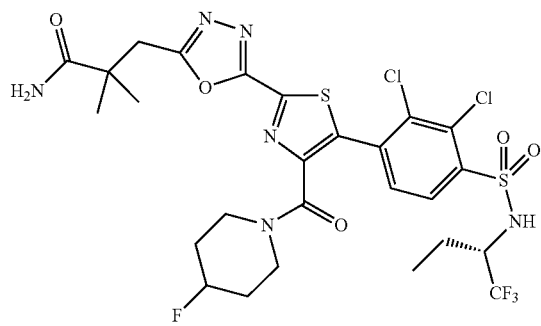 [SMILES: CC[C@H](NS(=O)(=O)c1ccc(-c2sc(-c3nnc(CC(C)(C)C(N)=O)o3)nc2C(=O)N2CCC(F)CC2)c(Cl)c1Cl)C(F)(F)F]

A solution of (S)-3-(5-(5-(2,3-dichloro-4-(N-(1,1,1-trifluorobutan-2-yl)sulfamoyl)phenyl)-4-(4-fluoropiperidine-1-carbonyl)thiazol-2-yl)-1,3,4-oxadiazol-2-yl)-2,2-dimethylpropanoic acid (90 mg, 0.13 mmol, Example 1/1, step a), NH$_4$Cl (53 mg, 1.0 mmol), HATU (75 mg, 0.20 mmol), and TEA (0.3 mL, 2.2 mmol) in MeCN (8 mL) was stirred at rt for 2 h, poured into H$_2$O (15 mL), and extracted with EtOAc (10 mL×3). The combined organic layers were washed with brine, dried over anhydrous Na$_2$SO$_4$, concentrated to dryness, and purified by prep-TLC (PE/EtOAc=1:1) to afford the title compound as a white solid.

Example 1/1

(S)-2,3-Dichloro-4-(2-(5-(2-cyano-2-methylpropyl)-1,3,4-oxadiazol-2-yl)-4-(4-fluoropiperidine-1-carbonyl)thiazol-5-yl)-N-(1,1,1-trifluorobutan-2-yl)benzenesulfonamide

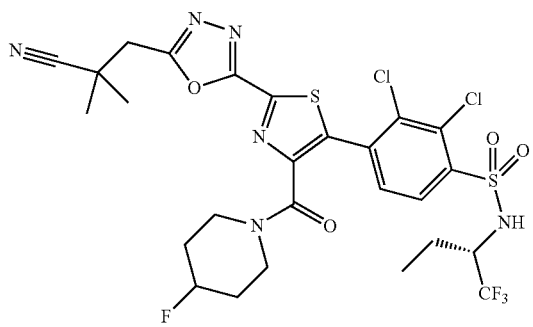 [SMILES: CC[C@H](NS(=O)(=O)c1ccc(-c2sc(-c3nnc(CC(C)(C)C#N)o3)nc2C(=O)N2CCC(F)CC2)c(Cl)c1Cl)C(F)(F)F]

A solution of (S)-3-(5-(5-(2,3-dichloro-4-(N-(1,1,1-trifluorobutan-2-yl)sulfamoyl)phenyl)-4-(4-fluoropiperidine-1-carbonyl)thiazol-2-yl)-1,3,4-oxadiazol-2-yl)-2,2-dimethylpropanamide (52 mg, 0.07 mmol, Example 1/1, step b) in DCM (8 mL) and pyridine (1 drop) was cooled to 0° C. and TFAA (29 mg, 0.14 mmol) was added dropwise. The mixture was warmed to rt and stirred for an additional 2 h. The reaction mixture was diluted with H$_2$O (10 mL), extracted with EtOAc (8 mL×3), and concentrated to dryness. The residue was purified by prep-HPLC to give the title compound as a white solid. $^1$H NMR (400 MHz, CDCl$_3$) δ ppm 8.09 (d, J=8.0 Hz, 1H), 7.65 (t, J=8.4 Hz, 1H), 5.46-5.42 (m, 1H), 4.93 (br d, J=46.8 Hz, 1H), 4.08-3.84 (m, 2H), 3.51-3.40 (m, 3H), 3.30 (s, 2H), 1.94-1.59 (m, 12H), 1.10 (t, J=7.2 Hz, 3H). MS (ESI): m/z 697.0 [M+H]$^+$.

Example 1/2

(S)-2,3-Dichloro-4-(4-(4,4-difluoropiperidine-1-carbonyl)-2-(5-(1-methoxycyclopropyl)-1,3,4-oxadiazol-2-yl)thiazol-5-yl)-N-(1,1,1-trifluoropropan-2-yl)benzenesulfonamide

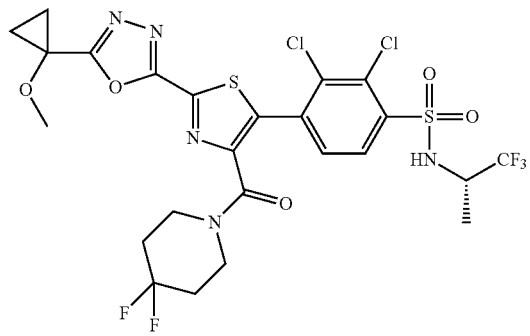 [SMILES: COC1(c2nnc(-c3nc(C(=O)N4CCC(F)(F)CC4)c(-c4ccc(S(=O)(=O)N[C@@H](C)C(F)(F)F)c(Cl)c4Cl)s3)o2)CC1]

The title compound was prepared as described for the synthesis of Example 1 (step a to step f), using in step c 4,4-difluoropiperidine in place of diethylamine and using in step e 1-methoxycyclopropanecarboxylic acid in place of 4-methoxy-3,3-dimethyl-4-oxobutanoic acid. $^1$HNMR (500 MHz, CDCl$_3$): δ ppm 8.11 (d, J=8.5 Hz, 1H), 7.63 (d, J=8.5 Hz, 1H), 5.46 (d, J=10.0 Hz, 1H), 4.10-4.04 (m, 1H), 3.84-3.73 (m, 2H), 3.63 (t, J=5.8 Hz, 2H), 3.56 (s, 3H), 2.04-1.97 (m, 4H), 1.45-1.52 (m, 4H), 1.42 (d, J=7.5 Hz, 3H). MS (ESI): m/z 690.1 [M+H]$^+$.

Example 1/3

(S)-2,3-Dichloro-4-(4-(4,4-difluoropiperidine-1-carbonyl)-2-(5-(1-(trifluoromethyl)cyclopropyl)-1,3,4-oxadiazol-2-yl)thiazol-5-yl)-N-(1,1,1-trifluoropropan-2-yl)benzenesulfonamide

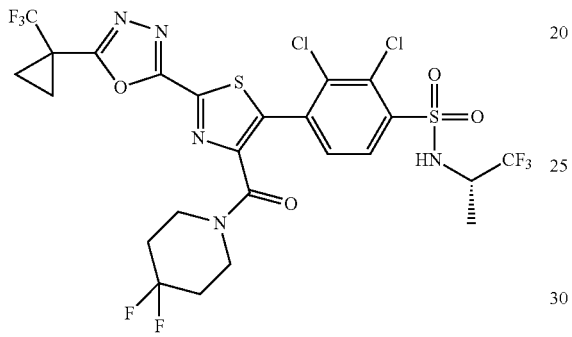

The title compound was prepared as described for the synthesis of Example 1 (step a to step f), using in step c 4,4-difluoropiperidine in place of diethylamine and using in step e 1-(trifluoromethyl)cyclopropanecarboxylic acid in place of 4-methoxy-3,3-dimethyl-4-oxobutanoic acid. $^1$H NMR (500 MHz, CDCl$_3$): δ ppm 8.11 (d, J=8.0 Hz, 1H), 7.62 (d, J=8.0 Hz, 1H), 5.39 (d, J=9.5 Hz, 1H), 4.10-4.06 (m, 1H), 3.84-3.74 (m, 2H), 3.66 (t, J=5.8 Hz, 2H), 2.08-2.00 (m, 4H), 1.73 (d, J=3.0 Hz, 4H), 1.42 (d, J=7.0 Hz, 3H). MS (ESI): m/z 728.0 [M+H]$^+$.

Example 1/4

(S)-2,3-Dichloro-4-(4-(4,4-difluoropiperidine-1-carbonyl)-2-(5-((methylsulfonyl)methyl)-1,3,4-oxadiazol-2-yl)thiazol-5-yl)-N-(1,1,1-trifluoropropan-2-yl)benzenesulfonamide

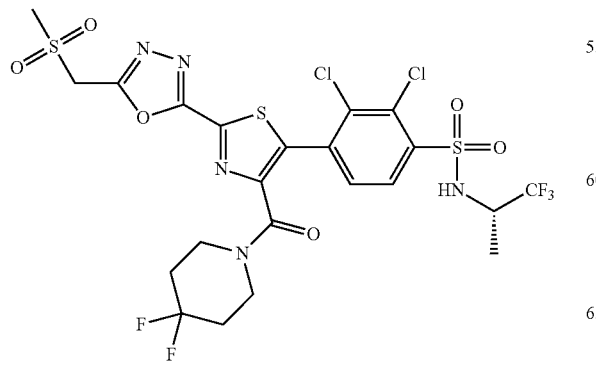

The title compound was prepared as described for the synthesis of Example 1 (step a to step f), using in step c 4,4-difluoropiperidine in place of diethylamine and using in step e 2-(methylsulfonyl)acetic acid in place of 4-methoxy-3,3-dimethyl-4-oxobutanoic acid. $^1$H NMR (500 MHz, CDCl$_3$): δ ppm 8.11 (d, J=9.0 Hz, 1H), 7.63 (d, J=8.5 Hz, 1H), 5.52-5.48 (m, 1H), 4.72 (s, 2H), 4.11-4.06 (m, 1H), 3.84-3.75 (m, 2H), 3.64 (t, J=5.5 Hz, 1H), 3.22 (s, 3H), 2.07-2.01 (m, 4H), 1.42 (d, J=7.0 Hz, 3H). MS (ESI): m/z 711.8 [M+H]$^+$.

Example 2

Step a (S)-Methyl 3-(5-(5-(2,3-dichloro-4-(N-(1,1,1-trifluorobutan-2-yl)sulfamoyl)phenyl)-4-(hydroxymethyl)thiazol-2-yl)-1,3,4-oxadiazol-2-yl)-2,2-dimethylpropanoate

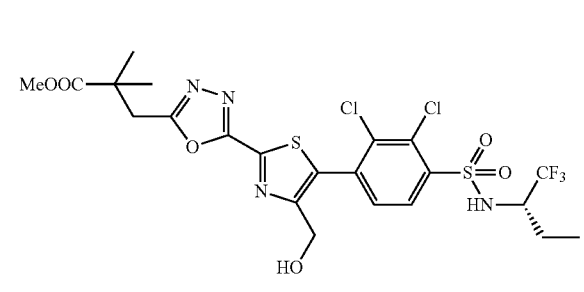 [SMILES: CC[C@H](NS(=O)(=O)c1ccc(-c2sc(-c3nnc(CC(C)(C)C(=O)OC)o3)nc2CO)c(Cl)c1Cl)C(F)(F)F]

To a solution of (S)-4-bromo-2,3-dichloro-N-(1,1,1-trifluorobutan-2-yl)benzenesulfonamide (620 mg, 1.6 mmol, Intermediate 12/4) and methyl 3-(5-(4-(hydroxymethyl)thiazol-2-yl)-1,3,4-oxadiazol-2-yl)-2,2-dimethylpropanoate (480 mg, 1.6 mmol, Intermediate 1, step f) in DMA (30 mL) was added P(Cy)$_3$·HBF$_4$ (200 mg, 0.54 mmol), pivalic acid (200 mg, 2.0 mmol), Pd(OAc)$_2$ (200 mg, 0.89 mmol), and K$_2$CO$_3$ (440 g, 3.2 mmol) under a N$_2$ atmosphere. The mixture was heated to 110° C. and stirred overnight. The mixture was cooled to rt and H$_2$O (50 mL) and EtOAc (50 mL) were added. The aqueous layer was extracted with EtOAc (50 mL×3) and the combined organic layers were dried over anhydrous MgSO$_4$, filtered and concentrated to dryness. The residue was purified by prep-TLC (PE/EtOAc=1:1) to afford the title compound as a brown oil.

Example 2

Step b (S)-5-(2,3-Dichloro-4-(N-(1,1,1-trifluorobutan-2-yl)sulfamoyl)phenyl)-2-(5-(3-methoxy-2,2-dimethyl-3-oxopropyl)-1,3,4-oxadiazol-2-yl)thiazole-4-carboxylic acid

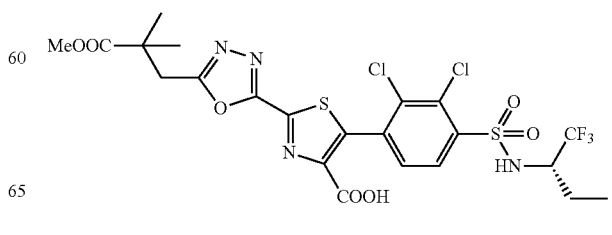

A solution of (S)-methyl 3-(5-(5-(2,3-dichloro-4-(N-(1,1,1-trifluorobutan-2-yl)sulfamoyl)phenyl)-4-(hydroxymethyl)thiazol-2-yl)-1,3,4-oxadiazol-2-yl)-2,2-dimethylpropanoate (450 mg, 0.72 mmol, Example 2, step a), TEMPO (134 mg, 0.858 mmol) and iodobenzene diacetate (920 mg, 2.88 mmoL) in H₂O (10 mL) and acetonitrile (20 mL) was stirred at rt overnight. H₂O (50 mL) and EtOAc (30 mL) were added. The aqueous layer was extracted with EtOAc (30 mL×2) and the combined organic layers were washed with brine, dried over anhydrous MgSO₄, and filtered. The filtrate was concentrated to dryness to give the title compound as a brown oil which was used in the next step directly.

Example 2

Step c

Methyl 3-(5-(5-(2,3-dichloro-4-(N—((S)-1,1,1-trifluorobutan-2-yl)sulfamoyl)phenyl)-4-((S)-2-methylpiperidine-1-carbonyl)thiazol-2-yl)-1,3,4-oxadiazol-2-yl)-2,2-dimethylpropanoate

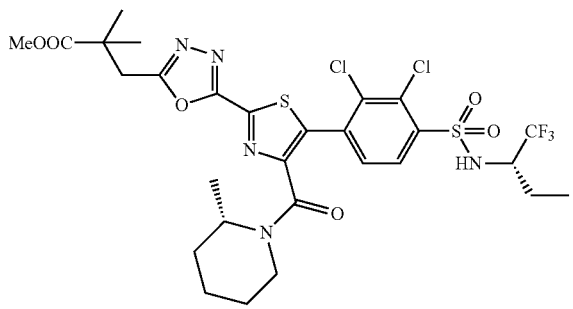 [SMILES: CC[C@H](NS(=O)(=O)c1ccc(-c2sc(-c3nnc(CC(C)(C)C(=O)OC)o3)nc2C(=O)N2CCCC[C@@H]2C)c(Cl)c1Cl)C(F)(F)F]

A solution of (S)-5-(2,3-dichloro-4-(N-(1,1,1-trifluorobutan-2-yl)sulfamoyl)phenyl)-2-(5-(3-methoxy-2,2-dimethyl-3-oxopropyl)-1,3,4-oxadiazol-2-yl)thiazole-4-carboxylic acid (270 mg, 0.43 mmol, Example 2, step b), (S)-2-methylpiperidine (85 mg, 0.85 mmol), HATU (240 mg, 0.63 mmol) and TEA (900 mg, 0.86 mmol) in acetonitrile (20 mL) was stirred at rt for 2 h. The mixture was poured into H₂O (20 mL) and extracted with EtOAc (30 mL×4). The combined organic layers were washed with brine, dried over anhydrous Na₂SO₄, filtered and concentrated to dryness. The residue was purified by prep-TLC (PE/EtOAc=1:2) to afford the title compound as a white solid.

Example 2

3-(5-(5-(2,3-Dichloro-4-(N—((S)-1,1,1-trifluorobutan-2-yl)sulfamoyl)phenyl)-4-((S)-2-methylpiperidine-1-carbonyl)thiazol-2-yl)-1,3,4-oxadiazol-2-yl)-2,2-dimethylpropanoic acid

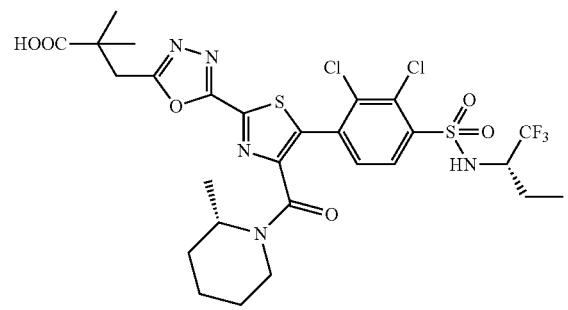 [SMILES: CC[C@H](NS(=O)(=O)c1ccc(-c2sc(-c3nnc(CC(C)(C)C(=O)O)o3)nc2C(=O)N2CCCC[C@@H]2C)c(Cl)c1Cl)C(F)(F)F]

A mixture of methyl 3-(5-(5-(2,3-dichloro-4-(N—((S)-1,1,1-trifluorobutan-2-yl)sulfamoyl)phenyl)-4-((S)-2-methylpiperidine-1-carbonyl)thiazol-2-yl)-1,3,4-oxadiazol-2-yl)-2,2-dimethylpropanoate (100 mg, 0.14 mmol, Example 2, step c) and LiOH monohydrate (12 mg, 0.28 mmol) in methanol (4 mL) and H₂O (2 mL) was stirred at rt overnight. The mixture was concentrated to dryness and water (10 mL) was added. The aqueous layer was extracted with EtOAc (8 mL×3). The combined organic layers were washed with brine, dried over anhydrous Na₂SO₄, filtered, and the filtrate was concentrated to dryness. The residue was purified by prep-HPLC to give the title compound as a white solid. ¹H NMR (400 MHz, CDCl₃): δ ppm 8.08-8.04 (m, 1H), 7.74-7.65 (m, 1H), 5.49 (br s, 1H), 4.88-4.42 (m, 1H), 3.95-3.81 (m, 1H), 3.46-3.40 (m, 1H), 3.28 (s, 2H), 2.95-2.78 (m, 1H), 1.94-1.86 (m, 1H), 1.69-1.56 (m, 5H), 1.42 (s, 6H), 1.17-1.16 (m, 8H). MS (ESI): m/z 712.1 [M+H]⁺.

Example 2/1

(S)-3-(5-(5-(2,3-Dichloro-4-(1,1,1,3,3,3-hexafluoro-2-hydroxypropan-2-yl)phenyl)-4-(2-methylpiperidine-1-carbonyl)thiazol-2-yl)-1,3,4-oxadiazol-2-yl)-2,2-dimethylpropanoic acid

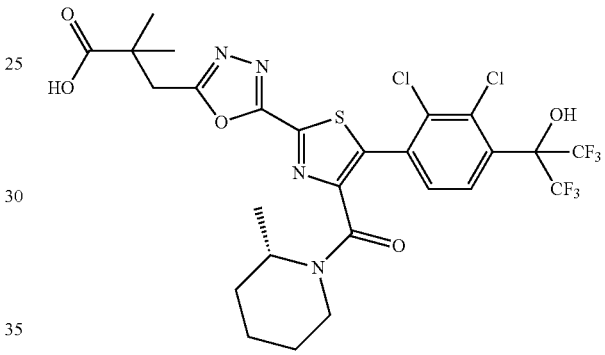

The title compound was prepared as described for the synthesis of Example 2, using in step a 2-(4-bromo-2,3-dichlorophenyl)-1,1,1,3,3,3-hexafluoropropan-2-ol (Intermediate 13, step b) in place of (S)-4-bromo-2,3-dichloro-N-(1,1,1-trifluorobutan-2-yl)benzenesulfonamide. ¹H NMR (400 MHz, CDCl₃): δ ppm 7.80-7.74 (m, 1H), 7.62-7.58 (m, 1H), 4.90-4.86 (m, 1H), 4.49-4.42 (m, 1H), 4.01-3.90 (m, 1H), 3.48-3.35 (m, 1H), 3.28 (s, 2H), 2.99-2.80 (m, 1H), 1.71-1.46 (m, 10H), 1.42-0.88 (m, 5H). MS (ESI): m/z 689.0 [M+H]⁺.

Example 2/2

Step a

Methyl 3-(5-(5-(3-(tert-butyl)-5-(1,1,1,3,3,3-hexafluoro-2-hydroxypropan-2-yl)phenyl)-4-(4-fluoropiperidine-1-carbonyl)thiazol-2-yl)-1,3,4-oxadiazol-2-yl)-2,2-dimethylpropanoate

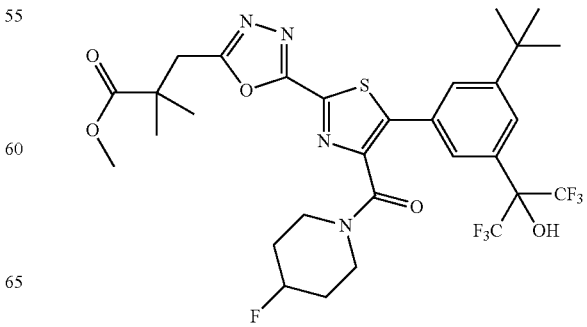

To a solution of methyl 3-(5-(4-(4-fluoropiperidine-1-carbonyl)thiazol-2-yl)-1,3,4-oxadiazol-2-yl)-2,2-dimethylpropanoate (120 mg, 0.30 mmol, Intermediate 2, step e), 2-(3-bromo-5-(tert-butyl)phenyl)-1,1,1,3,3,3-hexafluoropropan-2-ol (126 mg, 0.33 mmol, Intermediate 15, step b), PPh₃ (88 mg, 0.32 mmol) and KOAc (30 mg, 0.31 mmol) in DMF (15 mL) was added slowly Pd(OAc)₂ (7 mg, 0.03 mmol) at rt under nitrogen. The mixture was heated at 110° C. overnight, filtered, and the filter cake was washed with EtOAc. The organic layer was washed with water, brine, dried over anhydrous Na₂SO₄, filtered, concentrated to dryness, and purified by prep-TLC (PE/EtOAc=1/1) to give the title compound as an off-white solid.

Example 2/2

3-(5-(5-(3-(tert-Butyl)-5-(1,1,1,3,3,3-hexafluoro-2-hydroxypropan-2-yl)phenyl)-4-(4-fluoropiperidine-1-carbonyl)thiazol-2-yl)-1,3,4-oxadiazol-2-yl)-2,2-dimethylpropanoic acid

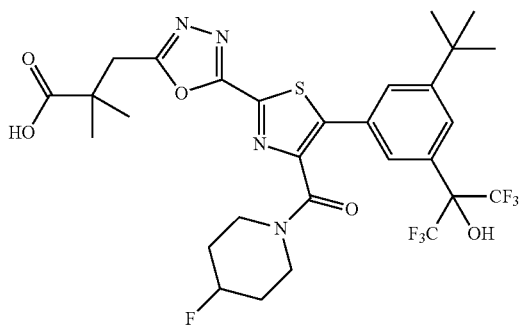 [SMILES: CC(C)(Cc1nnc(-c2nc(C(=O)N3CCC(F)CC3)c(-c3cc(C(C)(C)C)cc(C(O)(C(F)(F)F)C(F)(F)F)c3)s2)o1)C(=O)O]

To a solution of methyl 3-(5-(5-(3-(tert-butyl)-5-(1,1,1,3,3,3-hexafluoro-2-hydroxypropan-2-yl)phenyl)-4-(4-fluoropiperidine-1-carbonyl)thiazol-2-yl)-1,3,4-oxadiazol-2-yl)-2,2-dimethylpropanoate (40 mg, 0.06 mmol, Example 2/2, step a) in THF/H₂O (5.5 mL, 10:1) was added LiOH (7.2 mg, 1.9 mmol). The mixture was heated at 45° C. under nitrogen for 4 h, concentrated to dryness, diluted with H₂O (10 mL), adjusted to pH=5 with 1 M aqueous HCl and extracted with EtOAc. The organic layer was washed with brine, dried over anhydrous Na₂SO₄, filtered, concentrated to dryness, and purified by prep-HPLC to give the title compound as a yellow solid. ¹H NMR (CD₃OD, 300 MHz): δ ppm 7.91-7.90 (m, 1H), 7.79 (s, 1H), 7.78-7.77 (m, 1H), 3.72-4.64 (m, 1H), 3.92-3.27 (m, 6H), 1.88-1.81 (m, 2H), 1.57-1.49 (m, 2H), 1.38 (s, 9H), 1.34 (s, 6H). MS (ESI): m/z 681.2 [M+H]⁺.

Example 3

Step a (S)-2,3-Dichloro-4-(2-(5-(2-hydroxy-2-methylpropyl)-1,3,4-oxadiazol-2-yl)-4-(hydroxymethyl)thiazol-5-yl)-N-(1,1,1-trifluoropropan-2-yl)benzenesulfonamide

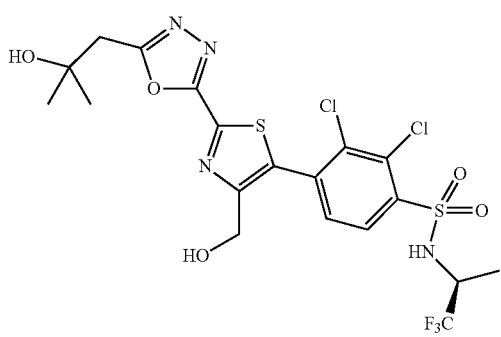 [SMILES: C[C@H](NS(=O)(=O)c1ccc(-c2sc(-c3nnc(CC(C)(C)O)o3)nc2CO)c(Cl)c1Cl)C(F)(F)F]

To a solution of 1-(5-(4-(hydroxymethyl)thiazol-2-yl)-1,3,4-oxadiazol-2-yl)-2-methylpropan-2-ol (340 mg, 1.3 mmol, Intermediate 3/1) and (S)-4-bromo-2,3-dichloro-N-(1,1,1-trifluoropropan-2-yl)benzenesulfonamide (520 mg, 1.3 mmol, Intermediate 12/3) in DMA (8 mL) was added P(Cy)₃·HBF₄ (60 mg, 0.16 mmol), PivOH (60 mg, 0.60 mmol), Pd(OAc)₂ (60 mg, 0.27 mmol), and K₂CO₃ (360 mg, 2.6 mmol) under a N₂ atmosphere. The mixture was heated to 100° C. overnight, cooled to rt, diluted with H₂O (30 mL), and extracted with EtOAc (30 mL×4). The combined organic layers were washed with H₂O (30 mL×3), brine, dried over anhydrous Na₂SO₄, filtered, concentrated to dryness, and purified by prep-TLC (PE/EtOAc=1:1) to afford the title compound as a brown solid.

Example 3

Step b (S)-5-(2,3-Dichloro-4-(N-(1,1,1-trifluoropropan-2-yl)sulfamoyl)phenyl)-2-(5-(2-hydroxy-2-methylpropyl)-1,3,4-oxadiazol-2-yl)thiazole-4-carboxylic acid

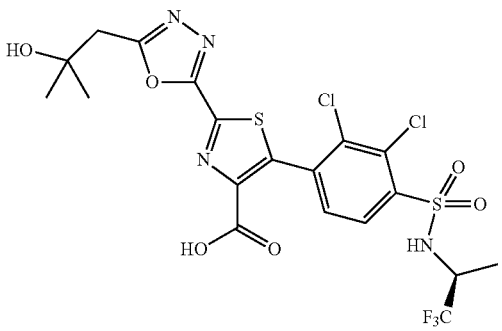 [SMILES: C[C@H](NS(=O)(=O)c1ccc(-c2sc(-c3nnc(CC(C)(C)O)o3)nc2C(=O)O)c(Cl)c1Cl)C(F)(F)F]

A mixture of (S)-2,3-dichloro-4-(2-(5-(2-hydroxy-2-methylpropyl)-1,3,4-oxadiazol-2-yl)-4-(hydroxymethyl)thiazol-5-yl)-N-(1,1,1-trifluoropropan-2-yl)benzenesulfonamide (450 mg, 0.78 mmol, Example 3, step a), TEMPO (145 mg, 0.928 mmol), iodobenzene diacetate (1.0 g, 3.2 mmoL), H₂O (8 mL), and MeCN (15 mL) was stirred at rt overnight, diluted with H₂O (20 mL), and extracted with EtOAc (30 mL×2). The combined organic layers were washed with brine, dried over anhydrous MgSO₄, filtered, and concentrated to dryness to give the title compound as a brown solid.

Example 3

(S)-2,3-Dichloro-4-(4-(4,4-difluoropiperidine-1-carbonyl)-2-(5-(2-hydroxy-2-methylpropyl)-1,3,4-oxadiazol-2-yl)thiazol-5-yl)-N-(1,1,1-trifluoropropan-2-yl)benzenesulfonamide

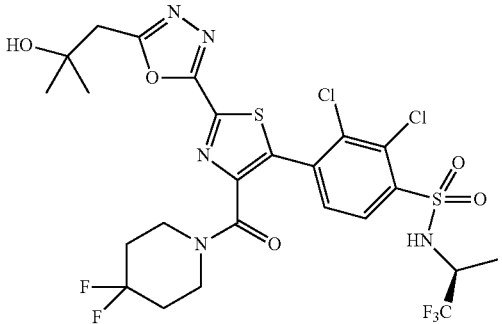 [SMILES: C[C@H](NS(=O)(=O)c1ccc(-c2sc(-c3nnc(CC(C)(C)O)o3)nc2C(=O)N2CCC(F)(F)CC2)c(Cl)c1Cl)C(F)(F)F]

A solution of (S)-5-(2,3-dichloro-4-(N-(1,1,1-trifluoropropan-2-yl)sulfamoyl)phenyl)-2-(5-(2-hydroxy-2-methylpropyl)-1,3,4-oxadiazol-2-yl)thiazole-4-carboxylic acid (150 mg, 0.26 mmol, Example 3, step b), 4,4-difluoropiperidine hydrochloride (80 mg, 0.52 mmol), HATU (150 mg, 0.4 mmol), TEA (130 mg, 1.3 mmol), and MeCN (15 mL) was stirred at rt for 2 h, poured into $H_2O$ (20 mL), and extracted with EtOAc (20 mL×4). The combined organic layers were washed with brine, dried over anhydrous $Na_2SO_4$, filtered, concentrated to dryness, and the residue was purified by prep-HPLC to afford the title compound as a white solid. $^1H$ NMR (400 MHz, $CDCl_3$): δ ppm 8.10 (d, J=6.4 Hz, 1H), 7.63 (d, J=6.8 Hz, 1H), 5.45 (d, J=8.0 Hz, 1H), 4.09-4.07 (m, 1H), 3.81-3.75 (m, 2H), 3.62 (t, J=4.4 Hz, 2H), 3.20 (s, 2H), 2.03-1.99 (m, 4H), 1.45-1.42 (m, 9H). MS (ESI): m/z 692.0 [M+H]⁺.

Example 3/1

(S)-2,3-Dichloro-4-(4-(3,3-difluoropyrrolidine-1-carbonyl)-2-(5-(2-hydroxy-2-methylpropyl)-1,3,4-oxadiazol-2-yl)thiazol-5-yl)-N-(1,1,1-trifluoropropan-2-yl)benzenesulfonamide

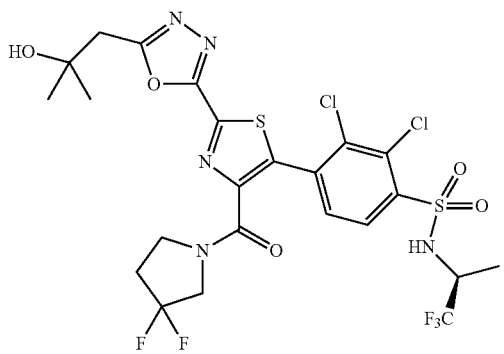 [SMILES: C[C@H](NS(=O)(=O)c1ccc(-c2sc(-c3nnc(CC(C)(C)O)o3)nc2C(=O)N2CCC(F)(F)C2)c(Cl)c1Cl)C(F)(F)F]

The title compound was prepared as described for the synthesis of Example 3 using 3,3-difluoropyrrolidine in place of 4,4-difluoropiperidine hydrochloride. $^1H$ NMR (400 MHz, $CDCl_3$): δ ppm 8.12 (d, J=6.8 Hz, 1H), 7.61 (t, J=7.2 Hz, 1H), 5.46 (br s, 1H), 4.26-4.20 (m, 1H), 4.12-4.06 (m, 2H), 3.96-3.83 (m, 2H), 3.23 (d, J=5.2 Hz, 2H), 2.50-2.41 (m, 2H), 1.48 (s, 6H), 1.42 (d, J=5.6 Hz, 3H). MS (ESI): m/z 678.0 [M+H]⁺.

Example 3/2

2,3-Dichloro-4-(4-((S)-4,4-difluoro-2-methylpyrrolidine-1-carbonyl)-2-(5-(2-hydroxy-2-methylpropyl)-1,3,4-oxadiazol-2-yl)thiazol-5-yl)-N—((S)-1,1,1-trifluoropropan-2-yl)benzenesulfonamide

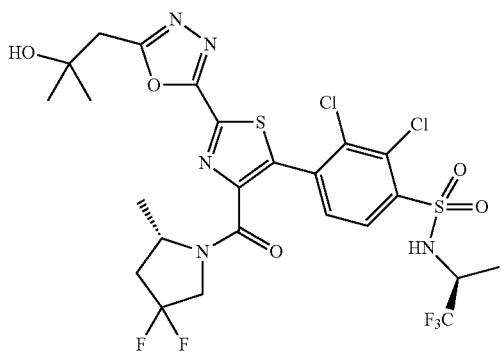 [SMILES: C[C@H](NS(=O)(=O)c1ccc(-c2sc(-c3nnc(CC(C)(C)O)o3)nc2C(=O)N2CC(F)(F)C[C@@H]2C)c(Cl)c1Cl)C(F)(F)F]

The title compound was prepared as described for the synthesis of Example 3 using (S)-4,4-difluoro-2-methylpyrrolidine hydrochloride (Intermediate 14, step b) in place of 4,4-difluoropiperidine hydrochloride. $^1H$ NMR (400 MHz, $CDCl_3$): δ ppm 8.10 (d, J=8.0 Hz, 1H), 7.61-7.56 (m, 1H), 5.51 (d, J=9.6 Hz, 1H), 4.99-4.50 (m, 1H), 4.24-3.90 (m, 3H), 3.21 (s, 2H), 2.67-2.57 (m, 1H), 2.17-2.09 (m, 1H), 1.45 (s, 6H), 1.42-1.28 (m, 6H). MS (ESI): m/z 692.0 [M+H]⁺.

Example 3/3

(S)-5-(2,3-Dichloro-4-(N-(1,1,1-trifluoropropan-2-yl)sulfamoyl)phenyl)-N,N-diethyl-2-(5-(2-hydroxy-2-methylpropyl)-1,3,4-oxadiazol-2-yl)thiazole-4-carboxamide

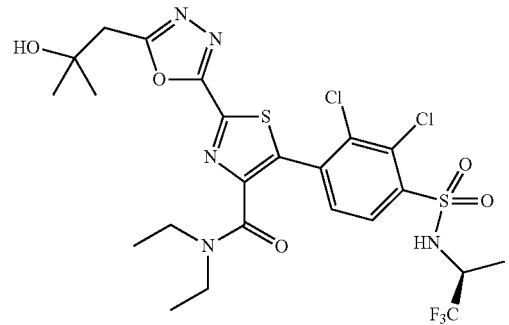 [SMILES: CCN(CC)C(=O)c1nc(-c2nnc(CC(C)(C)O)o2)sc1-c1ccc(S(=O)(=O)N[C@@H](C)C(F)(F)F)c(Cl)c1Cl]

The title compound was prepared as described for the synthesis of Example 3 using diethylamine in place of 4,4-difluoropiperidine hydrochloride. $^1H$ NMR (400 MHz, DMSO-$d_6$): δ ppm 9.23 (d, J=8.8 Hz, 1H), 8.09 (d, J=8.4 Hz, 1H), 7.75 (d, J=8.4 Hz, 1H), 4.19-4.13 (m, 1H), 3.39-3.24 (m, 4H), 3.10 (s, 2H), 1.27-1.25 (m, 9H), 1.07 (t, J=7.2 Hz, 3H), 1.00 (t, J=7.2 Hz, 3H). MS (ESI): m/z 644.1 [M+H]⁺.

Example 3/4

(5-(2,3-Dichloro-4-(1,1,1,3,3,3-hexafluoro-2-hydroxypropan-2-yl)phenyl)-2-(5-(2-hydroxy-2-methylpropyl)-1,3,4-oxadiazol-2-yl)thiazol-4-yl)(4-fluoropiperidin-1-yl)methanone

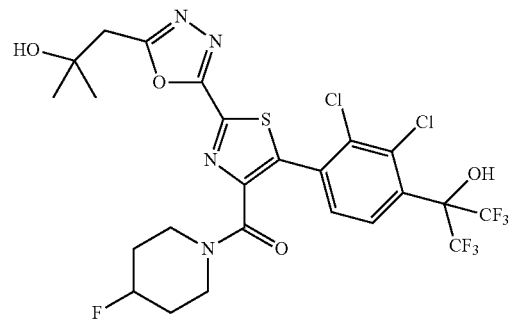 [SMILES: CC(C)(O)Cc1nnc(-c2nc(C(=O)N3CCC(F)CC3)c(-c3ccc(C(O)(C(F)(F)F)C(F)(F)F)c(Cl)c3Cl)s2)o1]

The title compound was prepared as described for the synthesis of Example 3, using in step a 2-(4-bromo-2,3-dichlorophenyl)-1,1,1,3,3,3-hexafluoropropan-2-ol (Intermediate 13, step b) in place of (S)-4-bromo-2,3-dichloro-N-(1,1,1-trifluoropropan-2-yl)benzenesulfonamide and 4-fluoropiperidine in place of 4,4-difluoropiperidine hydrochloride. $^1H$ NMR (400 MHz, $CDCl_3$): δ ppm 7.77-7.75 (m, 1H), 7.59 (d, J=8.8 Hz, 1H), 4.86 (d, J=47.6 Hz, 1H), 4.03-4.00 (m, 1H), 3.53-3.46 (m, 3H), 3.19 (s, 2H), 2.45 (br s, 1H), 1.90-1.59 (m, 4H), 1.44 (s, 6H). MS (ESI): m/z 665.0 [M+H]⁺.

Example 3/5

Step a (S)-2,3-Dichloro-4-(4-(4-fluoropiperidine-1-carbonyl)-2-(2-(3-hydroxy-3-methylbutanoyl)hydrazinecarbonyl)thiazol-5-yl)-N-(1,1,1-trifluorobutan-2-yl)benzenesulfonamide

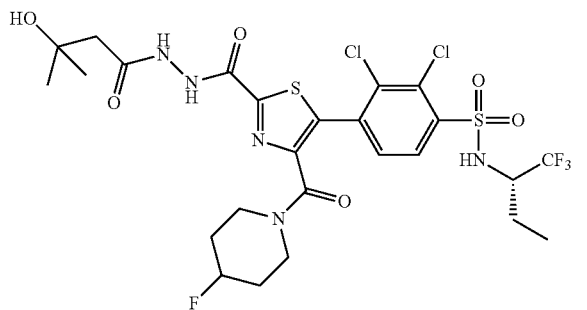 [SMILES: CC[C@H](NS(=O)(=O)c1ccc(-c2sc(C(=O)NNC(=O)CC(C)(C)O)nc2C(=O)N2CCC(F)CC2)c(Cl)c1Cl)C(F)(F)F]

A solution of (S)-2,3-dichloro-4-(4-(4-fluoropiperidine-1-carbonyl)-2-(hydrazinecarbonyl)thiazol-5-yl)-N-(1,1,1-trifluorobutan-2-yl)benzenesulfonamide (200 mg, 0.33 mmol, prepared as described for the synthesis of Example 1, step d, using in step a (S)-4-bromo-2,3-dichloro-N-(1,1,1-trifluorobutan-2-yl)benzenesulfonamide (Intermediate 12/4) in place of (S)-4-bromo-2,3-dichloro-N-(1,1,1-trifluoropropan-2-yl)benzenesulfonamide and in step c 4-fluoropiperidine in place of diethylamine), 3-hydroxy-3-methylbutanoic acid (80 mg, 0.66 mmol), HATU (190 mg, 0.5 mmol), and TEA (0.2 mL, 1.4 mmol) in MeCN (10 mL) was stirred at rt for 2 h, poured into H₂O (30 mL), and extracted with EtOAc (30 mL×4). The combined organic layers were washed with brine, dried over anhydrous Na₂SO₄, concentrated to dryness, and the residue was purified by prep-TLC (DCM/MeOH=10:1) to afford the title compound as a white solid.

Example 3/5

(S)-2,3-Dichloro-4-(4-(4-fluoropiperidine-1-carbonyl)-2-(5-(2-hydroxy-2-methylpropyl)-1,3,4-oxadiazol-2-yl)thiazol-5-yl)-N-(1,1,1-trifluorobutan-2-yl)benzenesulfonamide

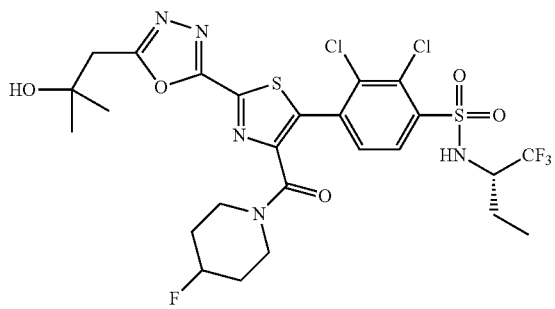 [SMILES: CC[C@H](NS(=O)(=O)c1ccc(-c2sc(-c3nnc(CC(C)(C)O)o3)nc2C(=O)N2CCC(F)CC2)c(Cl)c1Cl)C(F)(F)F]

A solution of (S)-2,3-dichloro-4-(4-(4-fluoropiperidine-1-carbonyl)-2-(2-(3-hydroxy-3-methylbutanoyl)hydrazinecarbonyl)thiazol-5-yl)-N-(1,1,1-trifluorobutan-2-yl)benzenesulfonamide (100 mg, 0.14 mmol, Example 3/5, step a), 4-methylbenzene-1-sulfonyl chloride (53 mg, 0.28 mmol) in TEA (0.1 mL, 0.7 mmol) and in DCM (10 mL) was stirred at rt overnight, poured into H₂O (20 mL), and extracted with EtOAc (15 mL×3). The combined organic layers were washed with brine, dried over anhydrous Na₂SO₄, filtered, and concentrated to dryness. The residue was purified by prep-TLC (EtOAc/PE=2:1) to give the title compound as a yellow solid. ¹H NMR (400 MHz, CDCl₃): δ ppm 8.08 (d, J=8.0 Hz, 1H), 7.65 (t, J=8.8 Hz, 1H), 5.36 (d, J=10.0 Hz, 1H), 4.85 (d, J=42.4 Hz, 1H), 4.07-3.85 (m, 2H), 3.49-3.37 (m, 3H), 3.20 (s, 2H), 1.94-1.55 (m, 6H), 1.44 (s, 6H), 1.11 (t, J=7.2 Hz, 3H). MS (ESI): m/z 687.9 [M+H]⁺.

Example 3/6

(S)-(5-(2,3-Dichloro-4-(1,1,1,3,3,3-hexafluoro-2-hydroxypropan-2-yl)phenyl)-2-(5-(2-hydroxy-2-methylpropyl)-1,3,4-oxadiazol-2-yl)thiazol-4-yl)(3-fluoropyrrolidin-1-yl)methanone

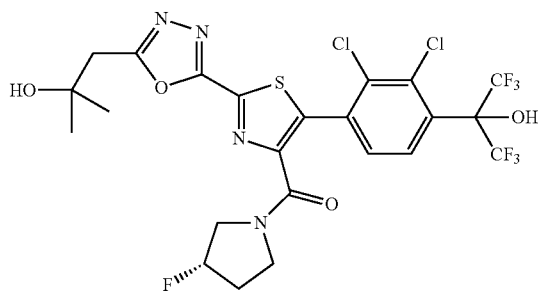 [SMILES: CC(C)(O)Cc1nnc(-c2nc(C(=O)N3CC[C@H](F)C3)c(-c3ccc(C(O)(C(F)(F)F)C(F)(F)F)c(Cl)c3Cl)s2)o1]

The title compound was prepared as described for the synthesis of Example 3, using in step a 2-(4-bromo-2,3-dichlorophenyl)-1,1,1,3,3,3-hexafluoropropan-2-ol (Intermediate 13, step b) in place of (S)-4-bromo-2,3-dichloro-N-(1,1,1-trifluoropropan-2-yl)benzenesulfonamide and in the final step (S)-3-fluoropyrrolidine hydrochloride in place of 4,4-difluoropiperidine hydrochloride. ¹H NMR (400 MHz, CDCl₃): δ ppm 7.76-7.72 (m, 1H), 7.57-7.53 (m, 1H), 5.30 (br d, J=52.4 Hz, 1H), 4.05-3.65 (m, 4H), 3.18 (s, 2H), 2.64-2.60 (m, 1H), 2.39-2.31 (m, 1H), 2.15-1.99 (m, 1H), 1.44 (s, 6H). MS (ESI): m/z 651.1 [M+H]⁺.

Example 3/7

(S)-3-(Difluoromethoxy)-4-(4-(4,4-difluoropiperidine-1-carbonyl)-2-(5-(2-hydroxy-2-methylpropyl)-1,3,4-oxadiazol-2-yl)thiazol-5-yl)-2-fluoro-N-(1,1,1-trifluoropropan-2-yl)benzenesulfonamide

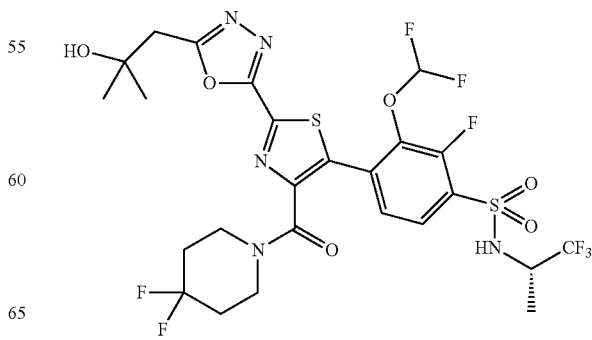

The title compound was prepared as described for the synthesis of Example 3, using in step a (S)-4-bromo-3-(difluoromethoxy)-2-fluoro-N-(1,1,1-trifluoropropan-2-yl)benzenesulfonamide (Intermediate 12/8, step b) in place of (S)-4-bromo-2,3-dichloro-N-(1,1,1-trifluoropropan-2-yl)benzenesulfonamide. $^1$H NMR (400 MHz, CDCl$_3$): δ ppm 7.86 (dd, J=8.0, 6.8 Hz, 1H), 7.57 (d, J=8.4 Hz, 1H), 6.59 (t, J=72.8 Hz, 1H), 5.57 (d, J=10.0 Hz, 1H), 4.15-4.08 (m, 1H), 3.91-3.76 (m, 2H), 3.56 (t, J=5.6 Hz, 2H), 3.21 (s, 2H), 2.09-1.93 (m, 4H), 1.45-1.42 (m, 9H). MS (ESI): m/z 708.1 [M+H]$^+$.

Example 4

Step a (S)-2-(Ethoxycarbonyl)-5-(4-(N-(1,1,1-trifluoropropan-2-yl)sulfamoyl)naphthalen-1-yl)thiazole-4-carboxylic acid

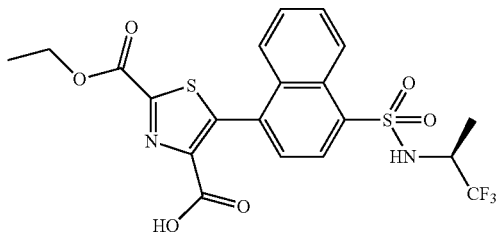 [SMILES: CCOC(=O)c1nc(C(=O)O)c(-c2ccc(S(=O)(=O)N[C@@H](C)C(F)(F)F)c3ccccc23)s1]

A mixture of (S)-ethyl 4-(hydroxymethyl)-5-(4-(N-(1,1,1-trifluoropropan-2-yl)sulfamoyl)naphthalen-1-yl)thiazole-2-carboxylate (488 mg, 1.00 mmol, prepared as described for the synthesis of Example 1, step a, using (S)-4-bromo-N-(1,1,1-trifluoropropan-2-yl)naphthalene-1-sulfonamide (Intermediate 12/7) in place of (S)-4-bromo-2,3-dichloro-N-(1,1,1-trifluoropropan-2-yl)benzenesulfonamide), TEMPO (187 mg, 1.2 mmol), iodobenzene diacetate (1.3 g, 4.0 mmol), H$_2$O (10 mL), and acetonitrile (20 mL) were stirred at rt overnight. H$_2$O (50 mL) and EtOAc (30 mL) were added and the aqueous layer was extracted with EtOAc (30 mL×2). The combined organic layers were washed with brine, dried over anhydrous MgSO$_4$, filtered, and concentrated to dryness to give the title compound as a brown solid, which was used in the next step without further purification.

Example 4

Step b (S)-Ethyl 4-(4-methylpiperidine-1-carbonyl)-5-(4-(N-(1,1,1-trifluoropropan-2-yl)sulfamoyl)naphthalen-1-yl)thiazole-2-carboxylate

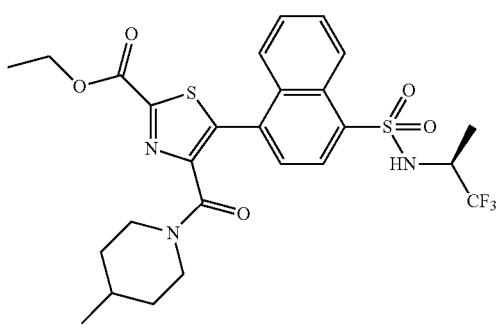 [SMILES: CCOC(=O)c1nc(C(=O)N2CCC(C)CC2)c(-c2ccc(S(=O)(=O)N[C@@H](C)C(F)(F)F)c3ccccc23)s1]

A solution of (S)-2-(ethoxycarbonyl)-5-(4-(N-(1,1,1-trifluoropropan-2-yl)sulfamoyl)naphthalen-1-yl)thiazole-4-carboxylic acid (490 mg, 0.98 mmol, Example 4, step a), 4-methylpiperidine (200 mg, 2 mmol), HATU (460 mg, 1.2 mmol), TEA (0.2 mL, 1.4 mmol), and acetonitrile (15 mL) was stirred at rt for 2 h. The mixture was poured into H$_2$O (30 mL) and extracted with EtOAc (30 mL×4). The combined organic layers were washed with brine, dried over anhydrous Na$_2$SO$_4$, filtered and concentrated to dryness. The residue was purified by prep-TLC (DCM/MeOH=10:1) to afford the title compound as a colorless solid.

Example 4

Step c (S)-4-(2-(Hydrazinecarbonyl)-4-(4-methylpiperidine-1-carbonyl)thiazol-5-yl)-N-(1,1,1-trifluoropropan-2-yl)naphthalene-1-sulfonamide

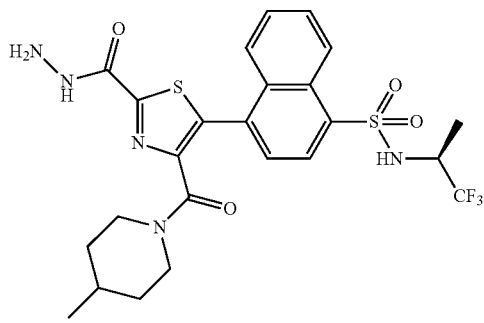 [SMILES: CC1CCN(C(=O)c2nc(C(=O)NN)sc2-c2ccc(S(=O)(=O)N[C@@H](C)C(F)(F)F)c3ccccc23)CC1]

A solution of (S)-ethyl 4-(4-methylpiperidine-1-carbonyl)-5-(4-(N-(1,1,1-trifluoropropan-2-yl)sulfamoyl)naphthalen-1-yl)thiazole-2-carboxylate (182 mg, 0.314 mmol, Example 4, step b), and hydrazine hydrate (0.40 mL, 13 mmol) in ethanol (10 mL) was stirred at 50° C. for 4 h. The mixture was concentrated to dryness and the residue was purified by prep-TLC (EtOAc) to give the title compound as a brown solid.

Example 4

Step d (S)-4-(2-(2-(2-Hydroxy-2-methylpropanoyl)hydrazinecarbonyl)-4-(4-methylpiperidine-1-carbonyl)thiazol-5-yl)-N-(1,1,1-trifluoropropan-2-yl)naphthalene-1-sulfonamide

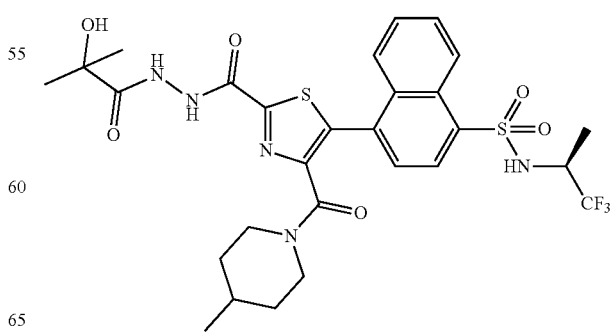

A solution of (S)-4-(2-(hydrazinecarbonyl)-4-(4-methylpiperidine-1-carbonyl)thiazol-5-yl)-N-(1,1,1-trifluoropropan-2-yl)naphthalene-1-sulfonamide (115 mg, 0.202 mmol, Example 4, step c), 2-hydroxy-2-methylpropanoic acid (42 mg, 0.40 mmol), HATU (114 mg, 0.300 mmol), TEA (0.10 mL, 0.70 mmol), and acetonitrile (5 mL) was stirred at rt for 2 h. The mixture was poured into H$_2$O (20 mL) and extracted with EtOAc (20 mL×4). The combined organic layers were washed with brine, dried over anhydrous Na$_2$SO$_4$, filtered and concentrated to dryness. The residue was purified by prep-TLC (DCM/MeOH=10:1) to afford the title compound as a colorless solid.

Example 4

(S)-4-(2-(5-(2-Hydroxypropan-2-yl)-1,3,4-oxadiazol-2-yl)-4-(4-methylpiperidine-1-carbonyl)thiazol-5-yl)-N-(1,1,1-trifluoropropan-2-yl)naphthalene-1-sulfonamide

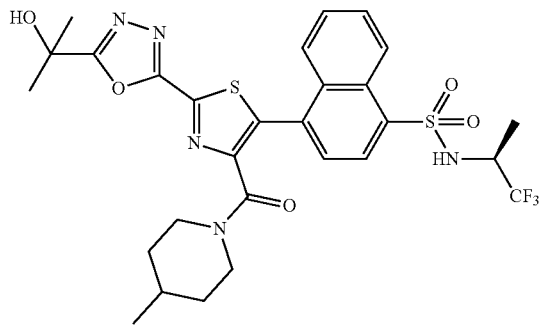 [SMILES: CC1CCN(C(=O)c2nc(-c3nnc(C(C)(C)O)o3)sc2-c2ccc(S(=O)(=O)N[C@@H](C)C(F)(F)F)c3ccccc23)CC1]

A mixture of (S)-4-(2-(2-(2-hydroxy-2-methylpropanoyl)hydrazinecarbonyl)-4-(4-methylpiperidine-1-carbonyl)thiazol-5-yl)-N-(1,1,1-trifluoropropan-2-yl)naphthalene-1-sulfonamide (55 mg, 0.083 mmol, Example 4, step d), 4-methylbenzene-1-sulfonyl chloride (23 mg, 0.12 mmol), TEA (0.05 mL, 0.4 mmol), and DCM (10 mL) was stirred at rt overnight. The mixture was poured into H$_2$O (10 mL) and extracted with EtOAc (8 mL×3). The combined organic layers were washed with brine, dried over anhydrous Na$_2$SO$_4$, filtered, and concentrated to dryness. The residue was purified by prep-TLC (EtOAc/PE=4:1) to give the title compound as a yellow solid. $^1$H NMR (400 MHz, DMSO-d$_6$): δ ppm 9.08 (s, 1H), 8.75 (d, J=8.8 Hz, 1H), 8.28 (d, J=7.6 Hz, 1H), 8.05 (d, J=8.4 Hz, 1H), 7.84-7.70 (m, 3H), 6.13 (s, 1H), 4.15-4.10 (m, 2H), 3.66-3.61 (m, 1H), 2.86-2.79 (m, 1H), 2.40-2.10 (m, 1H), 1.65 (s, 6H), 1.47-1.40 (m, 3H), 1.10-1.02 (m, 3H), 0.70 (d, J=4.0 Hz, 3H), 0.52-0.32 (m, 2H). MS (ESI): m/z 638.1 [M+H]$^1$.

Example 4/1

(S)-5-(2,3-Dichloro-4-(N-(1,1,1-trifluoropropan-2-yl)sulfamoyl)phenyl)-N,N-diethyl-2-(5-(2-hydroxypropan-2-yl)-1,3,4-oxadiazol-2-yl)thiazole-4-carboxamide

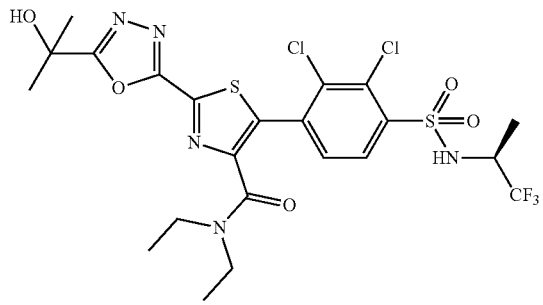 [SMILES: CCN(CC)C(=O)c1nc(-c2nnc(C(C)(C)O)o2)sc1-c1ccc(S(=O)(=O)N[C@@H](C)C(F)(F)F)c(Cl)c1Cl]

The title compound was prepared as described for the synthesis of Example 4, using in step a (S)-4-bromo-2,3-dichloro-N-(1,1,1-trifluoropropan-2-yl)benzenesulfonamide (Intermediate 12/3) in place of (S)-4-bromo-N-(1,1,1-trifluoropropan-2-yl)naphthalene-1-sulfonamide and in step b diethylamine in place of 4-methylpiperidine. 1H NMR (400 MHz, DMSO-d$_6$): δ ppm 9.24 (s, 1H), 8.09 (d, J=8.0 Hz, 1H), 7.74 (d, J=8.0 Hz, 1H), 6.10 (s, 1H), 4.17-4.15 (m, 1H), 3.37-3.33 (m, 2H), 3.28-3.23 (m, 2H), 1.63 (s, 6H), 1.26 (d, J=7.2 Hz, 3H), 1.03-0.98 (m, 6H). MS (ESI): m/z 630.0 [M+H]$^+$.

Example 4/2

(S)-2,3-Dichloro-4-(4-(4-fluoropiperidine-1-carbonyl)-2-(5-(2-hydroxypropan-2-yl)-1,3,4-oxadiazol-2-yl)thiazol-5-yl)-N-(1,1,1-trifluoropropan-2-yl)benzenesulfonamide

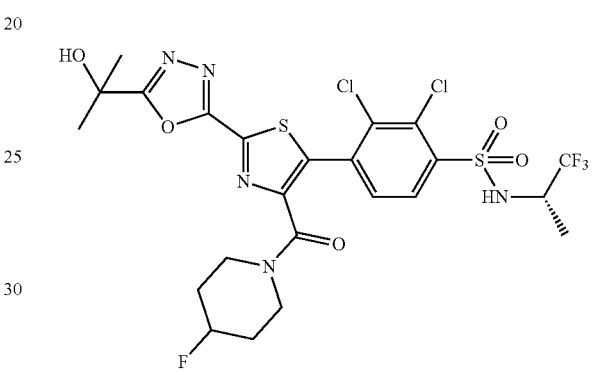

The title compound was prepared as described for the synthesis of Example 4, using in step a (S)-4-bromo-2,3-dichloro-N-(1,1,1-trifluoropropan-2-yl)benzenesulfonamide (Intermediate 12/3) in place of (S)-4-bromo-N-(1,1,1-trifluoropropan-2-yl)naphthalene-1-sulfonamide and in step b 4-fluoropiperidine in place of 4-methylpiperidine. $^1$H NMR (400 MHz, CDCl$_3$): δ ppm 8.10 (d, J=8.4 Hz, 1H), 7.68-7.64 (m, 1H), 5.42-5.37 (m, 1H), 4.93-4.80 (m, 1H), 4.12-3.95 (m, 2H), 3.51-3.41 (m, 3H), 1.83-1.57 (m, 10H), 1.43 (d, J=6.8 Hz, 3H). MS (ESI): m/z 660.2 [M+H]$^+$.

Example 4/3

2,3-Dichloro-4-(2-(5-(2-hydroxypropan-2-yl)-1,3,4-oxadiazol-2-yl)-4-((S)-2-methylpiperidine-1-carbonyl)thiazol-5-yl)-N—((S)-1,1,1-trifluoropropan-2-yl)benzenesulfonamide

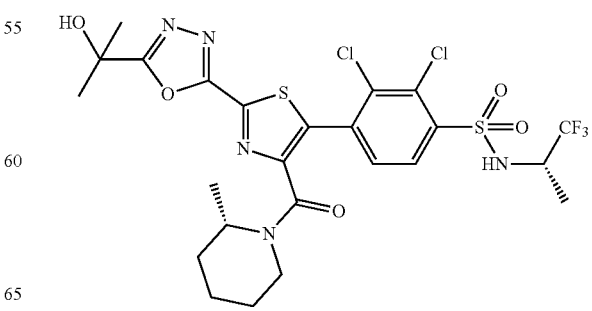

The title compound was prepared as described for the synthesis of Example 4, using in step a (S)-4-bromo-2,3-dichloro-N-(1,1,1-trifluoropropan-2-yl)benzenesulfonamide (Intermediate 12/3) in place of (S)-4-bromo-N-(1,1,1-trifluoropropan-2-yl)naphthalene-1-sulfonamide and in step b (S)-2-methylpiperidine in place of 4-methylpiperidine. ¹H NMR (400 MHz, CDCl₃): δ ppm 8.10-8.08 (m, 1H), 7.74-7.65 (m, 1H), 5.45 (d, J=9.6 Hz, 1H), 4.90-4.43 (m, 1H), 4.11-4.06 (m, 1H), 3.92-3.43 (m, 1H), 2.96-2.82 (m, 1H), 1.80 (s, 6H), 1.62-1.06 (m, 12H). MS (ESI): m/z 656.1 [M+H]⁺.

Example 4/4

(S)-2,3-Dichloro-4-(4-(4,4-difluoropiperidine-1-carbonyl)-2-(5-(2-hydroxypropan-2-yl)-1,3,4-oxadiazol-2-yl)thiazol-5-yl)-N-(1,1,1-trifluoropropan-2-yl)benzenesulfonamide

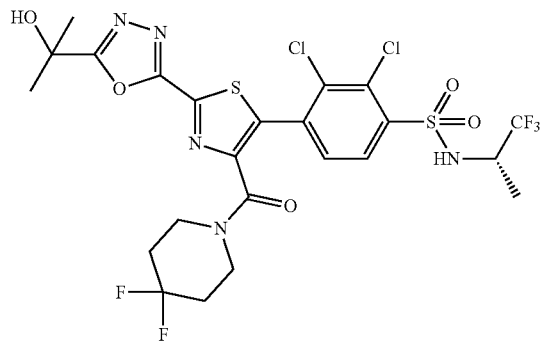 [SMILES: C[C@H](NS(=O)(=O)c1ccc(-c2sc(-c3nnc(C(C)(C)O)o3)nc2C(=O)N2CCC(F)(F)CC2)c(Cl)c1Cl)C(F)(F)F]

The title compound was prepared as described for the synthesis of Example 4, using in step a (S)-4-bromo-2,3-dichloro-N-(1,1,1-trifluoropropan-2-yl)benzenesulfonamide (Intermediate 12/3) in place of (S)-4-bromo-N-(1,1,1-trifluoropropan-2-yl)naphthalene-1-sulfonamide and in step b 4,4-difluoropiperidine in place of 4-methylpiperidine. ¹H NMR (400 MHz, CDCl₃): δ ppm 8.11 (d, J=8.4 Hz, 1H), 7.64 (d, J=8.4 Hz, 1H), 5.39 (d, J=10.0 Hz, 1H), 4.12-4.06 (m, 1H), 3.83-3.75 (m, 2H), 3.63-3.60 (m, 2H), 2.67 (br s, 1H), 2.08-1.94 (m, 4H), 1.80 (s, 6H), 1.42 (d, J=7.2 Hz, 3H). MS (ESI): m/z 678.0 [M+H]⁺.

Example 4/4 can Also be Prepared by the Following Route:

A mixture of (S)-4-bromo-2,3-dichloro-N-(1,1,1-trifluoropropan-2-yl)benzenesulfonamide (18.5 g, 46.0 mmol, Intermediate 12/3), (4,4-difluoropiperidin-1-yl)(2-(5-(2-hydroxypropan-2-yl)-1,3,4-oxadiazol-2-yl)thiazol-4-yl)methanone (15 g, 41.9 mmol, Intermediate 4, step d), palladium(II) acetate (0.47 g, 2.09 mmol), potassium acetate (8.22 g, 83.7 mmol), pivalic acid (1.71 g, 16.7 mmol), and butyronitrile (150 mL) was degassed for 15 minutes then heated to reflux for 10 h. The solvent was removed under vacuum and then partitioned between EtOAc (150 mL), water (75 mL), and saturated sodium carbonate solution (75 mL). The layers were separated and the aqueous layer was extracted with EtOAc (75 mL). The combined organic layers were dried over magnesium sulfate, filtered, and the solvent was removed under vacuum. The material was purified by FCC on silica gel (10-60% EtOAc in hexanes). The material was further purified via prep-HPLC using a 2000 g Lichroprep silicagel 25-40 um (Merck), 110 mm×40 cm column, 97.5% DCM/2.5% MeOH (0-25 min and 40-50 min), 95% DCM/5% MeOH (25-40 min) 500 mL/min flow to provide the title compound.

Example 4/5

(S)-2,3-Dichloro-4-(4-(4,4-difluoropiperidine-1-carbonyl)-2-(1,3,4-oxadiazol-2-yl)thiazol-5-yl)-N-(1,1,1-trifluoropropan-2-yl)benzenesulfonamide

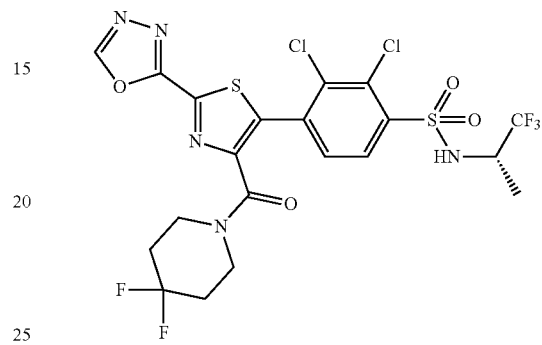

The title compound was obtained in the preparation of Example 4/4 as a by-product. Additional purification by Hyperprep C18 HS BDS column (35% 0.5% ammonium acetate in water/65% methanol, 80 mL/min) provided the title compound. ¹H NMR (400 MHz, CDCl₃) δ 8.67-8.58 (s, 1H), 8.16-8.09 (d, J=8.3 Hz, 1H), 7.68-7.61 (d, J=8.3 Hz, 1H), 5.39-5.28 (d, J=9.6 Hz, 1H), 4.16-4.00 (m, 1H), 3.87-3.71 (m, 2H), 3.71-3.60 (m, 2H), 2.15-1.90 (m, 4H), 1.48-1.39 (d, J=7.0 Hz, 3H). MS (ESI): m/z 619.8 [M+H]⁺.

Example 4/6

(S)-5-(2,3-Dichloro-4-(N-(1,1,1-trifluoropropan-2-yl)sulfamoyl)phenyl)-N-ethyl-2-(5-(2-hydroxypropan-2-yl)-1,3,4-oxadiazol-2-yl)-N-(2,2,2-trifluoroethyl)thiazole-4-carboxamide

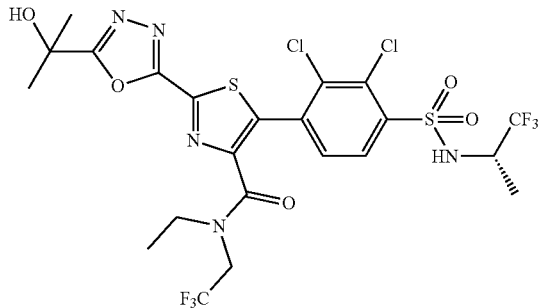 [SMILES: CCN(CC(F)(F)F)C(=O)c1nc(-c2nnc(C(C)(C)O)o2)sc1-c1ccc(S(=O)(=O)N[C@@H](C)C(F)(F)F)c(Cl)c1Cl]

The title compound was prepared as described for the synthesis of Example 4, using in step a (S)-4-bromo-2,3-dichloro-N-(1,1,1-trifluoropropan-2-yl)benzenesulfonamide (Intermediate 12/3) in place of (S)-4-bromo-N-(1,1,1-trifluoropropan-2-yl)naphthalene-1-sulfonamide and in step b N-ethyl-2,2,2-trifluoroethanamine in place of 4-methylpiperidine. ¹H NMR (400 MHz, CDCl₃): δ ppm 8.09 (d, J=8.4 Hz, 1H), 7.65-7.58 (m, 1H), 5.41 (br s, 1H), 4.42-4.02 (m, 3H), 3.60-3.49 (m, 2H), 1.81 (s, 6H), 1.41-1.38 (m, 3H), 1.22-1.18 (m, 3H). MS (ESI): m/z 683.9 [M+H]⁺.

Example 5

Step a (S)-2-(2-(4-(4-Methylpiperidine-1-carbonyl)-5-(4-(N-(1,1,1-trifluoropropan-2-yl)sulfamoyl)naphthalen-1-yl)thiazole-2-carbonyl)hydrazinyl)-2-oxoacetamide

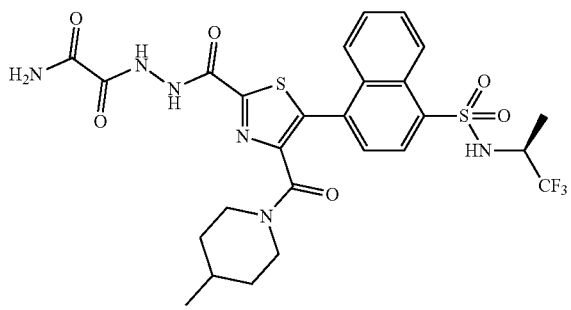 [SMILES: CC1CCN(C(=O)c2nc(C(=O)NNC(=O)C(N)=O)sc2-c2ccc(S(=O)(=O)N[C@@H](C)C(F)(F)F)c3ccccc23)CC1]

A solution of (S)-4-(2-(hydrazinecarbonyl)-4-(4-methylpiperidine-1-carbonyl)thiazol-5-yl)-N-(1,1,1-trifluoropropan-2-yl)naphthalene-1-sulfonamide (115 mg, 0.202 mmol, Example 4, step c), 2-amino-2-oxoacetic acid (36 mg, 0.40 mmol), HATU (114 mg, 0.300 mmol), and TEA (0.1 mL, 0.7 mmol) in acetonitrile (5 mL) was stirred at rt for 2 h. The mixture was poured into H₂O (10 mL) and extracted with EtOAc (8 mL×4). The combined organic layers were washed with brine, dried over anhydrous Na₂SO₄, filtered and concentrated to dryness. The residue was purified by prep-TLC (DCM/MeOH=9:1) to afford the title compound as a colorless solid.

Example 5

(S)-5-(4-(4-Methylpiperidine-1-carbonyl)-5-(4-(N-(1,1,1-trifluoropropan-2-yl)sulfamoyl)naphthalen-1-yl)thiazol-2-yl)-1,3,4-oxadiazole-2-carboxamide

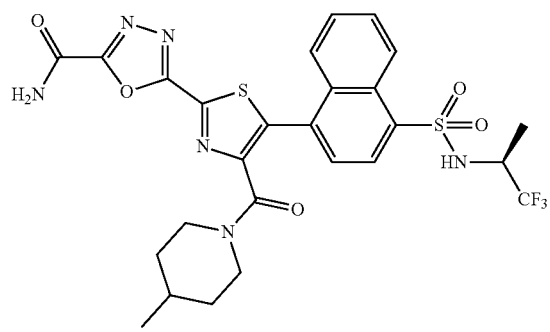 [SMILES: CC1CCN(C(=O)c2nc(-c3nnc(C(N)=O)o3)sc2-c2ccc(S(=O)(=O)N[C@@H](C)C(F)(F)F)c3ccccc23)CC1]

A solution of (S)-2-(2-(4-(4-methylpiperidine-1-carbonyl)-5-(4-(N-(1,1,1-trifluoropropan-2-yl)sulfamoyl)naphthalen-1-yl)thiazole-2-carbonyl)hydrazinyl)-2-oxoacetamide (50 mg, 0.078 mmol, Example 5, step a), 4-methylbenzene-1-sulfonyl chloride (23 mg, 0.12 mmol), and TEA (0.05 mL, 0.4 mmol) in DCM (10 mL) was stirred at rt overnight. The mixture was poured into H₂O (10 mL) and extracted with EtOAc (8 mL×3). The combined organic layers were washed with brine, dried over anhydrous Na₂SO₄, filtered, and concentrated to dryness. The residue was purified by prep-TLC (EtOAc/PE=5:1) to give the title compound as a yellow solid. ¹H NMR (400 MHz, DMSO-d₆): δ ppm 9.09 (s, 1H), 8.84 (s, 1H), 8.76 (d, J=8.4 Hz, 1H), 8.41 (s, 1H), 8.29 (d, J=7.6 Hz, 1H), 8.02 (d, J=8.8 Hz, 1H), 7.85-7.70 (m, 3H), 4.16-4.12 (m, 2H), 3.69-3.65 (m, 1H), 2.91-2.85 (m, 1H), 2.44-2.42 (m, 1H), 1.49-1.26 (m, 3H), 1.10-1.03 (m, 3H), 0.75-0.70 (m, 3H), 0.56-0.41 (m, 2H). MS (ESI): m/z 623.2 [M+H]⁺.

Example 5/1

(S)-5-(5-(2,3-Dichloro-4-(N-(1,1,1-trifluoropropan-2-yl)sulfamoyl)phenyl)-4-(diethylcarbamoyl)thiazol-2-yl)-1,3,4-oxadiazole-2-carboxamide

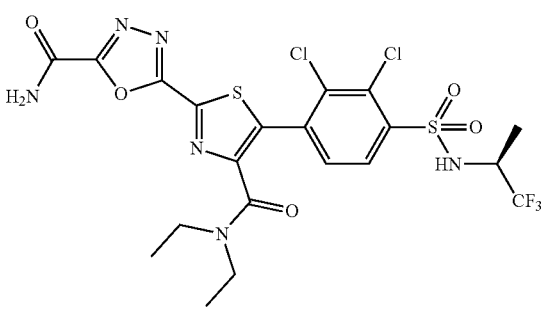 [SMILES: CCN(CC)C(=O)c1nc(-c2nnc(C(N)=O)o2)sc1-c1ccc(S(=O)(=O)N[C@@H](C)C(F)(F)F)c(Cl)c1Cl]

The title compound was prepared as described for the synthesis of Example 5 using (S)-4-bromo-2,3-dichloro-N-(1,1,1-trifluoropropan-2-yl)benzenesulfonamide (Intermediate 12/3) in place of (S)-4-bromo-N-(1,1,1-trifluoropropan-2-yl)naphthalene-1-sulfonamide and diethylamine in place of 4-methylpiperidine. ¹H NMR (400 MHz, DMSO-d₆): δ ppm 9.24 (s, 1H), 8.81 (s, 1H), 8.38 (s, 1H), 8.10 (d, J=7.6 Hz, 1H), 7.76 (d, J=8.4 Hz, 1H), 4.19-4.14 (m, 1H), 3.37-3.33 (m, 2H), 3.30-3.26 (m, 2H), 1.26 (d, J=6.8 Hz, 3H), 1.09 (t, J=6.8 Hz, 3H), 1.01 (t, J=6.8 Hz, 3H). MS (ESI): m/z 615.0 [M+H]⁺.

Example 6

Step a (S)-2,3-Dichloro-4-(4-(hydroxymethyl)-2-(5-(2-hydroxypropan-2-yl)-1,3,4-oxadiazol-2-yl)thiazol-5-yl)-N-(1,1,1-trifluorobutan-2-yl)benzenesulfonamide

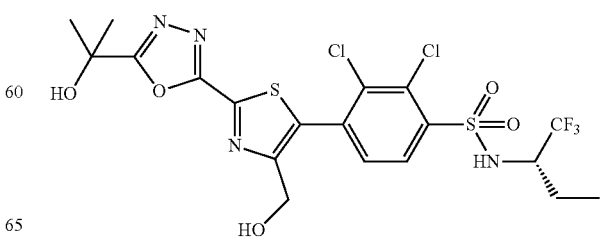

A mixture of 2-(5-(4-(hydroxymethyl)thiazol-2-yl)-1,3,4-oxadiazol-2-yl)propan-2-ol (180 mg, 0.75 mmol, Intermediate 3, step c), (S)-4-bromo-2,3-dichloro-N-(1,1,1-trifluorobutan-2-yl)benzenesulfonamide (310 mg, 0.75 mmol, Intermediate 12/4), Pd(OAc)$_2$ (56 mg, 0.25 mmol), P(Cy)$_3$·HBF$_4$ (56 mg, 0.15 mmol), pivalic acid (56 mg, 0.55 mmol), K$_2$CO$_3$ (154 mg, 1.12 mmol), and DMA (7 mL) was stirred at 100° C. overnight. The mixture was poured into water (20 mL) and extracted with EtOAc (50 mL×3). The combined organic layers were washed with brine, dried over anhydrous Na$_2$SO$_4$, filtered, concentrated to dryness, and the residue was purified by prep-TLC (PE/EtOAc=1:1) to give the title compound as a yellow solid.

Example 6

Step b (S)-5-(2,3-Dichloro-4-(N-(1,1,1-trifluorobutan-2-yl)sulfamoyl)phenyl)-2-(5-(2-hydroxypropan-2-yl)-1,3,4-oxadiazol-2-yl)thiazole-4-carboxylic acid

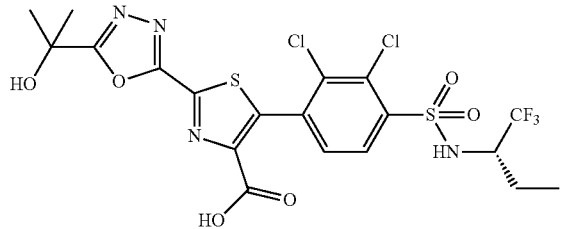 [SMILES: CC[C@H](NS(=O)(=O)c1ccc(-c2sc(-c3nnc(C(C)(C)O)o3)nc2C(=O)O)c(Cl)c1Cl)C(F)(F)F]

A mixture of (S)-2,3-dichloro-4-(4-(hydroxymethyl)-2-(5-(2-hydroxypropan-2-yl)-1,3,4-oxadiazol-2-yl)thiazol-5-yl)-N-(1,1,1-trifluorobutan-2-yl)benzenesulfonamide (215 mg, 0.374 mmol, Example 6, step a), TEMPO (89 mg, 0.57 mmol), iodobenzene diacetate (473 mg, 1.47 mmol), H$_2$O (1 mL), and acetonitrile (3 mL) was stirred at rt overnight. H$_2$O (5 mL) was added and the aqueous layer was extracted with EtOAc (10 mL×3). The combined organic layers were washed with brine, dried over anhydrous MgSO$_4$, filtered, and concentrated to dryness to give the title compound as a brown solid, which was used in next step without further purification.

Example 6

(S)-5-(2,3-Dichloro-4-(N-(1,1,1-trifluorobutan-2-yl)sulfamoyl)phenyl)-N,N-diethyl-2-(5-(2-hydroxypropan-2-yl)-1,3,4-oxadiazol-2-yl)thiazole-4-carboxamide

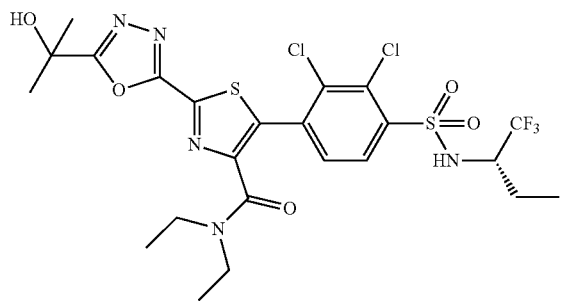 [SMILES: CC[C@H](NS(=O)(=O)c1ccc(-c2sc(-c3nnc(C(C)(C)O)o3)nc2C(=O)N(CC)CC)c(Cl)c1Cl)C(F)(F)F]

A mixture of (S)-5-(2,3-dichloro-4-(N-(1,1,1-trifluorobutan-2-yl)sulfamoyl)phenyl)-2-(5-(2-hydroxypropan-2-yl)-1,3,4-oxadiazol-2-yl)thiazole-4-carboxylic acid (100 mg, 0.17 mmol, Example 6, step b), diethylamine (20 mg, 0.26 mmol), HATU (99 mg, 0.26 mmol), TEA (0.1 mL, 0.7 mmol), and acetonitrile (2 mL) was stirred at rt for 2 h. The mixture was poured into H$_2$O (10 mL) and extracted with EtOAc (25 mL×3). The combined organic layers were washed with brine, dried over anhydrous Na$_2$SO$_4$, and concentrated to dryness. The residue was purified by prep-TLC (PE/EtOAc=1:2) to afford the title compound as a white solid. $^1$H NMR (400 MHz, CDCl$_3$): δ ppm 8.06 (d, J=8.2 Hz, 1H), 7.71 (d, J=8.2 Hz, 1H), 5.34-5.36 (m, 1H), 3.90-3.82 (m, 1H), 3.36-3.52 (m, 2H), 3.22-3.27 (m, 2H), 2.74 (s, 1H), 1.83-1.95 (m, 1H), 1.80 (s, 6H), 1.56-1.58 (m, 1H), 1.05-1.14 (m, 9H). MS (ESI): m/z 644.1 [M+H]$^+$.

Example 6/1

(S)-2,3-Dichloro-4-(4-(4-fluoropiperidine-1-carbonyl)-2-(5-(2-hydroxypropan-2-yl)-1,3,4-oxadiazol-2-yl)thiazol-5-yl)-N-(1,1,1-trifluorobutan-2-yl)benzenesulfonamide

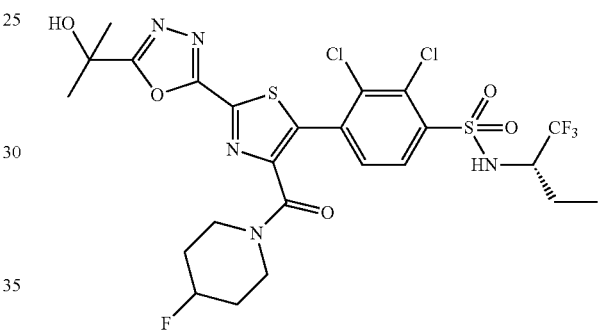

The title compound was prepared as described for the synthesis of Example 6, using 4-fluoropiperidine in place of diethylamine. $^1$H NMR (400 MHz, CDCl$_3$): δ ppm 8.08 (d, J=8.4 Hz, 1H), 7.66 (d, J=8.4 Hz, 1H), 5.45-5.44 (m, 1H), 4.91-4.78 (m, 1H), 4.06-3.87 (m, 2H), 3.51-3.38 (m, 3H), 2.88-2.91 (m, 1H), 1.98-1.80 (m, 11H), 1.63-1.55 (m, 1H), 1.11 (t, J=7.6 Hz, 3H). MS (ESI): m/z 674.1 [M+H]$^+$.

Example 6/2

(S)-2,3-Dichloro-4-(4-(3,3-difluoropyrrolidine-1-carbonyl)-2-(5-(2-hydroxypropan-2-yl)-1,3,4-oxadiazol-2-yl)thiazol-5-yl)-N-(1,1,1-trifluoropropan-2-yl)benzenesulfonamide

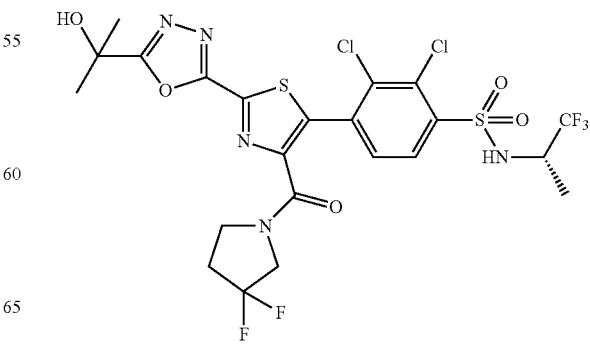

The title compound was prepared as described for the synthesis of Example 6, using in step a (S)-4-bromo-2,3-dichloro-N-(1,1,1-trifluoropropan-2-yl)benzenesulfonamide (Intermediate 12/3) in place of (S)-4-bromo-2,3-dichloro-N-(1,1,1-trifluorobutan-2-yl)benzenesulfonamide and in the final step 3,3-difluoropyrrolidine in place of diethylamine. $^1$H NMR (400 MHz, CDCl$_3$): δ ppm 8.10 (d, J=8.4 Hz, 1H), 7.60-7.56 (m, 1H), 5.39 (br s, 1H), 4.22-4.03 (m, 3H), 3.94-3.80 (m, 2H), 2.69 (br s, 1H), 2.49-2.40 (m, 2H), 1.81 (s, 6H), 1.40 (d, J=7.2 Hz, 3H). MS (ESI): m/z 664.0 [M+H]$^+$.

Example 6/3

(S)-3-(Difluoromethyl)-4-(4-(4,4-difluoropiperidine-1-carbonyl)-2-(5-(2-hydroxypropan-2-yl)-1,3,4-oxadiazol-2-yl)thiazol-5-yl)-2-fluoro-N-(1,1,1-trifluorobutan-2-yl)benzenesulfonamide

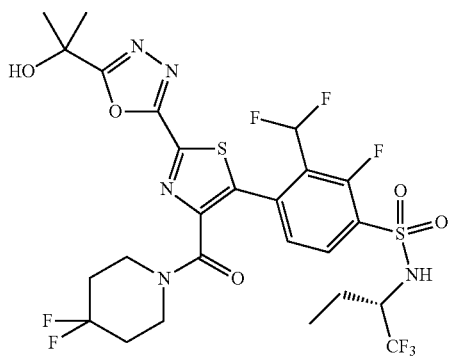 [SMILES: CC[C@H](NS(=O)(=O)c1ccc(-c2sc(-c3nnc(C(C)(C)O)o3)nc2C(=O)N2CCC(F)(F)CC2)c(C(F)F)c1F)C(F)(F)F]

The title compound was prepared as described for the synthesis of Example 6, using in step a (S)-4-bromo-3-(difluoromethyl)-2-fluoro-N-(1,1,1-trifluorobutan-2-yl)benzenesulfonamide (Intermediate 12/1, step e) in place of (S)-4-bromo-2,3-dichloro-N-(1,1,1-trifluorobutan-2-yl)benzenesulfonamide and in the final step 4,4-difluoropiperidine in place of diethylamine. $^1$H NMR (400 MHz, CDCl$_3$): δ ppm 8.06 (t, J=7.6 Hz, 1H), 7.50 (d, J=8.0 Hz, 1H), 6.95 (t, J=53.6 Hz, 1H), 5.13 (br s, 1H), 3.93-3.91 (m, 1H), 3.75-3.65 (m, 4H), 2.60 (s, 1H), 2.04-1.91 (m, 5H), 1.80 (s, 6H), 1.63-1.60 (m, 1H), 1.10 (t, J=7.6 Hz, 3H). MS (ESI): m/z 692.0 [M+H]$^+$.

Example 6/4

4-(4-((S)-4,4-Difluoro-2-methylpyrrolidine-1-carbonyl)-2-(5-(2-hydroxypropan-2-yl)-1,3,4-oxadiazol-2-yl)thiazol-5-yl)-3-(difluoromethyl)-2-fluoro-N—((S)-1,1,1-trifluoropropan-2-yl)benzenesulfonamide

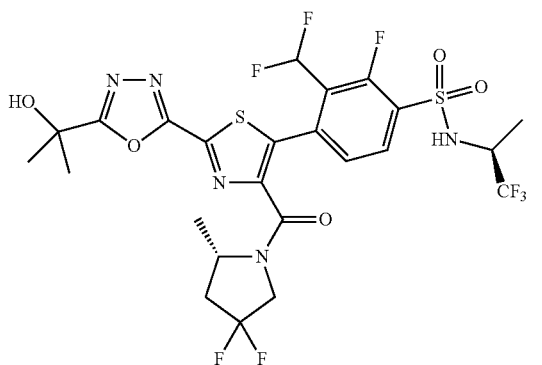 [SMILES: C[C@H](NS(=O)(=O)c1ccc(-c2sc(-c3nnc(C(C)(C)O)o3)nc2C(=O)N2CC(F)(F)C[C@@H]2C)c(C(F)F)c1F)C(F)(F)F]

The title compound was prepared as described for the synthesis of Example 6, using in step a (S)-4-bromo-3-(difluoromethyl)-2-fluoro-N-(1,1,1-trifluoropropan-2-yl)benzenesulfonamide (Intermediate 12/2) in place of (S)-4-bromo-2,3-dichloro-N-(1,1,1-trifluorobutan-2-yl)benzenesulfonamide and in the final step (S)-4,4-difluoro-2-methylpyrrolidine hydrochloride (Intermediate 14, step b) in place of diethylamine. $^1$H NMR (400 MHz, CDCl$_3$): δ ppm 8.07 (t, J=7.6 Hz, 1H), 7.46-7.44 (m, 1H), 6.90 (td, J=53.2, J=4.0 Hz, 1H), 5.18 (d, J=10.0 Hz, 1H), 4.50-4.44 (m, 1H), 4.32-4.02 (m, 3H), 2.63-2.53 (m, 2H), 2.16-2.05 (m, 1H), 1.82 (s, 6H), 1.44 (d, J=6.8 Hz, 3H), 1.36-1.32 (m, 3H). MS (ESI): m/z 678.2 [M+H]$^+$.

Example 6/5

2,3-Dichloro-4-(4-((S)-4,4-difluoro-2-methylpyrrolidine-1-carbonyl)-2-(5-(2-hydroxypropan-2-yl)-1,3,4-oxadiazol-2-yl)thiazol-5-yl)-N—((S)-1,1,1-trifluoropropan-2-yl)benzenesulfonamide

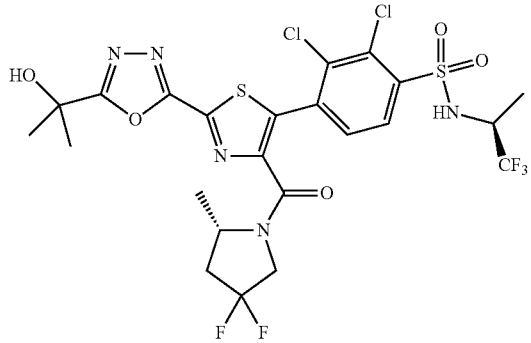 [SMILES: C[C@H](NS(=O)(=O)c1ccc(-c2sc(-c3nnc(C(C)(C)O)o3)nc2C(=O)N2CC(F)(F)C[C@@H]2C)c(Cl)c1Cl)C(F)(F)F]

The title compound was prepared as described for the synthesis of Example 6, using in step a (S)-4-bromo-2,3-dichloro-N-(1,1,1-trifluoropropan-2-yl)benzenesulfonamide (Intermediate 12/3) in place of (S)-4-bromo-2,3-dichloro-N-(1,1,1-trifluorobutan-2-yl)benzenesulfonamide and in the final step (S)-4,4-difluoro-2-methylpyrrolidine hydrochloride (Intermediate 14, step b) in place of diethylamine. $^1$H NMR (400 MHz, CDCl$_3$): δ ppm 8.10 (d, J=8.4 Hz, 1H), 7.62-7.57 (m, 1H), 5.33 (br s, 1H), 4.97-4.49 (m, 1H), 4.20-3.82 (m, 3H), 2.63-2.58 (m, 2H), 2.14-2.09 (m, 1H), 1.82 (s, 6H), 1.42-1.27 (m, 6H). MS (ESI): m/z 677.7 [M+H]$^+$.

Example 6/6

(S)-5-(2,3-Dichloro-4-(N-(1,1,1-trifluoropropan-2-yl)sulfamoyl)phenyl)-2-(5-(2-hydroxypropan-2-yl)-1,3,4-oxadiazol-2-yl)-N-methyl-N-propylthiazole-4-carboxamide

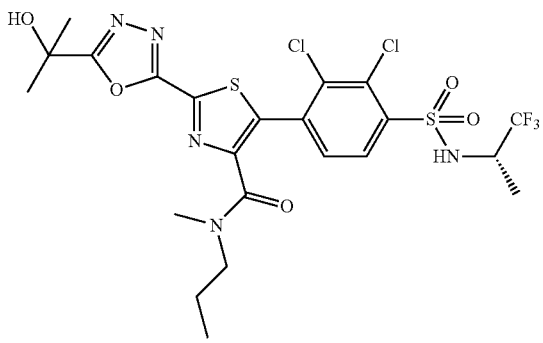 [SMILES: CCCN(C)C(=O)c1nc(-c2nnc(C(C)(C)O)o2)sc1-c1ccc(S(=O)(=O)N[C@@H](C)C(F)(F)F)c(Cl)c1Cl]

The title compound was prepared as described for the synthesis of Example 6, using in step a (S)-4-bromo-2,3-dichloro-N-(1,1,1-trifluoropropan-2-yl)benzenesulfonamide (Intermediate 12/3) in place of (S)-4-bromo-2,3-dichloro-N-(1,1,1-trifluorobutan-2-yl)benzenesulfonamide and in the final step N-methylpropan-1-amine in place of diethylamine.
$^1$H NMR (400 MHz, CDCl$_3$): δ ppm 8.10-8.07 (m, 1H), 7.72 and 7.67 (d, J=8.4 Hz, amide rotamers, 1H), 5.43 (br s, 1H), 4.10-4.05 (m, 1H), 3.42-3.30 (m, 1H), 3.22-3.18 (m, 1H), 2.98 and 2.92 (s, amide rotamers, 3H), 2.77 (br s, 1H), 1.80 (s, 6H), 1.56-1.49 (m, 2H), 1.42 (d, J=7.2 Hz, 3H), 0.84-0.79 (m, 3H). MS (ESI): m/z 629.8 [M+H]$^+$.

Example 6/7

(S)-5-(2,3-Dichloro-4-(N-(1,1,1-trifluoropropan-2-yl)sulfamoyl)phenyl)-N-ethyl-2-(5-(2-hydroxypropan-2-yl)-1,3,4-oxadiazol-2-yl)-N-isopropylthiazole-4-carboxamide

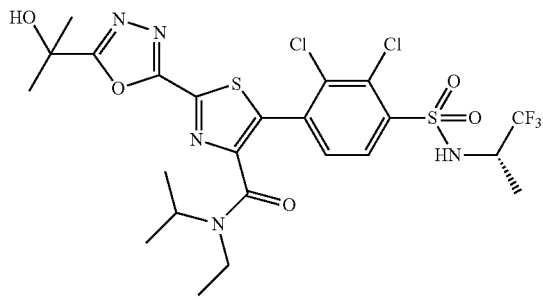 [SMILES: CCN(C(=O)c1nc(-c2nnc(C(C)(C)O)o2)sc1-c1ccc(S(=O)(=O)N[C@@H](C)C(F)(F)F)c(Cl)c1Cl)C(C)C]

The title compound was prepared as described for the synthesis of Example 6, using in step a (S)-4-bromo-2,3-dichloro-N-(1,1,1-trifluoropropan-2-yl)benzenesulfonamide (Intermediate 12/3) in place of (S)-4-bromo-2,3-dichloro-N-(1,1,1-trifluorobutan-2-yl)benzenesulfonamide and in the final step N-ethylpropan-2-amine in place of diethylamine.
$^1$H NMR (400 MHz, CDCl$_3$): δ ppm 8.07 (d, J=8.2 Hz, 1H), 7.74 (d, J=8.2 Hz, 1H), 5.46 (br s, 1H), 4.47-3.83 (m, 2H), 3.40-3.18 (m, 2H), 2.82 (br s, 1H), 1.78 (s, 6H), 1.42 (d, J=7.2 Hz, 3H), 1.13-1.10 (m, 9H). MS (ESI): m/z 643.8 [M+H]$^+$.

Example 6/8

(S)-5-(2,3-Dichloro-4-(N-(1,1,1-trifluoropropan-2-yl)sulfamoyl)phenyl)-N-ethyl-2-(5-(2-hydroxypropan-2-yl)-1,3,4-oxadiazol-2-yl)-N-propylthiazole-4-carboxamide

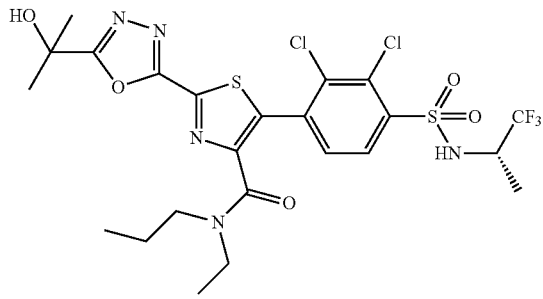 [SMILES: CCCN(CC)C(=O)c1nc(-c2nnc(C(C)(C)O)o2)sc1-c1ccc(S(=O)(=O)N[C@@H](C)C(F)(F)F)c(Cl)c1Cl]

The title compound was prepared as described for the synthesis of Example 6, using in step a (S)-4-bromo-2,3-dichloro-N-(1,1,1-trifluoropropan-2-yl)benzenesulfonamide (Intermediate 12/3) in place of (S)-4-bromo-2,3-dichloro-N-(1,1,1-trifluorobutan-2-yl)benzenesulfonamide and in the final step N-ethylpropan-1-amine in place of diethylamine.
$^1$H NMR (400 MHz, DMSO-d$_6$): δ ppm 9.24 (s, 1H), 8.09 (d, J=8.2 Hz, 1H), 7.75 (d, J=8.2 Hz, 1H), 6.09 (s, 1H), 4.15-1.16 (m, 1H), 3.36-3.33 (m, 1H), 3.28-3.23 (m, 2H), 3.16-3.12 (m, 1H), 1.63 (s, 6H), 1.51-1.41 (m, 2H), 1.25 (d, J=6.8 Hz, 3H), 1.07-0.97 (m, 3H), 0.74 (t, J=7.2 Hz, 3H). MS (ESI): m/z 643.8 [M+H]$^+$.

Example 6/9

2,3-Dichloro-4-(2-(5-(2-hydroxypropan-2-yl)-1,3,4-oxadiazol-2-yl)-4-((S)-3-methylmorpholine-4-carbonyl)thiazol-5-yl)-N—((S)-1,1,1-trifluoropropan-2-yl)benzenesulfonamide

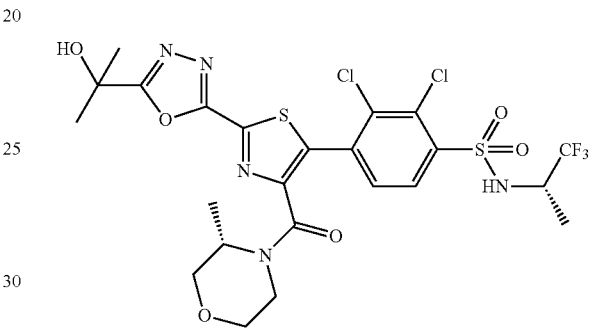

The title compound was prepared as described for the synthesis of Example 6, using in step a (S)-4-bromo-2,3-dichloro-N-(1,1,1-trifluoropropan-2-yl)benzenesulfonamide (Intermediate 12/3) in place of (S)-4-bromo-2,3-dichloro-N-(1,1,1-trifluorobutan-2-yl)benzenesulfonamide and in the final step (S)-3-methylmorpholine in place of diethylamine.
$^1$H NMR (400 MHz, CDCl$_3$): δ ppm 8.10 (d, J=8.0 Hz, 1H), 7.67 (d, J=8.4 Hz, 1H, amide rotamers), 5.47 (br s, 1H), 4.60-3.18 (m, 8H), 2.78 (s, 1H), 1.80 (s, 6H), 1.43 (d, J=6.8 Hz, 3H), 1.29 (d, J=6.4 Hz, 3H, amide rotamers). MS (ESI): m/z 657.8 [M+H]$^+$.

Example 6/10

(S)-3-(4-(4-Fluoropiperidine-1-carbonyl)-2-(5-(2-hydroxypropan-2-yl)-1,3,4-oxadiazol-2-yl)thiazol-5-yl)-5-(1-methylcyclopropyl)-N-(1,1,1-trifluoropropan-2-yl)benzamide

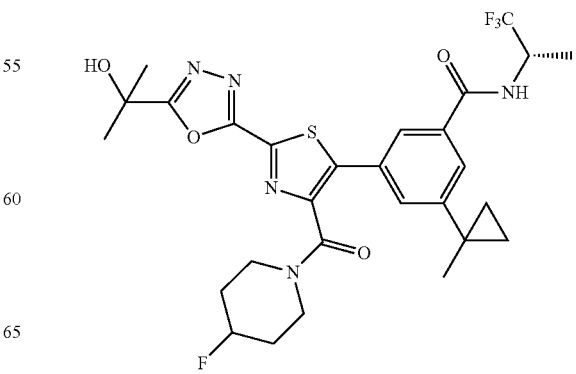

The title compound was prepared as described for the synthesis of Example 6, using in step a (S)-3-bromo-5-(1-methylcyclopropyl)-N-(1,1,1-trifluoropropan-2-yl)benzamide (Intermediate 16) in place of (S)-4-bromo-2,3-dichloro-N-(1,1,1-trifluorobutan-2-yl)benzenesulfonamide and in the final step 4-fluoropiperidine in place of diethylamine. ¹H NMR (400 MHz, CDCl₃): δ ppm 7.77-7.66 (m, 2H), 7.45-7.41 (m, 1H), 5.01-4.98 (m, 1H), 4.88-4.70 (m, 1H), 4.22-4.18 (m, 1H), 3.56-3.47 (m, 1H), 3.26-3.08 (m, 2H), 2.01-1.41 (m, 16H), 0.88-0.82 (m, 4H). MS (ESI): m/z 610.2 [M+H]⁺.

Example 6/11

(S)-3-Chloro-4-(4-(4-fluoropiperidine-1-carbonyl)-2-(5-(2-hydroxypropan-2-yl)-1,3,4-oxadiazol-2-yl)thiazol-5-yl)-N-(1,1,1-trifluorobutan-2-yl)benzenesulfonamide

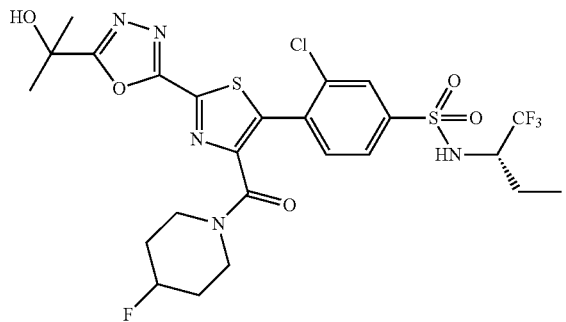 [SMILES: CC[C@H](NS(=O)(=O)c1ccc(-c2sc(-c3nnc(C(C)(C)O)o3)nc2C(=O)N2CCC(F)CC2)c(Cl)c1)C(F)(F)F]

The title compound was prepared as described for the synthesis of Example 6, using in step a (S)-4-bromo-3-chloro-N-(1,1,1-trifluorobutan-2-yl)benzenesulfonamide (Intermediate 12/9) in place of (S)-4-bromo-2,3-dichloro-N-(1,1,1-trifluorobutan-2-yl)benzenesulfonamide and in the final step 4-fluoropiperidine in place of diethylamine. ¹H NMR (400 MHz, CDCl₃): δ ppm 8.02 (s, 1H), 7.83 (d, J=8.0 Hz, 1H), 7.74 (d, J=8.0 Hz, 1H), 5.03 (d, J=9.6 Hz, 1H), 4.89-4.77 (m, 1H), 4.03-3.90 (m, 2H), 3.48-3.42 (m, 3H), 1.95-1.54 (m, 12H), 1.09 (t, J=7.6 Hz, 3H). MS (ESI): m/z 640.1 [M+H]⁺.

Example 6/12

(S)-3-Chloro-4-(4-(4,4-difluoropiperidine-1-carbonyl)-2-(5-(2-hydroxypropan-2-yl)-1,3,4-oxadiazol-2-yl)thiazol-5-yl)-N-(1,1,1-trifluorobutan-2-yl)benzenesulfonamide

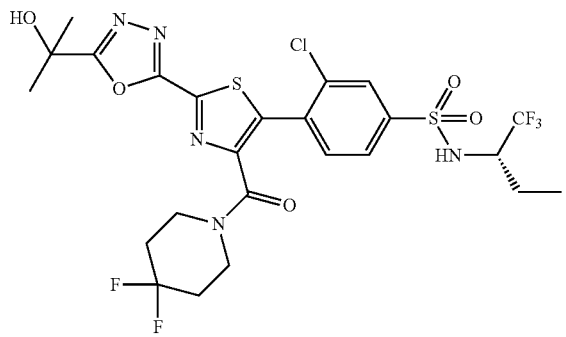 [SMILES: CC[C@H](NS(=O)(=O)c1ccc(-c2sc(-c3nnc(C(C)(C)O)o3)nc2C(=O)N2CCC(F)(F)CC2)c(Cl)c1)C(F)(F)F]

The title compound was prepared as described for the synthesis of Example 6, using in step a (S)-4-bromo-3-chloro-N-(1,1,1-trifluorobutan-2-yl)benzenesulfonamide (Intermediate 12/9) in place of (S)-4-bromo-2,3-dichloro-N-(1,1,1-trifluorobutan-2-yl)benzenesulfonamide and in the final step 4,4-difluoropiperidine in place of diethylamine. ¹H NMR (400 MHz, CDCl₃): δ ppm 8.01 (s, 1H), 7.84-7.82 (m, 1H), 7.70 (d, J=8.0 Hz, 1H), 5.34 (d, J=9.6 Hz, 1H), 3.94-3.87 (m, 1H), 3.80-3.76 (m, 2H), 3.57-3.54 (m, 2H), 2.04-1.86 (m, 5H), 1.79 (s, 6H), 1.62-1.54 (m, 1H), 1.07 (t, J=7.6 Hz, 3H). MS (ESI): m/z 658.1 [M+H]⁺.

Example 6/13

(S)-3-Chloro-4-(4-(3,3-difluoroazetidine-1-carbonyl)-2-(5-(2-hydroxypropan-2-yl)-1,3,4-oxadiazol-2-yl)thiazol-5-yl)-N-(1,1,1-trifluorobutan-2-yl)benzenesulfonamide

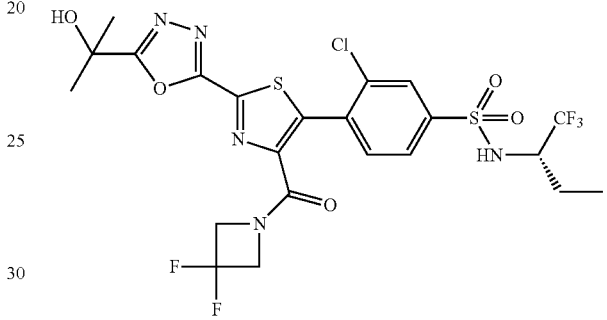

The title compound was prepared as described for the synthesis of Example 6, using in step a (S)-4-bromo-3-chloro-N-(1,1,1-trifluorobutan-2-yl)benzenesulfonamide (Intermediate 12/9) in place of (S)-4-bromo-2,3-dichloro-N-(1,1,1-trifluorobutan-2-yl)benzenesulfonamide and in the final step 3,3-difluoroazetidine in place of diethylamine. ¹H NMR (400 MHz, CDCl₃): δ ppm 7.99 (s, 1H), 7.81 (d, J=8.2 Hz, 1H), 7.58 (d, J=8.2 Hz, 1H), 5.21 (d, J=9.2 Hz, 1H), 4.98 (t, J=12.0 Hz, 2H), 4.45 (t, J=12.0 Hz, 2H), 3.91 (s, 1H), 1.92-1.87 (m, 1H), 1.80 (s, 6H), 1.59-1.53 (m, 1H), 1.05 (t, J=7.2 Hz, 3H). MS (ESI): m/z 630.0 [M+H]⁺.

Example 6/14

(S)-2-Chloro-3-(difluoromethyl)-4-(4-(4,4-difluoropiperidine-1-carbonyl)-2-(5-(2-hydroxypropan-2-yl)-1,3,4-oxadiazol-2-yl)thiazol-5-yl)-N-(1,1,1-trifluoropropan-2-yl)benzenesulfonamide

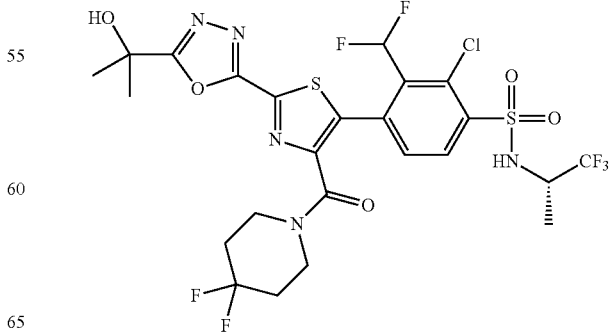

The title compound was prepared as described for the synthesis of Example 6, using in step a (S)-4-bromo-2-chloro-3-(difluoromethyl)-N-(1,1,1-trifluoropropan-2-yl)benzene sulfonamide (Intermediate 12/10) in place of (S)-4-bromo-2,3-dichloro-N-(1,1,1-trifluorobutan-2-yl)benzenesulfonamide and using in the final step 4,4-difluoropiperidine in place of diethylamine. $^1$H NMR (500 MHz, DMSO-d$_6$): δ ppm 9.21 (d, J=9.0 Hz, 1H), 8.26 (d, J=8.5 Hz, 1H), 7.74 (d, J=8.0 Hz, 1H), 7.28 (t, J=51.5 Hz, 1H), 4.22-4.17 (m, 1H), 3.63 (s, 4H), 1.97-1.91 (m, 4H), 1.63 (s, 6H), 1.25 (d, J=7.0 Hz, 3H). MS (ESI): m/z 694.1 [M+H]$^+$.

Example 6/15

(S)-3-Chloro-4-(4-(4,4-difluoropiperidine-1-carbonyl)-2-(5-(2-hydroxypropan-2-yl)-1,3,4-oxadiazol-2-yl)thiazol-5-yl)-2-fluoro-N-(1,1,1-trifluorobutan-2-yl)benzenesulfonamide

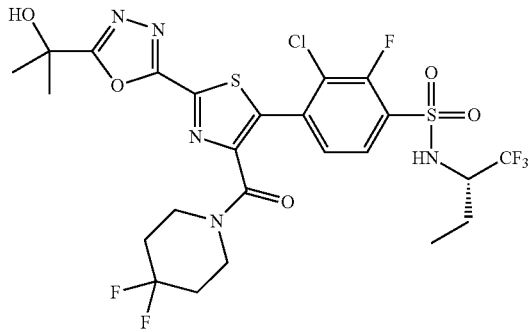 [SMILES: CC[C@H](NS(=O)(=O)c1ccc(-c2sc(-c3nnc(C(C)(C)O)o3)nc2C(=O)N2CCC(F)(F)CC2)c(Cl)c1F)C(F)(F)F]

The title compound was prepared as described for the synthesis of Example 6, using in step a (S)-4-bromo-3-chloro-2-fluoro-N-(1,1,1-trifluorobutan-2-yl)benzene sulfonamide (Intermediate 12/11) in place of (S)-4-bromo-2,3-dichloro-N-(1,1,1-trifluorobutan-2-yl)benzenesulfonamide and using in the final step 4,4-difluoropiperidine in place of diethylamine. $^1$H NMR (500 MHz, DMSO-d$_6$): δ ppm 9.30 (d, J=9.0 Hz, 1H), 7.91 (t, J=7.5 Hz, 1H), 7.63-7.61 (m, 1H), 3.97-3.93 (m, 1H), 3.68-3.51 (m, 4H), 1.97-1.91 (m, 4H), 1.73-1.68 (m, 1H), 1.63 (s, 6H), 1.57-1.51 (m, 1H), 0.83 (t, J=7.5 Hz, 3H). MS (ESI): m/z 676.1 [M+H]$^+$.

Example 6/16

(S)-2-(Difluoromethyl)-4-(4-(4,4-difluoropiperidine-1-carbonyl)-2-(5-(2-hydroxypropan-2-yl)-1,3,4-oxadiazol-2-yl)thiazol-5-yl)-3-fluoro-N-(1,1,1-trifluorobutan-2-yl)benzenesulfonamide

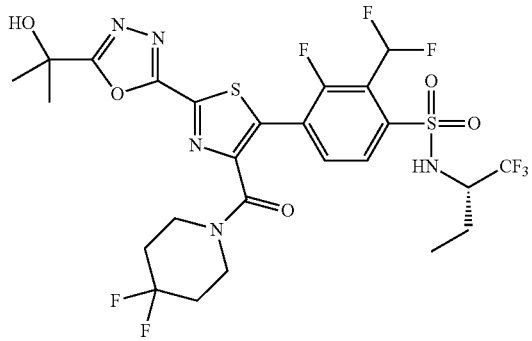 [SMILES: CC[C@H](NS(=O)(=O)c1ccc(-c2sc(-c3nnc(C(C)(C)O)o3)nc2C(=O)N2CCC(F)(F)CC2)c(F)c1C(F)F)C(F)(F)F]

The title compound was prepared as described for the synthesis of Example 6, using in step a (S)-4-bromo-2-(difluoromethyl)-3-fluoro-N-(1,1,1-trifluorobutan-2-yl)benzenesulfonamide (Intermediate 12/12) in place of (S)-4-bromo-2,3-dichloro-N-(1,1,1-trifluorobutan-2-yl)benzenesulfonamide and using in the final step 4,4-difluoropiperidine in place of diethylamine. $^1$H NMR (500 MHz, CDCl$_3$): δ ppm 7.92 (d, J=8.0 Hz, 1H), 7.82 (t, J=8.5 Hz, 1H), 7.53 (t, J=52.0 Hz, 1H), 5.68 (d, J=9.5 Hz, 1H) 3.87-3.82 (m, 3H), 3.63-3.62 (m, 2H), 2.11-1.99 (m, 4H), 1.92-1.87 (m, 1H), 1.80 (s, 6H), 1.81-1.57 (m, 1H), 1.06 (t, J=7.0 Hz, 3H). MS (ESI): m/z 692.1 [M+H]$^+$.

Example 6/17

3-Chloro-N-(1-(difluoromethyl)cyclopropyl)-4-(4-(4,4-difluoropiperidine-1-carbonyl)-2-(5-(2-hydroxypropan-2-yl)-1,3,4-oxadiazol-2-yl)thiazol-5-yl)-2-fluorobenzenesulfonamide

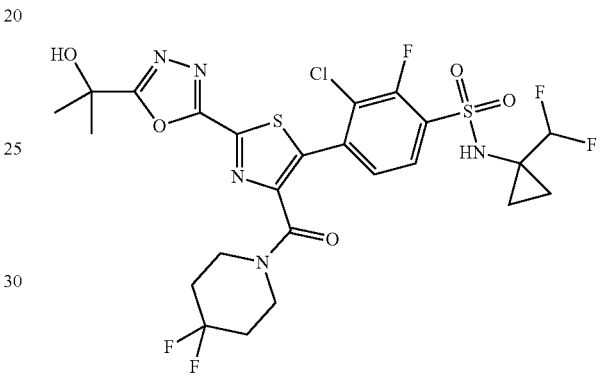

The title compound was prepared as described for the synthesis of Example 6, using in step a 4-bromo-3-chloro-N-(1-(difluoromethyl)cyclopropyl)-2-fluorobenzenesulfonamide (Intermediate 12/13) in place of (S)-4-bromo-2,3-dichloro-N-(1,1,1-trifluorobutan-2-yl)benzenesulfonamide and using in the final step 4,4-difluoropiperidine in place of diethylamine. $^1$H NMR (500 MHz, CDCl$_3$): δ ppm 7.90 (t, J=7.5 Hz, 1H), 7.51 (t, J=8.0 Hz, 1H), 5.79 (s, 1H), 5.51 (t, J=56.3 Hz, 1H), 3.79 (t, J=6.0 Hz, 2H), 3.58 (t, J=6.0 Hz, 2H), 2.03-1.93 (m, 4H), 1.80 (s, 6H), 1.19 (br s, 2H), 1.08 (t, J=7.5 Hz, 2H). MS (ESI): m/z 656.0 [M+H]$^+$.

Example 6/18

3-(Difluoromethyl)-2-fluoro-4-(2-(5-(2-hydroxypropan-2-yl)-1,3,4-oxadiazol-2-yl)-4-((S)-2-methylpiperidine-1-carbonyl)thiazol-5-yl)-N—((S)-1,1,1-trifluoropropan-2-yl)benzenesulfonamide

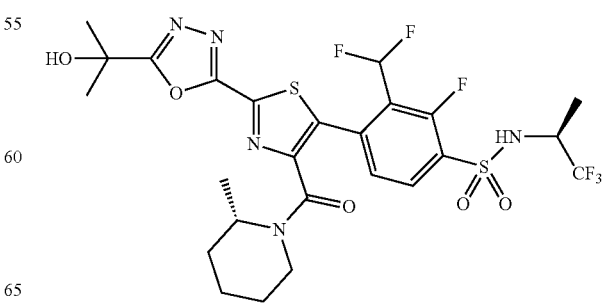

The title compound was prepared as described for the synthesis of Example 6, using in step a (S)-4-bromo-3-(difluoromethyl)-2-fluoro-N-(1,1,1-trifluoropropan-2-yl)benzenesulfonamide (Intermediate 12/2) in place of (S)-4-bromo-2,3-dichloro-N-(1,1,1-trifluorobutan-2-yl)benzenesulfonamide and using in the final step (S)-2-methylpiperidine in place of diethylamine. $^1$H NMR (500 MHz, CDCl$_3$, mixture of rotamers): δ ppm 8.06 (t, J=6.4 Hz, 1H), 7.58-7.52 (m, 1H), 6.93 (td, J$_1$=52.3 Hz, J$_2$=9.5 Hz, 1H), 5.42-5.40 (m, 1H), 4.83-4.40 (m, 1H), 4.17-4.11 (m, 1H), 4.01-2.80 (m, 2H), 1.80 (s, 6H), 1.70-1.10 (m, 12H). MS (ESI): m/z 656.2 [M+H]$^+$.

Example 6/19

3-Chloro-4-(4-(4,4-difluoropiperidine-1-carbonyl)-2-(5-(2-hydroxypropan-2-yl)-1,3,4-oxadiazol-2-yl)thiazol-5-yl)-2-fluoro-N-(1,1,1-trifluoro-2-methylpropan-2-yl)benzenesulfonamide

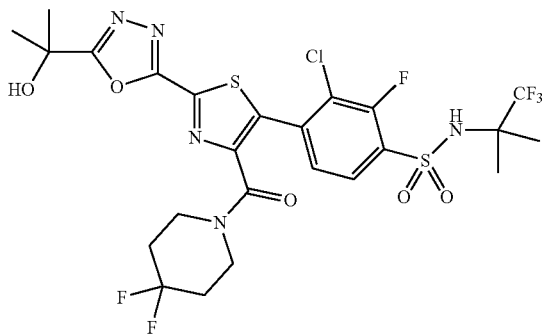 [SMILES: CC(C)(O)c1nnc(-c2nc(C(=O)N3CCC(F)(F)CC3)c(-c3ccc(S(=O)(=O)NC(C)(C)C(F)(F)F)c(F)c3Cl)s2)o1]

The title compound was prepared as described for the synthesis of Example 6, using in step a 4-bromo-3-chloro-2-fluoro-N-(1,1,1-trifluoro-2-methylpropan-2-yl)benzenesulfonamide (Intermediate 12/16) in place of (S)-4-bromo-2,3-dichloro-N-(1,1,1-trifluorobutan-2-yl)benzenesulfonamide and using in the final step 4,4-difluoropiperidine in place of diethylamine. $^1$H NMR (500 MHz, CDCl$_3$): δ ppm 7.88 (t, J=8.0 Hz, 1H), 7.50 (d, J=8.0 Hz, 1H), 5.31 (s, 1H), 3.81-3.78 (m, 2H), 3.62-3.60 (m, 2H), 2.06-1.97 (m, 4H), 1.80 (s, 6H), 1.51 (s, 6H). MS (ESI): m/z 676.1 [M+H]$^+$.

Example 6/20

(S)-5-(2-Chloro-3-fluoro-4-(N-(1,1,1-trifluorobutan-2-yl)sulfamoyl)phenyl)-N,N-diethyl-2-(5-(2-hydroxypropan-2-yl)-1,3,4-oxadiazol-2-yl)thiazole-4-carboxamide

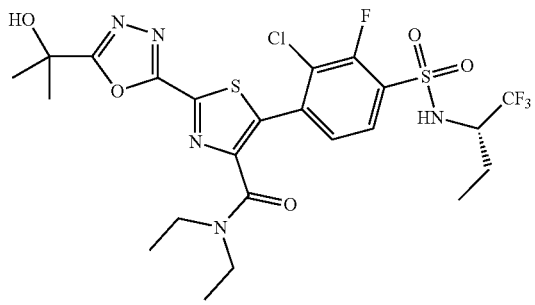 [SMILES: CC[C@H](NS(=O)(=O)c1ccc(-c2sc(-c3nnc(C(C)(C)O)o3)nc2C(=O)N(CC)CC)c(Cl)c1F)C(F)(F)F]

The title compound was prepared as described for the synthesis of Example 6, using in step a (S)-4-bromo-3-chloro-2-fluoro-N-(1,1,1-trifluorobutan-2-yl)benzene sulfonamide (Intermediate 12/11) in place of (S)-4-bromo-2,3-dichloro-N-(1,1,1-trifluorobutan-2-yl)benzenesulfonamide. $^1$H NMR (500 MHz, CDCl$_3$): δ ppm 7.83 (t, J=7.5 Hz, 1H), 7.58 (d, J=8.0 Hz, 1H), 5.37 (d, J=10.0 Hz, 1H), 3.93-3.89 (m, 1H), 3.51-3.40 (m, 2H), 3.27-3.23 (m, 2H), 1.96-1.89 (m, 1H), 1.79 (s, 6H), 1.64-1.57 (m, 1H), 1.13-1.08 (m, 9H). MS (ESI): m/z 628.1 [M+H]$^+$.

Example 6/21

3-(Difluoromethyl)-2-fluoro-4-(4-((2S)-4-fluoro-2-methylpyrrolidine-1-carbonyl)-2-(5-(2-hydroxypropan-2-yl)-1,3,4-oxadiazol-2-yl)thiazol-5-yl)-N—((S)-1,1,1-trifluoropropan-2-yl)benzenesulfonamide

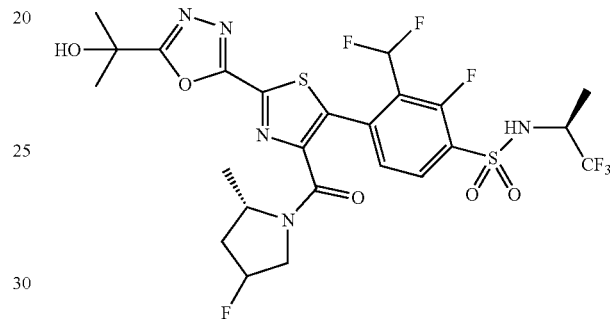

The title compound was prepared as described for the synthesis of Example 6, using in step a (S)-4-bromo-3-(difluoromethyl)-2-fluoro-N-(1,1,1-trifluoropropan-2-yl)benzenesulfonamide (Intermediate 12/2) in place of (S)-4-bromo-2,3-dichloro-N-(1,1,1-trifluorobutan-2-yl)benzenesulfonamide and using in the final step (2S)-4-fluoro-2-methylpyrrolidine hydrochloride (Intermediate 14/1) in place of diethylamine. $^1$H NMR (500 MHz, CDCl$_3$, mixture of rotamers): δ ppm 8.06 (t, J=7.5 Hz, 1H), 7.47-7.43 (m, 1H), 6.90 (t, J=53.3 Hz, 1H), 5.31-5.12 (m, 2H), 4.36-3.89 (m, 4H), 2.54-2.47 (m, 1H), 1.81-1.70 (m, 7H), 1.43-1.10 (m, 6H). MS (ESI): m/z 660.2 [M+H]$^+$.

Example 6/22

3-Chloro-4-(4-(4,4-difluoro-2,2-dimethylpyrrolidine-1-carbonyl)-2-(5-(2-hydroxypropan-2-yl)-1,3,4-oxadiazol-2-yl)thiazol-5-yl)-N-(1-(difluoromethyl)cyclopropyl)-2-fluorobenzenesulfonamide

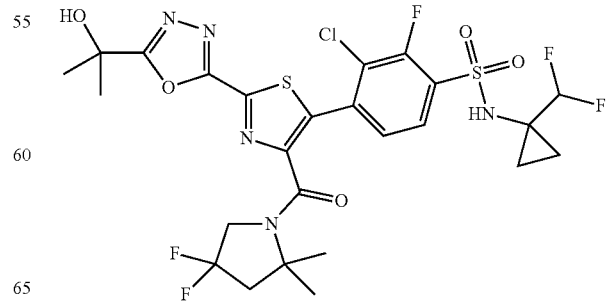

The title compound was prepared as described for the synthesis of Example 6, using in step a 4-bromo-3-chloro-N-(1-(difluoromethyl)cyclopropyl)-2-fluorobenzenesulfonamide (Intermediate 12/13) in place of (S)-4-bromo-2,3-dichloro-N-(1,1,1-trifluorobutan-2-yl)benzenesulfonamide and using in the final step 4,4-difluoro-2,2-dimethylpyrrolidine in place of diethylamine. $^1$H NMR (500 MHz, CDCl$_3$): δ ppm 7.90-7.87 (m, 1H), 7.46-7.44 (m, 1H), 5.82 (s, 1H), 5.66 (t, J=56.8 Hz, 1H), 4.07 (t, J=12.8 Hz, 2H), 2.36 (t, J=14.0 Hz, 2H), 1.82 (s, 6H), 1.61 (s, 6H), 1.07-1.15 (m, 4H). MS (ESI): m/z 670.1 [M+H]$^+$.

Example 6/23

3-Chloro-4-(4-(4,4-difluoropiperidine-1-carbonyl)-2-(5-(2-hydroxypropan-2-yl)-1,3,4-oxadiazol-2-yl)thiazol-5-yl)-2-fluoro-N-methyl-N-(2,2,2-trifluoroethyl)benzenesulfonamide

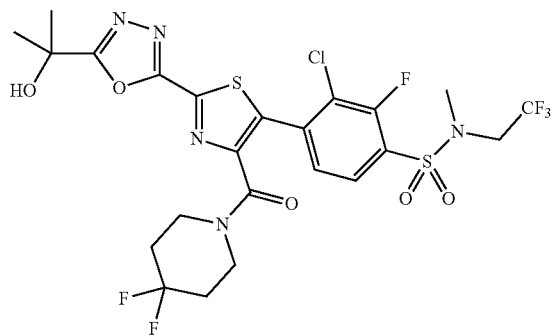 [SMILES: CN(CC(F)(F)F)S(=O)(=O)c1ccc(-c2sc(-c3nnc(C(C)(C)O)o3)nc2C(=O)N2CCC(F)(F)CC2)c(Cl)c1F]

The title compound was prepared as described for the synthesis of Example 6, using in step a 4-bromo-3-chloro-2-fluoro-N-methyl-N-(2,2,2-trifluoroethyl)benzenesulfonamide (Intermediate 12/17) in place of (S)-4-bromo-2,3-dichloro-N-(1,1,1-trifluorobutan-2-yl)benzenesulfonamide and using in the final step 4,4-difluoropiperidine in place of diethylamine. $^1$H NMR (500 MHz, CDCl$_3$): δ ppm 7.93-7.90 (m, 1H), 7.52-7.50 (m, 1H), 3.98-3.93 (m, 2H), 3.82-3.80 (m, 2H), 3.70-3.68 (m, 2H), 3.07 (s, 3H), 2.07-2.02 (m, 4H), 1.80 (s, 6H). MS (ESI): m/z 662.1 [M+H]$^+$.

Example 6/24

(S)-(2-(5-(2-Hydroxypropan-2-yl)-1,3,4-oxadiazol-2-yl)-5-(4-(3,3,3-trifluoro-2-hydroxy-2-(trifluoromethyl)propoxy)-2-(trifluoromethyl)phenyl)thiazol-4-yl)(2-methylpyrrolidin-1-yl)methanone

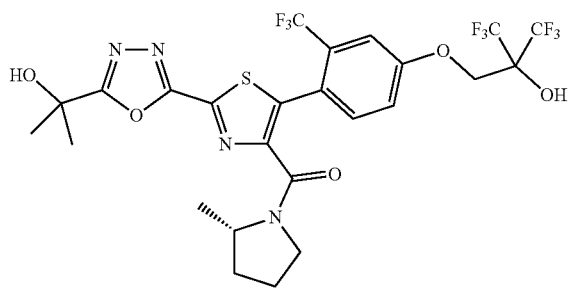 [SMILES: C[C@H]1CCCN1C(=O)c1nc(-c2nnc(C(C)(C)O)o2)sc1-c1ccc(OCC(O)(C(F)(F)F)C(F)(F)F)cc1C(F)(F)F]

The title compound was prepared as described for the synthesis of Example 6, using in step a 2-((4-bromo-3-(trifluoromethyl)phenoxy)methyl)-1,1,1,3,3,3-hexafluoropropan-2-ol (Intermediate 19) in place of (S)-4-bromo-2,3-dichloro-N-(1,1,1-trifluorobutan-2-yl)benzenesulfonamide and using in the final step (S)-2-methylpyrrolidine hydrochloride in place of diethylamine. $^1$H NMR (500 MHz, CDCl$_3$): δ ppm 7.60-7.52 (m, 1H), 7.30-7.28 (m, 1H), 7.16-7.14 (m, 1H), 4.62-4.16 (m, 3H), 3.80-3.53 (m, 2H), 2.08-1.95 (m, 2H), 1.82-1.78 (m, 7H), 1.60-1.57 (m, 1H), 1.23-1.15 (m, 3H). MS (ESI): m/z 663.2 [M+H]$^+$.

Example 7

Step a

Ethyl 4-(diethylcarbamoyl)thiazole-2-carboxylate

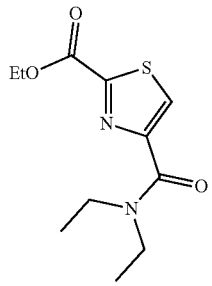

A solution of 2-(ethoxycarbonyl)thiazole-4-carboxylic acid (3.6 g, 1.8 mmol, Intermediate 2, step a), diethylamine (5.6 mL, 54 mmol), and HATU (8.17 g, 2.15 mmol) in DMF (20.0 mL) was stirred at rt overnight. The resulting solution was concentrated to dryness and the residue was purified by FCC on silica gel (PE/EtOAc=10/1) to give the title compound as a brown oil.

Example 7

Step b

N,N-Diethyl-2-(hydrazinecarbonyl)thiazole-4-carboxamide

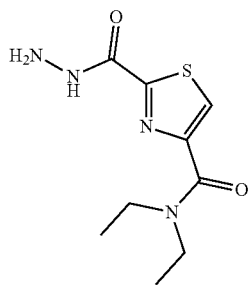 [SMILES: CCN(CC)C(=O)c1csc(C(=O)NN)n1]

To a solution of ethyl 4-(diethylcarbamoyl)thiazole-2-carboxylate (1.0 g, 3.9 mmol, Example 7, step a) in EtOH (10 mL) was added N$_2$H$_4$ (3.0 mL, 85%), and the solution was stirred at rt for 3 h. The resulting solution was poured into ice-water and extracted with DCM. The combined organic layers were washed with brine, dried over anhydrous Na₂SO₄, filtered, and concentrated to dryness to give the title compound as a yellow solid, which was used in the next step without further purification.

Example 7

Step c 2-(2-Acetylhydrazinecarbonyl)-N,N-diethylthiazole-4-carboxamide

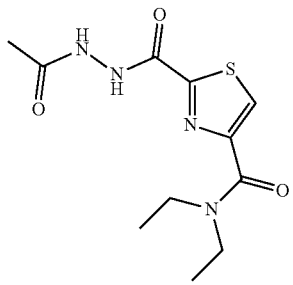 [SMILES: CCN(CC)C(=O)c1csc(C(=O)NNC(C)=O)n1]

To a solution of 2-(2-acetylhydrazinecarbonyl)-N,N-diethylthiazole-4-carboxamide (900 mg, 3.71 mmol, Example 7, step b) in DCM (20 mL) was slowly added Ac₂O (455 mg, 4.46 mmol; in 10 mL of DCM) at 0° C. The solution was stirred at 0° C. for 2 h. The mixture was quenched with H₂O at 0° C., the organic layer was separated and the aqueous layer was further extracted with DCM. The combined organic layers were washed with brine, dried over anhydrous Na₂SO₄, filtered, concentrated to dryness, and the residue was purified by FCC on silica gel (DCM/MeOH=50/1) to give the title compound as a yellow solid.

Example 7

Step d

N,N-Diethyl-2-(5-methyl-1,3,4-oxadiazol-2-yl)thiazole-4-carboxamide

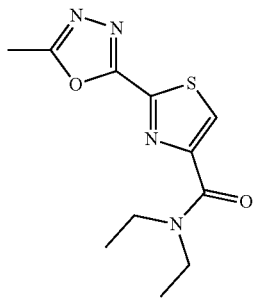 [SMILES: CCN(CC)C(=O)c1csc(-c2nnc(C)o2)n1]

To a solution of 2-(2-acetylhydrazinecarbonyl)-N,N-diethylthiazole-4-carboxamide (700 mg, 2.46 mmol, Example 7, step c) in DCM (21 mL) was added pyridine (585 mg, 7.39 mmol). Then Tf₂O (5.3 g, 19 mmol) was added dropwise at −10° C. The solution was slowly warmed to rt, stirred overnight at rt, concentrated to dryness, and the residue was purified by FCC on silica gel (PE/EtOAc=5/1) to give the title compound as a yellow oil.

Example 7

(S)-5-(2,3-Dichloro-4-(N-(1,1,1-trifluoropropan-2-yl)sulfamoyl)phenyl)-N,N-diethyl-2-(5-methyl-1,3,4-oxadiazol-2-yl)thiazole-4-carboxamide

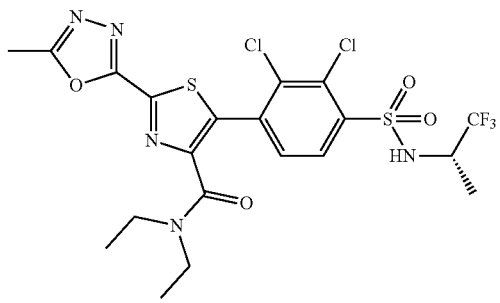 [SMILES: CCN(CC)C(=O)c1nc(-c2nnc(C)o2)sc1-c1ccc(S(=O)(=O)N[C@@H](C)C(F)(F)F)c(Cl)c1Cl]

A solution of N,N-diethyl-2-(5-methyl-1,3,4-oxadiazol-2-yl)thiazole-4-carboxamide (150 mg, 0.56 mmol, Example 7, step d), (S)-4-bromo-2,3-dichloro-N-(1,1,1-trifluoropropan-2-yl)benzenesulfonamide (248 mg, 0.618 mmol, Intermediate 12/3), KOAc (111 mg, 1.13 mmol), Pd(OAc)₂ (26 mg, 0.113 mmol), and PPh₃ (163 mg, 0.619 mmol) in DMF (10 mL) was stirred at rt while being purged with nitrogen for 5 min. Then the solution was stirred at 115° C. overnight. The resulting solution was cooled to rt, H₂O was added and the mixture was extracted with EtOAc. The combined organic layers were washed with brine, dried over anhydrous Na₂SO₄, concentrated to dryness, and the residue was purified by prep-HPLC to give the title compound as a white solid. ¹H NMR (CDCl₃, 300 MHz): δ ppm 8.08 (d, J=8.4, 1H), 7.72 (d, J=8.4 Hz, 1H), 5.31 (d, J=9.2 Hz, 1H), 4.12-4.02 (m, 1H), 3.39-3.49 (m, 2H), 3.31-3.25 (m, 2H), 2.70 (s, 3H), 1.40 (d, J=5.4 Hz, 3H), 1.09-1.13 (m, 6H). MS (ESI): m/z 586.0 [M+H]⁺.

Example 7/1

(S)-(5-(4-(1,1,1,3,3,3-hexafluoro-2-hydroxypropan-2-yl)-2-(trifluoromethyl)phenyl)-2-(5-(2-hydroxypropan-2-yl)-1,3,4-oxadiazol-2-yl)thiazol-4-yl)(2-methylpyrrolidin-1-yl)methanone

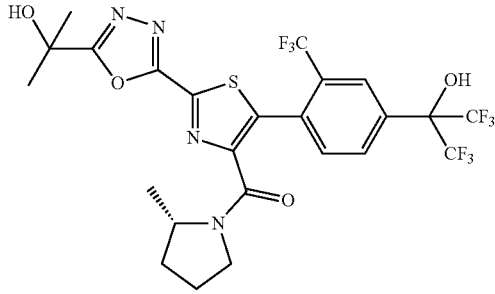 [SMILES: C[C@H]1CCCN1C(=O)c1nc(-c2nnc(C(C)(C)O)o2)sc1-c1ccc(C(O)(C(F)(F)F)C(F)(F)F)cc1C(F)(F)F]

To a solution of (S)-(2-(5-(2-hydroxypropan-2-yl)-1,3,4-oxadiazol-2-yl)thiazol-4-yl)(2-methylpyrrolidin-1-yl)methanone (2.0 g, 6.2 mmol, Intermediate 4/1, step b) in 30 mL of DMF was added 2-(4-bromo-3-(trifluoromethyl)phenyl)-1,1,1,3,3,3-hexafluoropropan-2-ol (3.6 g, 9.3 mmol, Intermediate 18, step e), Pd(PPh₃)₄ (2.0 g, 1.7 mmol) and KOAc (1.4 g, 14 mmol). The mixture was stirred at 120° C. overnight. The resulting solution was concentrated under reduced pressure, diluted with H$_2$O and extracted with DCM. The combined organic layers were washed with brine, dried over anhydrous Na$_2$SO$_4$, filtered and concentrated to dryness. The residue was purified by FCC on silica gel (EtOAc/PE, 1:1) followed by prep-HPLC to afford the title compound as a white solid. $^1$H NMR (300 MHz, DMSO-d$_6$): δ ppm 9.34 (s, 1H), 8.07-8.04 (m, 2H), 7.84-7.82 (m, 1H), 6.08 (s, 1H), 4.02-3.88 (m, 1H), 3.61-3.52 (m, 1H), 3.42-3.41 (m, 1H), 2.00-1.89 (m, 2H), 1.81-1.71 (m, 1H), 1.61 (s, 6H), 1.43-1.41 (m, 1H), 1.11-1.05 (m, 3H). MS (ESI): m/z 633.1 [M+H]$^+$.

Example 8

(R)-2,3-Dichloro-4-(4-(4,4-difluoropiperidine-1-carbonyl)-2-(5-(2-hydroxypropan-2-yl)-1,3,4-oxadiazol-2-yl)thiazol-5-yl)-N-(1,1,1-trifluoropropan-2-yl)benzenesulfonamide

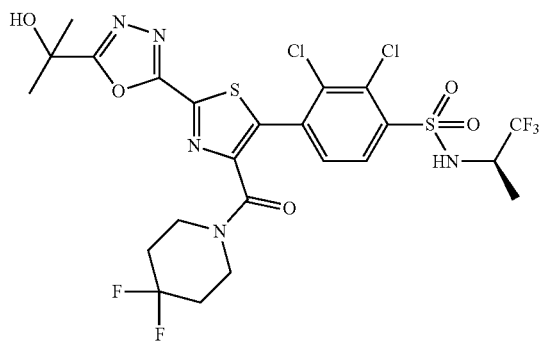 [SMILES: C[C@@H](NS(=O)(=O)c1ccc(-c2sc(-c3nnc(C(C)(C)O)o3)nc2C(=O)N2CCC(F)(F)CC2)c(Cl)c1Cl)C(F)(F)F]

Cs$_2$CO$_3$ (56.8 mg, 0.18 mmol) was added to (R)-4-bromo-2,3-dichloro-N-(1,1,1-trifluoropropan-2-yl)benzenesulfonamide (0.10 g, 0.18 mmol, Intermediate 12/5) and (4,4-difluoropiperidin-1-yl)(2-(5-(2-hydroxypropan-2-yl)-1,3,4-oxadiazol-2-yl)thiazol-4-yl)methanone (0.06 g, 0.18 mmol, Intermediate 4, step d) followed by Pd(OPiv)$_2$ (5.4 mg, 0.18 mmol) and DMF (1.3 mL). The reaction mixture was placed in a heating block already kept at 100° C. and stirred for 22 h. The reaction mixture was cooled to rt and additional Pd(OPiv)$_2$ (5.4 mg) was added, and then heated for another 2 days at 100° C. The mixture was cooled to rt, filtered through Celite® and the filter was washed with EtOAc. Water was added to the filtrate and the aqueous layer was extracted with EtOAc, and the combined organic layers were washed with brine, dried over anhydrous MgSO$_4$, filtered and concentrated. The crude product was purified by FCC on silica gel (0 to 10% MeOH-DCM) to provide the title compound as a white solid. $^1$H NMR (500 MHz, CDCl$_3$) δ ppm 8.11 (d, J=8.2 Hz, 1H), 7.64 (d, J=8.2 Hz, 1H), 5.41-5.36 (m, 1H), 4.10-4.05 (m, 1H), 3.83-3.75 (m, 2H), 3.62 (t, J=5.9 Hz, 2H), 2.66 (s, 1H), 2.10-1.92 (m, 4H), 1.80 (s, 6H), 1.42 (d, J=7.0 Hz, 3H). MS (ESI): m/z 677.7 [M+H]$^+$.

Example 8/1

(S)-3-Chloro-4-(4-(4,4-difluoropiperidine-1-carbonyl)-2-(5-(2-hydroxypropan-2-yl)-1,3,4-oxadiazol-2-yl)thiazol-5-yl)-2-fluoro-N-(1,1,1-trifluoropropan-2-yl)benzenesulfonamide

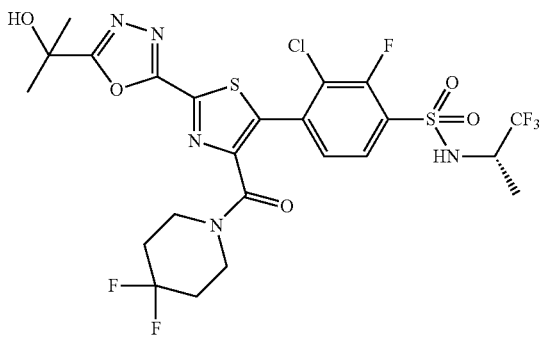 [SMILES: C[C@H](NS(=O)(=O)c1ccc(-c2sc(-c3nnc(C(C)(C)O)o3)nc2C(=O)N2CCC(F)(F)CC2)c(Cl)c1F)C(F)(F)F]

A mixture of (4,4-difluoropiperidin-1-yl)(2-(5-(2-hydroxypropan-2-yl)-1,3,4-oxadiazol-2-yl)thiazol-4-yl)methanone (154 mg, 0.43 mmol, Intermediate 4, step d), (S)-4-bromo-3-chloro-2-fluoro-N-(1,1,1-trifluoropropan-2-yl)benzenesulfonamide (169 mg, 0.44 mmol, Intermediate 12/6), Pd(OAc)$_2$ (8.0 mg, 0.036 mmol), pivalic acid (21.5 mg, 0.211 mmol) and potassium acetate (80 mg, 0.82 mmol) were combined in a dried round bottom flask, evacuated and back filled with nitrogen (3×). Butyronitrile (2 mL) was then added and the mixture flushed with nitrogen. The resulting mixture was heated to 120° C. for 3 h, cooled to rt, diluted with EtOAc, stirred overnight then filtered through Celite®. The filtrate was washed with saturated aqueous NaHCO$_3$, brine and dried over anhydrous Na$_2$SO$_4$. The mixture was filtered, evaporated to dryness and the residue was purified by FCC on silica gel (0 to 100% EtOAc in DCM) to provide the title compound as a tan solid. $^1$H NMR (400 MHz, CDCl$_3$) δ ppm 7.83-7.93 (m, 1H), 7.51 (d, J=8.1 Hz, 1H), 5.17 (d, J=9.6 Hz, 1H), 3.73-3.88 (m, 2H), 3.63 (t, J=5.6 Hz, 2H), 2.59 (br s, 1H), 1.94-2.12 (m, 4H), 1.81 (s, 6H), 1.58 (br s, 3H). MS (ESI): m/z 662 [M+H].

Example 8/2

(5-(2,3-Dichloro-4-(3,3,3-trifluoro-2-hydroxy-2-(trifluoromethyl)propyl)phenyl)-2-(5-(2-hydroxypropan-2-yl)-1,3,4-oxadiazol-2-yl)thiazol-4-yl)(4,4-difluoropiperidin-1-yl)methanone

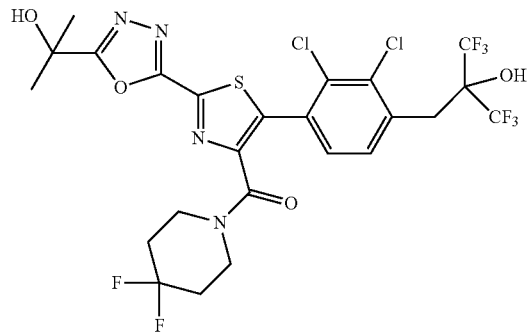 [SMILES: CC(C)(O)c1nnc(-c2nc(C(=O)N3CCC(F)(F)CC3)c(-c3ccc(CC(O)(C(F)(F)F)C(F)(F)F)c(Cl)c3Cl)s2)o1]

A mixture of 2-(4-bromo-2,3-dichlorobenzyl)-1,1,1,3,3,3-hexafluoropropan-2-ol (70 mg, 0.17 mmol, Intermediate 20), (4,4-difluoropiperidin-1-yl)(2-(5-(2-hydroxypropan-2-yl)-1,3,4-oxadiazol-2-yl)thiazol-4-yl)methanone (60 mg, 0.17 mmol, Intermediate 4, step d), Pd(OAc)$_2$ (10 mg, 0.045 mmol), RuPhos (21 mg, 0.045 mmol), KOAc (34 mg, 0.35 mmol), and pivalic acid (6.0 mg, 0.059 mmol) in butyronitrile (1.4 mL) was purged with N$_2$ for 5 min. The container was then sealed and heated at 120° C. for 18 h. After cooling the reaction to rt, the mixture was filtered through silica gel and the solids were washed with EtOAc. The filtrate was concentrated to dryness and the residue was purified by FCC on silica gel (0 to 100% EtOAc in heptanes) and then prep-HPLC (10 to 95% CH$_3$CN in H$_2$O, 0.1% TFA) to give the title compound. $^1$H NMR (400 MHz, CDCl$_3$) δ ppm 7.48 (d, J=8.1 Hz, 1H), 7.40 (d, J=8.1 Hz, 1H), 3.79 (t, J=5.8 Hz, 2H), 3.63-3.55 (m, 4H), 2.07-1.83 (m, 4H), 1.80 (s, 6H). MS (ESI): m/z 683.1 [M+H]$^+$.

Example 8/3

(5-(3-Chloro-4-(3,3,3-trifluoro-2-hydroxy-2-(trifluoromethyl)propyl)phenyl)-2-(5-(2-hydroxypropan-2-yl)-1,3,4-oxadiazol-2-yl)thiazol-4-yl)(4,4-difluoropiperidin-1-yl)methanone

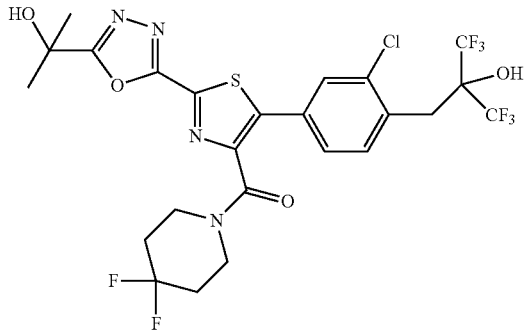 [SMILES: CC(C)(O)c1nnc(-c2nc(C(=O)N3CCC(F)(F)CC3)c(-c3ccc(CC(O)(C(F)(F)F)C(F)(F)F)c(Cl)c3)s2)o1]

The title compound was obtained in the preparation of Example 8/2 as a by-product. $^1$H NMR (400 MHz, CDCl$_3$) δ ppm 7.64 (d, J=2.0 Hz, 1H), 7.55 (d, J=8.1 Hz, 1H), 7.46 (dd, J=2.0, 8.1 Hz, 1H), 3.90 (t, J=5.8 Hz, 2H), 3.53 (s, 2H), 3.34 (t, J=3.3 Hz, 2H), 2.09-1.97 (m, 2H), 1.80 (s, 6H), 1.73-1.61 (m, 2H). MS (ESI) m/z 649.2 [M+H]$^+$.

Example 8/4

(5-(2,3-Dichloro-4-(hydroxy(1-(trifluoromethyl)cyclopropyl)methyl)phenyl)-2-(5-(2-hydroxypropan-2-yl)-1,3,4-oxadiazol-2-yl)thiazol-4-yl)(4,4-difluoropiperidin-1-yl)methanone

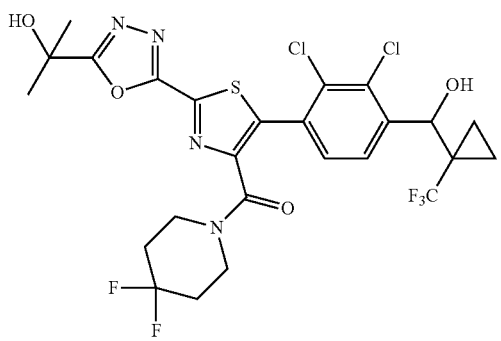 [SMILES: CC(C)(O)c1nnc(-c2nc(C(=O)N3CCC(F)(F)CC3)c(-c3ccc(C(O)C4(C(F)(F)F)CC4)c(Cl)c3Cl)s2)o1]

A mixture of (4-bromo-2,3-dichlorophenyl)(1-(trifluoromethyl)cyclopropyl)methanol (78 mg, 0.21 mmol, Intermediate 21, step c), (4,4-difluoropiperidin-1-yl)(2-(5-(2-hydroxypropan-2-yl)-1,3,4-oxadiazol-2-yl)thiazol-4-yl)methanone (66 mg, 0.18 mmol, Intermediate 4, step d), Pd(OAc)$_2$ (7 mg, 0.03 mmol), RuPhos (13 mg, 0.028 mmol), KOAc (44 mg, 0.45 mmol), and pivalic acid (12 mg, 0.12 mmol) in butyronitrile (1.4 mL) was degassed by bubbling N$_2$ through the solution for 5 min. The container was then sealed and heated at 120° C. for 10 h. After cooling the reaction to room temperature, the mixture was filtered through silica gel and the solids were washed with EtOAc. The filtrate was concentrated, purified by flash column chromatography (silica gel, 0-100% EtOAc in heptanes) and then reverse phase HPLC (10-95% CH$_3$CN in H$_2$O, 0.1% TFA) to give the title compound. $^1$H NMR (400 MHz, CDCl$_3$) δ 7.61 (d, J=8.08 Hz, 1H), 7.47 (d, J=8.08 Hz, 1H), 5.78 (s, 1H), 3.78-3.88 (m, 1H), 3.68-3.78 (m, 1H), 3.53-3.63 (m, 2H), 3.06-3.37 (m, 4H), 1.86-2.08 (m, 4H), 1.80 (s, 6H). MS (ESI) m/z 641.1 [M+H]$^+$.

Example 9

Step a 2-(2,3-Dichloro-4-(4-(hydroxymethyl)-2-(5-(2-hydroxypropan-2-yl)-4-(4-methoxybenzyl)-4H-1,2,4-triazol-3-yl)thiazol-5-yl)phenyl)-1,1,1,3,3,3-hexafluoropropan-2-ol

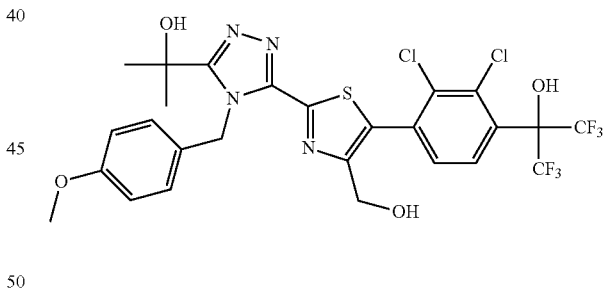

A solution of 2-(5-(4-(hydroxymethyl)thiazol-2-yl)-4-(4-methoxybenzyl)-4H-1,2,4-triazol-3-yl)propan-2-ol (250 mg, 0.69 mmol, Intermediate 5), 2-(4-bromo-2,3-dichlorophenyl)-1,1,1,3,3,3-hexafluoropropan-2-ol (351 mg, 0.89 mmol, Intermediate 13, step b), Pd(OAc)$_2$ (24 mg, 0.11 mmol), P(Cy)$_3$·HBF$_4$ (24 mg 0.07 mmol), and pivalic acid (24 mg 0.24 mmol), Na$_2$CO$_3$ (219 mg, 2.07 mmol) in DMA (10 mL) was heated at 90° C. overnight. The mixture was poured into water (20 mL) and extracted with EtOAc (50 mL×3). The combined organic layers were washed with brine, dried over anhydrous Na$_2$SO$_4$, and concentrated to dryness. The residue was purified by prep-TLC (PE/EtOAc=2:1) to give the title compound as a yellow solid.

Example 9

Step b 5-(2,3-Dichloro-4-(1,1,1,3,3,3-hexafluoro-2-hydroxypropan-2-yl)phenyl)-2-(5-(2-hydroxypropan-2-yl)-4-(4-methoxybenzyl)-4H-1,2,4-triazol-3-yl)thiazole-4-carboxylic acid

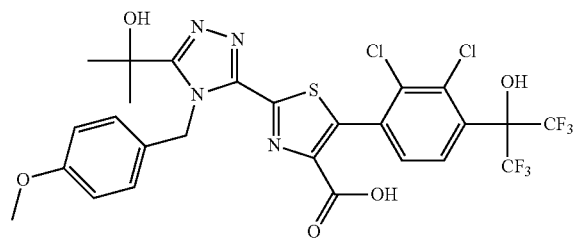 [SMILES: COc1ccc(Cn2c(-c3nc(C(=O)O)c(-c4ccc(C(O)(C(F)(F)F)C(F)(F)F)c(Cl)c4Cl)s3)nnc2C(C)(C)O)cc1]

To a solution of 2-(2,3-dichloro-4-(4-(hydroxymethyl)-2-(5-(2-hydroxypropan-2-yl)-4-(4-methoxybenzyl)-4H-1,2,4-triazol-3-yl)thiazol-5-yl)phenyl)-1,1,1,3,3,3-hexafluoropropan-2-ol (200 mg, 0.30 mmol, Example 9, step a) in $H_2O$ (5 mL), and acetonitrile (15 mL) were added TEMPO (94 mg, 0.60 mmol) and iodobenzene diacetate (530 g, 1.65 mmoL), and the mixture was stirred at rt overnight. $H_2O$ (15 mL) was added and the aqueous layer was extracted with EtOAc (30 mL×3). The combined organic phases were washed with brine, dried over anhydrous $MgSO_4$, filtered, and concentrated to dryness to give the crude title compound as a brown solid, which was used in the next step without purification.

Example 9

Step c 5-(2,3-Dichloro-4-(1,1,1,3,3,3-hexafluoro-2-hydroxypropan-2-yl)phenyl)-N,N-diethyl-2-(5-(2-hydroxypropan-2-yl)-4-(4-methoxybenzyl)-4H-1,2,4-triazol-3-yl)thiazole-4-carboxamide

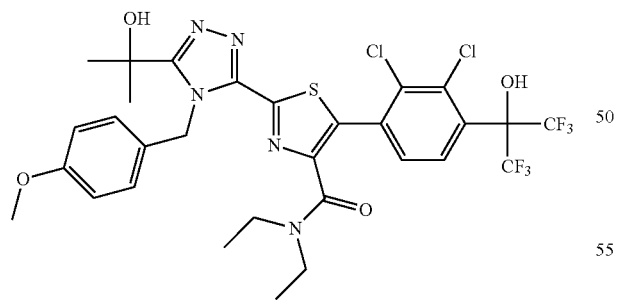

A solution of 5-(2,3-dichloro-4-(1,1,1,3,3,3-hexafluoro-2-hydroxypropan-2-yl)phenyl)-2-(5-(2-hydroxypropan-2-yl)-4-(4-methoxybenzyl)-4H-1,2,4-triazol-3-yl)thiazole-4-carboxylic acid (250 mg, crude Example 9, step b), diethylamine (62 mg, 0.85 mmol), and HATU (232 mg, 0.610 mmol), DIPEA (0.2 mL, 1.4 mmol) in acetonitrile (8 mL) was stirred at rt for 2 h. The mixture was poured into $H_2O$ (10 mL) and extracted with EtOAc (25 mL×3). The combined organic phases were washed with brine, dried over anhydrous $Na_2SO_4$, and concentrated to dryness. The residue was purified by FCC on silica gel (PE/EtOAc=1:1) to afford the title compound as a white solid.

Example 9

5-(2,3-Dichloro-4-(1,1,1,3,3,3-hexafluoro-2-hydroxypropan-2-yl)phenyl)-N,N-diethyl-2-(5-(2-hydroxypropan-2-yl)-4H-1,2,4-triazol-3-yl)thiazole-4-carboxamide

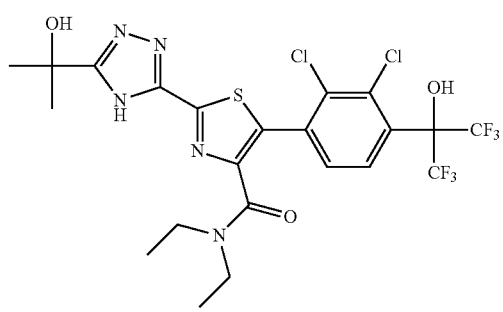 [SMILES: CCN(CC)C(=O)c1nc(-c2nnc(C(C)(C)O)[nH]2)sc1-c1ccc(C(O)(C(F)(F)F)C(F)(F)F)c(Cl)c1Cl]

A solution of 5-(2,3-dichloro-4-(1,1,1,3,3,3-hexafluoro-2-hydroxypropan-2-yl)phenyl)-N,N-diethyl-2-(5-(2-hydroxypropan-2-yl)-4-(4-methoxybenzyl)-4H-1,2,4-triazol-3-yl) thiazole-4-carboxamide (150 mg, 0.20 mmol, Example 9, step c) in a mixture of TFA (2 mL) and DCM (4 mL) was stirred at rt for 8 h. The mixture was poured into $H_2O$ (10 mL) and extracted with EtOAc (25 mL×3). The combined organic phases were washed with brine, dried over anhydrous $Na_2SO_4$, and concentrated to dryness. The residue was purified by prep-HPLC to afford the title compound as a white solid. $^1$H NMR (300 MHz, DMSO-$d_6$): δ ppm 14.37 (br s, 1H), 9.19 (br s, 1H), 7.85-7.66 (br m, 2H), 3.37-3.24 (m, 4H), 1.54 (s, 6H), 1.07-0.95 (m, 6H). MS (ESI): m/z 620.0 $[M+H]^+$.

Example 9/1

5-(2,3-Dichloro-4-(1,1,1,3,3,3-hexafluoro-2-hydroxypropan-2-yl)phenyl)-N,N-diethyl-2-(4-(2-hydroxy-2-methylpropyl)-4H-1,2,4-triazol-3-yl)thiazole-4-carboxamide

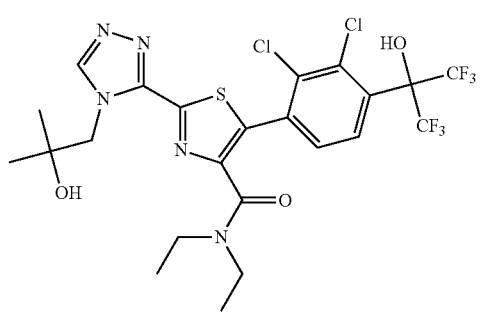 [SMILES: CCN(CC)C(=O)c1nc(-c2nncn2CC(C)(C)O)sc1-c1ccc(C(O)(C(F)(F)F)C(F)(F)F)c(Cl)c1Cl]

The title compound was prepared as described for Example 9, using in step a 1-(3-(4-(hydroxymethyl)thiazol-2-yl)-4H-1,2,4-triazol-4-yl)-2-methylpropan-2-ol (Intermediate 7, step c) in place of 2-(5-(4-(hydroxymethyl)thiazol- 2-yl)-4-(4-methoxybenzyl)-4H-1,2,4-triazol-3-yl)propan-2-ol. No final triazole deprotection step was performed. ¹H NMR (400 MHz, CD₃OD): δ ppm 8.74 (s, 1H), 7.95-7.63 (m, 2H), 4.73 (s, 2H) 3.52-3.47 (m, 2H), 3.43-3.40 (m, 2H), 1.21 (s, 6H), 1.20-1.06 (m, 6H). MS (ESI): m/z 634.0 [M+H]⁺.

Example 9/2

2,3-Dichloro-4-(4-((S)-4,4-difluoro-2-methylpyrrolidine-1-carbonyl)-2-(5-(2-hydroxypropan-2-yl)-4H-1,2,4-triazol-3-yl)thiazol-5-yl)-N—((S)-1,1,1-trifluoropropan-2-yl)benzenesulfonamide

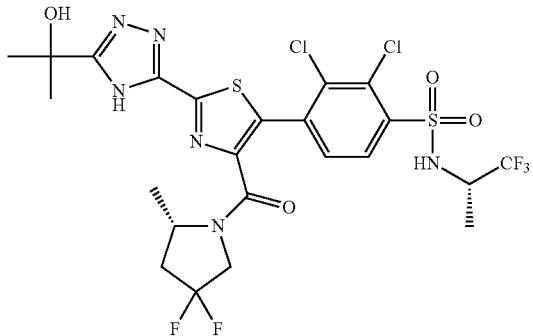 [SMILES: C[C@H](NS(=O)(=O)c1ccc(-c2sc(-c3nnc(C(C)(C)O)[nH]3)nc2C(=O)N2CC(F)(F)C[C@@H]2C)c(Cl)c1Cl)C(F)(F)F]

The title compound was prepared as described for the synthesis of Example 9, using in step a (S)-4-bromo-2,3-dichloro-N-(1,1,1-trifluoropropan-2-yl)benzenesulfonamide (Intermediate 12/3) in place of 2-(4-bromo-2,3-dichlorophenyl)-1,1,1,3,3,3-hexafluoropropan-2-ol and in step c (S)-4,4-difluoro-2-methylpyrrolidine hydrochloride (Intermediate 14, step b) in place of diethylamine. ¹H NMR (300 MHz, CDCl₃): δ ppm 8.08-8.05 (m, 1H), 7.66-7.57 (m, 1H), 5.67-5.20 (br s, 1H), 4.91-4.44 (m, 1H), 4.15-3.86 (m, 3H), 2.62-2.51 (m, 1H), 2.20-2.00 (m, 1H), 1.87 (s, 6H), 1.41-1.14 (m, 6H). MS (ESI): m/z 677.1 [M+H]⁺.

Example 9/3

(S)-2,3-Dichloro-4-(4-(4,4-difluoropiperidine-1-carbonyl)-2-(5-(2-hydroxypropan-2-yl)-4H-1,2,4-triazol-3-yl)thiazol-5-yl)-N-(1,1,1-trifluoropropan-2-yl)benzenesulfonamide

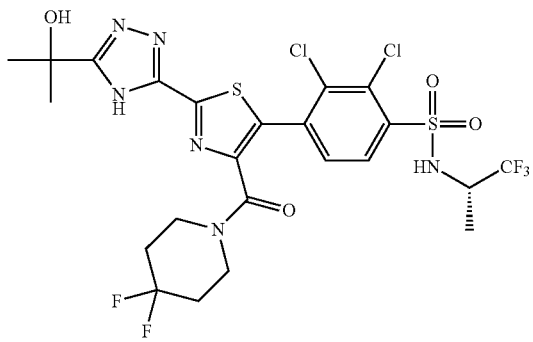 [SMILES: C[C@H](NS(=O)(=O)c1ccc(-c2sc(-c3nnc(C(C)(C)O)[nH]3)nc2C(=O)N2CCC(F)(F)CC2)c(Cl)c1Cl)C(F)(F)F]

The title compound was prepared as described for the synthesis of Example 9, using in step a (S)-4-bromo-2,3-dichloro-N-(1,1,1-trifluoropropan-2-yl)benzenesulfonamide (Intermediate 12/3) in place of 2-(4-bromo-2,3-dichlorophenyl)-1,1,1,3,3,3-hexafluoropropan-2-ol and in step c 4,4-difluoropiperidine in place of diethylamine. ¹H NMR (400 MHz, DMSO-d₆): δ ppm 14.37 (br s, 1H), 9.20-9.18 (m, 1H), 8.07 (d, J=6.8 Hz, 1H), 7.73 (d, J=6.8 Hz, 1H), 4.21-4.15 (m, 1H), 3.66-3.55 (m, 4H), 2.01-1.85 (m, 4H), 1.50 (s, 6H), 1.27-1.22 (m, 3H). MS (ESI): m/z 677.0 [M+H]⁺.

Example 9/4

(S)-2,3-Dichloro-4-(4-(4,4-difluoropiperidine-1-carbonyl)-2-(5-(2-hydroxypropan-2-yl)-4-methyl-4H-1,2,4-triazol-3-yl)thiazol-5-yl)-N-(1,1,1-trifluoropropan-2-yl)benzenesulfonamide

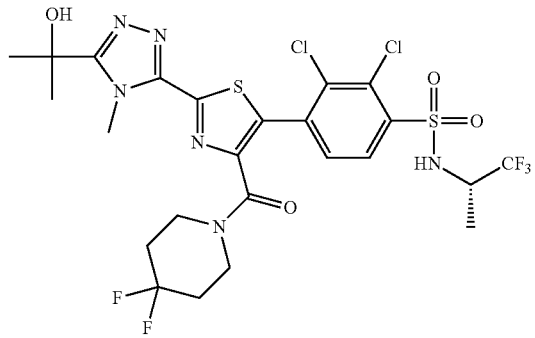 [SMILES: C[C@H](NS(=O)(=O)c1ccc(-c2sc(-c3nnc(C(C)(C)O)n3C)nc2C(=O)N2CCC(F)(F)CC2)c(Cl)c1Cl)C(F)(F)F]

The title compound was prepared as described for the synthesis of Example 9, using in step a 2-(5-(4-(hydroxymethyl)thiazol-2-yl)-4-methyl-4H-1,2,4-triazol-3-yl)propan-2-ol (Intermediate 6) and (S)-4-bromo-2,3-dichloro-N-(1,1,1-trifluoropropan-2-yl)benzenesulfonamide (Intermediate 12/3) in place of 2-(5-(4-(hydroxymethyl)thiazol-2-yl)-4-(4-methoxybenzyl)-4H-1,2,4-triazol-3-yl)propan-2-ol and 2-(4-bromo-2,3-dichlorophenyl)-1,1,1,3,3,3-hexafluoropropan-2-ol and in step c 4,4-difluoropiperidine in place of diethylamine. No final triazole deprotection step was performed. ¹H NMR (400 MHz, DMSO-d₆): δ ppm 9.18 (d, J=7.2 Hz, 1H), 8.07 (d, J=6.4 Hz, 1H), 7.75 (d, J=6.4 Hz, 1H), 4.23-4.16 (m, 4H), 3.69-3.66 (m, 4H), 2.00 (br s, 4H), 1.64 (s, 6H), 1.25 (d, J=5.6 Hz, 3H). MS (ESI): m/z 691.1 [M+H]⁺.

Example 10

Step a (S)-Methyl 3-(3-(5-(2,3-dichloro-4-(N-(1,1,1-trifluorobutan-2-yl)sulfamoyl)phenyl)-4-(hydroxymethyl)thiazol-2-yl)-1,2,4-oxadiazol-5-yl)-2,2-dimethylpropanoate

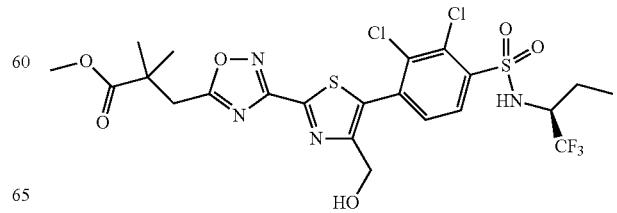

A mixture of methyl 3-(3-(4-(hydroxymethyl)thiazol-2-yl)-1,2,4-oxadiazol-5-yl)-2,2-dimethylpropanoate (250 mg, 0.82 mmol, Intermediate 8, step f), (S)-4-bromo-2,3-dichloro-N-(1,1,1-trifluorobutan-2-yl)benzenesulfonamide (340 mg, 0.86 mmol, Intermediate 12/4), Na₂CO₃ (360 mg, 2.58 mmol), Pd(OAc)₂ (70 mg, 0.30 mmol), P(Cy)₃·HBF₄ (75 mg 0.20 mmol), PivOH (30 mg 0.30 mmol), and DMA (8 mL) was heated under Ar at 88° C. overnight, cooled to rt, partitioned between EtOAc and H₂O and the layers were separated. The organic phase was washed with H₂O, brine, dried over anhydrous Na₂SO₄, filtered, concentrated to dryness, and the residue was purified by prep-TLC (EtOAc) to give the title compound as a light yellow solid.

Example 10

Step b

Methyl 3-(3-(5-(2,3-dichloro-4-(N—((S)-1,1,1-trifluorobutan-2-yl)sulfamoyl)phenyl)-4-((S)-2-methylpiperidine-1-carbonyl)thiazol-2-yl)-1,2,4-oxadiazol-5-yl)-2,2-dimethylpropanoate

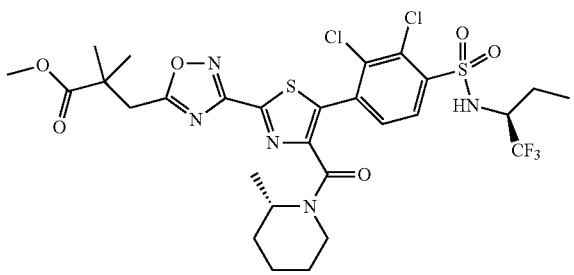 [SMILES: CC[C@H](NS(=O)(=O)c1ccc(-c2sc(-c3noc(CC(C)(C)C(=O)OC)n3)nc2C(=O)N2CCCC[C@@H]2C)c(Cl)c1Cl)C(F)(F)F]

A mixture of (5)-methyl 3-(3-(5-(2,3-dichloro-4-(N-(1,1,1-trifluorobutan-2-yl)sulfamoyl)phenyl)-4-(hydroxymethyl)thiazol-2-yl)-1,2,4-oxadiazol-5-yl)-2,2-dimethylpropanoate (100 mg, 0.16 mmol, Example 10, step a), TEMPO (31 mg, 0.2 mmol), iodobenzene diacetate (258 mg, 0.80 mmol), H₂O (5 mL), and MeCN (15 mL) was stirred at rt overnight, diluted with H₂O (15 mL), and extracted with EtOAc (30 mL×3). The combined organic layers were washed with brine, dried over anhydrous MgSO₄, filtered, and concentrated to dryness to give the crude intermediate as a brown solid, which was dissolved in DMF (10 mL). To the solution was added (S)-2-methylpiperidine (30 mg, 0.3 mmol), HATU (125 mg, 0.329 mmol), and DIPEA (0.117 mL, 0.661 mmol) at rt. The mixture was stirred for 2 h, poured into H₂O (120 mL), and extracted with EtOAc (100 mL×3). The combined organic layers were washed with brine, dried over anhydrous Na₂SO₄, filtered, concentrated to dryness, and the residue was purified by FCC on silica gel (PE/EtOAc=1:1) to afford the title compound as a yellow solid.

Example 10

3-(3-(5-(2,3-Dichloro-4-(N—((S)-1,1,1-trifluorobutan-2-yl)sulfamoyl)phenyl)-4-((S)-2-methylpiperidine-1-carbonyl)thiazol-2-yl)-1,2,4-oxadiazol-5-yl)-2,2-dimethylpropanoic acid

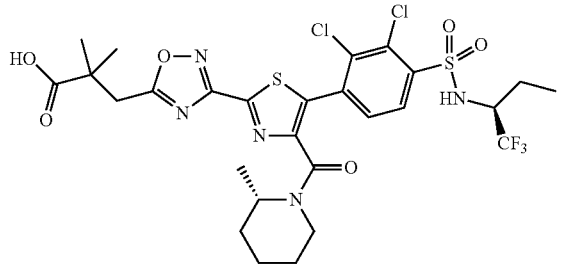 [SMILES: CC[C@H](NS(=O)(=O)c1ccc(-c2sc(-c3noc(CC(C)(C)C(=O)O)n3)nc2C(=O)N2CCCC[C@@H]2C)c(Cl)c1Cl)C(F)(F)F]

A mixture of methyl 3-(3-(5-(2,3-dichloro-4-(N—((S)-1,1,1-trifluorobutan-2-yl)sulfamoyl)phenyl)-4-((S)-2-methylpiperidine-1-carbonyl)thiazol-2-yl)-1,2,4-oxadiazol-5-yl)-2,2-dimethylpropanoate (80 mg, 0.11 mmol, Example 10, step b), LiOH·H₂O (43 mg, 1.0 mmol), MeOH (2 mL), and H₂O (1 mL) was stirred at rt overnight, concentrated to dryness, dissolved in aqueous HCl (1 N, 10 mL), and extracted with EtOAc (8 mL×3). The combined organic layers were washed with brine, dried over anhydrous Na₂SO₄, filtered, concentrated to dryness, and the residue was purified by prep-HPLC to give the title compound as a white solid. ¹H NMR (300 MHz, CDCl₃, mixture of rotamers): δ ppm 8.08-8.05 (m, 1H), 7.75-7.67 (m, 1H), 5.63 (d, J=7.5 Hz, 1H), 4.88-4.42 (br s, 0.6H), 4.45-4.42 (br s, 0.4H), 3.94-3.85 (m, 1.4H), 3.47-3.44 (m, 0.6H), 3.30 (s, 2H), 3.30-2.80 (m, 1H), 1.93-1.85 (m, 1H), 1.69-1.56 (m, 6H), 1.41 (s, 6H), 1.35-1.07 (m, 7H). MS (ESI): m/z 712.0 [M+H]⁺.

Example 10/1

(S)-3-(3-(5-(3-Chloro-2-(difluoromethyl)-4-(N-(1,1,1-trifluorobutan-2-yl)sulfamoyl)phenyl)-4-(4,4-difluoropiperidine-1-carbonyl)thiazol-2-yl)-1,2,4-oxadiazol-5-yl)-2,2-dimethylpropanoic acid

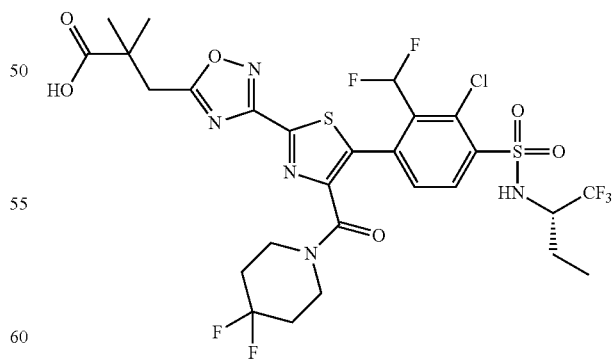

The title compound was prepared as described for the synthesis of Example 10, using in step a (S)-4-bromo-2-chloro-3-(difluoromethyl)-N-(1,1,1-trifluorobutan-2-yl)benzenesulfonamide (Intermediate 12/14) in place of (S)-4-bromo-2,3-dichloro-N-(1,1,1-trifluorobutan-2-yl)

benzenesulfonamide and using in step b 4,4-difluoropiperidine in place of (S)-2-methylpiperidine. ¹H NMR (500 MHz, CDCl₃): δ ppm 8.21 (d, J=10.0 Hz, 1H), 7.66 (d, J=10.0 Hz, 1H), 7.19 (t, J=66.5 Hz, 1H), 5.48 (br s, 1H), 3.89-3.85 (m, 1H), 3.69 (br s, 4H), 3.28 (s, 2H), 2.03-1.87 (m, 5H), 1.64-1.56 (m, 1H), 1.38 (s, 6H), 1.12-1.08 (m, 3H). MS (ESI): m/z 750.1 [M+H]⁺.

Example 10/2

(S)-3-(3-(4-(4,4-Difluoropiperidine-1-carbonyl)-5-(4-(N-(1,1,1-trifluorobutan-2-yl)sulfamoyl)-2-(trifluoromethoxy)phenyl)thiazol-2-yl)-1,2,4-oxadiazol-5-yl)-2,2-dimethylpropanoic acid

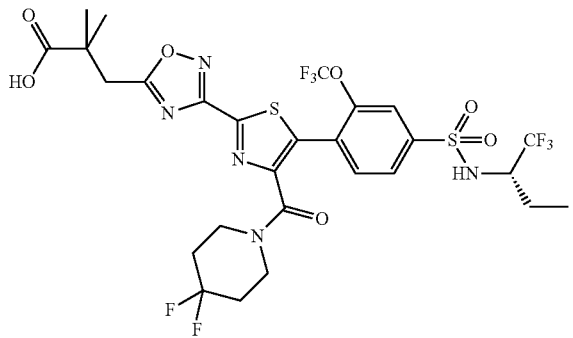 [SMILES: CC[C@H](NS(=O)(=O)c1ccc(-c2sc(-c3noc(CC(C)(C)C(=O)O)n3)nc2C(=O)N2CCC(F)(F)CC2)c(OC(F)(F)F)c1)C(F)(F)F]

The title compound was prepared as described for the synthesis of Example 10, using in step a (S)-4-bromo-N-(1,1,1-trifluorobutan-2-yl)-3-(trifluoromethoxy)benzenesulfonamide (Intermediate 12/15) in place of (S)-4-bromo-2,3-dichloro-N-(1,1,1-trifluorobutan-2-yl)benzenesulfonamide and using in step b 4,4-difluoropiperidine in place of (S)-2-methylpiperidine. ¹H NMR (500 MHz, DMSO-d₆): δ ppm 7.99-7.90 (m, 3H), 4.06-4.01 (m, 1H), 3.70-3.68 (m, 2H), 3.48-3.45 (m, 2H), 3.28 (s, 2H), 2.04-1.88 (m, 4H), 1.69-1.64 (m, 1H), 1.47-1.41 (m, 1H), 1.29 (s, 6H), 0.70 (t, J=7.5 Hz, 3H). MS (ESI): m/z 750.3 [M+H]⁺.

Example 10/3

3-(3-(5-(3-Chloro-2-(difluoromethyl)-4-(N—((S)-1,1,1-trifluorobutan-2-yl)sulfamoyl)phenyl)-4-((S)-4,4-difluoro-2-methylpyrrolidine-1-carbonyl)thiazol-2-yl)-1,2,4-oxadiazol-5-yl)-2,2-dimethylpropanoic acid

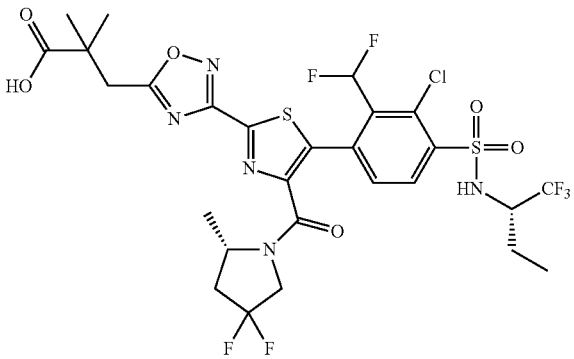 [SMILES: CC[C@H](NS(=O)(=O)c1ccc(-c2sc(-c3noc(CC(C)(C)C(=O)O)n3)nc2C(=O)N2CC(F)(F)C[C@@H]2C)c(C(F)F)c1Cl)C(F)(F)F]

The title compound was prepared as described for the synthesis of Example 10, using in step a (S)-4-bromo-2-chloro-3-(difluoromethyl)-N-(1,1,1-trifluorobutan-2-yl)benzenesulfonamide (Intermediate 12/14) in place of (S)-4-bromo-2,3-dichloro-N-(1,1,1-trifluorobutan-2-yl)benzenesulfonamide and using in step b (S)-4,4-difluoro-2-methylpyrrolidine (Intermediate 14, step b) in place of (S)-2-methylpiperidine. ¹H NMR (500 MHz, CDCl₃, mixture of rotamers): δ 8.25-8.22 (m, 1H), 7.60-7.56 (m, 1H), 7.26-7.06 (m, 1H), 5.39 (br s, 1H), 4.45-3.85 (m, 4H), 3.29 (s, 2H), 2.58-2.48 (m, 1H), 2.09-2.02 (m, 1H), 1.92-1.87 (m, 1H), 1.63-1.56 (m, 1H), 1.41 (s, 6H), 1.32-1.26 (m, 3H), 1.10-1.07 (m, 3H). MS (ESI): m/z 750.1 [M+H]⁺.

Example 10/4

3-(3-(5-(3-Chloro-2-(difluoromethyl)-4-(N—((S)-1,1,1-trifluorobutan-2-yl)sulfamoyl)phenyl)-4-((S)-2-methylpiperidine-1-carbonyl)thiazol-2-yl)-1,2,4-oxadiazol-5-yl)-2,2-dimethylpropanoic acid

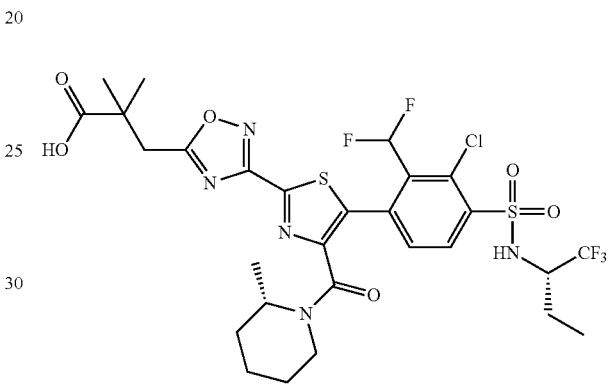

The title compound was prepared as described for the synthesis of Example 10, using in step a (S)-4-bromo-2-chloro-3-(difluoromethyl)-N-(1,1,1-trifluorobutan-2-yl)benzenesulfonamide (Intermediate 12/14) in place of (S)-4-bromo-2,3-dichloro-N-(1,1,1-trifluorobutan-2-yl)benzenesulfonamide. ¹H NMR (500 MHz, DMSO-d₆, mixture of rotamers): δ ppm 8.23 (d, J=8.0 Hz, 1H), 7.69-7.66 (m, 1H), 7.40-7.15 (m, 1H), 4.64-3.51 (m, 4H), 3.26 (s, 2H), 3.00-2.74 (m, 1H), 1.70-1.40 (m, 7H), 1.28 (s, 6H), 1.15-1.01 (m, 4H), 0.86 (t, J=7.0 Hz, 3H). MS (ESI): m/z 728.1 [M+H]⁺.

Example 11

Step a (S)-2,3-Dichloro-4-(4-(hydroxymethyl)-2-(5-(2-hydroxypropan-2-yl)-1,2,4-oxadiazol-3-yl)thiazol-5-yl)-N-(1,1,1-trifluoropropan-2-yl)benzenesulfonamide

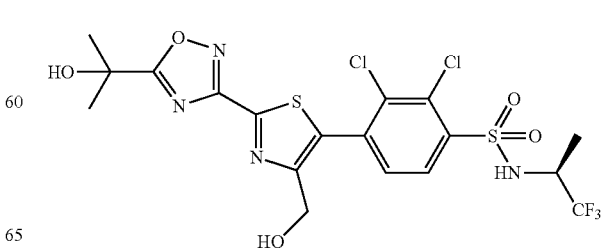

A solution of 2-(3-(4-(hydroxymethyl)thiazol-2-yl)-1,2,4-oxadiazol-5-yl)propan-2-ol (105 mg, 0.435 mmol, Intermediate 9, step b), (S)-4-bromo-2,3-dichloro-N-(1,1,1-trifluoropropan-2-yl)benzenesulfonamide (170 mg, 0.43 mmol, Intermediate 12/3), $K_2CO_3$ (120 mg, 0.86 mmol), Pd(OAc)$_2$ (23 mg, 0.10 mmol), P(Cy)$_3$·HBF$_4$ (20 mg, 0.058 mmol), and PivOH (10 mg, 0.086 mmol) in DMA (2 mL) was stirred under argon at 95° C. overnight. The solution was cooled to rt, partitioned between EtOAc and water and the layers were separated. The organic layer was washed with water and brine, dried over anhydrous $Na_2SO_4$, filtered, concentrated to dryness, and the residue was purified by prep-TLC to give the title compound as a light yellow solid.

Example 11

Step b (S)-5-(2,3-Dichloro-4-(N-(1,1,1-trifluoropropan-2-yl)sulfamoyl)phenyl)-2-(5-(2-hydroxypropan-2-yl)-1,2,4-oxadiazol-3-yl)thiazole-4-carboxylic acid

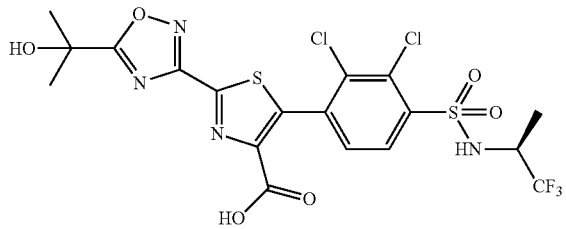 [SMILES: C[C@H](NS(=O)(=O)c1ccc(-c2sc(-c3noc(C(C)(C)O)n3)nc2C(=O)O)c(Cl)c1Cl)C(F)(F)F]

To a solution of (S)-2,3-dichloro-4-(4-(hydroxymethyl)-2-(5-(2-hydroxypropan-2-yl)-1,2,4-oxadiazol-3-yl)thiazol-5-yl)-N-(1,1,1-trifluoropropan-2-yl)benzene sulfonamide (110 mg, 0.19 mmol, Example 11, step a) in a mixture of MeCN (5 mL) and $H_2O$ (2.5 mL) were added iodobenzene diacetate (250 mg, 0.78 mmol) and TEMPO (36 mg, 0.23 mmol). The mixture was stirred for 12 h at rt and concentrated to dryness. The residue was extracted with EtOAc (10 mL×2) and the organic layer was washed with brine and dried over anhydrous $Na_2SO_4$. The mixture was concentrated to dryness and the residue purified by prep-TLC (EtOAc) to give the title compound as a white solid.

Example 11

(S)-2,3-Dichloro-4-(4-(4-fluoropiperidine-1-carbonyl)-2-(5-(2-hydroxypropan-2-yl)-1,2,4-oxadiazol-3-yl)thiazol-5-yl)-N-(1,1,1-trifluoropropan-2-yl)benzenesulfonamide

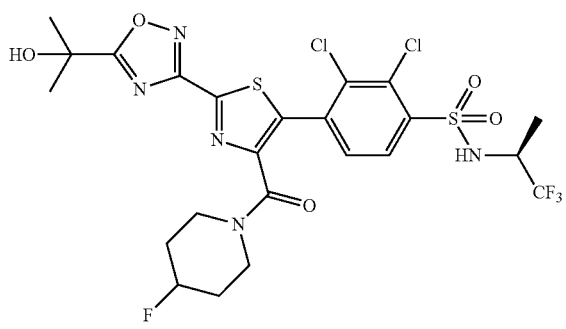 [SMILES: C[C@H](NS(=O)(=O)c1ccc(-c2sc(-c3noc(C(C)(C)O)n3)nc2C(=O)N2CCC(F)CC2)c(Cl)c1Cl)C(F)(F)F]

To a solution of (S)-5-(2,3-dichloro-4-(N-(1,1,1-trifluoropropan-2-yl)sulfamoyl)phenyl)-2-(5-(2-hydroxypropan-2-yl)-1,2,4-oxadiazol-3-yl)thiazole-4-carboxylic acid (95 mg, 0.17 mmol, Example 11, step b) in DMA (3.0 mL) were added HATU (94 mg, 0.25 mmol) and TEA (50 mg, 0.5 mmol). The mixture was stirred at rt for 20 min. 4-Fluoropiperidine (34 mg, 0.36 mmol) was added and the mixture was stirred overnight. Water was added and the mixture was extracted with EtOAc. The organic layer was separated, washed with brine, dried over anhydrous $Na_2SO_4$, and filtered. The filtrate was concentrated to dryness and the residue was purified by prep-HPLC to give the title compound. $^1H$ NMR (400 MHz, CDCl$_3$): δ ppm 8.10-8.08 (m, 1H), 7.70-7.66 (m, 1H), 5.56 (s, 1H), 4.94-4.81 (m, 1H), 4.10-3.93 (m, 2H), 3.52-3.40 (m, 3H), 3.04 (s, 1H), 1.92-1.69 (m, 10H), 1.44-1.40 (m, 3H). MS (ESI): m/z 660.0 [M+H]$^+$.

Example 11/1

(S)-3-(Difluoromethyl)-2-fluoro-4-(4-(4-fluoropiperidine-1-carbonyl)-2-(5-(2-hydroxypropan-2-yl)-1,2,4-oxadiazol-3-yl)thiazol-5-yl)-N-(1,1,1-trifluoropropan-2-yl)benzenesulfonamide

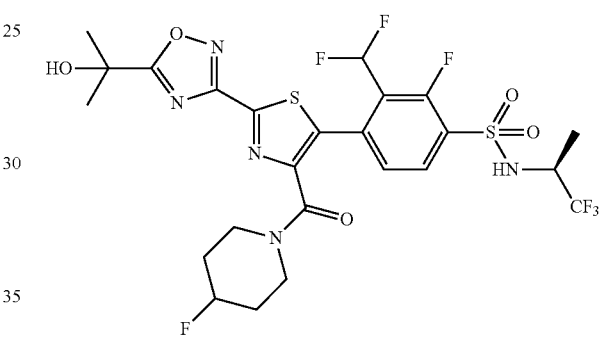

The title compound was prepared as described for the synthesis of Example 11, using in step a (S)-4-bromo-3-(difluoromethyl)-2-fluoro-N-(1,1,1-trifluoropropan-2-yl)benzenesulfonamide4-fluoropiperidine (Intermediate 12/2) in place (S)-4-bromo-2,3-dichloro-N-(1,1,1-trifluoropropan-2-yl)benzenesulfonamide. $^1$HNMR (500 MHz, CDCl$_3$): δ 8.07-8.05 (m, 1H), 7.52-7.50 (m, 1H), 6.92 (t, J=53.0 Hz, 1H), 5.41-5.39 (m, 1H), 4.93-4.83 (m, 1H), 4.17-4.13 (m, 1H), 3.98-3.93 (m, 1H), 3.62-3.60 (m, 2H), 3.49-3.43 (m, 1H), 1.90-1.78 (m, 10H), 1.43 (d, J=7.0 Hz, 3H). MS (ESI): m/z 660.2 [M+H]$^+$.

Example 11/2

(S)-3-(Difluoromethyl)-4-(4-(4,4-difluoropiperidine-1-carbonyl)-2-(5-(2-hydroxypropan-2-yl)-1,2,4-oxadiazol-3-yl)thiazol-5-yl)-2-fluoro-N-(1,1,1-trifluoropropan-2-yl)benzenesulfonamide

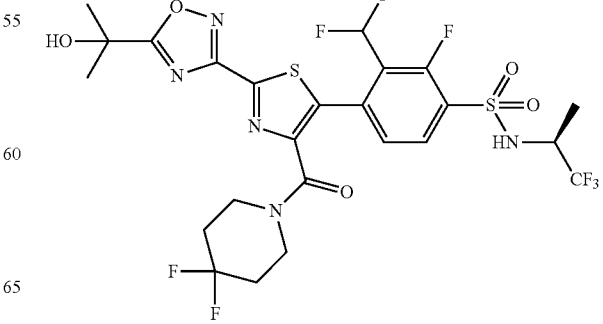

The title compound was prepared as described for the synthesis of Example 11, using in step a (S)-4-bromo-3-(difluoromethyl)-2-fluoro-N-(1,1,1-trifluoropropan-2-yl)benzenesulfonamide (Intermediate 12/2) in place (S)-4-bromo-2,3-dichloro-N-(1,1,1-trifluoropropan-2-yl)benzenesulfonamide and 4,4-difluoropiperidine in place of 4-fluoropiperidine. $^1$HNMR (500 MHz, CDCl$_3$): δ 8.08-8.05 (m, 1H), 7.50 (d, J=7.5 Hz, 1H), 6.93 (t, J=53.0 Hz, 1H), 5.32 (s, 1H), 4.17-4.12 (m, 1H), 3.75-3.70 (m, 4H), 2.07-1.98 (m, 4H), 1.78 (s, 6H), 1.44 (d, J=7.0 Hz, 3H). MS (ESI): m/z 678.0 [M+H]$^+$.

Example 12

Step a (S)-3-(Difluoromethyl)-2-fluoro-4-(2-(5-(2-hydroxy-2-methylpropyl)-1,2,4-oxadiazol-3-yl)-4-(hydroxymethyl)thiazol-5-yl)-N-(1,1,1-trifluorobutan-2-yl)benzenesulfonamide

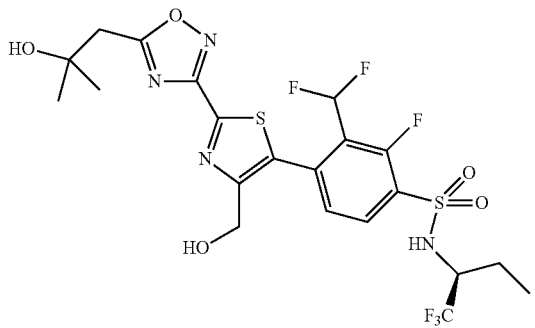 [SMILES: CC[C@H](NS(=O)(=O)c1ccc(-c2sc(-c3noc(CC(C)(C)O)n3)nc2CO)c(C(F)F)c1F)C(F)(F)F]

A solution of 1-(3-(4-(hydroxymethyl)thiazol-2-yl)-1,2,4-oxadiazol-5-yl)-2-methylpropan-2-ol (240 mg, 0.93 mmol, Intermediate 9/1), (S)—N-(4-bromo-3-(difluoromethyl)-2-fluorophenyl)-1,1,1-trifluorobutane-2-sulfonamide (384 mg, 0.927 mmol, Intermediate 12/1, step e), K$_2$CO$_3$ (128 mg, 0.926 mmol), Pd(OAc)$_2$ (50 mg 0.22 mmol), P(Cy)$_3$.HBF$_4$ (50 mg 0.14 mmol), and PivOH (20 mg, 0.20 mmol) in DMA (3 mL) was stirred under Ar at 95° C. overnight, cooled to rt, diluted with EtOAc and H$_2$O, and the organic layer was separated. The organic phase was washed with H$_2$O and brine, dried over anhydrous Na$_2$SO$_4$, filtered, concentrated to dryness, and the residue was purified by prep-TLC (EtOAc) to give the title compound as a light yellow solid.

Example 12

Step b (S)-5-(2-(Difluoromethyl)-3-fluoro-4-(N-(1,1,1-trifluorobutan-2-yl)sulfamoyl)phenyl)-2-(5-(2-hydroxy-2-methylpropyl)-1,2,4-oxadiazol-3-yl)thiazole-4-carboxylic acid

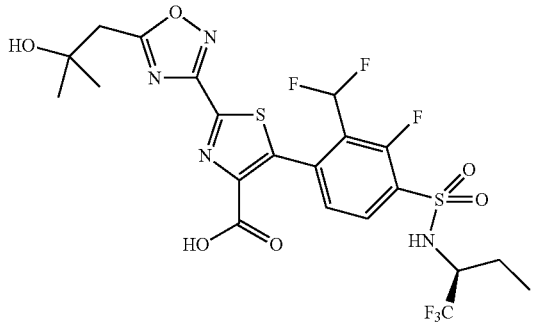 [SMILES: CC[C@H](NS(=O)(=O)c1ccc(-c2sc(-c3noc(CC(C)(C)O)n3)nc2C(=O)O)c(C(F)F)c1F)C(F)(F)F]

To a solution of (S)-3-(difluoromethyl)-2-fluoro-4-(2-(5-(2-hydroxy-2-methylpropyl)-1,2,4-oxadiazol-3-yl)-4-(hydroxymethyl)thiazol-5-yl)-N-(1,1,1-trifluorobutan-2-yl)benzene sulfonamide (230 mg, 0.39 mmol, Example 12, step a) in a mixture of MeCN (5 mL) and H$_2$O (2.5 mL) were added iodobenzene diacetate (250 mg, 0.78 mmol) and TEMPO (90 mg, 0.59 mmol). The mixture was stirred for 12 h at rt, concentrated to dryness, and extracted with EtOAc (10 mL×3). The combined organic layers were washed with brine, dried over anhydrous Na$_2$SO$_4$, filtered, concentrated to dryness, and the residue was purified by prep-TLC (EtOAc) to give the title compound as a white solid.

Example 12

(S)-3-(Difluoromethyl)-2-fluoro-4-(4-(4-fluoropiperidine-1-carbonyl)-2-(5-(2-hydroxy-2-methylpropyl)-1,2,4-oxadiazol-3-yl)thiazol-5-yl)-N-(1,1,1-trifluorobutan-2-yl)benzenesulfonamide

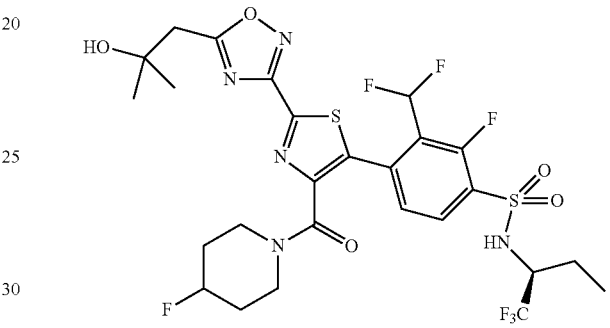

To a solution of (S)-5-(2-(difluoromethyl)-3-fluoro-4-(N-(1,1,1-trifluorobutan-2-yl)sulfamoyl)phenyl)-2-(5-(2-hydroxy-2-methylpropyl)-1,2,4-oxadiazol-3-yl)thiazole-4-carboxylic acid (100 mg, 0.17 mmol, Example 12, step b) in DMA (3 mL) were added HATU (94 mg, 0.25 mmol) and TEA (50 mg, 0.5 mmol). The mixture was stirred for 20 min, and 4-fluoropiperidine (34 mg, 0.36 mmol) was added. The reaction mixture was stirred overnight, quenched with H$_2$O, and extracted with EtOAc. The organic layer was separated, washed with brine, dried over anhydrous Na$_2$SO$_4$, filtered, concentrated to dryness, and the residue was purified by prep-HPLC to give the title compound. $^1$H NMR (400 MHz, CDCl$_3$): δ ppm 8.05 (t, J=7.6 Hz, 1H), 7.52-7.49 (m, 1H), 6.92 (t, J=52.8 Hz, 1H), 5.32 (d, J=9.6 Hz, 1H), 4.94-4.82 (m, 1H), 4.00-3.91 (m, 2H), 3.66-3.59 (m, 2H), 3.46-3.44 (m, 1H), 3.22 (s, 2H), 1.95-1.58 (m, 6H), 1.43 (s, 6H), 1.09 (t, J=7.4 Hz, 3H). MS (ESI): m/z 688.1 [M+H]$^+$.

Example 12/1

(S)-3-(Difluoromethyl)-4-(4-(3,3-difluoropyrrolidine-1-carbonyl)-2-(5-(2-hydroxy-2-methylpropyl)-1,2,4-oxadiazol-3-yl)thiazol-5-yl)-2-fluoro-N-(1,1,1-trifluorobutan-2-yl)benzenesulfonamide

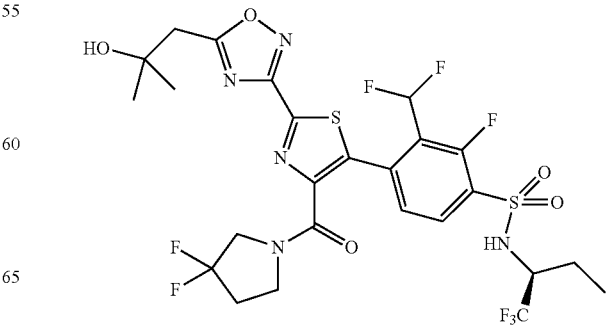

The title compound was prepared as described for the synthesis of Example 12, using in the final step, 3,3-difluoropyrrolidine in place of 4-fluoropiperidine. ¹H NMR (400 MHz, CDCl₃): δ ppm 8.04 (dd, J=7.6, 7.4 Hz, 1H), 7.42 (dd, J=8.0, 6.0 Hz, 1H), 6.88 (dd, J=53.0, 5.5 Hz, 1H), 5.23 (d, J=9.6 Hz, 1H), 4.27-4.09 (m, 2H), 3.91-3.74 (m, 3H), 3.22 (s, 2H), 2.43-2.34 (m, 2H), 1.93-1.89 (m, 1H), 1.62-1.56 (m, 1H), 1.43 (s, 6H), 1.09 (t, J=7.2 Hz, 3H). MS (ESI): m/z 692.0 [M+H]⁺.

Example 13

Step a (S)-2,3-Dichloro-4-(4-(hydroxymethyl)-2-(5-(2-hydroxypropan-2-yl)isoxazol-3-yl)thiazol-5-yl)-N-(1,1,1-trifluoropropan-2-yl)benzenesulfonamide

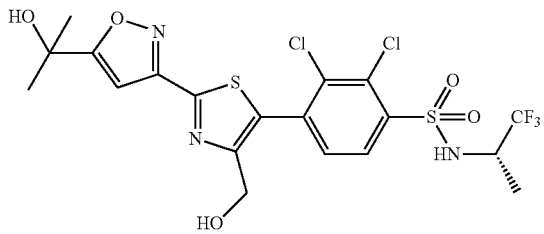 [SMILES: C[C@H](NS(=O)(=O)c1ccc(-c2sc(-c3cc(C(C)(C)O)on3)nc2CO)c(Cl)c1Cl)C(F)(F)F]

To a solution of 2-(3-(4-(hydroxymethyl)thiazol-2-yl)isoxazol-5-yl)propan-2-ol (178 mg, 0.742 mmol, Intermediate 10, step e), (S)-4-bromo-2,3-dichloro-N-(1,1,1-trifluoropropan-2-yl)benzenesulfonamide (300 mg, 0.723 mmol, Intermediate 12/3), and Na₂CO₃ (160 mg, 1.5 mmol) in DMA (3 mL) were added P(Cy)₃.HBF₄ (55 mg, 0.15 mmol), PivOH (15 mg, 0.15 mmol), and Pd(OAc)₂ (50 mg, 0.22 mmol) under an Ar atmosphere. The solution was stirred at 95° C. overnight. The mixture was cooled to rt, partitioned between EtOAc and water, and the layers were separated. The organic layer was washed with water, brine, dried over anhydrous Na₂SO₄, and filtered. The filtrate was concentrated to dryness and the yellow residue was purified by FCC on silica gel (PE/EtOAc=3:1) to give the title compound as a yellow solid.

Example 13

Step b (S)-5-(2,3-Dichloro-4-(N-(1,1,1-trifluoropropan-2-yl)sulfamoyl)phenyl)-2-(5-(2-hydroxypropan-2-yl)isoxazol-3-yl)thiazole-4-carboxylic acid

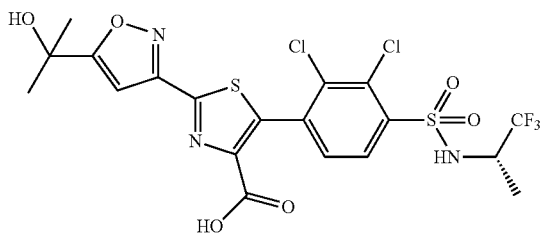 [SMILES: C[C@H](NS(=O)(=O)c1ccc(-c2sc(-c3cc(C(C)(C)O)on3)nc2C(=O)O)c(Cl)c1Cl)C(F)(F)F]

To a solution of (S)-2,3-dichloro-4-(4-(hydroxymethyl)-2-(5-(2-hydroxypropan-2-yl)isoxazol-3-yl)thiazol-5-yl)-N-(1,1,1-trifluoropropan-2-yl)benzenesulfonamide (175 mg, 0.312 mmol, Example 13, step a) in a mixture of MeCN (5 mL) and H₂O (2.5 mL) were added iodobenzene diacetate (386 mg, 1.20 mmol) and TEMPO (56 mg, 0.36 mmol). The mixture was stirred for 12 h at rt and concentrated to dryness. The residue was extracted with EtOAc (20 mL×2) and the organic layer was washed with brine, dried with anhydrous Na₂SO₄, filtered and concentrated to dryness. The residue was purified by prep-TLC (EtOAc) to give the title compound as a white solid.

Example 13

(S)-2,3-Dichloro-4-(4-(4,4-difluoropiperidine-1-carbonyl)-2-(5-(2-hydroxypropan-2-yl)isoxazol-3-yl)thiazol-5-yl)-N-(1,1,1-trifluoropropan-2-yl)benzenesulfonamide

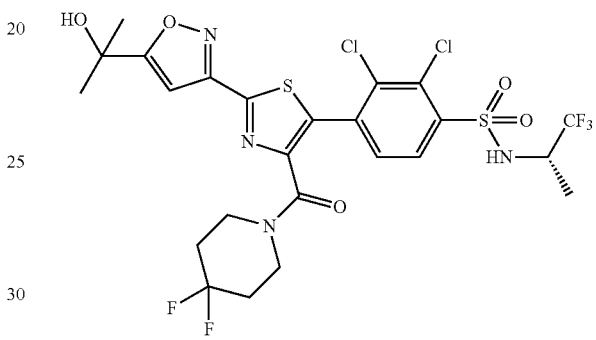

To a solution of (S)-5-(2,3-dichloro-4-(N-(1,1,1-trifluoropropan-2-yl)sulfamoyl)phenyl)-2-(5-(2-hydroxypropan-2-yl)isoxazol-3-yl)thiazole-4-carboxylic acid (95 mg, 0.17 mmol, Example 13, step b) in DMA (3.0 mL) were added HATU (94 mg, 0.25 mmol) and TEA (50 mg, 0.5 mmol). The mixture was stirred for 20 min and then 4,4-difluoropiperidine (44 mg, 0.36 mmol) was added. The mixture was stirred overnight, quenched with water, and extracted with EtOAc. The organic layer was separated, washed with brine, dried over anhydrous Na₂SO₄, and filtered. The filtrate was concentrated to dryness and the residue was purified by prep-HPLC to give the title compound. ¹H NMR (400 MHz, CDCl₃): δ ppm 8.08 (d, J=8.2 Hz, 1H), 7.61 (d, J=8.2 Hz, 1H), 6.76 (s, 1H), 5.47 (d, J=9.6 Hz, 1H), 4.10-4.04 (m, 1H), 3.82-3.76 (m, 2H), 3.64-3.61 (m, 2H), 2.07-1.96 (m, 4H), 1.70 (s, 6H), 1.41 (d, J=6.8 Hz, 3H). MS (ESI): m/z 676.8 [M+H]⁺.

Example 13/1

(S)-2,3-Dichloro-4-(4-(4-fluoropiperidine-1-carbonyl)-2-(5-(2-hydroxypropan-2-yl)isoxazol-3-yl)thiazol-5-yl)-N-(1,1,1-trifluoropropan-2-yl)benzenesulfonamide

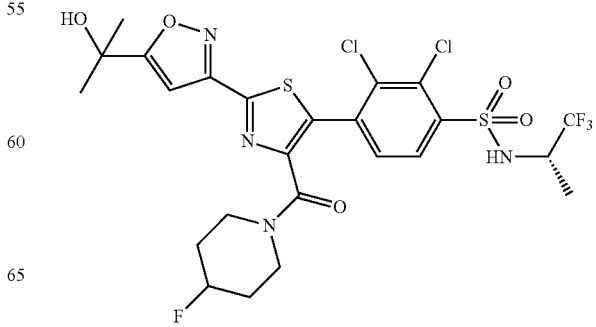

The title compound was prepared as described for the synthesis of Example 13, using in the final step, 4-fluoropiperidine in place of 4,4-difluoropiperidine. ¹H NMR (400 MHz, CDCl₃): δ ppm 8.08 (d, J=8.0 Hz, 1H), 7.64-7.60 (m, 1H), 6.78 (s, 1H), 5.44 (d, J=9.2 Hz, 1H), 4.95-4.79 (m, 1H), 4.10-3.99 (m, 1H), 3.66-3.44 (m, 3H), 1.94-1.70 (m, 10H) 1.41 (d, J=6.8 Hz, 3H). MS (ESI): 658.8 [M+H]⁺.

Example 14

Step a (S)-5-(2,3-Dichloro-4-(N-(1,1,1-trifluoropropan-2-yl)sulfamoyl)phenyl)-4-(4-fluoropiperidine-1-carbonyl)thiazole-2-carboxamide

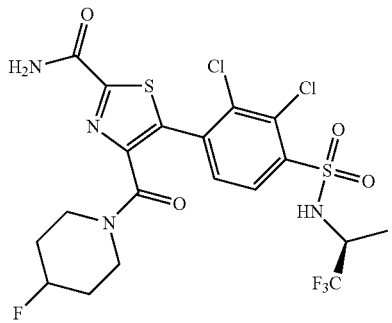 [SMILES: C[C@H](NS(=O)(=O)c1ccc(-c2sc(C(N)=O)nc2C(=O)N2CCC(F)CC2)c(Cl)c1Cl)C(F)(F)F]

A solution of potassium (S)-5-(2,3-dichloro-4-(N-(1,1,1-trifluoropropan-2-yl)sulfamoyl)phenyl)-4-(4-fluoropiperidine-1-carbonyl)thiazole-2-carboxylate (400 mg, 0.65 mmol, prepared as described in WO2013/178362, Example 301, using in step 2 4-fluoropiperidine in place of 4-methylpiperidine and in step 3 (S)-4-bromo-2,3-dichloro-N-(1,1,1-trifluoropropan-2-yl)benzenesulfonamide (Intermediate 12/3) in place of 4-bromo-3-chloro-2-methyl-N-(tert-pentyl)benzenesulfonamide), HATU (177 mg, 1.31 mmol), and DIPEA (1.68 g, 13.0 mmol) in DCM (20 mL) was stirred for 0.5 h at rt. Then NH₄Cl (348 mg, 6.5 mmol) was added and the solution was stirred for another 0.5 h, concentrated to dryness, and the residue was purified by FCC on silica gel (PE/EtOAc=5/1) to give the title compound as a white solid.

Example 14

Step b (S)-2,3-Dichloro-4-(2-cyano-4-(4-fluoropiperidine-1-carbonyl)thiazol-5-yl)-N-(1,1,1-trifluoropropan-2-yl)benzenesulfonamide

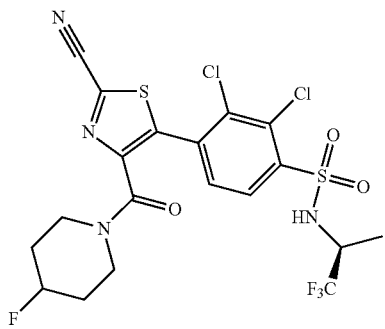 [SMILES: C[C@H](NS(=O)(=O)c1ccc(-c2sc(C#N)nc2C(=O)N2CCC(F)CC2)c(Cl)c1Cl)C(F)(F)F]

To a solution of (S)-5-(2,3-dichloro-4-(N-(1,1,1-trifluoropropan-2-yl)sulfamoyl)phenyl)-4-(4-fluoropiperidine-1-carbonyl)thiazole-2-carboxamide (220 mg, 0.38 mmol, Example 14, step a), and DIPEA (292 mg, 2.28 mmol) in anhydrous THF (5 mL) was added a solution of TFAA (241 mg, 1.15 mmol) in anhydrous DCM (5 mL) at 0° C. under nitrogen. The solution was stirred at rt for 2 h, quenched with saturated aqueous NaHCO₃, and the organic layer was separated. The organic layer was washed with H₂O, brine, dried over anhydrous Na₂SO₄, filtered, concentrated to dryness, and the residue was purified by FCC on silica gel (PE/EtOAc=10/1) to give the title compound as a white solid.

Example 14

Step c (S)-5-(2,3-Dichloro-4-(N-(1,1,1-trifluoropropan-2-yl)sulfamoyl)phenyl)-4-(4-fluoropiperidine-1-carbonyl)-N'-hydroxythiazole-2-carboximidamide

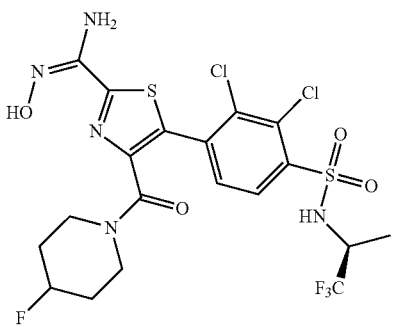 [SMILES: C[C@H](NS(=O)(=O)c1ccc(-c2sc(/C(N)=N\O)nc2C(=O)N2CCC(F)CC2)c(Cl)c1Cl)C(F)(F)F]

To a solution of (S)-2,3-dichloro-4-(2-cyano-4-(4-fluoropiperidine-1-carbonyl)thiazol-5-yl)-N-(1,1,1-trifluoropropan-2-yl)benzenesulfonamide (170 mg, 0.30 mmol, Example 14, step b) in MeOH (5 mL) were added TEA (303 mg, 3.00 mmol) and NH₂OH.HCl (42 mg, 0.60 mmol). The solution was heated for 3 h at reflux, and concentrated to dryness. Addition of water resulted in the formation of a solid that was isolated by filtration and dried under vacuum to give the title compound as a pale yellow solid.

Example 14

(S)-2,3-Dichloro-4-(4-(4-fluoropiperidine-1-carbonyl)-2-(5-oxo-4,5-dihydro-1,2,4-oxadiazol-3-yl)thiazol-5-yl)-N-(1,1,1-trifluoropropan-2-yl)benzenesulfonamide

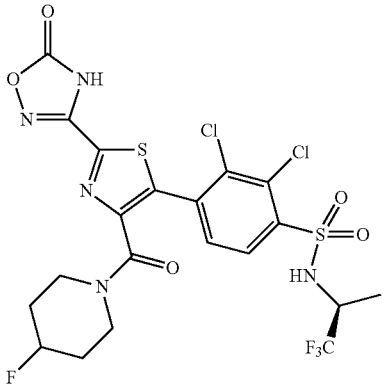 [SMILES: C[C@H](NS(=O)(=O)c1ccc(-c2sc(-c3noc(=O)[nH]3)nc2C(=O)N2CCC(F)CC2)c(Cl)c1Cl)C(F)(F)F]

To a solution of (S)-5-(2,3-dichloro-4-(N-(1,1,1-trifluoropropan-2-yl)sulfamoyl)phenyl)-4-(4-fluoropiperidine-1-carbonyl)-N'-hydroxythiazole-2-carboximidamide (120 mg, 0.20 mmol, Example 14, step c), and TEA 113 mg, 1.07 mmol) in anhydrous THF (3 mL) was added triphosgene (24 mg, 81 μmol) at 0° C. The solution was stirred for 1 h, diluted with water, stirred for another 30 min, and extracted with EtOAc. The organic layer was dried over anhydrous Na$_2$SO$_4$, filtered, concentrated to dryness, and the residue was purified by prep-HPLC to give the title compound as a white solid. $^1$H NMR (300 MHz, CD$_3$OD): δ ppm 8.11 (d, J=8.4 Hz, 1H), 7.64 (d, J=8.4 Hz, 1H), 4.92 (br s, 0.5H), 4.74 (br s, 0.5H), 4.12-4.02 (m, 1H), 3.85-3.76 (m, 1H), 3.56-3.55 (m, 3H), 1.80-1.75 (m, 4H), 1.33-1.28 (m, 3H). MS: m/z 616.0 [M−1]$^-$.

Example 15

2,3-Dichloro-4-(4-((S)-2-methylpiperidine-1-carbonyl)-2-(1H-tetrazol-5-yl)thiazol-5-yl)-N—((S)-1,1,1-trifluorobutan-2-yl)benzenesulfonamide

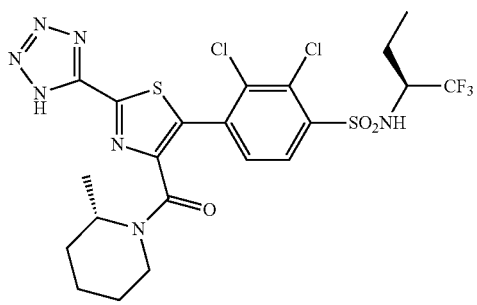

To a solution of 2,3-dichloro-4-(2-cyano-4-((S)-2-methylpiperidine-1-carbonyl)thiazol-5-yl)-N—((S)-1,1,1-trifluorobutan-2-yl)benzenesulfonamide (97 mg, 0.17 mmol, prepared as described for Example 14, step b, using (S)-4-bromo-2,3-dichloro-N-(1,1,1-trifluorobutan-2-yl) benzenesulfonamide (Intermediate 12/4) in place of (S)-4-bromo-2,3-dichloro-N-(1,1,1-trifluoropropan-2-yl) benzenesulfonamide and (S)-2-methylpiperidine in place of 4-fluoropiperidine) in DMF (3 mL) was added NaN$_3$ (55 mg, 0.85 mmol) and the mixture was stirred at 100° C. overnight. Water was added and the mixture was extracted with EtOAc three times. The combined organic layers were washed with brine, dried over anhydrous Na$_2$SO$_4$, filtered and concentrated to dryness. The residue was purified by prep-HPLC to give the title compound as a white solid. $^1$H NMR (400 MHz, CD$_3$OD): δ ppm 8.00 (d, J=6.8 Hz, 1H), 7.60-7.55 (m, 1H), 4.72-4.68 (m, 0.6H), 4.28-4.25 (m, 0.4H), 4.01-3.90 (m, 0.4H), 3.83-3.71 (m, 1H), 3.60-3.53 (m, 0.6H), 3.11-2.99 (m, 0.6H), 2.85-2.73 (m, 0.4H), 1.69-1.66 (m, 1H), 1.58-0.92 (m, 10H), 0.91 (t, J=5.6 Hz, 3H). MS (ESI): m/z 612.1 [M+H]$^+$.

Example 16

Step a 2,3-Dichloro-4-(2-(hydroxymethyl)-4-((S)-2-methylpiperidine-1-carbonyl)thiazol-5-yl)-N—((S)-1,1,1-trifluoropropan-2-yl)benzenesulfonamide

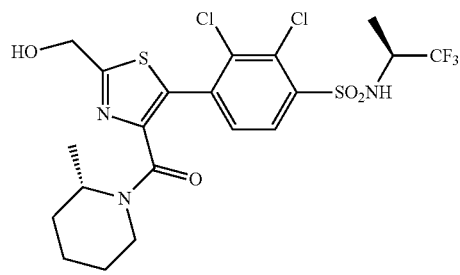

To a solution of ethyl 5-(2,3-dichloro-4-(N—((S)-1,1,1-trifluoropropan-2-yl)sulfamoyl)phenyl)-4-((S)-2-methylpiperidine-1-carbonyl)thiazole-2-carboxylate (216 mg, 0.36 mmol, prepared as described for the synthesis of Example 1, step c using in step c (S)-2-methylpiperidine in place of diethylamine) in MeOH (10 mL) was added NaBH$_4$ (34 mg, 0.90 mmol). The resulting mixture was stirred at rt for 1 h. Then the mixture was quenched with water and extracted with EtOAc. The organic layer was separated, washed with brine and dried over anhydrous Na$_2$SO$_4$. After filtration, the filtrate was concentrated to dryness to give the title compound as a white solid.

Example 16

Step b 2,3-Dichloro-4-(2-formyl-4-((S)-2-methylpiperidine-1-carbonyl)thiazol-5-yl)-N—((S)-1,1,1-trifluoropropan-2-yl)benzenesulfonamide

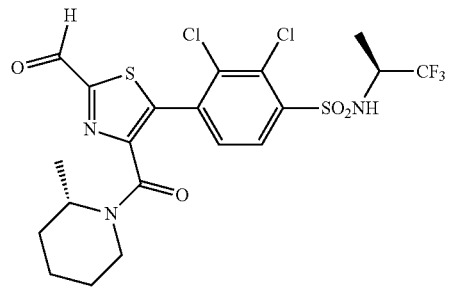

To a solution of 2,3-dichloro-4-(2-(hydroxymethyl)-4-((S)-2-methylpiperidine-1-carbonyl)thiazol-5-yl)-N—((S)-1,1,1-trifluoropropan-2-yl)benzenesulfonamide (193 mg, 0.35 mmol, Example 16, step a) in acetone (5 mL) was added IBX (234 mg, 0.70 mmol), the solution was stirred at rt overnight. Then the mixture was filtered and the filtrate was concentrated to dryness to give the title compound as a white solid.

Example 16

Step c 2,3-Dichloro-4-(2-ethynyl-4-((S)-2-methylpiperidine-1-carbonyl)thiazol-5-yl)-N—((S)-1,1,1-trifluoropropan-2-yl)benzenesulfonamide

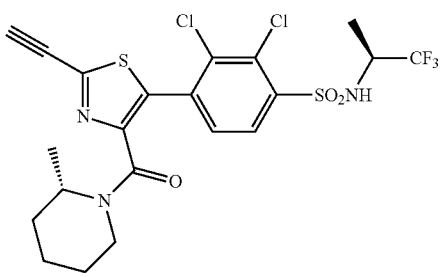

To a solution of 2,3-dichloro-4-(2-formyl-4-((S)-2-methylpiperidine-1-carbonyl)thiazol-5-yl)-N—((S)-1,1,1-trifluoropropan-2-yl)benzenesulfonamide (171 mg, 0.31 mmol, Example 16, step b) in MeOH (10 mL) was added dimethyl (1-diazo-2-oxopropyl)phosphonate (89 mg, 0.47 mmol) and $K_2CO_3$ (65 mg, 0.47 mmol) and the mixture was stirred at rt for 2 h. Then the mixture was quenched with water and extracted with EtOAc. The organic layer was separated, washed with brine, dried over anhydrous $Na_2SO_4$, filtered and the filtrate was concentrated to dryness. The yellow residue was purified by FCC on silica gel (PE/EtOAc=5:1) to give the title compound as a white solid.

Example 16

2,3-Dichloro-4-(4-((S)-2-methylpiperidine-1-carbonyl)-2-(1H-1,2,3-triazol-5-yl)thiazol-5-yl)-N—((S)-1,1,1-trifluoropropan-2-yl)benzenesulfonamide

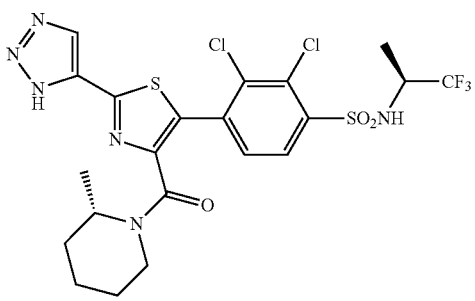

To a solution of 2,3-dichloro-4-(2-ethynyl-4-((S)-2-methylpiperidine-1-carbonyl)thiazol-5-yl)-N—((S)-1,1,1-trifluoropropan-2-yl)benzenesulfonamide (70 mg, 0.13 mmol, Example 16, step c) in DMF (2 mL) was added $NaN_3$ (42 mg, 0.65 mmol) and $NH_4Cl$ (41 mg, 0.65 mmol), the mixture was stirred at 100° C. overnight, then water was added and the mixture was extracted with EtOAc three times. The combined organic layers were washed with brine, dried over anhydrous $Na_2SO_4$, filtered and concentrated to dryness. The residue was purified by prep-HPLC to give the title compound as a white solid. $^1H$ NMR (400 MHz, $CD_3OD$): δ ppm 8.42-8.40 (br s, 1H), 8.15 (d, J=6.4 Hz, 1H), 7.70-7.66 (m, 1H), 4.84-4.70 (m, 0.6H), 4.24-4.36 (m, 0.4H), 4.13-4.06 (m, 1.4H), 3.62-3.56 (m, 0.6H), 3.16-3.04 (m, 0.6H), 2.96-2.84 (m, 0.4H), 1.73-1.50 (m, 5H), 1.40-1.34 (m, 3H), 1.25-1.17 (m, 4H). MS (ESI): m/z 597.1 $[M+H]^+$.

Example 17

Step a (S)-2,3-Dichloro-4-(4-(hydroxymethyl)-2-(6-(2-hydroxypropan-2-yl)pyridin-2-yl)thiazol-5-yl)-N-(1,1,1-trifluoropropan-2-yl)benzenesulfonamide

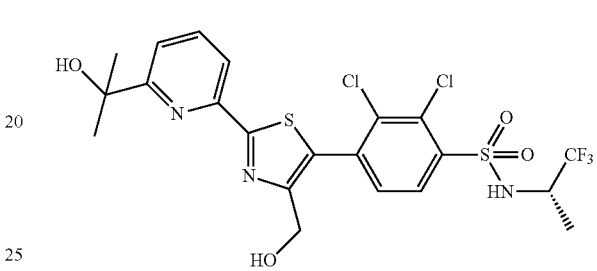

To a solution of 2-(6-(4-(hydroxymethyl)thiazol-2-yl)pyridin-2-yl)propan-2-ol (74 mg, 0.29 mmol, Intermediate 11, step f), (S)-4-bromo-2,3-dichloro-N-(1,1,1-trifluoropropan-2-yl)benzenesulfonamide (139 mg, 0.347 mmol, Intermediate 12/3), and $K_2CO_3$ (80 mg, 0.58 mmol) in DMA (5 mL) were added $P(Cy)_3 \cdot BF_4$ (12 mg, 0.032 mmol), PivOH (10 mg, 0.10 mmol), and $Pd(OAc)_2$ (15 mg, 0.067 mmol) under Ar. The solution was stirred at 95° C. overnight. The mixture was cooled to rt, partitioned between EtOAc and water, and the layers were separated. The organic layer was washed with brine, dried over anhydrous $Na_2SO_4$, filtered, and concentrated to dryness. The yellow residue was purified by FCC on silica gel (PE/EtOAc=3:1) to give the title compound as a white solid.

Example 17

Step b (S)-5-(2,3-Dichloro-4-(N-(1,1,1-trifluoropropan-2-yl)sulfamoyl)phenyl)-2-(6-(2-hydroxypropan-2-yl)pyridin-2-yl)thiazole-4-carboxylic acid

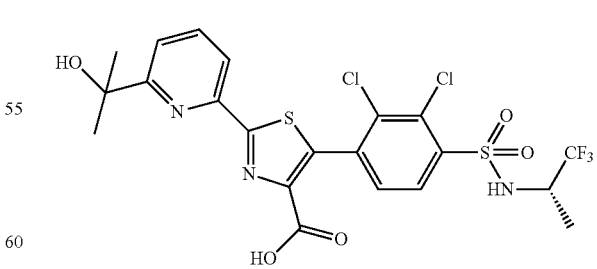

To a solution of (S)-2,3-dichloro-4-(4-(hydroxymethyl)-2-(6-(2-hydroxypropan-2-yl)pyridin-2-yl)thiazol-5-yl)-N-(1,1,1-trifluoropropan-2-yl)benzenesulfonamide (125 mg, 0.219 mmol, Example 17, step a) in a mixture of MeCN (8 mL) and $H_2O$ (4 mL) were added TEMPO (151 mg, 1.10 mmol) and iodobenzene diacetate (354 mg, 1.10 mmol). The resulting mixture was stirred at rt for 1 h. The mixture was quenched with water and extracted with EtOAc. The organic layer was separated, washed with brine, and dried over anhydrous $Na_2SO_4$. After filtration, the filtrate was concentrated to dryness to give the title compound as a yellow solid.

Example 17

(S)-5-(2,3-Dichloro-4-(N-(1,1,1-trifluoropropan-2-yl)sulfamoyl)phenyl)-N,N-diethyl-2-(6-(2-hydroxypropan-2-yl)pyridin-2-yl)thiazole-4-carboxamide

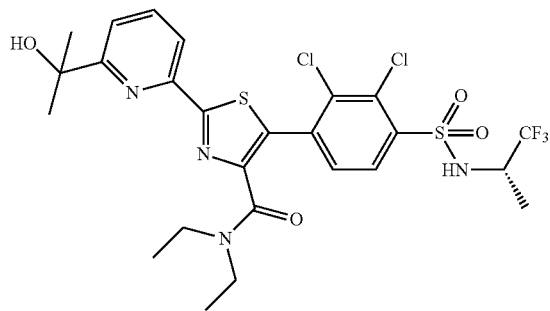 [SMILES: CCN(CC)C(=O)c1nc(-c2cccc(C(C)(C)O)n2)sc1-c1ccc(S(=O)(=O)N[C@@H](C)C(F)(F)F)c(Cl)c1Cl]

To a solution of (S)-5-(2,3-dichloro-4-(N-(1,1,1-trifluoropropan-2-yl)sulfamoyl)phenyl)-2-(6-(2-hydroxypropan-2-yl)pyridin-2-yl)thiazole-4-carboxylic acid (104 mg, 0.178 mmol, Example 17, step b), HATU (103 mg, 0.271 mmol), and TEA (46 mg, 0.45 mmol) in DMA (5 mL) was added diethylamine (16 mg, 0.22 mmol). The solution was stirred at rt for 10 min. The mixture was partitioned between EtOAc and water, and the layers were separated. The organic layer was washed with water, brine, dried over anhydrous $Na_2SO_4$, filtered, concentrated to dryness, and the yellow residue was purified by prep-HPLC to give the title compound as a white solid. $^1H$ NMR (400 MHz, $CDCl_3$): δ ppm 8.12 (d, J=8.0 Hz, 1H), 8.05 (d, J=8.4 Hz, 1H), 7.87 (dd, $J_1=J_2=8.0$ Hz, 1H), 7.68 (d, J=8.4 Hz, 1H), 7.50 (d, J=8.0 Hz, 1H), 5.43 (d, J=10.0 Hz, 1H), 4.08-4.02 (m, 1H), 3.52-3.40 (m, 2H), 3.36-3.31 (m, 2H), 1.61 (s, 6H), 1.39 (d, J=6.8 Hz, 3H), 1.19-1.10 (m, 6H). MS (ESI): m/z 639.0 $[M+H]^+$.

Example 17/1

(S)-5-(2,3-Dichloro-4-(N-(1,1,1-trifluoropropan-2-yl)sulfamoyl)phenyl)-N,N-diethyl-2-(4-(2-hydroxypropan-2-yl)pyridin-2-yl)thiazole-4-carboxamide

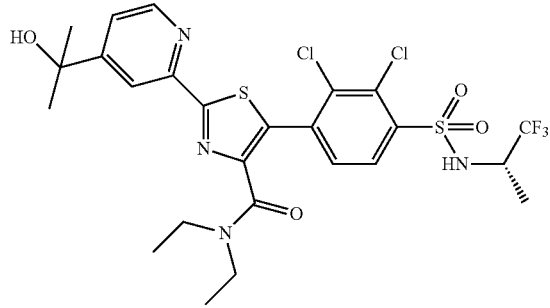 [SMILES: CCN(CC)C(=O)c1nc(-c2cc(C(C)(C)O)ccn2)sc1-c1ccc(S(=O)(=O)N[C@@H](C)C(F)(F)F)c(Cl)c1Cl]

The title compound was prepared as described for the synthesis of Example 17, using in step a 2-(2-(4-(hydroxymethyl)thiazol-2-yl)pyridin-4-yl)propan-2-ol (Intermediate 11/1, step b) in place of 2-(6-(4-(hydroxymethyl)thiazol-2-yl)pyridin-2-yl)propan-2-ol. $^1H$ NMR (400 MHz, DMSO-$d_6$): δ ppm 9.20 (d, J=9.2 Hz, 1H), 8.60 (d, J=5.4 Hz, 1H), 8.28 (s, 1H), 8.06 (d, J=8.2 Hz, 1H), 7.73 (d, J=8.2 Hz, 1H), 7.63 (d, J=5.4 Hz, 1H), 4.18-4.16 (m, 1H), 3.38-3.29 (m, 4H), 1.48 (s, 6H), 1.25 (d, J=7.2 Hz, 3H), 1.14 (t, J=6.8 Hz, 3H), 1.02 (t, J=6.8 Hz, 3H). MS (ESI): m/z 639.1 $[M+H]^+$.

Example 17/2

(S)-5-(2,3-Dichloro-4-(N-(1,1,1-trifluoropropan-2-yl)sulfamoyl)phenyl)-N,N-diethyl-2-(6-(2-hydroxypropan-2-yl)pyrimidin-4-yl)thiazole-4-carboxamide

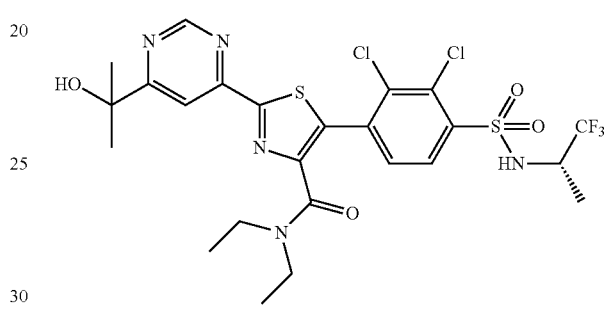

The title compound was prepared as described for the synthesis of Example 17, using in step a 2-(6-(4-(hydroxymethyl)thiazol-2-yl)pyrimidin-4-yl)propan-2-ol (Intermediate 11/2, step b) in place of 2-(6-(4-(hydroxymethyl)thiazol-2-yl)pyridin-2-yl)propan-2-ol. $^1H$ NMR (400 MHz, $CDCl_3$): δ ppm 9.18 (s, 1H), 9.25 (s, 1H), 8.06 (d, J=8.0 Hz, 1H), 7.70 (d, J=8.0 Hz, 1H), 5.35 (br s, 1H), 4.09-4.02 (m, 2H), 3.53-3.40 (m, 2H), 3.31-3.25 (m, 2H), 1.62 (s, 6H), 1.41 (d, J=7 Hz, 3H), 1.14-1.10 (m, 6H). MS (ESI): m/z 640.0 $[M+H]^+$.

Example 18

Step a (S)-Methyl 3-(3-(5-(2-(difluoromethyl)-3-fluoro-4-(N-(1,1,1-trifluoropropan-2-yl)sulfamoyl)phenyl)-4-(hydroxymethyl)thiazol-2-yl)isoxazol-5-yl)-2,2-dimethylpropanoate

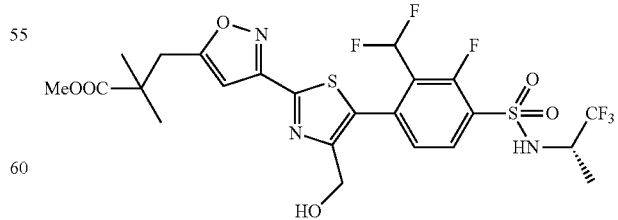

To a solution of methyl 3-(3-(4-(hydroxymethyl)thiazol-2-yl)isoxazol-5-yl)-2,2-dimethylpropanoate (266 mg, 0.90 mmol, Intermediate 10/1), (S)-4-bromo-3-(difluoromethyl)-2-fluoro-N-(1,1,1-trifluoropropan-2-yl)benzenesulfonamide (360 mg, 0.90 mmol, Intermediate 12/2) and Na₂CO₃ (160 mg, 1.5 mmol) in DMA (3 mL) was added P(Cy)₃.HBF₄ (80 mg, 0.22 mmol), PivOH (20 mg, 0.20 mmol) and Pd(OAc)₂ (80 mg, 0.36 mmol) under Ar. The solution was stirred at 95° C. overnight. The mixture was cooled to rt and partitioned between EtOAc and water. The organic layer was washed with water and brine, dried over Na₂SO₄, filtered and concentrated to dryness. The residue was purified by FCC on silica gel (PE/EtOAc=3:1) to afford the title compound as a yellow solid.

Example 18

Step b (S)-5-(2-(Difluoromethyl)-3-fluoro-4-(N-(1,1,1-trifluoropropan-2-yl)sulfamoyl)phenyl)-2-(5-(3-methoxy-2,2-dimethyl-3-oxopropyl)isoxazol-3-yl)thiazole-4-carboxylic acid

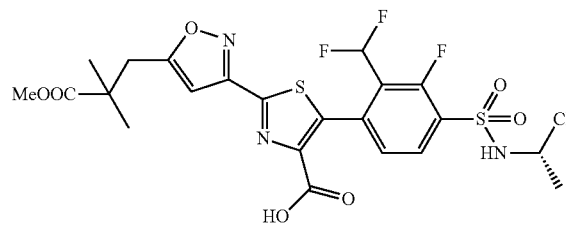

To a solution of (5)-methyl 3-(3-(5-(2-(difluoromethyl)-3-fluoro-4-(N-(1,1,1-trifluoropropan-2-yl)sulfamoyl)phenyl)-4-(hydroxymethyl)thiazol-2-yl)isoxazol-5-yl)-2,2-dimethylpropanoate (232 mg, 0.38 mmol, Example 18, step a) in MeCN/H₂O (7.5 mL, 2:1) was added iodobenzene diacetate (386 mg, 1.20 mmol) and TEMPO (70 mg, 0.45 mmol). The mixture was stirred for 12 h at rt, concentrated and the residue was extracted with EtOAc (20 mL×2). The combined organic layers were washed with brine, dried over anhydrous Na₂SO₄, filtered and concentrated to dryness. The residue was purified by prep-TLC (EtOAc) to afford the title compound as a white solid.

Example 18

Step c (S)-Methyl 3-(3-(5-(2-(difluoromethyl)-3-fluoro-4-(N-(1,1,1-trifluoropropan-2-yl)sulfamoyl)phenyl)-4-(4,4-difluoropiperidine-1-carbonyl)thiazol-2-yl)isoxazol-5-yl)-2,2-dimethylpropanoate

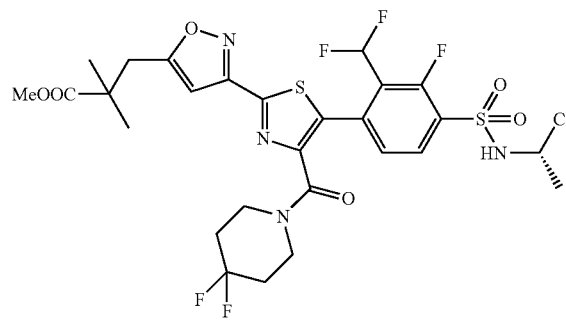

To a solution of (S)-5-(2-(difluoromethyl)-3-fluoro-4-(N-(1,1,1-trifluoropropan-2-yl)sulfamoyl)phenyl)-2-(5-(3-methoxy-2,2-dimethyl-3-oxopropyl)isoxazol-3-yl)thiazole-4-carboxylic acid (100 mg, 0.16 mmol, Example 18, step b) in DMA (3.0 mL) was added HATU (94 mg, 0.25 mmol) and TEA (50 mg, 0.5 mmol). The mixture was stirred for 20 min at rt. 4,4-Difluoropiperidine (44 mg, 0.36 mmol) was added and the mixture was stirred overnight at rt, quenched with water and extracted with EtOAc. The combined organic layers were washed with brine, dried over anhydrous Na₂SO₄, filtered and concentrated to dryness. The residue was purified by prep-TLC (EtOAc) to afford the title compound.

Example 18

(S)-3-(3-(5-(2-(Difluoromethyl)-3-fluoro-4-(N-(1,1,1-trifluoropropan-2-yl)sulfamoyl)phenyl)-4-(4,4-difluoropiperidine-1-carbonyl)thiazol-2-yl)isoxazol-5-yl)-2,2-dimethylpropanoic acid

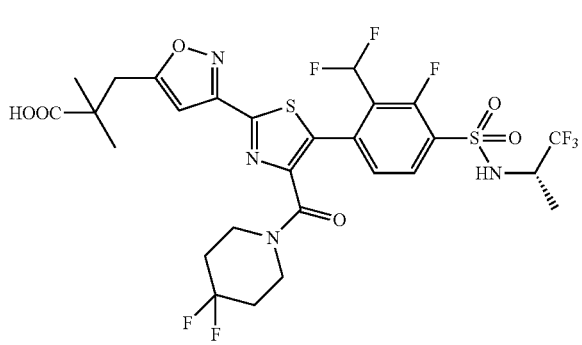 [SMILES: C[C@H](NS(=O)(=O)c1ccc(-c2sc(-c3cc(CC(C)(C)C(=O)O)on3)nc2C(=O)N2CCC(F)(F)CC2)c(C(F)F)c1F)C(F)(F)F]

A mixture of (5)-methyl 3-(3-(5-(2-(difluoromethyl)-3-fluoro-4-(N-(1,1,1-trifluoropropan-2-yl)sulfamoyl)phenyl)-4-(4,4-difluoropiperidine-1-carbonyl)thiazol-2-yl)isoxazol-5-yl)-2,2-dimethylpropanoate (95 mg, 0.13 mmol, Example 18, step c), LiOH.H₂O (1 mg, 0.02 mmol) in methanol/H₂O (3 mL, 2:1) was stirred at rt overnight. The mixture was concentrated and 1 M aqueous HCl (10 mL) was added. The mixture was extracted with EtOAc (8 mL×3) and the combined organic layers were washed with brine, dried over Na₂SO₄, filtered and concentrated to dryness. The residue was purified by prep-HPLC to afford the title compound as a white solid. ¹H NMR (500 MHz, CDCl₃): δ ppm 8.05-8.02 (m, 1H), 7.50 (d, J=8.0 Hz, 1H), 6.88 (t, J=53.0 Hz, 1H), 6.66 (s, 1H), 5.46 (d, J=10.0 Hz, 1H), 4.16-4.11 (m, 1H), 3.75-3.67 (m, 4H), 3.16 (s, 2H), 2.04-1.98 (m, 4H), 1.43 (d, J=7.0 Hz, 3H), 1.35 (s, 6H). MS (ESI): m/z 719.0 [M+H]⁺.

Example 18/1

3-(3-(4-((S)-4,4-Difluoro-2-methylpyrrolidine-1-carbonyl)-5-(2-(difluoromethyl)-3-fluoro-4-(N—((S)-1,1,1-trifluoropropan-2-yl)sulfamoyl)phenyl)thiazol-2-yl)isoxazol-5-yl)-2,2-dimethylpropanoic acid

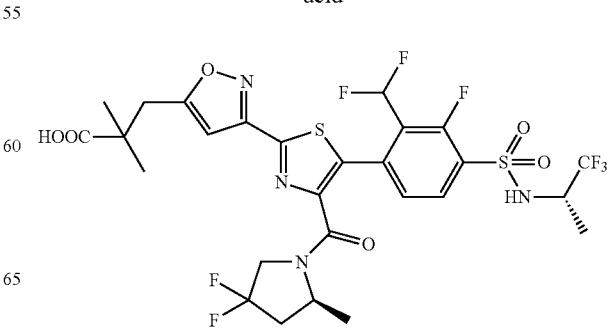

The title compound was prepared as described for the synthesis of Example 18, using in step c (S)-4,4-difluoro-2-methylpyrrolidine hydrochloride (Intermediate 14, step b) in place of 4,4-difluoropiperidine. $^1$H NMR (500 MHz, CDCl$_3$): δ ppm 8.04-8.01 (m, 1H), 7.40-7.36 (m, 1H), 6.94-6.63 (m, 2H), 4.95-4.46 (m, 1H), 4.23-4.06 (m, 3H), 3.15 (s, 2H), 2.56-2.52 (m, 1H), 2.17-2.06 (m, 1H), 1.41 (d, J=7.0 Hz, 3H), 1.34-1.31 (m, 9H). MS (ESI): m/z 719.1 [M+H]$^+$.

Example 19

(S)-3-(6-(5-(2-(Difluoromethyl)-3-fluoro-4-(N-(1,1,1-trifluorobutan-2-yl)sulfamoyl)phenyl)-4-(4,4-difluoropiperidine-1-carbonyl)thiazol-2-yl)pyridin-2-yl)-2,2-dimethylpropanoic acid

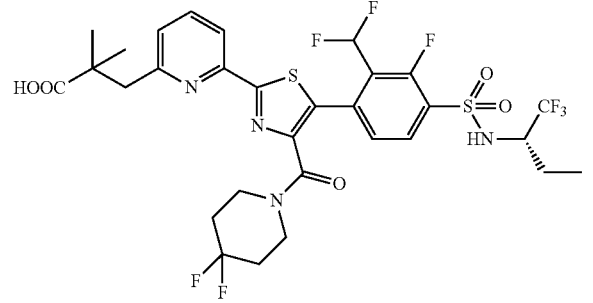 [SMILES: CC[C@H](NS(=O)(=O)c1ccc(-c2sc(-c3cccc(CC(C)(C)C(=O)O)n3)nc2C(=O)N2CCC(F)(F)CC2)c(C(F)F)c1F)C(F)(F)F]

The title compound was prepared as described for the synthesis of Example 18, using in step a ethyl 3-(6-(4-(hydroxymethyl)thiazol-2-yl)pyridin-2-yl)-2,2-dimethylpropanoate (Intermediate 17, step d) in place of methyl 3-(3-(4-(hydroxymethyl)thiazol-2-yl)isoxazol-5-yl)-2,2-dimethylpropanoate and using in the final step (S)-4-bromo-3-(difluoromethyl)-2-fluoro-N-(1,1,1-trifluorobutan-2-yl)benzenesulfonamide (Intermediate 12/1, step e) in place of (S)-4-bromo-3-(difluoromethyl)-2-fluoro-N-(1,1,1-trifluoropropan-2-yl)benzenesulfonamide. $^1$HNMR (500 MHz, CDCl$_3$): δ ppm 8.02-7.96 (m, 2H), 7.77 (t, J=8.0 Hz, 1H), 7.39 (d, J=8.0 Hz, 1H), 7.24 (d, J=8.0 Hz, 1H), 6.82 (t, J=52.5 Hz, 1H), 5.21 (d, J=10.0 Hz, 1H), 3.93-3.88 (m, 1H), 3.77-3.71 (m, 4H), 3.13 (s, 2H), 2.07-1.99 (m, 4H), 1.93-1.87 (m, 1H), 1.63-1.56 (m, 1H), 1.27 (s, 6H), 1.08 (t, J=7.5 Hz, 3H). MS (ESI): m/z 743.2 [M+H]$^+$.

Example 19/1

3-(6-(4-((S)-4,4-Difluoro-2-methylpyrrolidine-1-carbonyl)-5-(2-(difluoromethyl)-3-fluoro-4-(N-((S)-1,1,1-trifluorobutan-2-yl)sulfamoyl)phenyl)thiazol-2-yl)pyridin-2-yl)-2,2-dimethylpropanoic acid

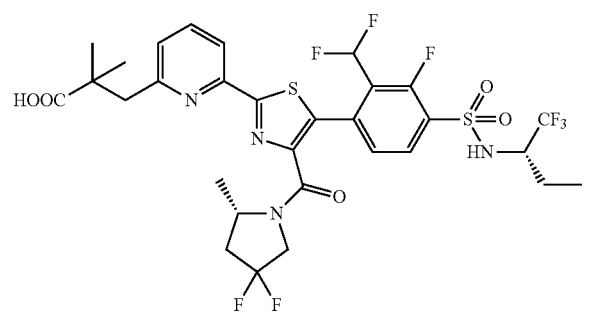 [SMILES: CC[C@H](NS(=O)(=O)c1ccc(-c2sc(-c3cccc(CC(C)(C)C(=O)O)n3)nc2C(=O)N2CC(F)(F)C[C@@H]2C)c(C(F)F)c1F)C(F)(F)F]

The title compound was prepared as described for the synthesis of Example 19, using in the amide coupling step (S)-4,4-difluoro-2-methylpyrrolidine hydrochloride (Intermediate 14, step b) in place of 4,4-difluoropiperidine. $^1$H NMR (500 MHz, CDCl$_3$): δ ppm 8.04-7.97 (m, 2H), 7.79-7.77 (m, 1H), 7.35-7.24 (m, 2H), 6.77 (t, J=52.5 Hz, 1H), 5.19 (d, J=10.0 Hz, 1H), 4.51-4.47 (m, 1H), 4.31-3.87 (m, 3H), 3.12 (s, 2H), 2.58-2.53 (m, 1H), 2.11-2.08 (m, 1H), 1.92-1.87 (m, 1H), 1.62-1.56 (m, 1H), 1.38-1.33 (m, 3H), 1.27 (s, 6H), 1.26-1.05 (m, 3H). MS (ESI): m/z 743.2 [M+H]$^+$.

Example 20

Step a 2-(5-(3-Methoxy-2,2-dimethyl-3-oxopropyl)-1,2,4-oxadiazol-3-yl)thiazole-4-carboxylic acid

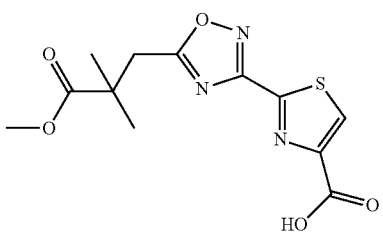 [SMILES: COC(=O)C(C)(C)Cc1nc(-c2nc(C(=O)O)cs2)no1]

To a solution of methyl 3-(3-(4-(hydroxymethyl)thiazol-2-yl)-1,2,4-oxadiazol-5-yl)-2,2-dimethylpropanoate (1.3 g, 4.4 mmol, Intermediate 8, step f) in CH$_3$CN/H$_2$O (60 mL, 5:1) was added TEMPO (690 mg, 4.4 mmol) and iodobenzene diacetate (2.8 g, 8.8 mmol) at 0° C. The mixture was stirred at rt overnight. The mixture was diluted with H$_2$O and extracted with EtOAc. The combined organic layers were washed with brine, dried over anhydrous Na$_2$SO$_4$, filtered and concentrated to dryness. The residue was purified by FCC on silica gel (EtOAc) to afford the title compound as a white solid.

Example 20

Step b (S)-Methyl 2,2-dimethyl-3-(3-(4-(2-methylpiperidine-1-carbonyl)thiazol-2-yl)-1,2,4-oxadiazol-5-yl)propanoate

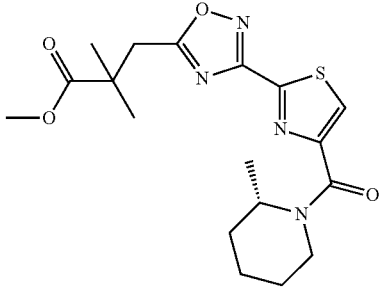 [SMILES: COC(=O)C(C)(C)Cc1nc(-c2nc(C(=O)N3CCCC[C@@H]3C)cs2)no1]

To a solution of 2-(5-(3-methoxy-2,2-dimethyl-3-oxopropyl)-1,2,4-oxadiazol-3-yl)thiazole-4-carboxylic acid (300 mg, 0.97 mmol, Example 20, step a) in DCM (10 mL) was added HATU (366 mg, 1.06 mmol) and DIEA (374 mg, 2.90 mmol). The mixture was stirred at rt for 30 min. (S)-2-Methylpiperidine hydrochloride (130 mg, 0.965 mmol) was added and the mixture was stirred at rt for 2 h. The resulting solution was diluted with H₂O and extracted with DCM. The combined organic layers were washed with brine, dried over anhydrous Na₂SO₄, filtered and concentrated to dryness. The residue was purified by prep-TLC to afford the title compound as a yellow oil.

Example 20

Step c (S)-Methyl 3-(3-(5-(2,3-dichloro-4-(1,1,1,3,3,3-hexafluoro-2-hydroxypropan-2-yl)phenyl)-4-(2-methylpiperidine-1-carbonyl)thiazol-2-yl)-1,2,4-oxadiazol-5-yl)-2,2-dimethylpropanoate

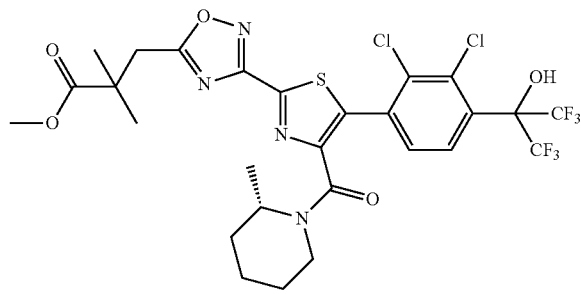 [SMILES: COC(=O)C(C)(C)Cc1nc(-c2nc(C(=O)N3CCCC[C@@H]3C)c(-c3ccc(C(O)(C(F)(F)F)C(F)(F)F)c(Cl)c3Cl)s2)no1]

A solution of (5)-methyl 2,2-dimethyl-3-(3-(4-(2-methylpiperidine-1-carbonyl)thiazol-2-yl)-1,2,4-oxadiazol-5-yl)propanoate (110 mg, 0.28 mmol, Example 20, step b), 2-(4-bromo-2,3-dichlorophenyl)-1,1,1,3,3,3-hexafluoropropan-2-ol (109 mg, 0.28 mmol, Intermediate 13, step b), KOAc (55 mg, 0.56 mmol), Pd(PPh₃)₄ (65 mg, 0.056 mmol) in DMF (5 mL) was purged with nitrogen for 5 min and then stirred at 120° C. overnight. The resulting solution was cooled to rt, diluted with H₂O and extracted with EtOAc. The combined organic layers were washed with brine, dried over anhydrous Na₂SO₄, filtered and concentrated to dryness. The residue was purified by prep-HPLC to afford the title compound as a yellow solid.

Example 20

(S)-3-(3-(5-(2,3-Dichloro-4-(1,1,1,3,3,3-hexafluoro-2-hydroxypropan-2-yl)phenyl)-4-(2-methylpiperidine-1-carbonyl)thiazol-2-yl)-1,2,4-oxadiazol-5-yl)-2,2-dimethylpropanoic acid

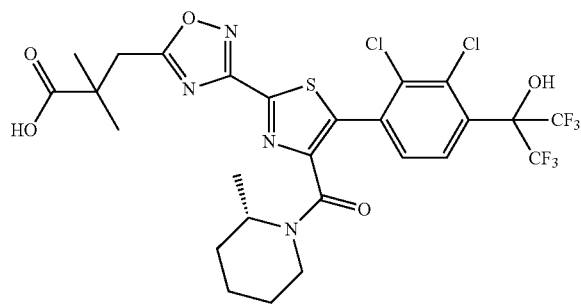 [SMILES: C[C@H]1CCCCN1C(=O)c1nc(-c2noc(CC(C)(C)C(=O)O)n2)sc1-c1ccc(C(O)(C(F)(F)F)C(F)(F)F)c(Cl)c1Cl]

To a solution of (S)-methyl 3-(3-(5-(2,3-dichloro-4-(1,1,1,3,3,3-hexafluoro-2-hydroxypropan-2-yl)phenyl)-4-(2-methylpiperidine-1-carbonyl)thiazol-2-yl)-1,2,4-oxadiazol-5-yl)-2,2-dimethylpropanoate (77 mg, 0.11 mmol, Example 20, step c) in THF/H₂O (4 mL, 3:1) was added LiOH.H₂O (12 mg, 0.27 mmol) and the mixture was stirred at 50° C. for 2 h. The resulting solution was concentrated under reduced pressure and diluted with H₂O. 1 M Aqueous HCl was added to acidify to pH=3-4 and the mixture was extracted with EtOAc. The combined organic layers were washed with brine, dried over anhydrous Na₂SO₄, filtered and concentrated to dryness. The residue was purified by prep-HPLC to afford the title compound as a white solid. ¹HNMR (300 MHz, DMSO-d₆): δ ppm 9.25 (br s, 1H), 7.97-7.91 (m, 1H), 7.68-7.65 (m, 1H), 4.65-3.90 (m, 2H), 3.50-3.34 (m, 2H), 3.20-2.70 (m, 1H), 1.49-1.41 (m, 5H), 1.28-1.23 (m, 6H), 1.11-1.05 (m, 5H). MS (ESI): m/z 689.1 [M+H]⁺.

Example 21

Step a

Benzyl(4-bromo-2,3-dichlorophenyl)sulfane

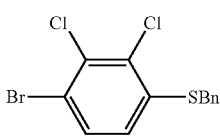

To a solution of 1-bromo-2,3-dichloro-4-iodobenzene (2.6 g, 7.5 mmol), and DIPEA (1.45 g, 11.3 mmol) in 1,4-dioxane (20 mL) were added 2-dicyclohexylphosphino-2',4',6'-triisopropylbiphenyl (357 mg, 0.75 mmol) and Pd₂(dba)₃ (686 mg, 0.75 mmol) under Ar and the mixture was heated to 80° C. Benzyl mercaptan (1.12 g, 9.0 mmol) was added slowly and the mixture was stirred at 80° C. overnight, cooled to rt, diluted with H₂O and extracted with EtOAc (×3). The combined organic layers were washed with brine, dried over anhydrous Na₂SO₄, filtered and concentrated to dryness. The residue was purified by FCC on silica gel (PE/EtOAc=50:1) to give the title compound as a white solid.

Example 21

Step b 2-(5-(5-(4-(Benzylthio)-2,3-dichlorophenyl)-4-(hydroxymethyl)thiazol-2-yl)-1,3,4-oxadiazol-2-yl)propan-2-ol

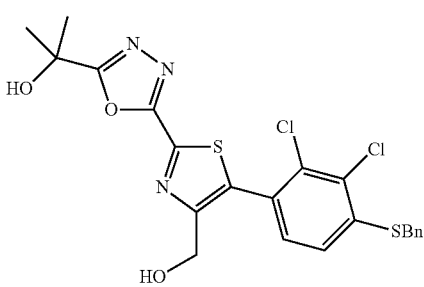

To a solution of benzyl(4-bromo-2,3-dichlorophenyl)sulfane (197 mg, 0.75 mmol, Example 21, step a), 2-(5-(4-(hydroxymethyl)thiazol-2-yl)-1,3,4-oxadiazol-2-yl)propan-2-ol (180 mg, 0.75 mmol, Intermediate 3, step c), and Na₂CO₃ (199 mg, 1.88 mmol) in DMA (5 mL) were added P(Cy)₃·HBF₄ (18 mg, 0.05 mmol), PivOH (16 mg, 0.16 mmol), and Pd(OAc)₂ (20 mg, 0.09 mmol) under Ar. The solution was stirred at 95° C. overnight, cooled to rt, partitioned between EtOAc and H₂O, and the layers were separated. The organic layer was washed with brine, dried over anhydrous Na₂SO₄, filtered and concentrated to dryness. The residue was purified by FCC on silica gel (PE/EtOAc=3:1) to give the title compound as a white solid.

Example 21

Step c 5-(4-(Benzylthio)-2,3-dichlorophenyl)-2-(5-(2-hydroxypropan-2-yl)-1,3,4-oxadiazol-2-yl)thiazole-4-carboxylic acid

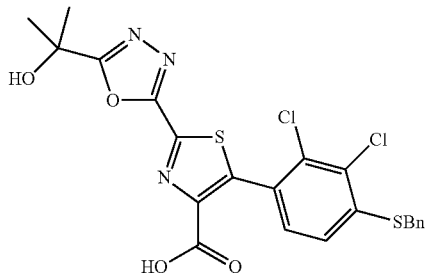

To a solution of 2-(5-(5-(4-(benzylthio)-2,3-dichlorophenyl)-4-(hydroxymethyl)thiazol-2-yl)-1,3,4-oxadiazol-2-yl)propan-2-ol (220 mg, 0.43 mmol, Example 21, step b) in a mixture of MeCN/water (2:1, 15 mL) was added TEMPO (146 mg, 1.08 mmol) and iodobenzene diacetate (346 mg, 1.08 mmol). The mixture was stirred at rt for 1 h, diluted with H₂O and extracted with EtOAc. The combined organic layers were washed with brine, dried over anhydrous Na₂SO₄, filtered, and concentrated to dryness to give the title compound as a yellow solid.

Example 21

Step d (5-(4-(Benzylthio)-2,3-dichlorophenyl)-2-(5-(2-hydroxypropan-2-yl)-1,3,4-oxadiazol-2-yl)thiazol-4-yl)(4,4-difluoropiperidin-1-yl)methanone

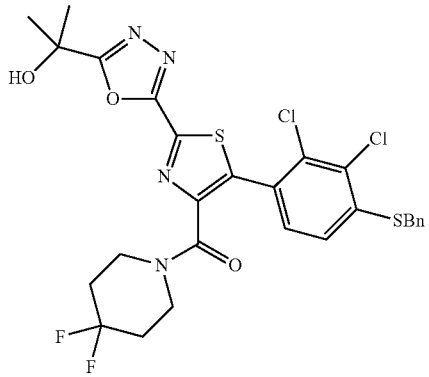

To a solution of 5-(4-(benzylthio)-2,3-dichlorophenyl)-2-(5-(2-hydroxypropan-2-yl)-1,3,4-oxadiazol-2-yl)thiazole-4-carboxylic acid (193 mg, 0.370 mmol, Example 21, step c), HATU (211 mg, 0.555 mmol), TEA (93 mg, 0.93 mmol), in DMA (5 mL) was added 4,4-difluoropiperidine (53 mg, 0.44 mmol) and the solution was stirred at rt for 10 min, partitioned between EtOAc and H₂O, and the layers were separated. The organic layer was washed with H₂O, brine, dried over anhydrous Na₂SO₄, filtered and concentrated to dryness. The residue was purified by FCC on silica gel (PE/EtOAc=1:1) to give the title compound as a white solid.

Example 21

Step e 2,3-Dichloro-4-(4-(4,4-difluoropiperidine-1-carbonyl)-2-(5-(2-hydroxypropan-2-yl)-1,3,4-oxadiazol-2-yl)thiazol-5-yl)benzene-1-sulfonyl chloride

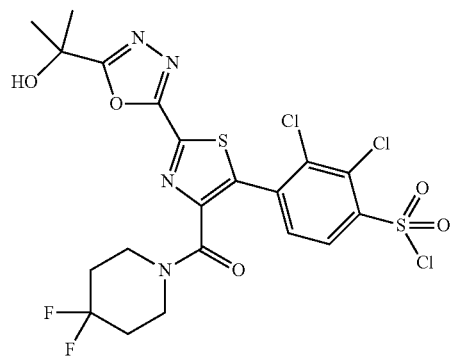 [SMILES: CC(C)(O)c1nnc(-c2nc(C(=O)N3CCC(F)(F)CC3)c(-c3ccc(S(=O)(=O)Cl)c(Cl)c3Cl)s2)o1]

To a solution of (5-(4-(benzylthio)-2,3-dichlorophenyl)-2-(5-(2-hydroxypropan-2-yl)-1,3,4-oxadiazol-2-yl)thiazol-4-yl)(4,4-difluoropiperidin-1-yl)methanone (170 mg, 0.27 mmol, Example 21, step d) in DCM (5 mL) was added sulfuryl dichloride (72 mg, 0.54 mmol) at −10° C. and the mixture was stirred at rt for 10 min, diluted with ice water, and extracted with DCM (3×). The combined organic layers were washed with ice water, brine, dried over anhydrous Na₂SO₄, filtered, and concentrated to dryness to give the title compound as a yellow solid, which was used immediately in the next step without purification.

Example 21

2,3-Dichloro-4-(4-(4,4-difluoropiperidine-1-carbonyl)-2-(5-(2-hydroxypropan-2-yl)-1,3,4-oxadiazol-2-yl)thiazol-5-yl)-N-(1-methylcyclopropyl)benzenesulfonamide

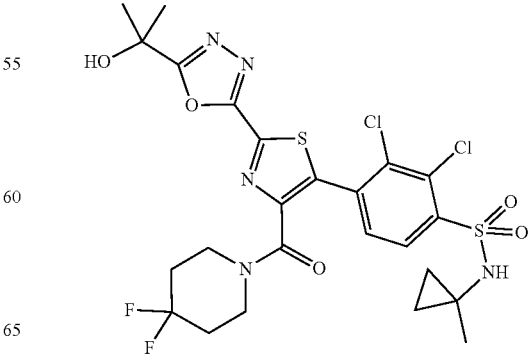

To a solution of 2,3-dichloro-4-(4-(4,4-difluoropiperidin-1-carbonyl)-2-(5-(2-hydroxypropan-2-yl)-1,3,4-oxadiazol-2-yl)thiazol-5-yl)benzene-1-sulfonyl chloride (133 mg, 0.220 mmol, Example 21, step e), DMAP (4 mg, 30 μmol), and DIPEA (43 mg, 0.33 mmol) in DCM (3 mL) was added 1-methylcyclopropanamine (19 mg, 0.27 mmol). The mixture was stirred at rt for 1 h, diluted with H₂O, and extracted with DCM (3×). The combined organic layers were washed with brine, dried over anhydrous Na₂SO₄, filtered, and concentrated to dryness. The residue was purified by prep-HPLC to give the title compound as a white solid. $^1$H NMR (400 MHz, CDCl₃): δ ppm 8.19 (d, J=8.4 Hz, 1H), 7.64 (d, J=8.0 Hz, 1H), 5.53 (s, 1H), 3.79 (t, J=5.3 Hz, 2H), 3.64 (t, J=5.3 Hz, 2H), 2.62 (s, 1H), 2.06-1.97 (m, 4H), 1.81 (s, 6H), 1.24 (s, 3H), 0.87 (t, J=5.8 Hz, 2H), 0.57 (t, J=5.8 Hz, 2H). MS (ESI): m/z 636.1 [M+H]$^+$.

Example 22

Step a 2-(5-(2-Hydroxypropan-2-yl)-4-methyl-4H-1,2,4-triazol-3-yl)thiazole-4-carboxylic acid

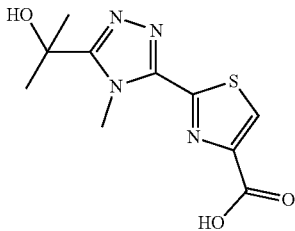 [SMILES: Cn1c(-c2nc(C(=O)O)cs2)nnc1C(C)(C)O]

To a solution of 2-(5-(4-(hydroxymethyl)thiazol-2-yl)-4-methyl-4H-1,2,4-triazol-3-yl)propan-2-ol (204 mg, 0.80 mmol, Intermediate 6) in acetonitrile/H₂O (13 mL, 3:1) was added TEMPO (125 mg, 0.80 mmol) and iodobenzene diacetate (958 mg, 2.98 mmol). The mixture was stirred at rt for 2 h. The resulting solution was basified with saturated aqueous Na₂CO₃ to pH=11 and extracted with EtOAc. The aqueous layer was acidified with 6 M aqueous HCl to pH=3 and extracted with EtOAc. The combined organic layers were washed with brine, dried over anhydrous Na₂SO₄, filtered and concentrated to dryness to afford the title compound as a yellow solid.

Example 22

Step b (S)-(2-(5-(2-Hydroxypropan-2-yl)-4-methyl-4H-1,2,4-triazol-3-yl)thiazol-4-yl)(2-methylpyrrolidin-1-yl)methanone

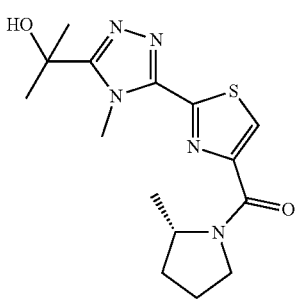 [SMILES: C[C@H]1CCCN1C(=O)c1csc(-c2nnc(C(C)(C)O)n2C)n1]

To a solution of 2-(5-(2-hydroxypropan-2-yl)-4-methyl-4H-1,2,4-triazol-3-yl)thiazole-4-carboxylic acid (168 mg, 0.626 mmol, Example 22, step a) in anhydrous DMF (5.0 mL) was added (S)-2-methylpyrrolidine hydrochloride (85 mg, 0.70 mmol) and DIEA (260 mg, 2.0 mmol). The mixture was stirred for 30 min, then HATU (270 mg, 0.70 mmol) was added. The mixture was stirred for 3 h. The solution was quenched with H₂O and extracted with EtOAc. The combined organic layers were washed with brine, dried over anhydrous Na₂SO₄, filtered and concentrated to dryness. The residue was purified by FCC on silica gel (EtOAc) to afford the title compound as a white solid.

Example 22

(S)-(5-(4-(1,1,1,3,3,3-Hexafluoro-2-hydroxypropan-2-yl)-2-(trifluoromethyl)phenyl)-2-(5-(2-hydroxypropan-2-yl)-4-methyl-4H-1,2,4-triazol-3-yl)thiazol-4-yl)(2-methylpyrrolidin-1-yl)methanone

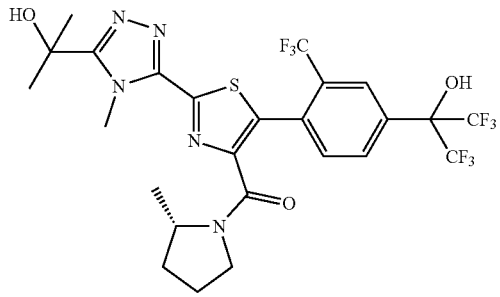 [SMILES: C[C@H]1CCCN1C(=O)c1nc(-c2nnc(C(C)(C)O)n2C)sc1-c1ccc(C(O)(C(F)(F)F)C(F)(F)F)cc1C(F)(F)F]

To a solution of (S)-(2-(5-(2-hydroxypropan-2-yl)-4-methyl-4H-1,2,4-triazol-3-yl)thiazol-4-yl)(2-methylpyrrolidin-1-yl)methanone (165 mg, 0.49 mmol, Example 22, step b) in 3.0 mL of DMF was added 2-(4-bromo-3-(trifluoromethyl)phenyl)-1,1,1,3,3,3-hexafluoropropan-2-ol (274 mg, 0.70 mmol, Intermediate 18, step e), Pd(PPh₃)₄ (20 mg, 0.017 mmol) and KOAc (141 mg, 1.50 mmol). The mixture was stirred at 120° C. overnight. The solution was concentrated under reduced pressure, diluted with H₂O and extracted with DCM. The combined organic layers were washed with brine, dried over anhydrous Na₂SO₄, filtered and concentrated to dryness. The residue was purified by FCC on silica gel (EtOAc/PE=1:1) followed by prep-HPLC to afford the title compound as a white solid. $^1$H NMR (300 MHz, DMSO-d₆): δ ppm 9.31 (s, 1H), 8.05-8.01 (m, 2H), 7.81-7.78 (m, 1H), 5.74 (s, 1H), 4.22 (s, 3H), 4.02-3.98 (m, 1H), 3.62-3.59 (m, 1H), 3.36-3.34 (m, 1H), 2.00-1.89 (m, 2H), 1.81-1.71 (m, 1H), 1.61 (s, 6H), 1.43-1.41 (m, 1H), 1.10-1.05 (m, 3H). MS (ESI): m/z 646.2 [M+H]$^+$.

Example 23

(S)-2,3-Dichloro-4-(2-(4-cyclopropyl-5-(2-hydroxypropan-2-yl)-4H-1,2,4-triazol-3-yl)-4-(4,4-difluoropiperidine-1-carbonyl)thiazol-5-yl)-N-(1,1,1-trifluoropropan-2-yl)benzenesulfonamide

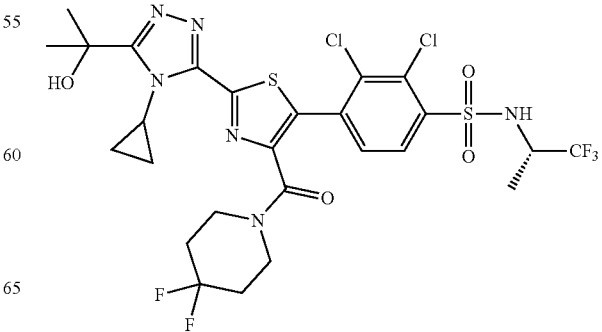

To a glass tube was added a mixture of 2,3-dichloro-4-[4-(4,4-difluoropiperidine-1-carbonyl)-2-[5-(1-hydroxy-1-methyl-ethyl)-1,3,4-oxadiazol-2-yl]thiazol-5-yl]-N-[(1S)-2,2,2-trifluoro-1-methyl-ethyl]benzenesulfonamide (102 mg, 0.15 mmol Example 4/4), p-toluenesulfonic acid monohydrate (21 mg, 0.11 mmol), cyclopropylamine (0.33 mL, 4.8 mmol), and methanol (2.5 mL). The tube was sealed and warmed to 65° C. After 24 hours the mixture was cooled to 23° C. and concentrated to dryness. The residue was dissolved in methanol (1 mL) and then the solution was filtered through a syringe-tip filter. The filtrate was purified by prep-HPLC to provide the tile compound as a white solid after lyophilization. $^1$H NMR (500 MHz, CDCl$_3$) δ 8.09 (d, J=8.2 Hz, 1H), 7.64 (d, J=8.3 Hz, 1H), 5.30 (d, J=9.7 Hz, 1H), 4.14-4.03 (m, 1H), 3.86-3.71 (m, 2H), 3.66-3.59 (m, 2H), 3.59-3.51 (m, 1H), 2.07-1.86 (m, 10H), 1.42 (d, J=7.0 Hz, 3H), 1.30-1.24 (m, 2H), 1.20-1.14 (m, 2H). MS (ESI): m/z 717.1 [M+H]$^+$.

Example 24

Step a

8-Bromochroman-5-amine

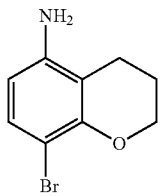 [SMILES: Nc1ccc(Br)c2c1CCCO2]

To a mixture of chroman-5-amine (1.0 g, 6.7 mmol) in DCM (30 mL) was added NBS (1.19 g, 6.7 mmol) at rt and the resulting mixture stirred at rt for 4 h then concentrated to dryness. The residue was purified by FCC on silica gel (PE:EtOAc=20:1) to give the title compound as a white solid.

Example 24

Step b

8-Bromochroman-5-sulfonyl chloride

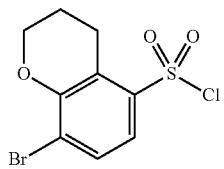 [SMILES: O=S(=O)(Cl)c1ccc(Br)c2c1CCCO2]

A mixture of 8-bromochroman-5-amine (400 mg, 1.75 mmol, Example 24, step a), concentrated HCl (6 mL) and HOAc (2 mL) was stirred at rt for 18 h then added to a solution of NaNO$_2$ (138 mg, 2.0 mmol) in H$_2$O (0.5 mL) at −10° C. The resulting mixture was stirred at −10-0° C. for 1 hour. Meanwhile, a mixture of SO$_2$, AcOH, CuCl and CuCl$_2$ in AcOH (6 mL) was placed in a 50 mL flask and cooled to 0° C. The diazotization mixture was then added dropwise to the reaction mixture at 0° C., and the solution was stirred at rt for 18 h. The resulting reaction mixture was added to cold water (100 mL) and extracted with DCM (3×50 mL). The combined organic phase was dried over anhydrous Na$_2$SO$_4$, filtered and concentrated to dryness to give the title compound as a yellow oil.

Example 24

Step c (S)-8-Bromo-N-(1,1,1-trifluoropropan-2-yl)chroman-5-sulfonamide

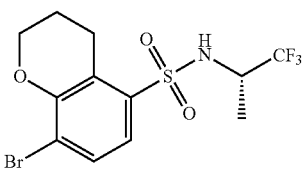 [SMILES: C[C@H](NS(=O)(=O)c1ccc(Br)c2c1CCCO2)C(F)(F)F]

A solution of 8-bromochroman-5-sulfonyl chloride (100 mg, 0.83 mmol, Example 24, step b) and (S)-1,1,1-trifluoropropan-2-amine hydrochloride (136 mg, 1.2 mmol) in pyridine (3 mL) in a 50 mL flask was stirred at rt for 18 hours. The mixture concentrated and purified by FCC on silica gel (EtOAc:PE=1:15) to give the title compound as a white solid.

Example 24

8-(4-(4,4-Difluoropiperidine-1-carbonyl)-2-(5-(2-hydroxypropan-2-yl)-1,3,4-oxadiazol-2-yl)thiazol-5-yl)-N—((S)-1,1,1-trifluoropropan-2-yl)chroman-5-sulfonamide

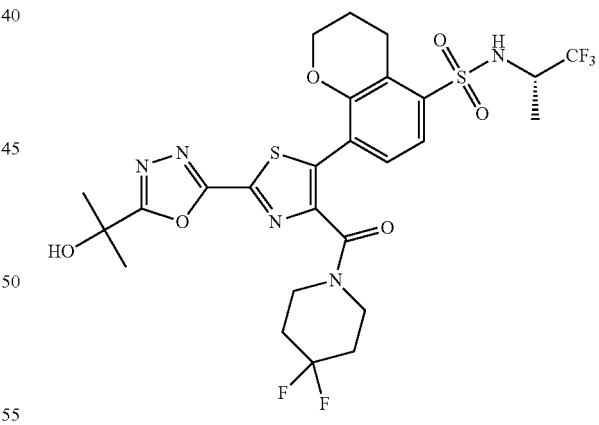

A mixture of (4,4-difluoropiperidin-1-yl)(2-(5-(2-hydroxypropan-2-yl)-1,3,4-oxadiazol-2-yl)thiazol-4-yl)methanone (93 mg, 0.26 mmol, Intermediate 4, step d), (S)-8-bromo-N-(1,1,1-trifluoropropan-2-yl)chroman-5-sulfonamide (100 mg, 0.26 mmol, Example 24, step c), pivalic acid (10 mg, 0.1 mmol), di(1-adamantyl)-n-butylphosphine (19 mg, 0.05 mmol) and K$_2$CO$_3$ (98 mg, 0.5 mmol) in DMA (8 mL) in a 100 mL round-bottomed flask was added Pd(OAc)$_2$ (6.7 mg, 0.03 mmol) under N$_2$. The mixture was stirred at 110° C. for 5 h then concentrated to dryness. The residue was purified by FCC on silica gel (DCM: MeOH=30:1 to 10:1) to give the solid which was further purified by prep-HPLC (ACN-H$_2$O, 45-55, 0.1% TFA) to give the title compound as a white solid. $^1$H NMR (400 MHz, DMSO-d$_6$) δ 8.81 (s, 1H), 7.59 (d, J=8.3 Hz, 1H), 7.49 (d, J=8.3 Hz, 1H), 6.09 (s, 1H), 4.38-4.25 (m, 2H), 3.99-3.92 (m, 1H), 3.76 (t, J=5.7 Hz, 2H), 3.34-3.31 (m, 2H), 3.23-3.07 (m, 2H), 2.10-1.95 (m, 4H), 1.82-1.72 (m, 2H), 1.63 (s, 6H), 1.18 (d, J=6.9 Hz, 3H). MS (ESI): m/z 666.1 [M+H]$^+$.

Example 25

4-(4-(4,4-Difluoropiperidine-1-carbonyl)-2-(5-(2-hydroxypropan-2-yl)-1,3,4-oxadiazol-2-yl)thiazol-5-yl)-3-fluoro-2-(trifluoromethyl)-N—((S)-1,1,1-trifluoropropan-2-yl)benzenesulfonamide

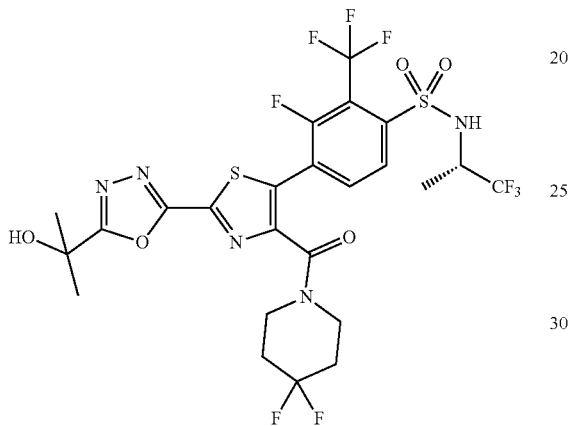

The title compound was prepared as described for the synthesis of Example 24, using in step a 3-fluoro-2-(trifluoromethyl)benzenamine in place of chroman-5-amine. $^1$H NMR (400 MHz, DMSO-d$_6$) δ 9.28 (s, 1H), 8.23-8.16 (m, 1H), 8.13 (d, J=8.4 Hz, 1H), 6.12 (s, 1H), 4.22 (s, 1H), 3.81-3.66 (m, 2H), 3.59 (s, 2H), 2.03 (s, 2H), 1.91 (s, 2H), 1.64 (s, 6H), 1.33 (d, J=6.7 Hz, 3H). MS (ESI): m/z 695.5 [M+H]$^+$.

Example 26

4-(4-(4,4-Difluoropiperidine-1-carbonyl)-2-(5-(2-hydroxypropan-2-yl)-1,3,4-oxadiazol-2-yl)thiazol-5-yl)-3-fluoro-2-methyl-N—((S)-1,1,1-trifluoropropan-2-yl)benzenesulfonamide

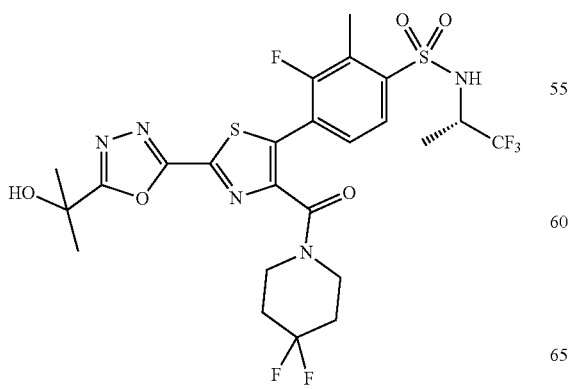

The title compound was prepared as described for the synthesis of Example 24, using in step a 3-fluoro-2-methylbenzenamine in place of chroman-5-amine. The title compound was isolated as a white solid. $^1$H NMR (400 MHz, DMSO-d$_6$) δ 7.90-7.83 (m, 1H), 7.66 (s, 1H), 6.11 (s, 1H), 4.03 (s, 1H), 3.74 (s, 2H), 3.46 (s, 2H), 2.54 (s, 3H), 2.05 (s, 2H), 1.84 (s, 2H), 1.65-1.64 (m, 6H), 1.19 (brs, 3H). MS (ESI): m/z 641.9 [M+H]$^+$.

Example 27

3-Chloro-4-(4-(4,4-difluoropiperidine-1-carbonyl)-2-(5-(2-hydroxypropan-2-yl)-1,3,4-oxadiazol-2-yl)thiazol-5-yl)-2-methyl-N—((S)-1,1,1-trifluoropropan-2-yl)benzenesulfonamide

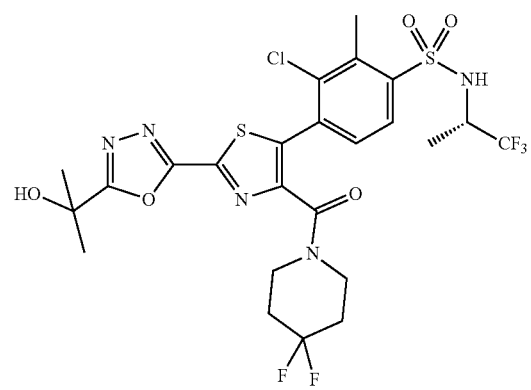 [SMILES: Cc1c(S(=O)(=O)N[C@@H](C)C(F)(F)F)ccc(-c2sc(-c3nnc(C(C)(C)O)o3)nc2C(=O)N2CCC(F)(F)CC2)c1Cl]

The title compound was prepared as described for the synthesis of Example 24, using in step a 3-chloro-2-methylbenzenamine instead of chroman-5-amine. The title compound was isolated as a white solid. $^1$H NMR (400 MHz, DMSO-d$_6$) δ 8.00 (d, J=8.3 Hz, 1H), 7.62 (d, J=8.2 Hz, 1H), 6.11 (s, 1H), 4.13-4.00 (m, 1H), 3.65 (s, 2H), 3.49 (s, 2H), 2.70 (s, 3H), 1.90 (br s, 4H), 1.64 (s, 6H), 1.20 (d, J=6.9 Hz, 3H). MS (ESI): m/z 657.9 [M+H]$^+$.

Example 28

(5-(2-(difluoromethyl)-4-(1,1,1,3,3,3-hexafluoro-2-hydroxypropan-2-yl)phenyl)-2-(5-(2-hydroxypropan-2-yl)-1,3,4-oxadiazol-2-yl)thiazol-4-yl)(4,4-difluoropiperidin-1-yl)methanone

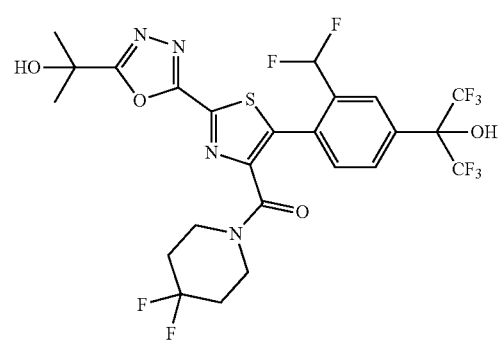 [SMILES: CC(C)(O)c1nnc(-c2nc(C(=O)N3CCC(F)(F)CC3)c(-c3ccc(C(O)(C(F)(F)F)C(F)(F)F)cc3C(F)F)s2)o1]

Butyronitrile (2 mL) that had been sparged with argon for 1 h was added to a mixture of (4,4-difluoropiperidin-1-yl)(2-(5-(2-hydroxypropan-2-yl)-1,3,4-oxadiazol-2-yl)thiazol-4-yl)methanone (116 mg, 0.324 mmol, Intermediate 4, step d), 2-(4-bromo-3-(difluoromethyl)phenyl)-1,1,1,3,3,3-hexafluoropropan-2-ol (172 mg, 0.461 mmol, Intermediate 23), KOAc (0.066 g, 0.672 mmol), pivalic acid (17 mg, 0.17 mmol) and tricyclohexylphosphonium tetrafluoroborate (27 mg, 0.07 mmol). The mixture was sparged with nitrogen for 25 minutes. Then Pd(OAc)$_2$ (16.2 mg, 0.072 mmol) was added at rt under nitrogen and the mixture was sparged with nitrogen for 2 minutes. The mixture was placed in a heating block already at 100° C. for 18 h, cooled to rt and filtered through Celite®. The filter cake was washed with EtOAc and transferred to a separatory funnel. The organic layer was washed with aqueous saturated NaHCO$_3$ solution, aqueous sodium chloride solution, dried over anhydrous MgSO$_4$, filtered, concentrated to dryness and the residue was purified by FCC on silica gel (0 to 60% EtOAc in DCM). Further purification by FCC on silica gel (0 to 5% MeOH in DCM) furnished the title compound. $^1$H NMR (CDCl$_3$, 500 MHz): δ ppm 8.09 (s, 1H), 7.96-7.88 (m, 1H), 7.61 (d, J=8.2 Hz, 1H), 6.92-6.70 (m, 1H), 4.30 (s, 1H), 3.76 (t, J=5.9 Hz, 2H), 3.59 (t, J=5.9 Hz, 2H), 2.65 (s, 1H), 2.09-1.83 (m, 4H), 1.80 (d, J=1.3 Hz, 6H). MS (ESI): m/z 650.5 [M+H]$^+$.

Example 29

(S)-(5-(2-(difluoromethyl)-4-(1,1,1,3,3,3-hexafluoro-2-hydroxypropan-2-yl)phenyl)-2-(5-(2-hydroxypropan-2-yl)-1,3,4-oxadiazol-2-yl)thiazol-4-yl)(2-methylpyrrolidin-1-yl)methanone

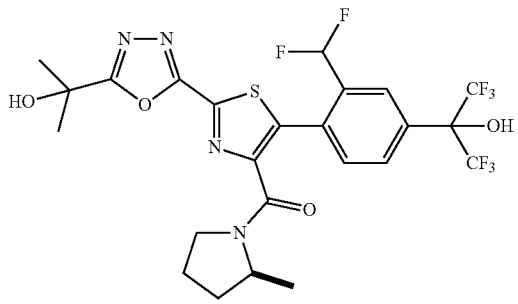

Butyronitrile (1.9 mL) that had been sparged with argon for 1 h was added to a mixture of (S)-(2-(5-(2-hydroxypropan-2-yl)-1,3,4-oxadiazol-2-yl)-5-methylthiazol-4-yl)(2-methylpyrrolidin-1-yl)methanone (100 mg, 0.310 mmol, Intermediate 4/1, step b), 2-(4-bromo-3-(difluoromethyl)phenyl)-1,1,1,3,3,3-hexafluoropropan-2-ol (165 mg, 0.442 mmol, Intermediate 23), K$_2$CO$_3$ (0.17 g, 1.2 mmol), and pivalic acid (13 mg, 0.12 mmol). The mixture was sparged with nitrogen for 25 minutes. Then Pd$_2$dba$_3$ (42.6 mg, 0.046 mmol) and butyl-di-1-adamantyl phosphine (35.1 mg, 0.093 mmol) were added at rt under nitrogen and the mixture was sparged with nitrogen for 2 minutes. The mixture was placed in a heating block already at 100° C. for 48 h, cooled to rt and filtered through Celite®. The filter cake was washed with EtOAc and transferred to a separatory funnel. The organic layer was washed with aqueous saturated NaHCO$_3$ solution, aqueous sodium chloride solution, dried over anhydrous MgSO$_4$, filtered, concentrated to dryness and the residue was purified by FCC on silica gel (0 to 60% EtOAc in DCM) to provide the title compound. $^1$H NMR (400 MHz, CDCl$_3$) δ 8.13-8.06 (m, 1H), 7.88-7.84 (m, 1H), 7.59-7.50 (m, 1H), 7.04-6.69 (m, 1H), 4.63-4.5 (m, 1.3H), 4.27-4.13 (m, 0.7H), 3.69-3.42 (m, 2H), 2.71-2.69 (m, 1H), 2.12-1.72 (m, 8H), 1.72-1.43 (m, 2H), 1.17 (d, J=6.3 Hz, 2H), 1.08 (d, J=6.4 Hz, 1H). MS (ESI): m/z 615.1 [M+H]$^+$.

Example 30

(S)-(5-(2-(difluoromethyl)-4-(1,1,1,3,3,3-hexafluoro-2-hydroxypropan-2-yl)phenyl)-2-(5-(2-hydroxypropan-2-yl)-1,2,4-oxadiazol-3-yl)thiazol-4-yl)(2-methylpyrrolidin-1-yl)methanone

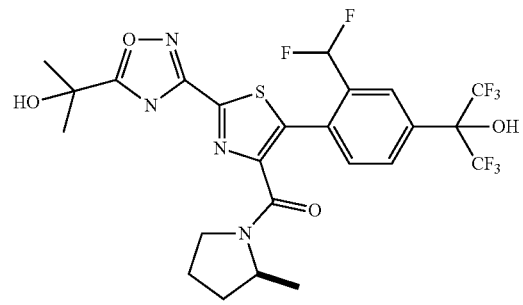

The title compound was prepared as described in Example 29, using (S)-(2-(5-(2-hydroxypropan-2-yl)-1,2,4-oxadiazol-3-yl)thiazol-4-yl)(2-methylpyrrolidin-1-yl)methanone (Intermediate 24) in place of (S)-(2-(5-(2-hydroxypropan-2-yl)-1,3,4-oxadiazol-2-yl)-5-methylthiazol-4-yl)(2-methylpyrrolidin-1-yl)methanone. $^1$H NMR (500 MHz, CDCl$_3$) δ 8.14-8.07 (m, 1H), 7.89-7.81 (m, 1H), 7.58-7.50 (m, 1H), 7.06-6.69 (m, 1H), 4.68-4.63 (m, 0.4H), 4.57-4.46 (m, 1H), 4.20-4.16 (m, 0.6H), 3.74-3.69 (m, 0.7H), 3.61-3.44 (m, 1.3H), 2.81-2.80 (m, 1H), 2.16-1.71 (m, 8H), 1.70-1.47 (m, 2H), 1.17 (d, J=6.3 Hz, 2H), 1.04 (d, J=6.4 Hz, 1H). MS (ESI): m/z 615.1 [M+H]$^+$.

Example 31

(S)-(5-(4-(1,1,1,3,3,3-hexafluoro-2-hydroxypropan-2-yl)-2-methylphenyl)-2-(5-(2-hydroxypropan-2-yl)-1,3,4-oxadiazol-2-yl)thiazol-4-yl)(2-methylpyrrolidin-1-yl)methanone

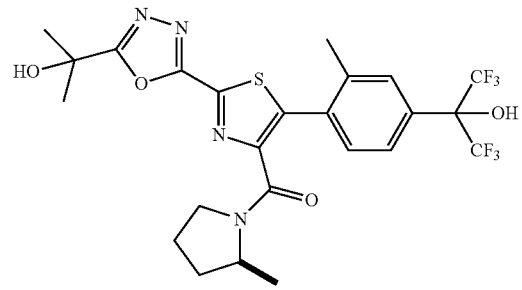 [SMILES: Cc1cc(C(O)(C(F)(F)F)C(F)(F)F)ccc1-c1sc(-c2nnc(C(C)(C)O)o2)nc1C(=O)N1CCC[C@@H]1C]

An oven-dried vial under nitrogen, was charged with (S)-(2-(5-(2-hydroxypropan-2-yl)-1,3,4-oxadiazol-2-yl)thiazol-4-yl)(2-methylpyrrolidin-1-yl)methanone (105 mg, 0.33 mmol, Intermediate 4/1, step b), 2-(4-bromo-3-methylphenyl)-1,1,1,3,3,3-hexafluoropropan-2-ol (100 mg, 0.3 mmol, Intermediate 22), K$_2$CO$_3$ (164 mg, 1.19 mmol), pivalic acid (12 mg, 0.12 mmol), Pd$_2$(dba)$_3$ (41 mg, 0.045 mmol), di-(1-adamantyl)-N-butylphosphine (34 mg, 0.089 mmol) and butyronitrile (1.85 mL). The resulting solution was stirred for 16.5 h at 100° C. The reaction mixture was then cooled to room temperature, diluted with H$_2$O (15 mL), and the aqueous phase was extracted with EtOAc (2×20 mL). The combined organic layers were washed with brine, dried over anhydrous Na$_2$SO$_4$, filtered and concentrated to dryness. The crude product was purified by FCC on silica gel (EtOAc/DCM=0/100 to 60/40) to provide the title compound as a cream-colored solid. $^1$H NMR (500 MHz, CDCl$_3$) δ 7.68-7.64 (m, 1H), 7.61-7.54 (m, 1H), 7.47-7.41 (m, 1H), 5.09-4.77 (m, 1H), 4.26-4.16 (m, 1H), 3.59-3.01 (m, 3H), 2.41-2.35 (m, 3H), 2.03-1.95 (m, 1H), 1.88-1.81 (m, 1H), 1.80-1.77 (m, 6H), 1.71-1.66 (m, 1H), 1.62-1.44 (m, 1H), 1.14 (d, J=6.3 Hz, 2H), 1.01 (d, J=6.4 Hz, 1H). MS (ESI): m/z 579.0 [M+H]$^+$.

Example 32

(S)-(5-(4-(1,1,1,3,3,3-hexafluoro-2-hydroxypropan-2-yl)-2-methylphenyl)-2-(5-(2-hydroxypropan-2-yl)-1,2,4-oxadiazol-3-yl)thiazol-4-yl)(2-methylpyrrolidin-1-yl)methanone

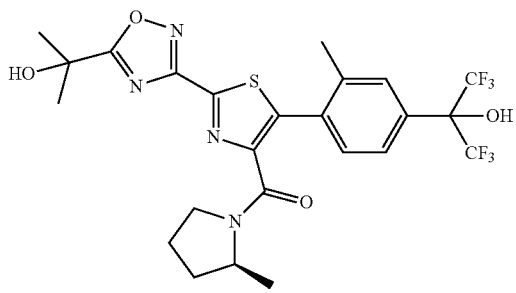 [SMILES: Cc1cc(C(O)(C(F)(F)F)C(F)(F)F)ccc1-c1sc(-c2noc(C(C)(C)O)n2)nc1C(=O)N1CCC[C@@H]1C]

The title compound was prepared as described in Example 31, using (S)-(2-(5-(2-hydroxypropan-2-yl)-1,2,4-oxadiazol-3-yl)thiazol-4-yl)(2-methylpyrrolidin-1-yl)methanone (Intermediate 24) in place of (S)-(2-(5-(2-hydroxypropan-2-yl)-1,3,4-oxadiazol-2-yl)thiazol-4-yl)(2-methylpyrrolidin-1-yl)methanone. $^1$H NMR (500 MHz, CDCl$_3$) δ 7.66-7.62 (m, 1H), 7.59-7.50 (m, 1H), 7.48-7.44 (m, 1H), 4.74-4.47 (m, 1H), 4.40-4.17 (m, 1H), 3.59-3.01 (m, 3H), 2.38 (s, 3H), 2.03-1.94 (m, 1H), 1.86-1.80 (m, 1H), 1.78-1.75 (m, 6H), 1.75-1.70 (m, 1H), 1.61-1.44 (m, 1H), 1.14 (d, J=6.3 Hz, 2H), 1.00 (d, J=6.4 Hz, 1H). MS (ESI): m/z 579.0 [M+H]$^+$.

The compounds of Example 33-40 can be made according to the procedures described below.

Example 33

(S)-(5-(2-(Difluoromethyl)-4-(1,1,1,3,3,3-hexafluoro-2-hydroxypropan-2-yl)phenyl)-2-(5-(2-hydroxypropan-2-yl)-4-methyl-4H-1,2,4-triazol-3-yl)thiazol-4-yl)(2-methylpyrrolidin-1-yl)methanone

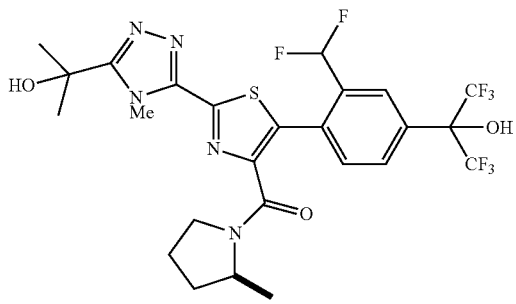 [SMILES: C[C@H]1CCCN1C(=O)c1nc(-c2nnc(C(C)(C)O)n2C)sc1-c1ccc(C(O)(C(F)(F)F)C(F)(F)F)cc1C(F)F]

The title compound can be prepared as described in Example 9/4, using in step a 2-(4-bromo-3-(difluoromethyl)phenyl)-1,1,1,3,3,3-hexafluoropropan-2-ol (Intermediate 23) in place of (S)-4-bromo-2,3-dichloro-N-(1,1,1-trifluoropropan-2-yl)benzenesulfonamide and in step c (S)-2-methylpyrrolidine in place of 4,4-difluoropiperidine.

Example 34

(S)-(5-(4-(1,1,1,3,3,3-Hexafluoro-2-hydroxypropan-2-yl)-2-methylphenyl)-2-(5-(2-hydroxypropan-2-yl)-4-methyl-4H-1,2,4-triazol-3-yl)thiazol-4-yl)(2-methylpyrrolidin-1-yl)methanone

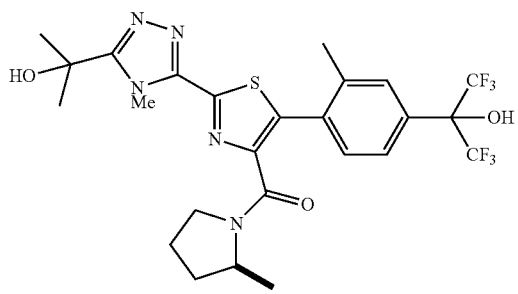 [SMILES: Cc1cc(C(O)(C(F)(F)F)C(F)(F)F)ccc1-c1sc(-c2nnc(C(C)(C)O)n2C)nc1C(=O)N1CCC[C@@H]1C]

The title compound can be prepared as described in Example 9/4, using in step a 2-(4-bromo-3-methylphenyl)-1,1,1,3,3,3-hexafluoropropan-2-ol (Intermediate 22) in place of (S)-4-bromo-2,3-dichloro-N-(1,1,1-trifluoropropan-2-yl)benzenesulfonamide and in step c (S)-2-methylpyrrolidine in place of 4,4-difluoropiperidine.

Example 35

Step a 1-(5-Bromo-4-(trifluoromethyl)pyridin-2-yl)-2,2,2-trifluoroethanone

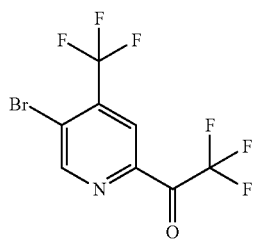 [SMILES: O=C(c1cc(C(F)(F)F)c(Br)cn1)C(F)(F)F]

A solution of 5-bromo-2-iodo-4-(trifluoromethyl)pyridine (3.5 g, 9.95 mmol) in toluene (30 mL) is cooled to −78° C. Then, n-BuLi (4.14 mL, 9.95 mmol, 2.5 M in THF) is added and the resulting mixture is stirred at −78° C. for 30 minutes. Then ethyl 2,2,2-trifluoroacetate (1.7 g, 11.94 mmol) is added and the mixture is stirred at −78° C. for 1 h. The mixture is quenched by the addition of saturated aqueous NH$_4$Cl (5 mL), then it can be diluted with brine and extracted with EtOAc (2×30 mL). The organic layers are combined, then wash with brine, dry over anhydrous MgSO$_4$, filter and concentrate to dryness. The residue can be purified by FCC on silica gel (EtOAc/PE=1/50 to 1/20) to provide the title compound as a yellow oil.

Example 35

Step b 2-(5-Bromo-4-(trifluoromethyl)pyridin-2-yl)-1,1,1,3,3,3-hexafluoropropan-2-ol

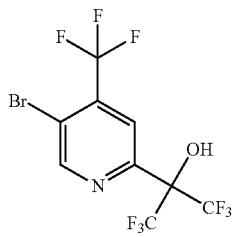 [SMILES: OC(c1cc(C(F)(F)F)c(Br)cn1)(C(F)(F)F)C(F)(F)F]

A solution of 1-(5-bromo-4-(trifluoromethyl)pyridin-2-yl)-2,2,2-trifluoroethanone (1.2 g, 3.73 mmol, Intermediate 23, step a) and TMSCF$_3$ (2.65 g, 18.64 mmol) in anhydrous THF (20 mL) is cooled to −10° C. Then, a solution of TBAF (974 mg, 3.73 mmol) in THF (10 mL) is added followed immediately by the addition of 1 N aqueous HCl (6 mL). The resulting mixture is stirred at rt for 10 minutes. The mixture is then partitioned between saturated aqueous NaHCO$_3$ (10 mL) and EtOAc (20 mL). The aqueous layer is further extracted with EtOAc (20 mL), then the organic layers are combined, wash with brine, dry over anhydrous Na$_2$SO$_4$, filter and concentrate to dryness. The residue can be purified by FCC on silica gel (PE) to afford the title compound as a white solid.

Example 35

(S)-(5-(6-(1,1,1,3,3,3-Hexafluoro-2-hydroxypropan-2-yl)-4-(trifluoromethyl)pyridin-3-yl)-2-(5-(2-hydroxypropan-2-yl)-1,3,4-oxadiazol-2-yl)thiazol-4-yl)(2-methylpyrrolidin-1-yl)methanone

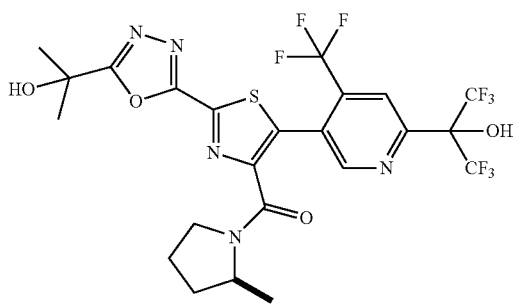 [SMILES: C[C@H]1CCCN1C(=O)c1nc(-c2noc(C(C)(C)O)n2)sc1-c1cnc(C(O)(C(F)(F)F)C(F)(F)F)cc1C(F)(F)F]

The title compound can be prepared as described in Example 31, using 2-(5-bromo-4-(trifluoromethyl)pyridin-2-yl)-1,1,1,3,3,3-hexafluoropropan-2-ol (Example 35, step b) in place of 2-(4-bromo-3-methylphenyl)-1,1,1,3,3,3-hexafluoropropan-2-ol.

Example 36

(S)-(5-(6-(1,1,1,3,3,3-Hexafluoro-2-hydroxypropan-2-yl)-4-(trifluoromethyl)pyridin-3-yl)-2-(5-(2-hydroxypropan-2-yl)-1,2,4-oxadiazol-3-yl)thiazol-4-yl)(2-methylpyrrolidin-1-yl)methanone

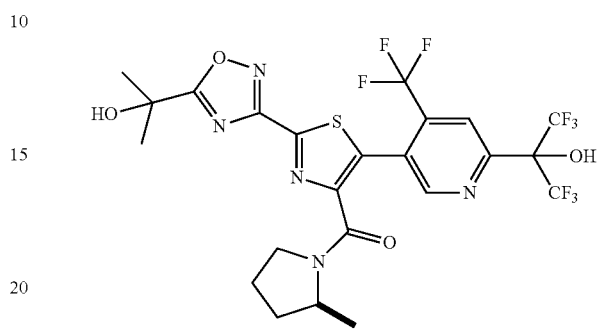

The title compound can be prepared as described in Example 31, using (S)-(2-(5-(2-hydroxypropan-2-yl)-1,2,4-oxadiazol-3-yl)thiazol-4-yl)(2-methylpyrrolidin-1-yl)methanone (Intermediate 24) in place of (S)-(2-(5-(2-hydroxypropan-2-yl)-1,3,4-oxadiazol-2-yl)thiazol-4-yl)(2-methylpyrrolidin-1-yl)methanone and 2-(5-bromo-4-(trifluoromethyl)pyridin-2-yl)-1,1,1,3,3,3-hexafluoropropan-2-ol (Example 35, step b) in place of 2-(4-bromo-3-methylphenyl)-1,1,1,3,3,3-hexafluoropropan-2-ol.

Example 37

(S)-(5-(6-(1,1,1,3,3,3-Hexafluoro-2-hydroxypropan-2-yl)-4-(trifluoromethyl)pyridin-3-yl)-2-(5-(2-hydroxypropan-2-yl)-4-methyl-4H-1,2,4-triazol-3-yl)thiazol-4-yl)(2-methylpyrrolidin-1-yl)methanone

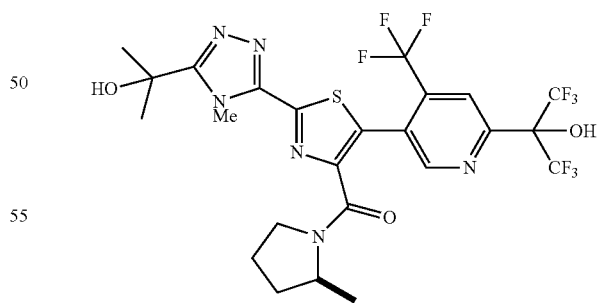

The title compound can be prepared as described in Example 9/4, using in step a 2-(5-bromo-4-(trifluoromethyl)pyridin-2-yl)-1,1,1,3,3,3-hexafluoropropan-2-ol (Example 35, step b) in place of (S)-4-bromo-2,3-dichloro-N-(1,1,1-trifluoropropan-2-yl)benzenesulfonamide and in step c (S)-2-methylpyrrolidine in place of 4,4-difluoropiperidine.

Example 38

(S)-3-(3-(5-(6-(1,1,1,3,3,3-Hexafluoro-2-hydroxy-propan-2-yl)-4-(trifluoromethyl)pyridin-3-yl)-4-(2-methylpyrrolidine-1-carbonyl)thiazol-2-yl)-1,2,4-oxadiazol-5-yl)-2,2-dimethylpropanoic acid

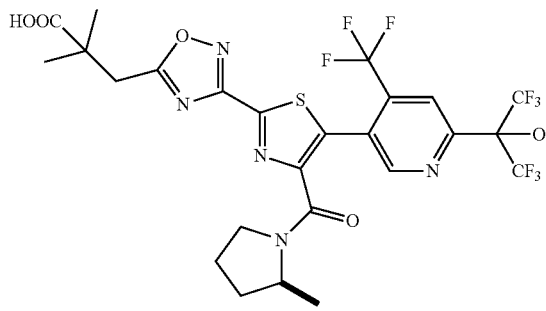

The title compound can be prepared as described for the synthesis of Example 10, using in step a 2-(5-bromo-4-(trifluoromethyl)pyridin-2-yl)-1,1,1,3,3,3-hexafluoropropan-2-ol (Example 35, step b) in place of (S)-4-bromo-2,3-dichloro-N-(1,1,1-trifluorobutan-2-yl)benzenesulfonamide and using in step b (S)-2-methylpyrrolidine in place of (S)-2-methylpiperidine.

Example 39

(S)-3-(3-(5-(2-(Difluoromethyl)-4-(1,1,1,3,3,3-hexafluoro-2-hydroxypropan-2-yl)phenyl)-4-(2-methylpyrrolidine-1-carbonyl)thiazol-2-yl)-1,2,4-oxadiazol-5-yl)-2,2-dimethylpropanoic acid

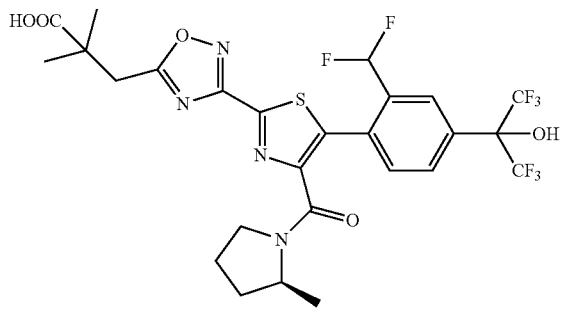 [SMILES: C[C@H]1CCCN1C(=O)c1nc(-c2noc(CC(C)(C)C(=O)O)n2)sc1-c1ccc(C(O)(C(F)(F)F)C(F)(F)F)cc1C(F)F]

The title compound can be prepared as described for the synthesis of Example 10, using in step a 2-(4-bromo-3-(difluoromethyl)phenyl)-1,1,1,3,3,3-hexafluoropropan-2-ol (Intermediate 23) in place of (S)-4-bromo-2,3-dichloro-N-(1,1,1-trifluorobutan-2-yl)benzenesulfonamide and using in step b (S)-2-methylpyrrolidine in place of (S)-2-methylpiperidine.

Example 40

(S)-3-(3-(5-(4-(1,1,1,3,3,3-Hexafluoro-2-hydroxy-propan-2-yl)-2-methylphenyl)-4-(2-methylpyrrolidine-1-carbonyl)thiazol-2-yl)-1,2,4-oxadiazol-5-yl)-2,2-dimethylpropanoic acid

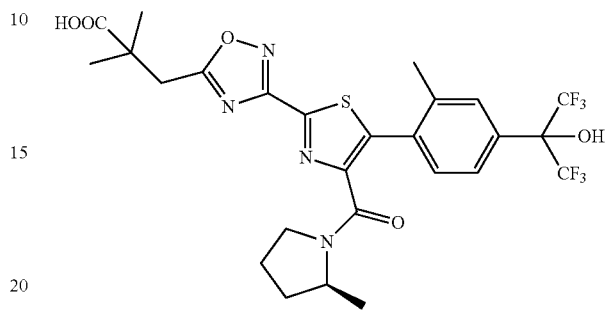

The title compound can be prepared as described for the synthesis of Example 10, using in step a 2-(4-bromo-3-methylphenyl)-1,1,1,3,3,3-hexafluoropropan-2-ol (Intermediate 22) in place of (S)-4-bromo-2,3-dichloro-N-(1,1,1-trifluorobutan-2-yl)benzenesulfonamide and using in step b (S)-2-methylpyrrolidine in place of (S)-2-methylpiperidine.

In Vitro Biological Data

ThermoFluor® Assay

ThermoFluor® is a fluorescence based assay that estimates ligand binding affinities by measuring the effect of a ligand on protein thermal stability (Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) High-density miniaturized thermal shift assays as a general strategy for drug discovery. *J Biomol Screen* 6, 429-40, and Matulis, D., Kranz, J. K., Salemme, F. R., and Todd, M. J. (2005) Thermodynamic stability of carbonic anhydrase: measurements of binding affinity and stoichiometry using ThermoFluor. *Biochemistry* 44, 5258-66). This approach is applicable to a wide variety of systems, and rigorous in theoretical interpretation through quantitation of equilibrium binding constants ($K_D$).

In a ThermoFluor® experiment where protein stability is monitored as the temperature is steadily increased, an equilibrium binding ligand causes the midpoint of an unfolding transition ($T_m$) to occur at a higher temperature. The shift in the melting point described as a $\Delta T_m$ is proportional to the concentration and affinity of the ligand. The compound potency may be compared as a rank order of either $\Delta T_m$ values at a single compound concentration or in terms of $K_D$ values, estimated from concentration response curves.

RORγt ThermoFluor® Assay Construct

For the RORγt construct used in the ThermoFluor® assay, numbering for the nucleotide sequences was based on the reference sequence for human RORγt, transcript variant 2, NCBI Accession: NM 001001523.1 (SEQ ID NO:1). Nucleotides 850-1635 (SEQ ID NO:2) coding for the wild type human RORγt ligand binding domain (RORγt LBD) were cloned into the pHIS1 vector, a modified pET *E. coli* expression vector (Accelagen, San Diego), containing an in-frame N-terminal His-tag and a TurboTEV protease cleavage site (ENLYFQG, SEQ ID NO:3) upstream of the cloned insert sequence. The amino acid sequence for the RORγt construct used in the Thermofluor assay is shown as SEQ ID NO:4.

ThermoFluor® experiments were carried out using instruments owned by Janssen Research and Discovery, L.L.C. through its acquisition of 3-Dimensional Pharmaceuticals, Inc. 1,8-ANS (Invitrogen) was used as a fluorescent dye. Protein and compound solutions are dispensed into black 384-well polypropylene PCR microplates (Abgene) and overlayed with silicone oil (1 µL, Fluka, type DC 200) to prevent evaporation.

Bar-coded assay plates are robotically loaded onto a thermostatically controlled PCR-type thermal block and then heated at a typical ramp-rate of 1° C./min for all experiments.

Fluorescence was measured by continuous illumination with UV light (Hamamatsu LC6) supplied via fiber optic and filtered through a band-pass filter (380-400 nm; >6 OD cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. Images were collected at each temperature, and the sum of the pixel intensity in a given area of the assay plate was recorded versus temperature. Reference wells contained RORγt without compounds, and the assay conditions were as follows:

0.065 mg/mL RORγt
60 µM 1,8-ANS
100 mM Hepes, pH 7.0
10 mM NaCl
2.5 mM GSH
0.002% Tween-20

Project compounds were arranged in a pre-dosed mother plate (Greiner Bio-one) wherein compounds are serially diluted in 100% DMSO by 1:2 from a high concentration of 10 mM over 12 columns within a series (column 12 is a reference well containing DMSO, no compound). The compounds were robotically dispensed directly into assay plates (1×=46 nL) using a Hummingbird capillary liquid handling instrument (Digilab). Following compound dispense, protein and dye in buffer was added to achieve the final assay volume of 3 µL, followed by 1 µL of silicone oil.

The binding affinity was estimated as described previously (Matulis, D., Kranz, J. K., Salemme, F. R., and Todd, M. J. (2005) Thermodynamic stability of carbonic anhydrase: measurements of binding affinity and stoichiometry using ThermoFluor®. *Biochemistry* 44, 5258-66) using the following thermodynamic parameters of protein unfolding:

Reference RORγt $T_m$: 47.8° C.
$\Delta H_{(Tm)}$=115 kcal/mol
$\Delta C_{p(Tm)}$=3 kcal/mol Cell Based Biological Data RORγt (full-length human) Reporter Assay Three similar protocols, shown below, have been used to test the functional activity of RORγt modulatory compounds on transcriptional activation driven by full-length human RORγt. All three provide similar data and can be used interchangeably.

Conditions A

Cells used in this assay were transiently co-transfected with three different plasmids, one expressing the GAL4-DNA binding domain (DBD)-RORγt fusion protein under control of a CMV promoter (NH2-Gal4-DBD:RORC—COOH in pCMV-BD, Stratagene #211342), and two reporter plasmids—the firefly luciferase reporter under control of a GAL4 promoter (pFR-Luc 2× GAL4) and *Renilla luciferase* reporter under control of CMV promoter (pRL-CMV, Promega #E2261). The full-length coding sequence was used for human RORγt, i.e., nucleotides 142-1635 of human RORγt, transcript variant 2, NCBI Accession: NM 001001523.1 (SEQ ID NO:1). HEK293T cells were plated at 35000 per well in 96-well plate in medium of MEM with 8.6% FBS. After 18-22 hours incubation, the transfection was carried out by using a PEI solution with 170.5 ng total DNA/well (50 ng pCMV-BD-ROR plus 20 ng of pFR-Luc reporter and 0.5 ng of pRL-CMV reporter plus 100 ng Carrier DNA (Clontech #630440) for each well). 4-6 hours after transfection, cells were treated with compounds for overnight in the medium with final concentration of FBS 1.1% and DMSO 0.1%. After overnight (16 to 20 hours) incubation, media were removed and cells were lysed with 20 µL 1× Passive Lysis Buffer (Promega) for 10-15 minutes. Luminescence was measured using a BMG LUMIstar OPTIMA plate reader, after addition of 75 µL/well firefly luciferase buffer, followed by 75 µL/well *Renilla luciferase* buffer. To calculate the effect of compounds on RORγt activity, firefly values were normalized against values of DMSO only and values of reference compound at saturating concentration, then further normalized against *Renilla* signals. IC50s were generated by plotting final *Renilla* normalized data against compound concentration and percent inhibition was calculated against DMSO control.

Conditions B

Cells used in this assay were transiently co-transfected with three different plasmids, one expressing the GAL4-DNA binding domain (DBD)-RORγt fusion protein under control of a CMV promoter (NH2-Gal4-DBD:RORC—COOH in pCMV-BD, Stratagene #211342), and two reporter plasmids—the firefly luciferase reporter under control of a GAL4 promoter (pFR-Luc 2×GAL4) and *Renilla luciferase* reporter under control of CMV promoter (pRL-CMV, Promega #E2261). The full-length coding sequence was used for human RORγt, i.e., nucleotides 142-1635 of human RORγt, transcript variant 2, NCBI Accession: NM 001001523.1 (SEQ ID NO:1). HEK293T cells were plated at 35,000 per well in 96-well plate in medium of DMEM with 10% FBS. After 18-22 hours incubation, the transfection was carried out by using a PEI solution with 170.5 ng total DNA/well (50 ng pCMV-BD-ROR plus 20 ng of pFR-Luc reporter and 0.5 ng of pRL-CMV reporter plus 100 ng Carrier DNA (Clontech #630440) for each well). 4-6 hours after transfection, cells were treated with compounds for overnight in the medium with final concentration of FBS 1.3% and DMSO 0.1%. After overnight (16 to 20 hours) incubation, media were removed and cells were lysed with 50 µL Glo Lysis Buffer (Promega) for 10-15 minutes followed by 10 minute incubation with 50 uL Dual Glo reagent (Promega) at room temperature. Firefly luciferase luminescence was measured using a BMG Pherastar plate reader. To each well, 50 uL Stop and Glo reagent was added and incubated for 10 minutes at room temperature. *Renilla* luminescence was measured using a BMG Pherastar plate reader. To calculate the effect of compounds on RORγt activity, firefly values were normalized against values of DMSO only and values of reference compound at saturating concentration, then further normalized against *Renilla* signals. IC50s were generated by plotting final *Renilla* normalized data against compound concentration and percent inhibition was calculated against DMSO control.

Conditions C

Cells used in this assay were transiently co-transfected with three different plasmids, one expressing the GAL4-DNA binding domain (DBD)-RORγt fusion protein under control of a CMV promoter (NH2-Gal4-DBD:RORC—COOH in pCMV-BD, Stratagene #211342), and two reporter plasmids—the firefly luciferase reporter under control of a GAL4 promoter (pFR-Luc 2×GAL4) and *Renilla luciferase* reporter under control of CMV promoter (pRL-CMV, Promega #E2261). The full-length coding sequence was used for human RORγt, i.e., nucleotides 142-1635 of human RORγt, transcript variant 2, NCBI Accession: NM 001001523.1 (SEQ ID NO:1). HEK293T cells were plated at 8750 cells per well in 384-well plate in medium of DMEM with 10% FBS. After 18-22 hours incubation, the transfection was carried out by using a PEI solution with 42.6 ng total DNA/well (12.5 ng pCMV-BD-ROR plus 5 ng of pFR-Luc reporter and 0.125 ng of pRL-CMV reporter plus 25 ng Carrier DNA (Clontech #630440) for each well). 4-6 hours after transfection, cells were treated with compounds for overnight in the medium with final concentration of FBS 1.3% and DMSO 0.1%. After overnight (16 to 20 hours) incubation, media were removed and cells were lysed with 20 μL Glo Lysis Buffer (Promega) for 10-15 minutes followed by 10 minute incubation with 20 uL Dual Glo reagent (Promega) at room temperature. Firefly luciferase luminescence was measured using a BMG Pherastar plate reader. To each well, 20 uL Stop and Glo reagent was added and incubated for 10 minutes at room temperature. *Renilla* luminescence was measured using a BMG Pherastar plate reader. To calculate the effect of compounds on RORγt activity, firefly values were normalized against values of DMSO only and values of reference compound at saturating concentration, then further normalized against *Renilla* signals. IC50s were generated by plotting final *Renilla* normalized data against compound concentration and percent inhibition was calculated against DMSO control.

Human Th17 Assay

The human Th17 assay tests the effect of RORγt modulatory compounds on IL-17 production by CD4 T cells under conditions which favor Th17 differentiation. Total $CD4^+$ T cells were isolated from the peripheral blood mononuclear cells (PBMC) of healthy donors using a $CD4^+$ T cell isolation kit II, following the manufacturer's instructions (Miltenyi Biotec). Cells were resuspended in a medium of RPMI-1640 supplemented with 10% fetal bovine serum, penicillin, streptomycin, glutamate, and β-mercaptoethanol and were added to 96-well plates at $1.5 \times 10^5$ per 100 μL per well. 50 μL of compound at titrated concentrations in DMSO were added into each well at final DMSO concentration at 0.2%. Cells were incubated for 1 hour, then 50 μL of Th17 cell differentiation medium was added to each well. The final concentrations of antibodies and cytokines (R&D Systems) in differentiation medium were: $3 \times 10^6$/mL anti-CD3/CD28 beads (prepared using human T cell activation/expansion kit, Miltenyi Biotec), 10 μg/mL anti-IL4, 10 μg/mL anti-IFNγ, 10 ng/mL IL1β, 10 ng/mL IL23, 50 ng/mL IL6, 3 ng/mL TGFβ and 20 U/mL IL2. Cells were cultured at 37° C. and 5% $CO_2$ for 3 days. Supernatants were collected and the accumulated IL-17 in culture was measured by using MULTI-SPOT® Cytokine Plate following manufacture's instruction (Meso Scale Discovery). The plate was read using Sector Imager 6000, and IL-17 concentration was extrapolated from the standard curve. The IC50s were determined by GraphPad.

TABLE 1

| Example # | ThermoFluor® Assay, Kd (μM) | RORγt (FL) Reporter Assay A, $IC_{50}$ (μM) | RORγt (FL) Reporter Assay A, % inhibition @ 6 μM | RORγt (FL) Reporter Assay B or C, $IC_{50}$ (μM) | RORγt (FL) Reporter Assay B or C, % inhibition @ 6 μM | Human Th17 Assay, $IC_{50}$ (μM) |
|---|---|---|---|---|---|---|
| 1 | 0.0013 | 1.1 | 89 | ND | ND | 0.054 |
| 1/1 | 0.0010 | 0.010 | 106 | ND | ND | ND |
| 1/2 | 0.00042 | 0.011 | 105** | ND | ND | ND |
| 1/3 | 0.00070 | 0.0045 | 103** | ND | ND | ND |
| 1/4 | 0.0047 | 0.055 | 101 | ND | ND | ND |
| 2 | 0.0000030 | 0.10 | 104 | ND | ND | ND |
| 2/1 | 0.00098 | 0.23 | 102 | ND | ND | ND |
| 2/2 | 0.0020 | 0.15 | 104 | ND | ND | 0.15 |
| 3 | 0.0016 | 0.026 | 107 | ND | ND | ND |
| 3/1 | 0.016 | 0.057 | 109 | ND | ND | ND |
| 3/2 | 0.00059 | 0.023 | 107 | ND | ND | ND |
| 3/3 | 0.010 | 0.027 | 107 | ND | ND | ND |
| 3/4 | 0.024 | 0.050 | 106* | ND | ND | ND |
| 3/5 | 0.0032 | 0.014 | 108 | ND | ND | ND |
| 3/6 | 0.076 | 0.37 | 104 | ND | ND | ND |
| 3/7 | 0.081 | 0.29 | 103 | ND | ND | ND |
| 4 | 0.0015 | 0.019 | 103* | ND | ND | ND |
| 4/1 | 0.0050 | 0.021 | 104 | ND | ND | ND |
| 4/2 | 0.011 | 0.045 | 103 | ND | ND | ND |
| 4/3 | 0.00038 | 0.026 | 105 | ND | ND | ND |
| 4/4 | 0.00074 | 0.032 | 108 | ND | ND | 0.015 |
| 4/5 | 0.012 | 0.052 | 110 | ND | ND | ND |
| 4/6 | 0.0063 | 0.023 | 101 | ND | ND | ND |
| 5 | 0.037 | 0.17 | 106 | ND | ND | ND |
| 5/1 | 0.12 | 0.28 | 105 | ND | ND | ND |
| 6 | 0.00099 | 0.013 | 105* | ND | ND | ND |
| 6/1 | 0.00036 | 0.018 | 102* | ND | ND | ND |
| 6/2 | 0.0076 | 0.038 | 108 | ND | ND | ND |
| 6/3 | 0.0017 | 0.027 | 110 | ND | ND | ND |
| 6/4 | 0.0068 | 0.082 | 108 | ND | ND | ND |
| 6/5 | 0.00060 | 0.023 | 103 | ND | ND | ND |
| 6/6 | 0.016 | 0.072 | 110 | ND | ND | ND |
| 6/7 | 0.0017 | 0.038 | 113 | ND | ND | ND |
| 6/8 | 0.0045 | 0.030 | 108 | ND | ND | ND |
| 6/9 | 0.0065 | 0.11 | 108 | ND | ND | 0.10 |
| 6/10 | 0.045 | 0.21 | 101 | ND | ND | ND |
| 6/11 | 0.0093 | 0.069 | 104 | ND | ND | ND |

TABLE 1-continued

| Example # | ThermoFluor ® Assay, Kd (μM) | RORγt (FL) Reporter Assay A, IC$_{50}$ (μM) | RORγt (FL) Reporter Assay A, % inhibition @ 6 μM | RORγt (FL) Reporter Assay B or C, IC$_{50}$ (μM) | RORγt (FL) Reporter Assay B or C, % inhibition @ 6 μM | Human Th17 Assay, IC$_{50}$ (μM) |
|---|---|---|---|---|---|---|
| 6/12 | 0.010 | 0.055 | 103 | ND | ND | ND |
| 6/13 | 0.59 | 1.1 | 90 | ND | ND | ND |
| 6/14 | 0.0033 | 0.073 | 105 | ND | ND | ND |
| 6/15 | 0.00089 | 0.033 | 107 | ND | ND | ND |
| 6/16 | 0.00047 | 0.038 | 104 | ND | ND | ND |
| 6/17 | 0.021 | 0.10 | 105 | ND | ND | ND |
| 6/18 | 0.0010 | 0.082 | 104 | ND | ND | ND |
| 6/19 | 0.0061 | 0.076 | 107 | ND | ND | ND |
| 6/20 | 0.011 | 0.043 | 102* | ND | ND | ND |
| 6/21 | 0.27 | 0.41 | 102 | ND | ND | ND |
| 6/22 | 1.2 | 1.6 | 74 | ND | ND | ND |
| 6/23 | 6.0 | 2.3 | 40 | ND | ND | ND |
| 6/24 | 0.011 | 0.13 | 96* | ND | ND | ND |
| 7 | 0.29 | 0.12 | 102 | ND | ND | ND |
| 7/1 | 0.0010 | 0.038 | 102* | 0.0060 | 108* | 0.064 |
| 8 | 0.029 | 0.11 | 102 | ND | ND | ND |
| 8/1 | 0.0056 | 0.061 | 108 | ND | ND | ND |
| 8/2 | 0.0017 | 0.051 | 104* | ND | ND | ND |
| 8/3 | 0.0063 | 0.083 | 104* | ND | ND | ND |
| 8/4 | 0.012 | 0.32 | 47 | ND | ND | ~6 |
| 9 | 0.032 | 0.12 | 99* | ND | ND | ND |
| 9/1 | 0.027 | 0.067 | 99* | ND | ND | ND |
| 9/2 | 0.00071 | 0.028 | 104* | ND | ND | ND |
| 9/3 | 0.0012 | 0.061 | 104* | ND | ND | ND |
| 9/4 | 0.0015 | 0.024 | 108 | 0.065 | 102 | ND |
| 10 | 0.00000039 | 0.0090 | 104 | ND | ND | ND |
| 10/1 | 0.0000014 | 0.066 | 104 | ND | ND | ND |
| 10/2 | 0.000040 | 0.057 | 106 | ND | ND | 0.076 |
| 10/3 | 0.0000036 | 0.050 | 97 | ND | ND | ND |
| 10/4 | 0.00000014 | 0.033 | 99 | ND | ND | ND |
| 11 | 0.0039 | 0.027 | 104* | ND | ND | ND |
| 11/1 | 0.031 | 0.12 | 103 | ND | ND | ND |
| 11/2 | 0.012 | 0.046 | 108 | ND | ND | ND |
| 12 | 0.0094 | 0.068 | 103 | ND | ND | ND |
| 12/1 | 0.030 | 0.12 | 102 | ND | ND | ND |
| 13 | 0.0013 | 0.012 | 105* | ND | ND | ND |
| 13/1 | 0.0049 | 0.021 | 101* | ND | ND | ND |
| 14 | 0.28 | >2 | −25* | ND | ND | ND |
| 15 | 0.00064 | 1.9 | 59 | ND | ND | 6.0 |
| 16 | 0.0066 | 0.014 | 100* | ND | ND | ND |
| 17 | 0.0071 | 0.014 | 104* | ND | ND | ND |
| 17/1 | 0.0078 | 0.027 | 91*** | ND | ND | ND |
| 17/2 | 0.0028 | 0.031 | 106** | ND | ND | ND |
| 18 | 0.0037 | 0.35 | 103 | ND | ND | 0.41 |
| 18/1 | 0.0056 | 0.17 | 104 | ND | ND | 0.47 |
| 19 | 0.000013 | 0.0080 | 99* | ND | ND | 0.0090 |
| 19/1 | 0.000023 | 0.010 | 98* | ND | ND | ND |
| 20 | 0.000026 | 0.012 | 101* | ND | ND | ND |
| 21 | 0.0047 | 0.067 | 107 | ND | ND | ND |
| 22 | 0.0050 | 0.11 | 99* | 0.083 | 87 | ND |
| 23 | 0.0031 | ND | ND | 0.040 | 109 | ND |
| 24 | 0.0052 | 0.19 | 97 | ND | ND | ND |
| 25 | 0.010 | 0.093 | 98 | ND | ND | ND |
| 26 | 0.0050 | 0.086 | 107 | ND | ND | ND |
| 27 | 0.00038 | 0.030 | 107 | ND | ND | 0.0090 |
| 28 | 0.0055 | ND | ND | ND | ND | ND |
| 29 | 0.017 | ND | ND | ND | ND | ND |
| 30 | 0.022 | ND | ND | ND | ND | ND |
| 31 | 0.018 | ND | ND | ND | ND | ND |
| 32 | 0.027 | ND | ND | ND | ND | ND |

All data shown in Table 1 is either the value of one data point or the average of more than one data point.
ND: value not determined.
*% inhibition is shown at 2 μM compound concentration,
**% inhibition is shown at 0.67 μM compound concentration,
***% inhibition at 0.22 μM compound concentration While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All documents cited herein are incorporated by reference.

We claim:
1. A compound of Formula I:

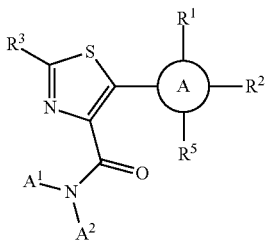

Formula I wherein:

is phenyl, pyridyl, pyrimidyl, pyrazinyl, or pyridazyl;
$R^1$ is Cl, —CN, H, F, $OC_{(1-4)}$alkyl, $OCHF_2$,

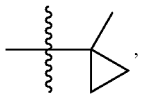

$OCF_3$, $C_{(1-4)}$alkyl, Br, I, or cyclopropyl; wherein said $C_{(1-4)}$alkyl is optionally substituted with up to six fluorine atoms;
$R^2$ is F, Cl, —CN, H, $OC_{(1-4)}$alkyl, $OCHF_2$, $OCF_3$, cyclopropyl, or $C_{(1-4)}$alkyl; wherein said $C_{(1-4)}$alkyl is optionally substituted with up to five fluorine atoms, and said cyclopropyl is optionally substituted with OH, $CH_3$, $CF_3$, and up to five fluorine atoms; or $R^1$ and $R^2$ may be taken together with their attached ring A to form a fused ring system selected from the group consisting of naphthalenyl, tetrahydronaphthalenyl, isoquinolinyl, quinolinyl, 2,3-dihydro-1H-indenyl, chromanyl, isochromanyl, and naphthyridinyl; wherein said naphthalenyl, tetrahydronaphthalenyl, isoquinolinyl, quinolinyl, 2,3-dihydro-1H-indenyl, chromanyl, isochromanyl, and naphthyridinyl may optionally be substituted with up to three substituents independently selected from the group consisting of F, $OC_{(1-3)}$alkyl or $C_{(1-3)}$alkyl wherein said $OC_{(1-3)}$alkyl and $C_{(1-3)}$ alkyl is optionally substituted with up to five fluorine atoms (including $CHF_2$, $CH_2F$, $CF_3$, and $CH_3$; provided that $R^2$ may not be H if $R^1$ is H;
$R^3$ is thiadiazolyl, oxadiazolyl, isoxadiazolyl, oxazolyl, isoxazolyl, triazolyl, tetrazolyl, 1,2,4-oxadiazol-5(4H)-on-3-yl, pyridyl, thiazolyl, pyrimidyl, pyridazyl, pyrazyl, imidazolyl, pyrrolyl, furanyl, or phenyl; wherein said thiadiazolyl, oxadiazolyl, isoxadiazolyl, oxazolyl, isoxazolyl, triazolyl, pyridyl, thiazolyl, pyrimidyl, pyridazyl, pyrazyl, imidazolyl, pyrrolyl, furanyl, or phenyl is optionally substituted with $R^4$, and further optionally substituted with one substituent selected from the group consisting of F, $CH_3$, $CF_3$, and cyclopropyl;
$R^4$ is H, $C_{(1-6)}$alkyl$SO_2C_{(1-6)}$alkyl, $C(O)NH_2$, $C_{(1-6)}$alkyl, CN, $C_{(3-6)}$cycloalkyl, $NH_2$, $NH(C_{(1-6)}$alkyl), $N(C_{(1-6)}$alkyl)$_2$, $NHCO(C_{(1-6)}$alkyl), $N(C_{(1-6)}$alkyl)$CO(C_{(1-6)}$alkyl), $NHSO_2(C_{(1-6)}$alkyl), $N(C_{(1-6)}$alkyl)$SO_2(C_{(1-6)}$alkyl), $O(C_{(1-6)}$alkyl), $C(O)NH_2$, $CONH(C_{(1-6)}$alkyl), $CON(C_{(1-6)}$alkyl)$_2$, $SO_2NH_2$, $SO_2NH(C_{(1-6)}$alkyl), $SO_2NH(COC_{(1-6)}$alkyl), or $SO_2N(C_{(1-6)}$ alkyl)$_2$; wherein said $C_{(1-6)}$alkyl or $C_{(3-6)}$cycloalkyl is optionally substituted independently with up to six fluorine atoms, $CF_3$, $CO_2H$, OH, —CN, $C(O)NH_2$, $NH_2$, $OCH_3$, $OCHF_2$, $OCF_3$, —$(CX_2)_m$—, or $N(CH_3)_2$;
m is 2, 3, 4, or 5;
X is H, or F; wherein each occurance of X in a single molecule is independently defined;
$A^1$ is H, or $C_{(1-4)}$alkyl; wherein said $C_{(1-4)}$alkyl is optionally substituted with up to six fluorine atoms, Cl, —CN, $OCH_3$, $OCHF_2$, or $OCF_3$;
$A^2$ is $C_{(1-6)}$alkyl, $C_{(0-2)}$alkyl-$C_{(3-6)}$cycloalkyl,

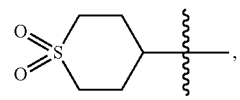

$CH_2$—$C_6H_4$—$C(O)NH_2$, —$C_6H_4$—F, $CH_2$—CCH, or $CH_2$—CC—$CH_3$; wherein said $C_{(1-6)}$alkyl, and said $C_{(0-2)}$ alkyl-$C_{(3-6)}$cycloalkyl are optionally substituted with up to six fluorine atoms, Cl, —CN, $OCH_3$, $OCHF_2$, or $OCF_3$;
or $A^1$ and $A^2$ may be taken together with their attached nitrogen to form a ring selected from the group consisting of:
thiomorpholinyl, piperidinyl, pyrrolidinyl, piperazinyl, morpholinyl, azetidinyl, and aziridinyl;
wherein said piperidinyl, pyrrolidinyl, piperazinyl, morpholinyl, azetidinyl, and aziridinyl are optionally substituted with $CF_3$, $CH_2CH_2F$, $C_{(1-2)}$cycloalkyl, —CN, OH, $CH_2OH$, $CH_2F$, F, Cl, $OCH_3$, $OCHF_2$, $OCF_3$, —$(CX_2)_nO(CX_2)_n$—, or —$(CX_2)_n$—, and up to three additional substituents selected from the group consisting of $CH_3$ and F;
n is independently 0, 1, 2, 3, or 4;
X is H, or F; wherein each occurrence of X in a single molecule is independently defined;
$R^5$ is $SO_2NA^3A^4$, $CONA^3A^4$, $NA^3A^4$, $OCH_2C(CF_3)_2OH$, $C_{(3-6)}$cycloalkyl, or $C_{(1-6)}$alkyl; wherein said $C_{(3-6)}$ cycloalkyl and said $C_{(1-6)}$alkyl are optionally substituted with OH, Cl, —CN, H, $OCH_3$, $OCHF_2$, $OCF_3$, or $NA^3A^4$, further optionally substituted with —$CH_2CH_2$— attached to the same carbon atom, and up to seven fluorine atoms;
$A^3$ is H, or $C_{(1-4)}$alkyl; wherein said $C_{(1-4)}$alkyl is optionally substituted with OH, Cl, —CN, $OCH_3$, $OCHF_2$, or $OCF_3$; and up to six fluorine atoms;
$A^4$ is H, $C_{(1-6)}$alkyl, $C_{(3-6)}$cycloalkyl, or $C_{(3-6)}$heterocycloalkyl; wherein said $C_{(1-6)}$alkyl is optionally substituted with cyclopropyl, morpholinyl, OH, $OCH_3$, $C(O)NH_2$, Cl, —CN, $OCHF_2$, $OCF_3$ and additionally substituted with up to three fluorine atoms; and wherein said $C_{(3-6)}$cycloalkyl, and $C_{(3-6)}$heterocycloalkyl are optionally substituted with $CF_3$, $CH_3$, —CN, $C(O)NH_2$, and up to three fluorine atoms;
or $A^3$ and $A^4$ can be taken together with their attached nitrogen to form a ring selected from the group consisting of piperidinyl, morpholinyl, piperazinyl, pyrrolidinyl, aziridinyl, and azetidinyl wherein said piperidinyl, morpholinyl, piperazinyl, pyrrolidinyl, aziridinyl, and azetidinyl are optionally substituted with up to four groups selected from the group consisting of $CF_3$, OH, $CH_3$, $CH_2F$, and $CHF_2$; and further optionally substituted with up to four groups selected from the group consisting of CF$_3$, OH, CH$_3$, CH$_2$F, and CHF$_2$; and further optionally substituted with up to six fluorine atoms;

and pharmaceutically acceptable salts thereof.

2. The compound of claim 1, wherein:

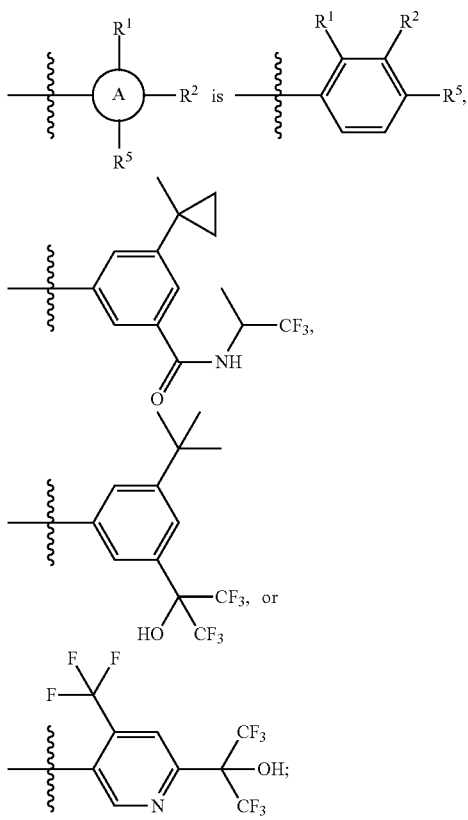

R$^1$ is Cl, —CN, H, F, OCH$_3$,

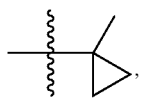 [SMILES: *C1(C)CC1]

OCHF$_2$, OCF$_3$, C$_{(1-2)}$alkyl, Br, or I; wherein said C$_{(1-2)}$alkyl is optionally substituted with up to five fluorine atoms;

R$^2$ is F, Cl, —CN, H, OCH$_3$, OCHF$_2$, OCF$_3$, cyclopropyl or C$_{(1-2)}$alkyl; wherein said C$_{(1-2)}$alkyl is optionally substituted with up to five fluorine atoms, and said cyclopropyl is optionally substituted with OH, CH$_3$, CF$_3$, and up to five fluorine atoms; or R$^1$ and R$^2$ may be taken together with their attached phenyl to form a fused ring system selected from the group consisting of naphthalenyl, tetrahydronaphthalenyl, isoqinolinyl, quinolinyl, and chromanyl; provided that R$^2$ may not be H if R$^1$ is H;

R$^3$ is oxadiazolyl, isoxadiazolyl, oxazolyl, isoxazolyl, triazolyl, tetrazolyl, 1,2,4-oxadiazol-5(4H)-on-3-yl, pyridyl, thiazolyl, pyrimidyl, pyridazyl, pyrazyl, imidazolyl, or pyrrolyl; wherein said oxadiazolyl, isoxadiazolyl, oxazolyl, isoxazolyl, triazolyl, pyridyl, thiazolyl, pyrimidyl, pyridazyl, pyrazyl, imidazolyl, or pyrrolyl is optionally substituted with R$^4$, and said triazolyl may be additionally substituted with one substituent selected from the group consisting of CH$_3$ and cyclopropyl;

R$^4$ is H, CH$_2$SO$_2$CH$_3$, C(O)NH$_2$, C$_{(1-4)}$alkyl,

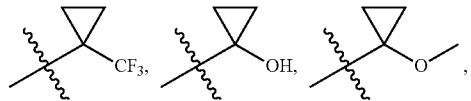

or —CN; wherein said C$_{(1-4)}$alkyl is optionally substituted with up to six fluorine atoms, CO$_2$H, OH, or —CN;

A$^1$ is H, or C$_{(1-3)}$alkyl; wherein said C$_{(1-3)}$alkyl is optionally substituted with up to five fluorine atoms, Cl, —CN, OCH$_3$, OCHF$_2$, or OCF$_3$;

A$^2$ is C$_{(1-4)}$alkyl, C$_{(0-2)}$alkyl-C$_{(3-6)}$cycloalkyl, CH$_2$—C$_6$H$_4$—C(O)NH$_2$, —C$_6$H$_4$—F, CH$_2$—CCH, or CH$_2$—CC—CH$_3$; wherein said C$_{(1-4)}$alkyl, and said C$_{(0-2)}$alkyl-C$_{(3-6)}$cycloalkyl are optionally substituted with up to three fluorine atoms, Cl, —CN, OCH$_3$, OCHF$_2$, or OCF$_3$;

or A$^1$ and A$^2$ may be taken together with their attached nitrogen to form a ring selected from the group consisting of:

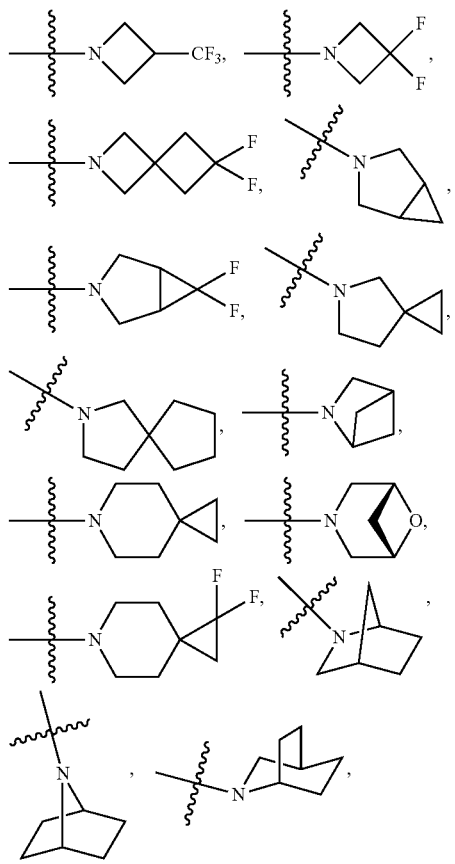

thiomorpholinyl, piperidinyl, pyrrolidinyl, piperazinyl, and morpholinyl; wherein said piperidinyl, pyrrolidinyl, piperazinyl, and morpholinyl are optionally substituted with CF$_3$, CH$_2$CH$_2$F, C$_{(1-2)}$alkyl, —CN, OH,

215

CH$_2$OH, CH$_2$F, F, Cl, OCH$_3$, OCHF$_2$, or OCF$_3$, and up to three additional substituents selected from the group consisting of CH$_3$ and F;

R$^5$ is SO$_2$NA$_3$A$_4$,

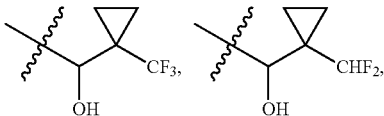

OCH$_2$C(CF$_3$)$_2$OH, or C$_{(1-6)}$alkyl; wherein said C$_{(1-6)}$alkyl is optionally substituted with OH, Cl, —CN, H, OCH$_3$, OCHF$_2$, or OCF$_3$; and up to six fluorine atoms;

A$^4$ is C$_{(1-6)}$alkyl, C$_{(3-6)}$cycloalkyl, oxetanyl, or tetrahydrofuranyl; wherein said C$_{(1-6)}$alkyl is optionally substituted with cyclopropyl, morpholinyl, OH, OCH$_3$, or C(O)NH$_2$, and additionally substituted with up to three fluorine atoms; and wherein said C$_{(3-6)}$cycloalkyl, oxetanyl, and tetrahydrofuranyl are optionally substituted with CF$_3$, CH$_3$, —CN, or C(O)NH$_2$;

or A$^3$ and A$^4$ can be taken together with their attached nitrogen to form a ring selected from the group consisting of piperidinyl, morpholinyl, piperazinyl, and pyrrolidinyl, wherein said piperidinyl, morpholinyl, and piperazinyl are optionally substituted with up to four methyl groups and up to six fluorine atoms;

and pharmaceutically acceptable salts thereof.

3. The compound of claim 2, wherein:

R$^1$ is Cl, —CN, H, F, OCH$_3$,

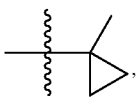

OCHF$_2$, OCF$_3$, or C$_{(1-2)}$alkyl; wherein said C$_{(1-2)}$alkyl is optionally substituted with up to five fluorine atoms;

R$^2$ is F, Cl, —CN, CHF$_2$, CF$_3$, CH$_3$, or H; or R$^1$ and R$^2$ may be taken together with their attached phenyl to form a fused ring system selected from the group consisting of naphthalenyl, tetrahydronaphthalenyl, isoqinolinyl, quinolinyl, and chromanyl; provided that R$^2$ may not be H if R$^1$ is H;

R$^3$ is oxadiazolyl, isoxadiazolyl, oxazolyl, isoxazolyl, triazolyl, tetrazolyl, 1,2,4-oxadiazol-5(4H)-on-3-yl, pyridyl, thiazolyl, pyrimidyl, pyridazyl, or pyrazyl; wherein said oxadiazolyl, isoxadiazolyl, oxazolyl, isoxazolyl, triazolyl, pyridyl, thiazolyl, pyrimidyl, pyridazyl, or pyrazyl is optionally substituted with R$^4$, and said triazolyl may be additionally substituted with one substituent selected from the group consisting of CH$_3$ and cyclopropyl;

R$^4$ is H, CH$_2$SO$_2$CH$_3$, C(O)NH$_2$, CH$_2$C(CH$_3$)$_2$CO$_2$H, CH$_2$C(CH$_3$)$_2$CN, C$_{(0-1)}$alkylC(CH$_3$)$_2$OH,

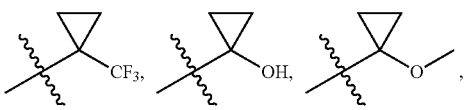

—CN, or C$_{(1-2)}$alkyl; wherein said C$_{(1-2)}$alkyl is optionally substituted with up to five fluorine atoms;

216

A$^1$ is H, or C$_{(1-3)}$alkyl; wherein said C$_{(1-3)}$alkyl is optionally substituted with up to five fluorine atoms;

A$^2$ is C$_{(1-4)}$alkyl, C$_{(0-2)}$alkyl-C$_{(3-6)}$cycloalkyl, CH$_2$—C$_6$H$_4$—C(O)NH$_2$, —C$_6$H$_4$—F, CH$_2$—CCH, CH$_2$—CC—CH$_3$, or CH$_2$CH$_2$—CN; wherein said C$_{(1-4)}$alkyl, and said C$_{(0-2)}$alkyl-C$_{(3-6)}$cycloalkyl are optionally substituted with up to three fluorine atoms;

or A$^1$ and A$^2$ may be taken together with their attached nitrogen to form a ring selected from the group consisting of:

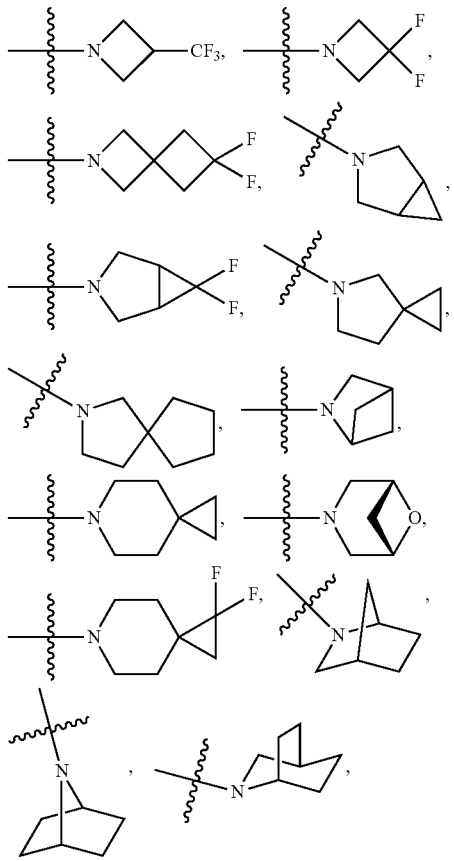

thiomorpholinyl, piperidinyl, pyrrolidinyl, piperazinyl, and morpholinyl; wherein said piperidinyl, pyrrolidinyl, piperazinyl, and morpholinyl are optionally substituted with CF$_3$, CH$_2$CH$_2$F, C$_{(1-2)}$alkyl, —CN, OH, CH$_2$OH, CH$_2$F, or F, and up to three additional substituents selected from the group consisting of CH$_3$ and F;

R$^5$ is SO$_2$NA$_3$A$_4$,

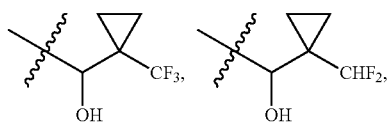 [SMILES: *C(O)C1(C(F)(F)F)CC1 ; *C(O)C1(C(F)F)CC1]

OCH$_2$C(CF$_3$)$_2$OH, or C$_{(1-6)}$alkyl; wherein said C$_{(1-6)}$alkyl is optionally substituted with one OH group and up to six fluorine atoms;

A$^3$ is H, or C$_{(1-4)}$alkyl;

A$^4$ is C$_{(1-6)}$alkyl, cyclopropyl, cyclobutyl, oxetanyl, or tetrahydrofuranyl; wherein said C$_{(1-6)}$ alkyl is optionally substituted with cyclopropyl, morpholinyl, OH, OCH₃, or C(O)NH₂, and additionally substituted with up to three fluorine atoms; and wherein said cyclopropyl cyclobutyl, oxetanyl, and tetrahydrofuranyl are optionally substituted with CF₃, CH₃, —CN, or C(O)NH₂;

or $A^3$ and $A^4$ can be taken together with their attached nitrogen to form a ring selected from the group consisting of piperidinyl, morpholinyl, piperazinyl, and pyrrolidinyl, wherein said piperidinyl, morpholinyl, and piperazinyl are optionally substituted with one or two methyl groups and up to three fluorine atoms;

and pharmaceutically acceptable salts thereof.

4. The compound of claim 3, wherein:
$R^1$ is Cl, CHF₂, CF₃, CH₃, CH₂CH₃, —CN, H, F, OCH₃, OCHF₂, or OCF₃;
$R^2$ is F, Cl, CHF₂, CF₃, CH₃, or H; or $R^1$ and $R^2$ may be taken together with their attached phenyl to form a fused ring system selected from the group consisting of naphthalenyl, tetrahydronaphthalenyl, isoqinolinyl, and chromanyl; provided that $R^2$ may not be H if $R^1$ is H;
$R^3$ is oxadiazolyl, isoxadiazolyl, oxazolyl, isoxazolyl, triazolyl, tetrazolyl, 1,2,4-oxadiazol-5(4H)-on-3-yl, pyridyl, or thiazolyl, wherein said oxadiazolyl, isoxadiazolyl, oxazolyl, isoxazolyl, triazolyl, pyridyl, or thiazolyl is optionally substituted with $R^4$, and said triazolyl may be additionally substituted with one substituent selected from the group consisting of CH₃ and cyclopropyl;
$R^4$ is H, CH₂SO₂CH₃, C(O)NH₂, CH₃, CH₂C(CH₃)₂CO₂H, CH₂C(CH₃)₂CN, $C_{(0-1)}$alkylC(CH₃)₂OH,

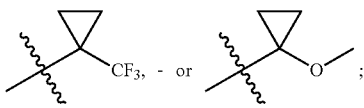

$A^1$ is H, $C_{(1-3)}$alkyl, or CH₂CH₂F;
$A^2$ is $C_{(2-4)}$alkyl, CH₂-cyclopentyl, CH₂CH₂-cyclopropyl, $C_{(3-4)}$cycloalkyl,

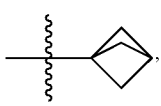 [SMILES: *C12CC(C1)C2]

CH₂—C₆H₄—C(O)NH₂, —C₆H₄—F, CH₂—CCH, CH₂CH₂—CN, CH₂—CC—CH₃; wherein said $C_{(3-4)}$cycloalkyl is optionally substituted with one fluorine atom and said $C_{(2-4)}$alkyl is optionally substituted with up to three fluorine atoms;

or $A^1$ and $A^2$ may be taken together with their attached nitrogen to form a ring selected from the group consisting of:

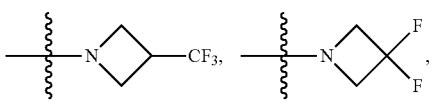

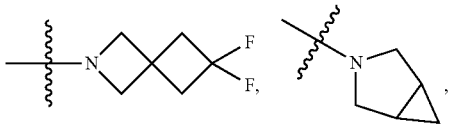

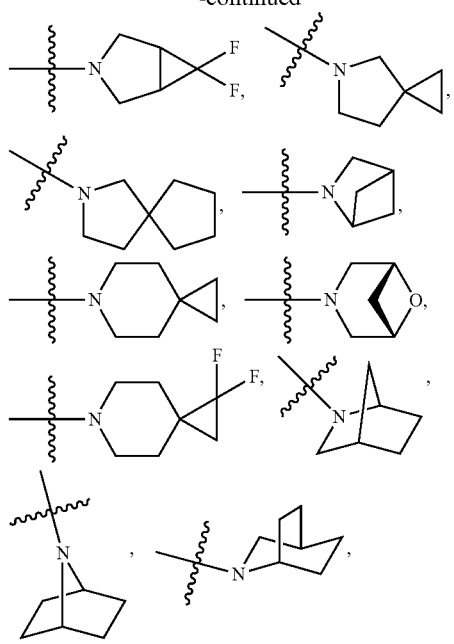

thiomorpholinyl, piperidinyl, pyrrolidinyl, and morpholinyl; wherein said piperidinyl, pyrrolidinyl, and morpholinyl are optionally substituted with CF₃, CH₂CH₂F, $C_{(1-2)}$alkyl, —CN, OH, CH₂OH, or CH₂F and up to three additional substituents selected from the group consisting of CH₃ and F;
$R^5$ is SO₂NA₃A₄,

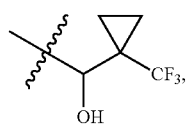

CH₂C(CF₃)₂OH, OCH₂C(CF₃)₂OH, or C(CF₃)₂OH;
$A^3$ is H, CH₃, or $C_{(1-4)}$alkyl;
$A^4$ is $C_{(1-6)}$alkyl,

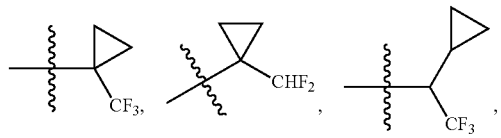

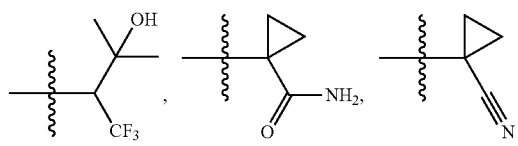

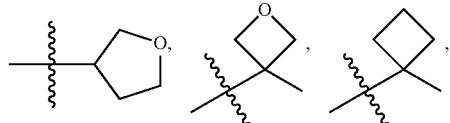

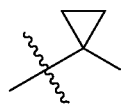

C(CH₃)₂CH₂OCH₃, C(CH₃)₂CH₂OH, C(CH₃)₂CH₂-morpholinyl, C(CH₃)₂CH₂CH₂OH, C(CH₃)₂CH₂C(O)NH₂, or CH₂C(CH₃)₂OH; wherein said $C_{(1-6)}$alkyl is optionally substituted with up to three fluorine atoms;

or A³ and A⁴ can be taken together with their attached nitrogen to form a ring selected from the group consisting of

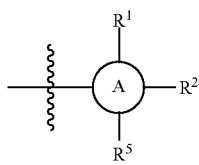

and pharmaceutically acceptable salts thereof.

5. The compound of claim 4, wherein:

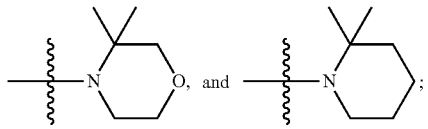

is

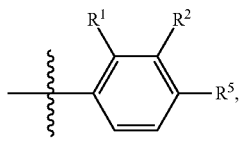

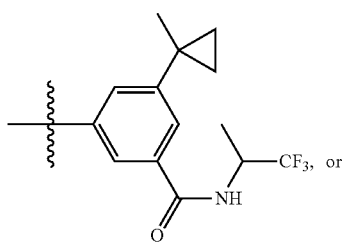

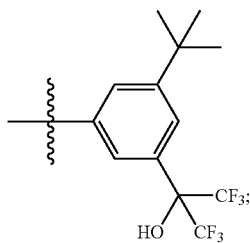

R¹ is H, Cl, CHF₂, CF₃, CH₃, F, OCHF₂, or OCF₃;

R² is F, Cl, CHF₂, CF₃, CH₃, or H; or R¹ and R² may be taken together with their attached phenyl to form a fused ring system selected from the group consisting of naphthalenyl, and chromanyl;

provided that R² may not be H if R¹ is H;

R³ is

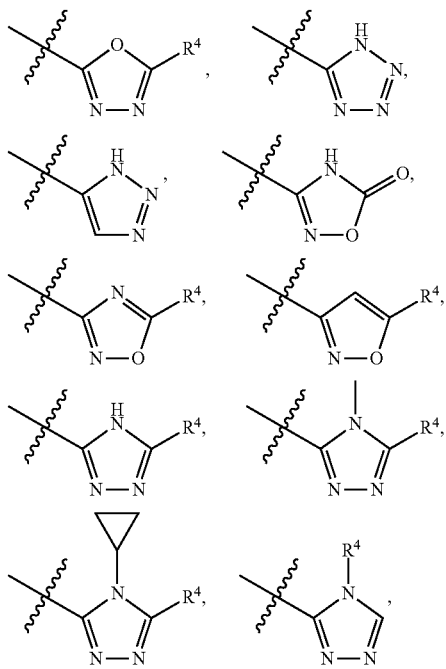

pyridyl, or pyrimidyl, wherein said pyridyl or pyrimidyl is optionally substituted with R⁴;

A¹ is CH₃, CH₂CH₃;

A² is CH₂CH₂CH₃, CH(CH₃)₂, CH₂CH₃, or CH₂CF₃;

or A¹ and A² may be taken together with their attached nitrogen to form a ring selected from the group consisting of:

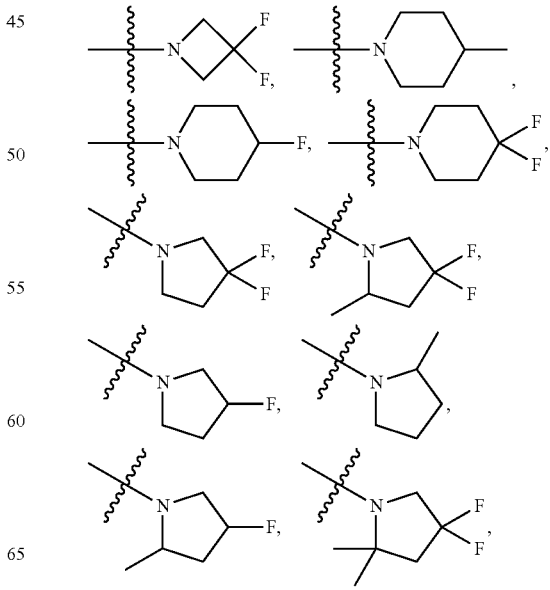

-continued
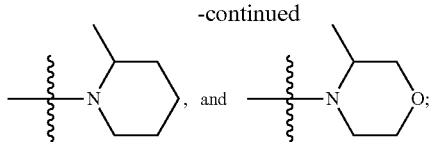
$A^3$ is H, or $CH_3$;
$A^4$ is
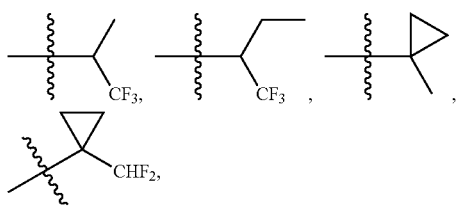
$CH_2CF_3$, or $C(CH_3)_2CF_3$;
and pharmaceutically acceptable salts thereof.
6. The compound of claim 5 selected from the group consisting of:
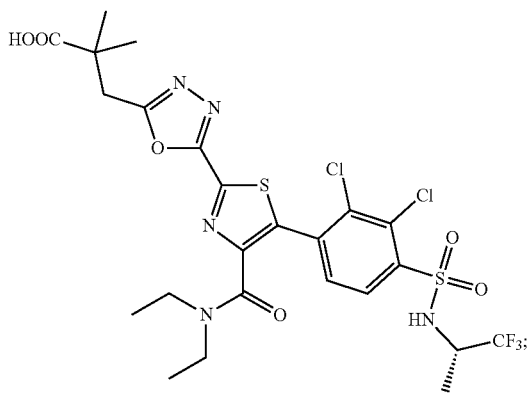
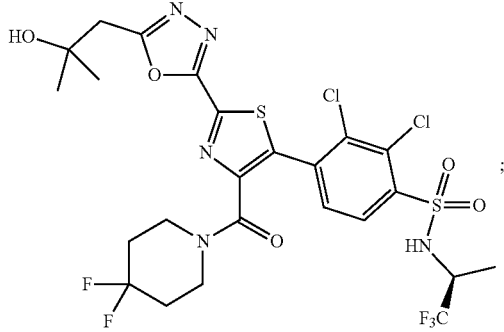
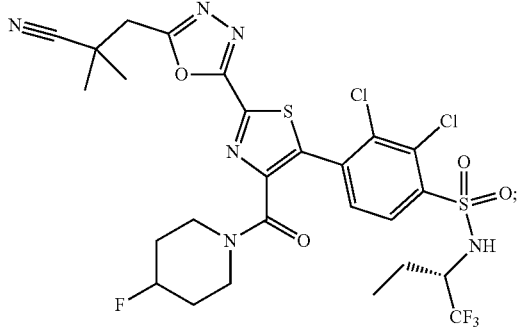
-continued
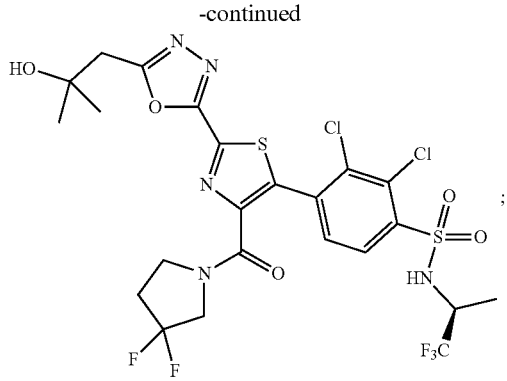
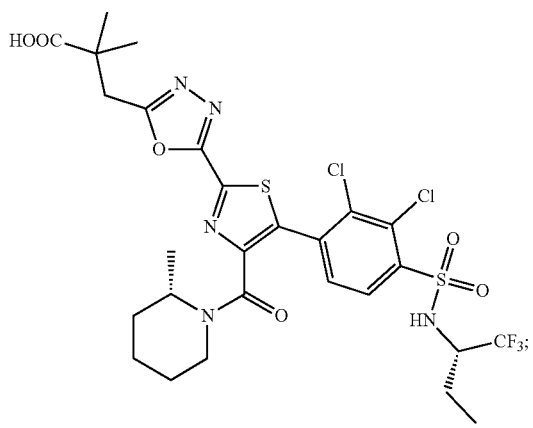
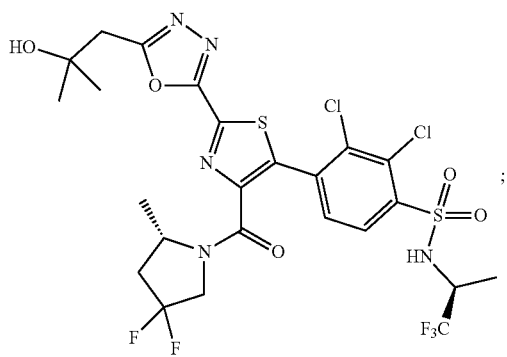
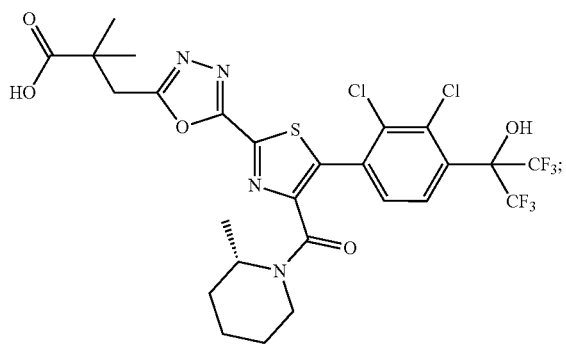

223
-continued
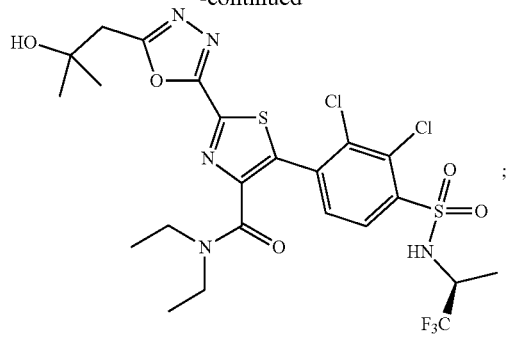
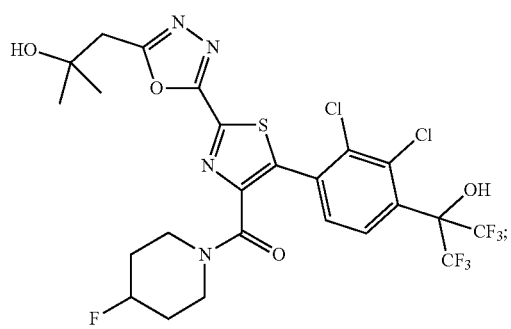
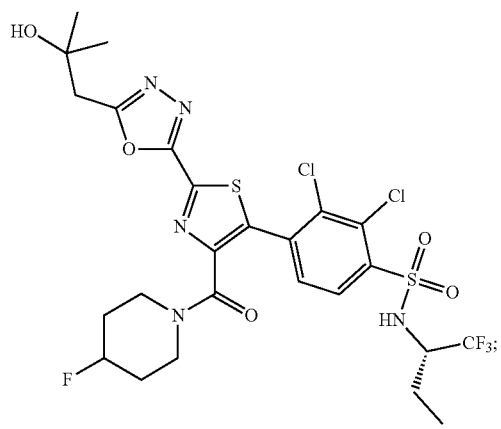
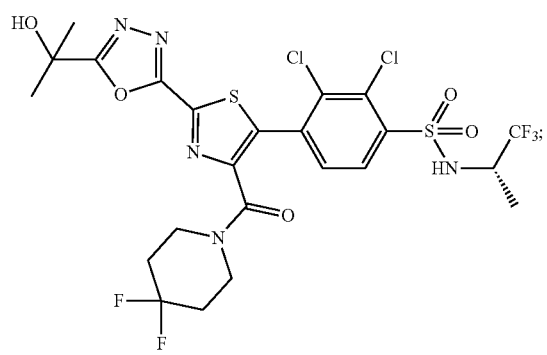
224
-continued
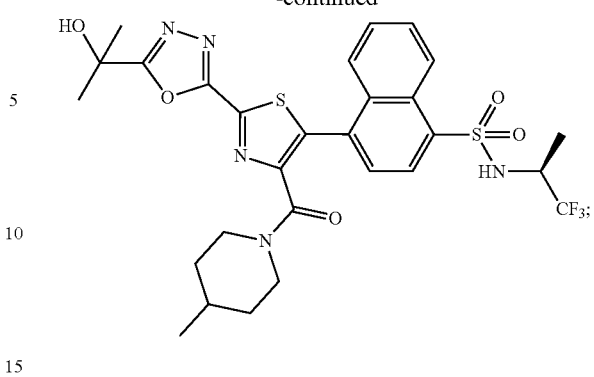
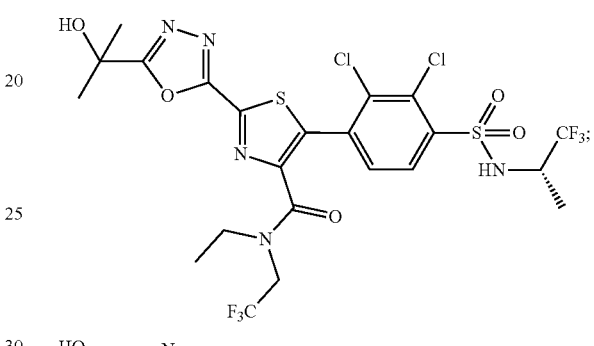
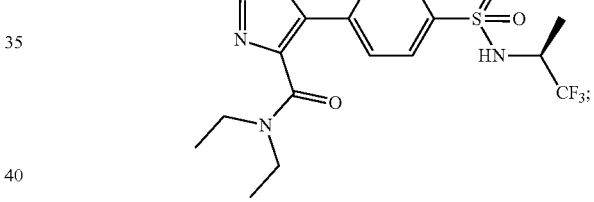
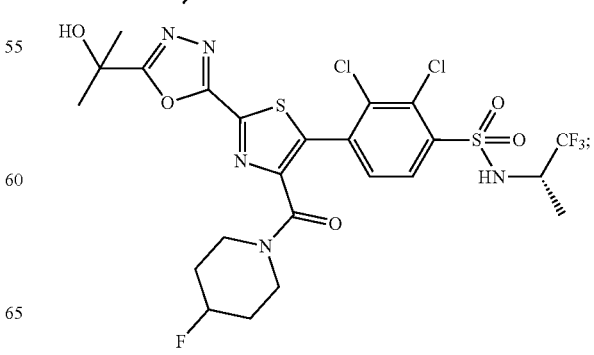

225
-continued
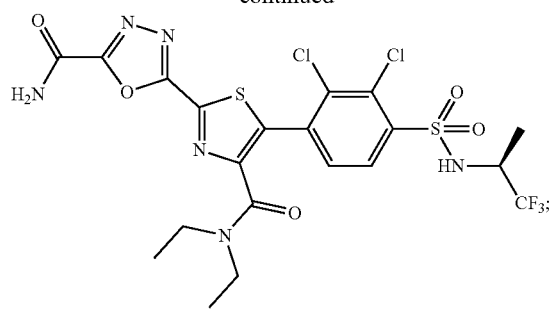
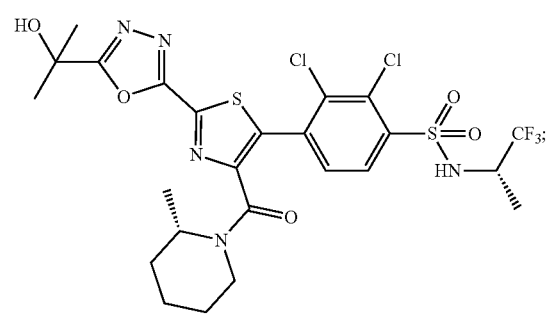
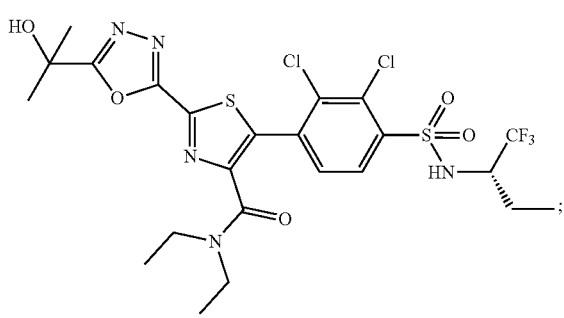
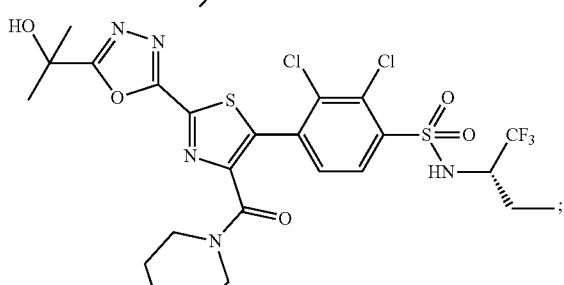
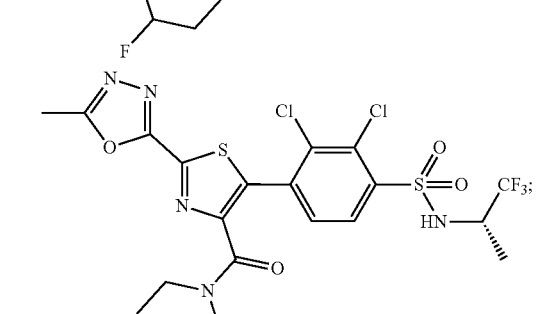
226
-continued
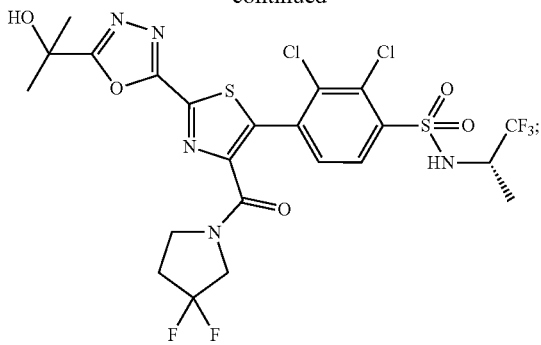
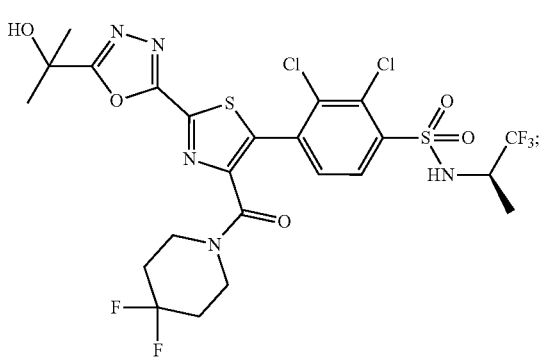
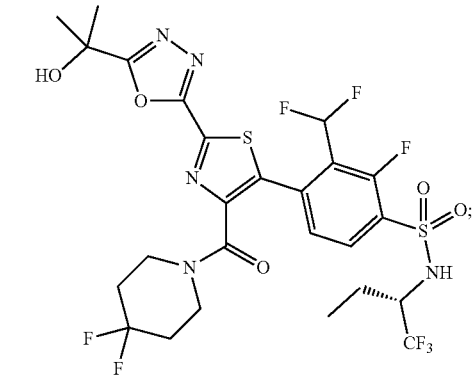
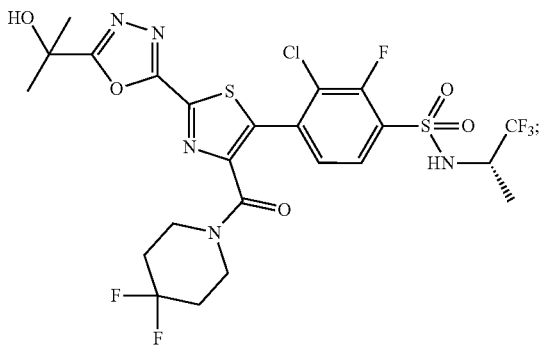

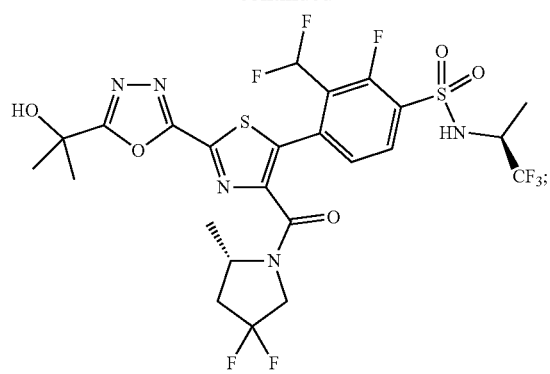
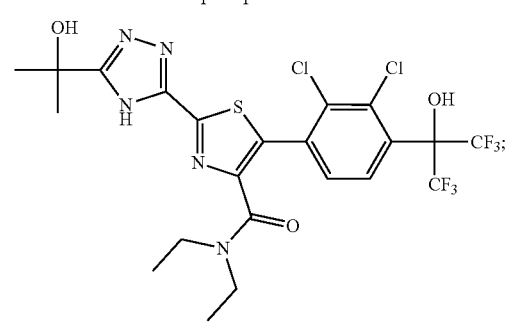
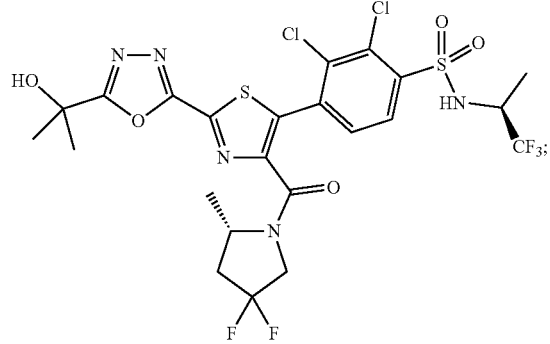
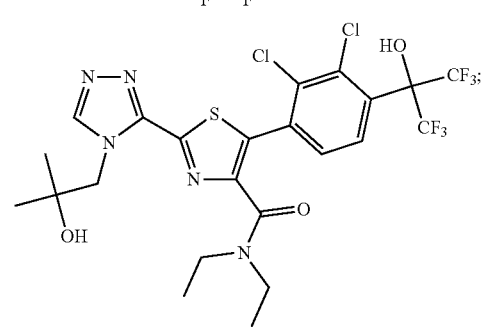
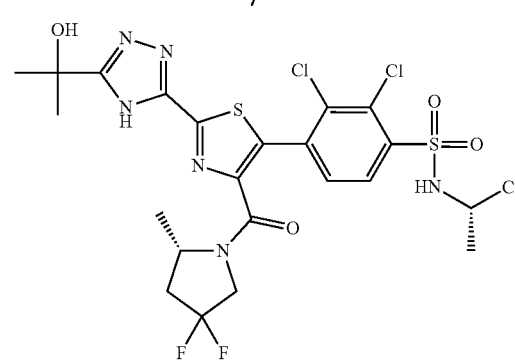
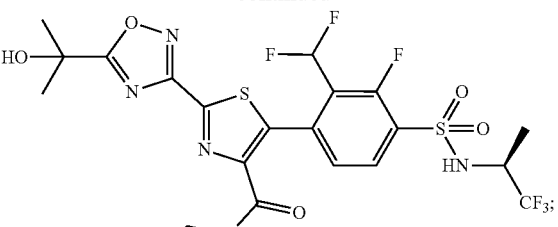
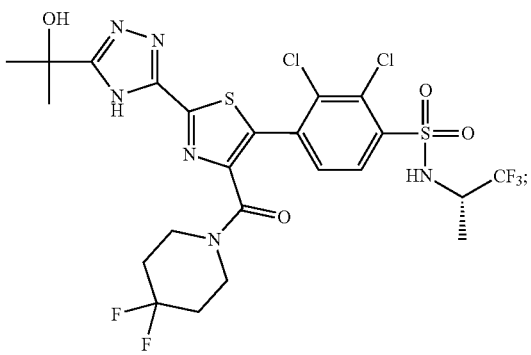
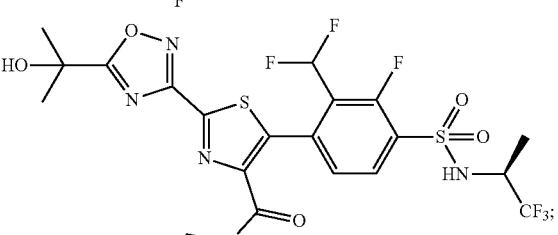
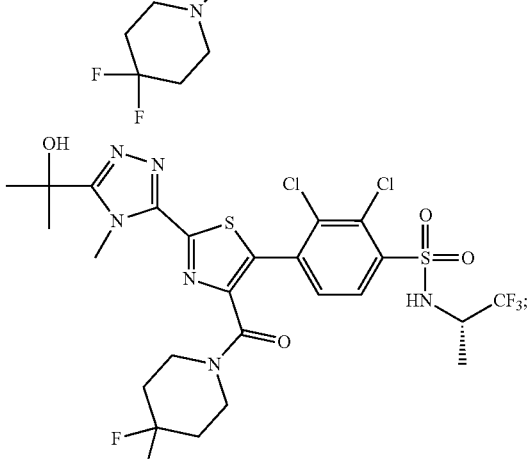
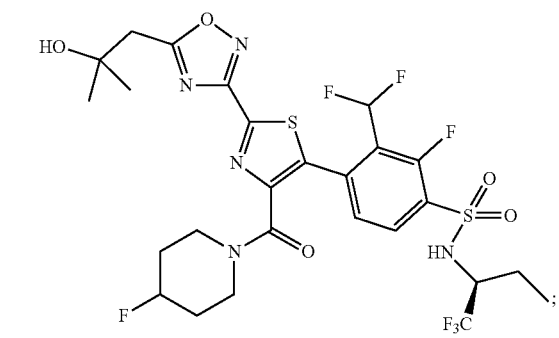

229
-continued
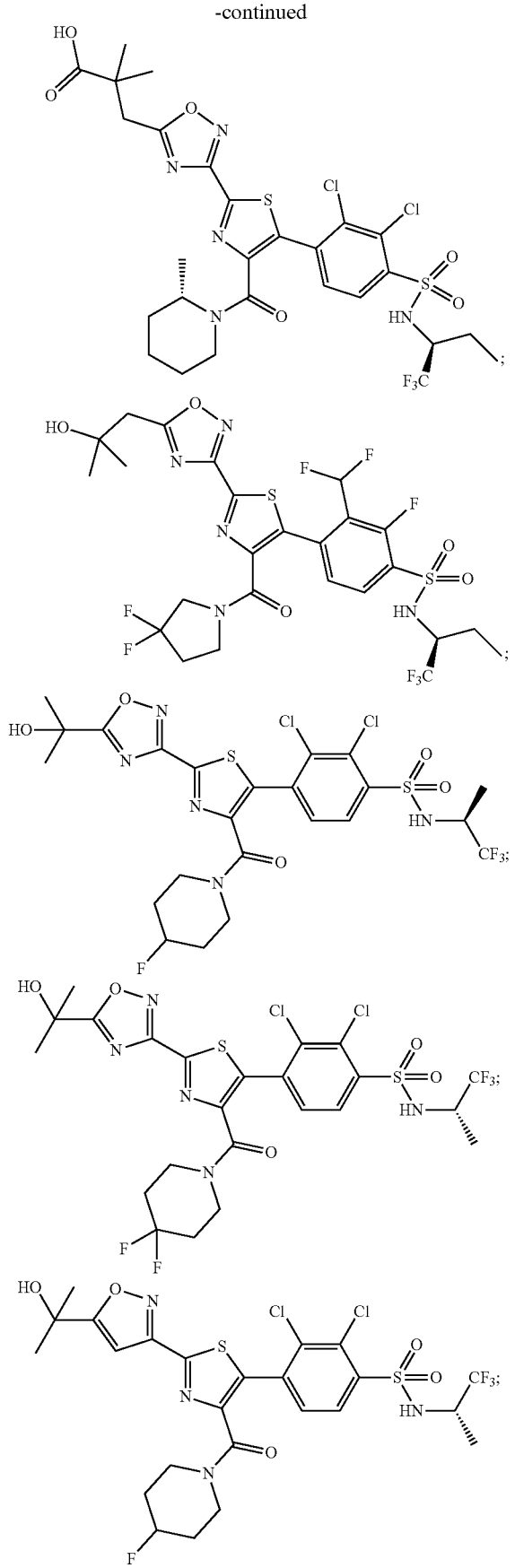
230
-continued
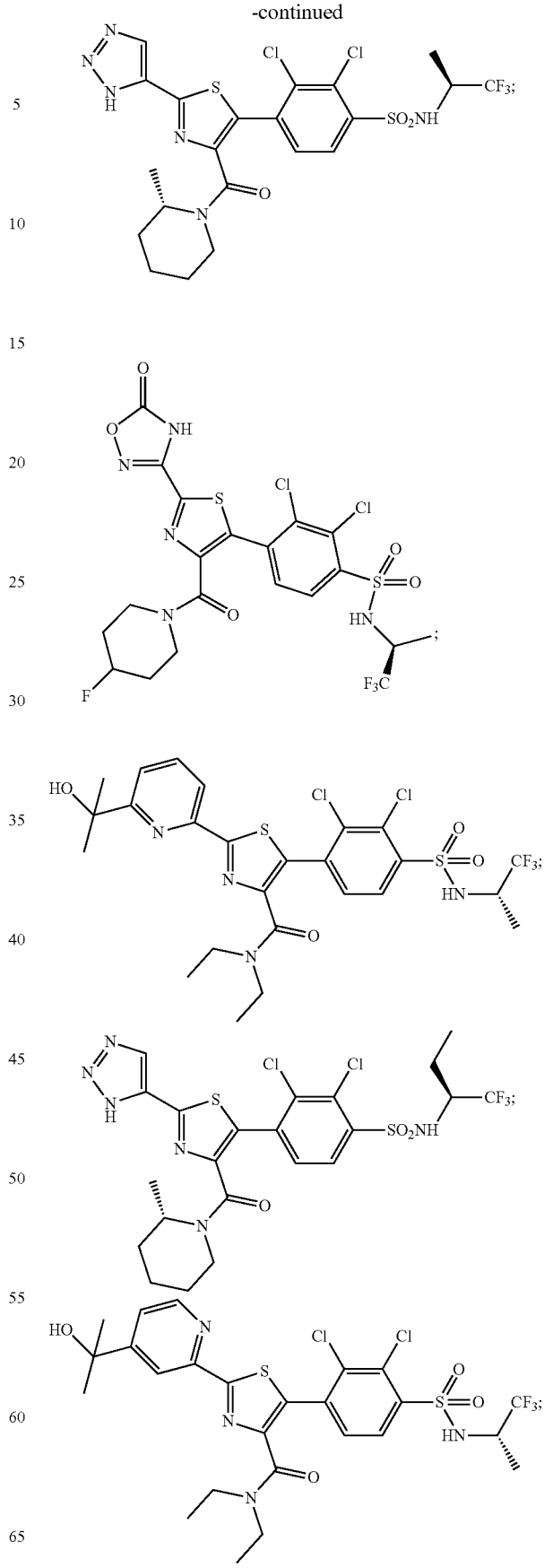

231
-continued
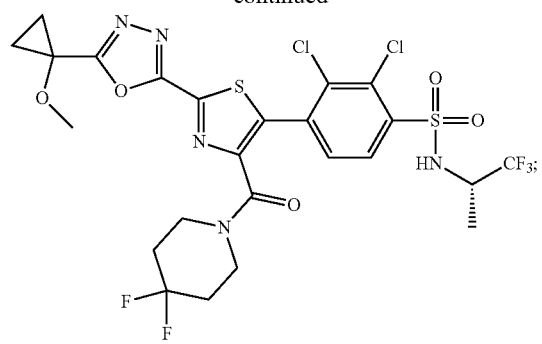
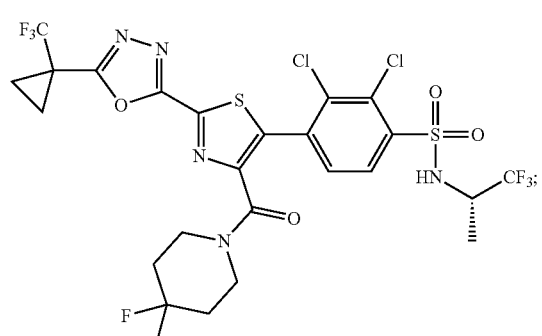
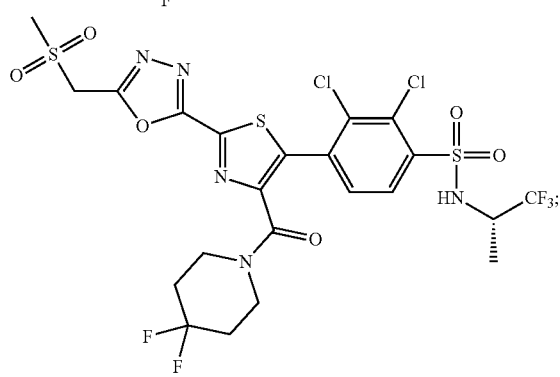
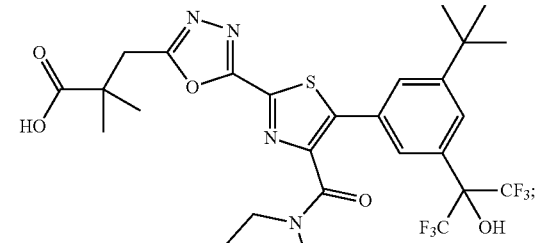
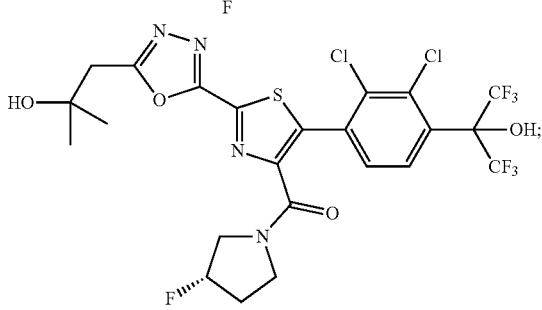
232
-continued
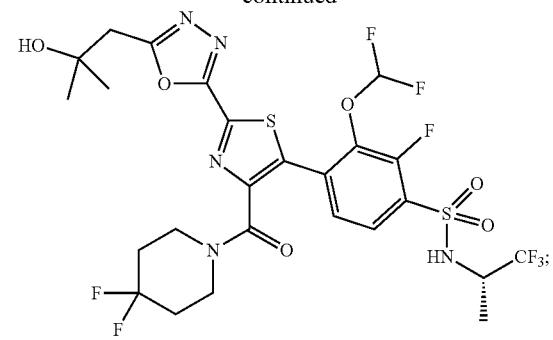
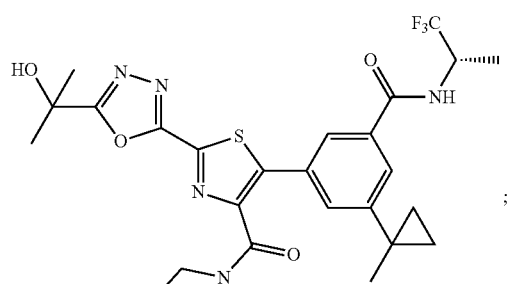
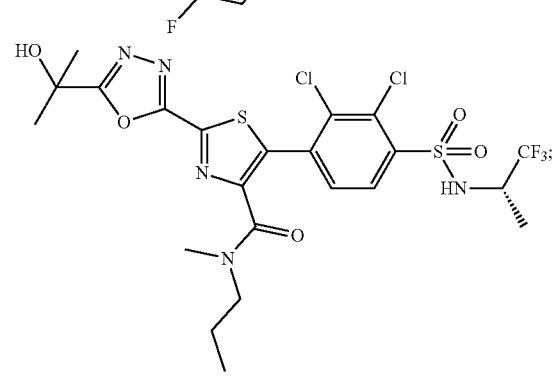
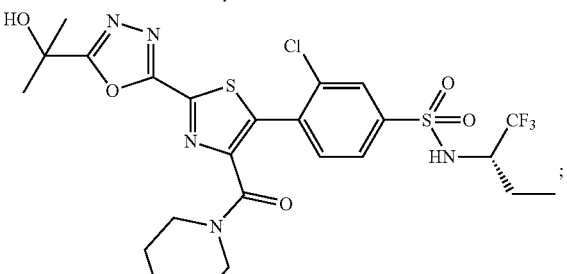
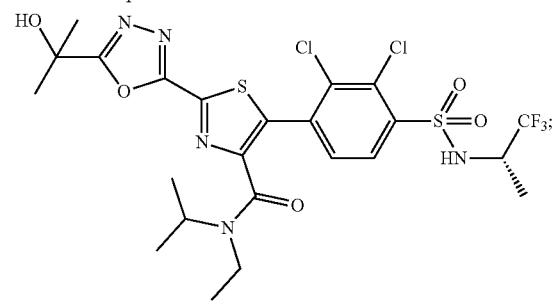

233
-continued
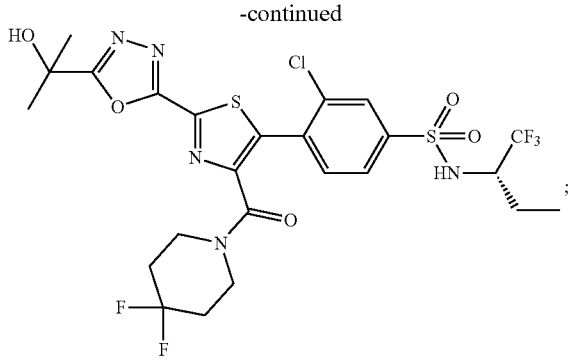
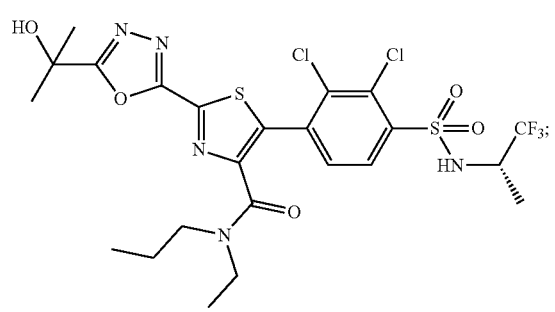
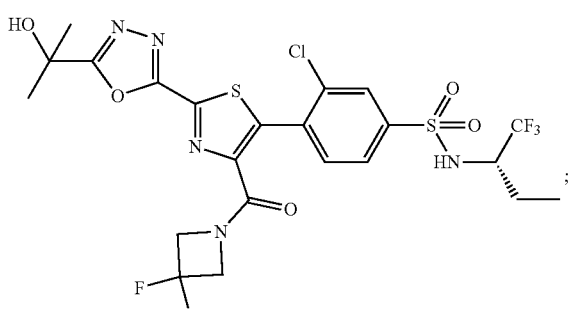
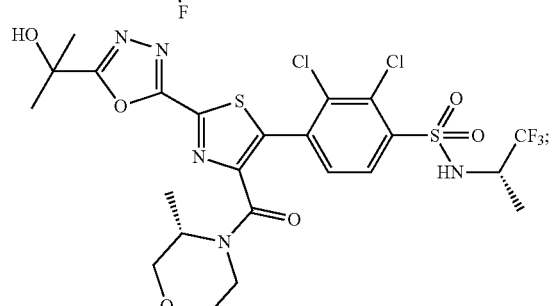
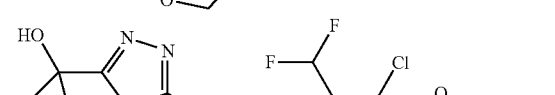
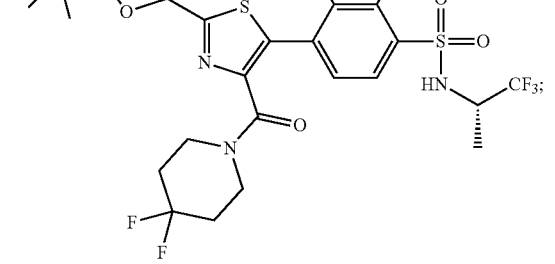
234
-continued
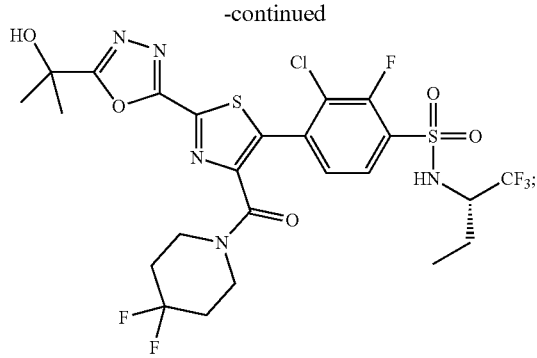
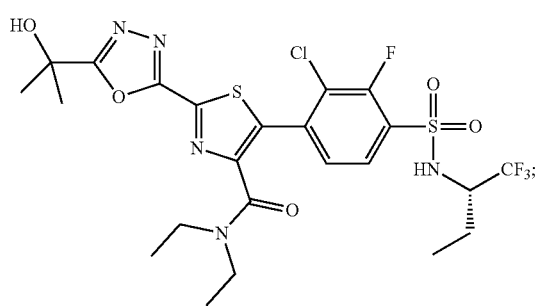
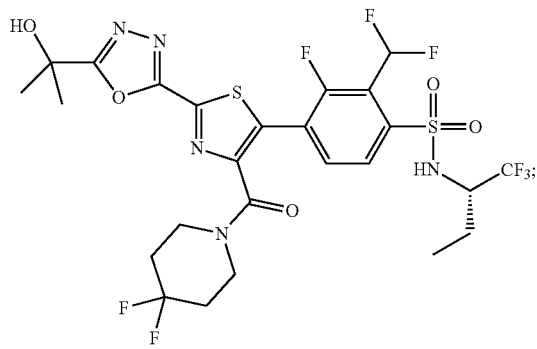
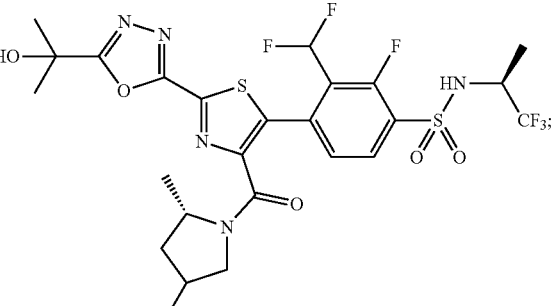
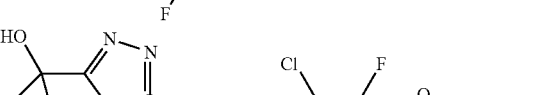
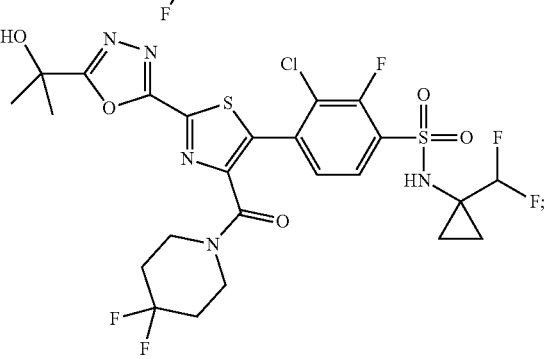

235
-continued
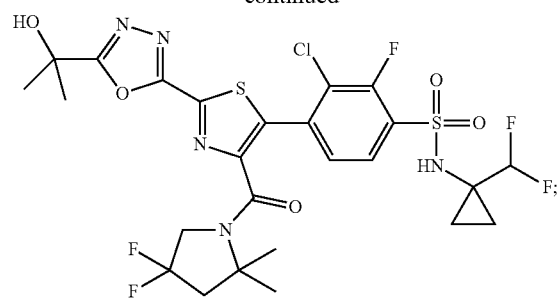
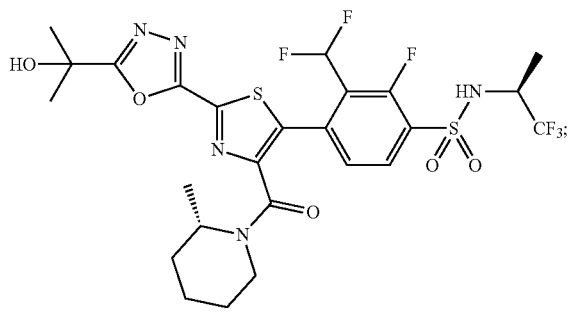
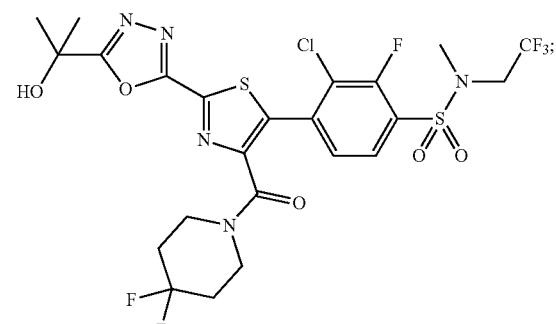
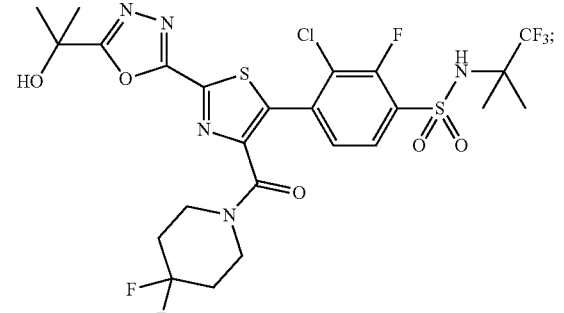
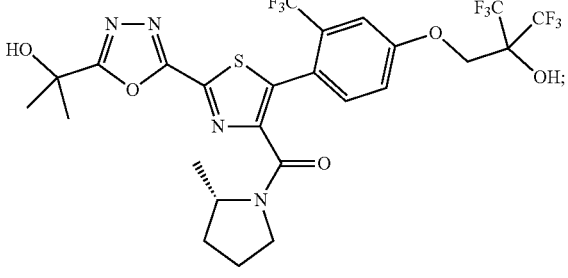
236
-continued
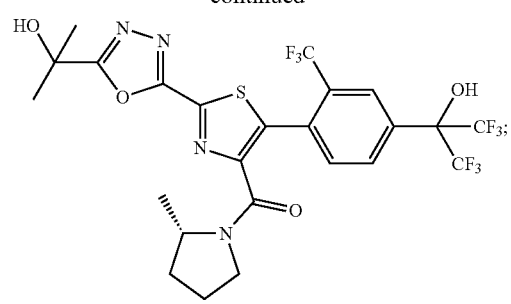
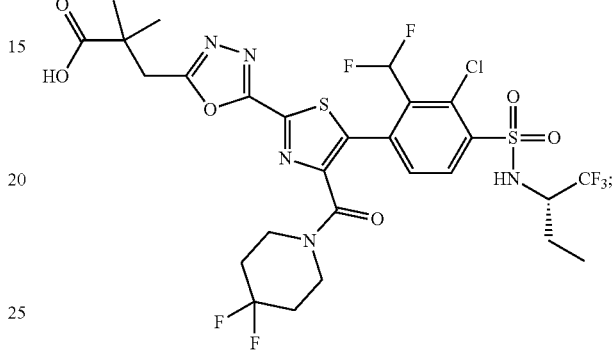
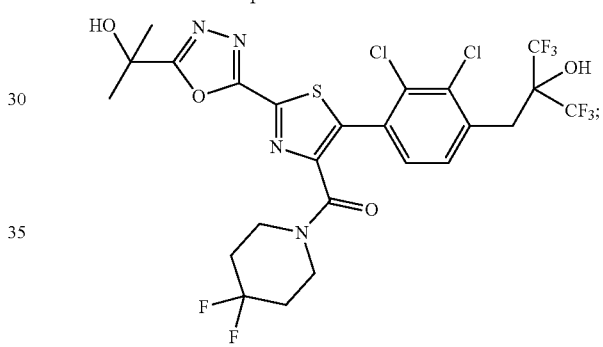
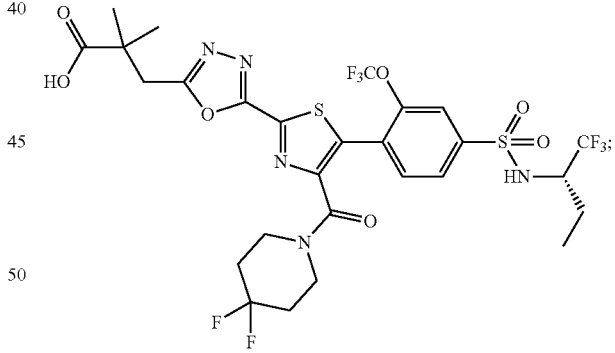
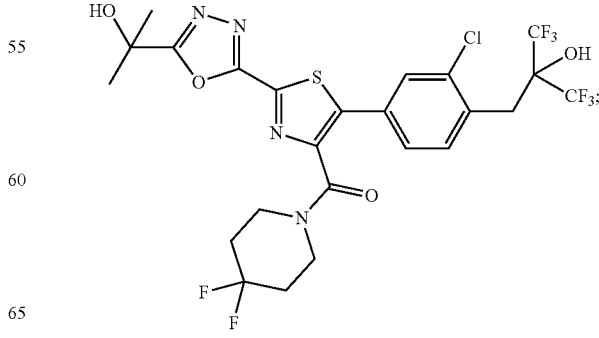

237
-continued
238
-continued
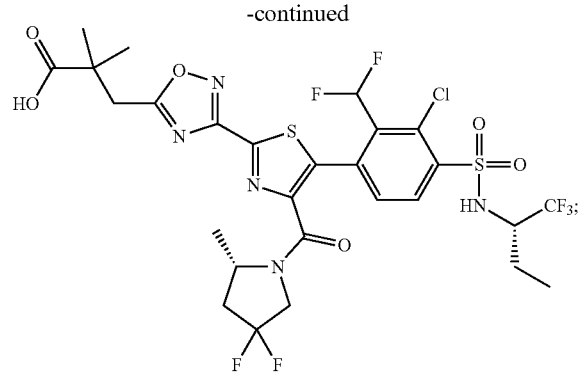
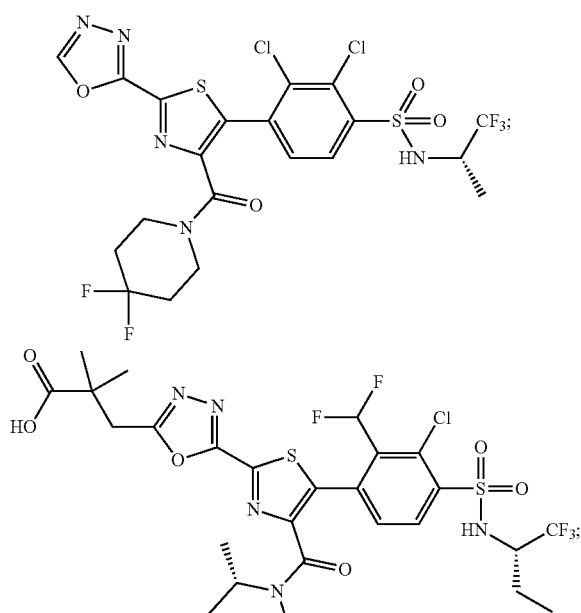
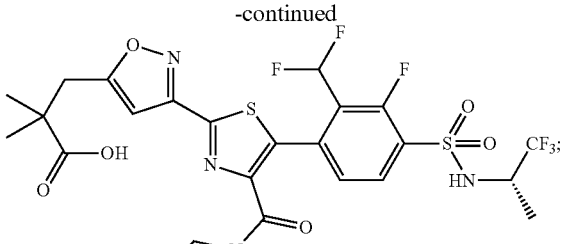
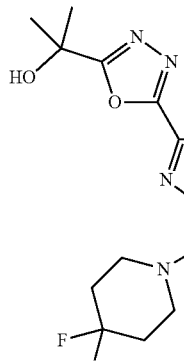
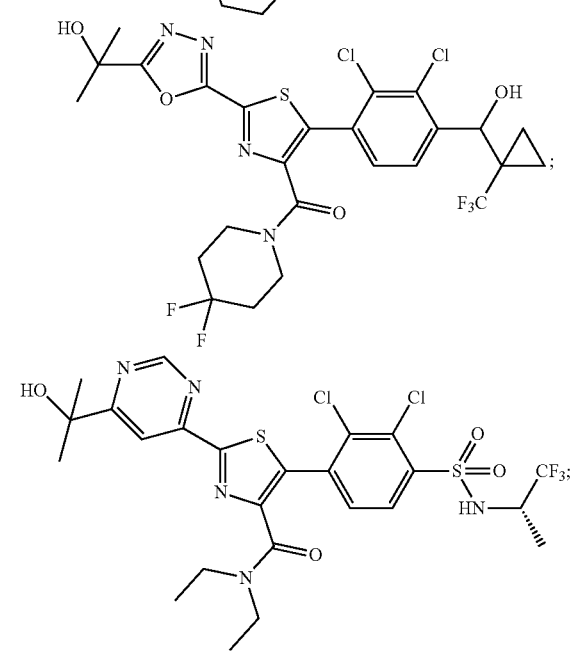
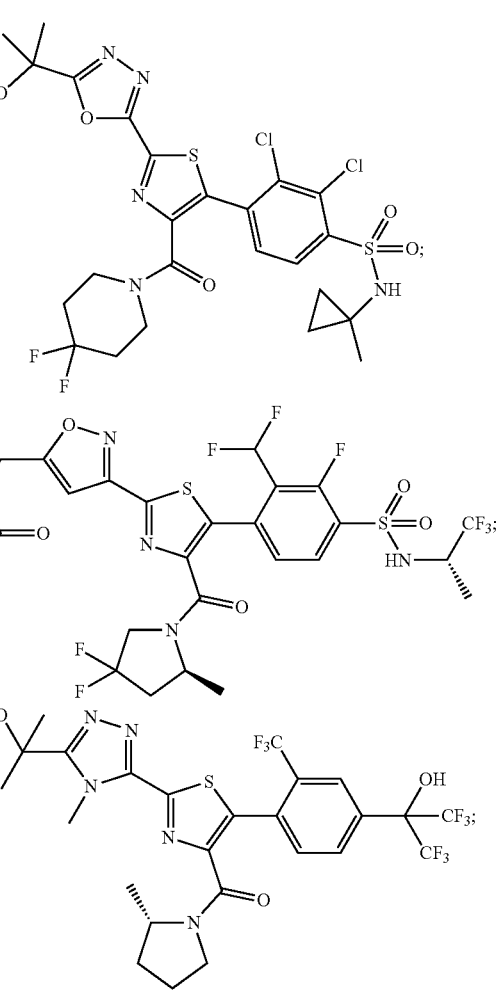
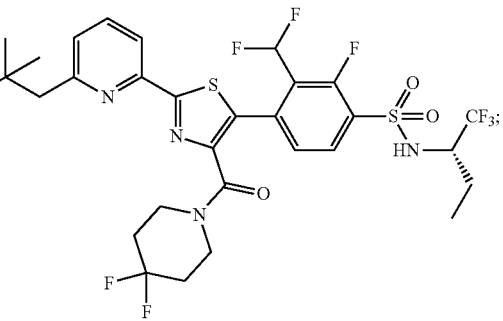

239
-continued
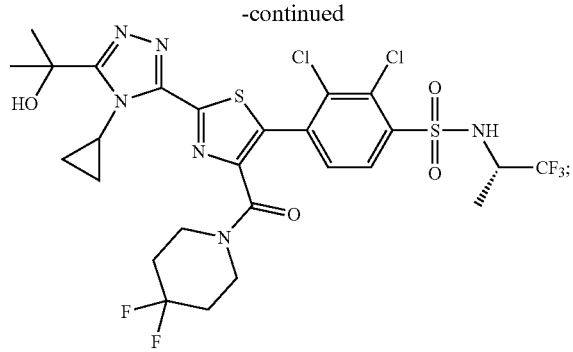
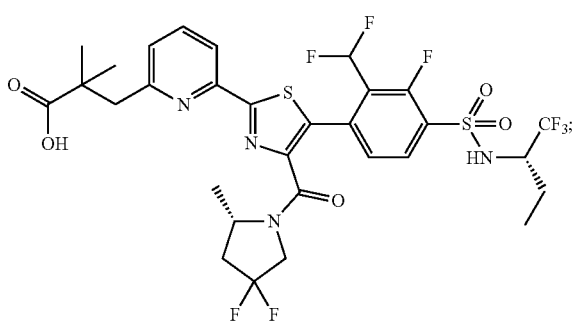
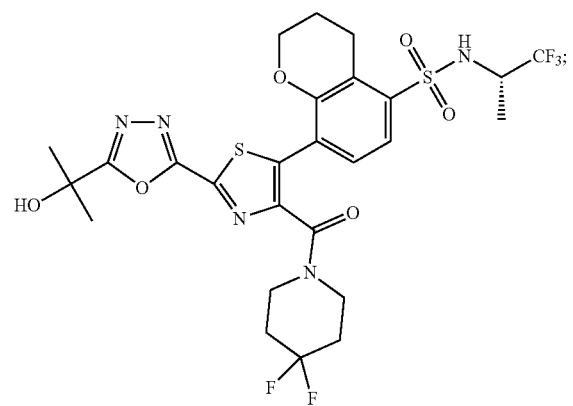
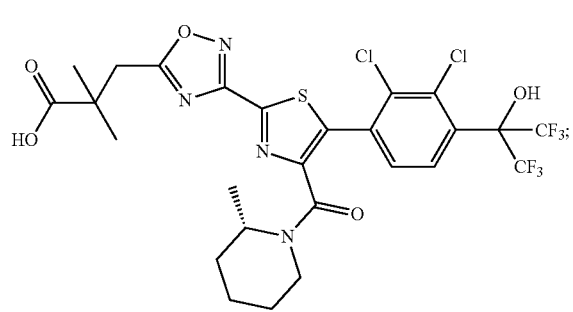
240
-continued
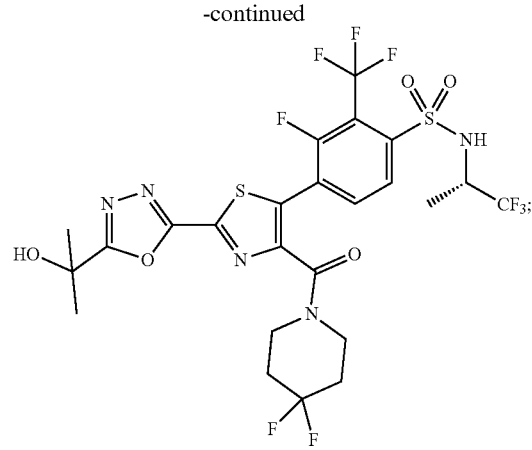
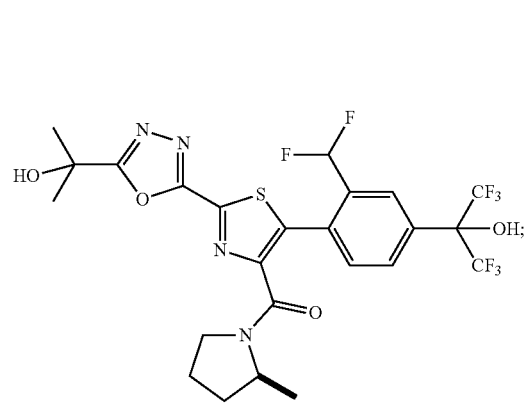
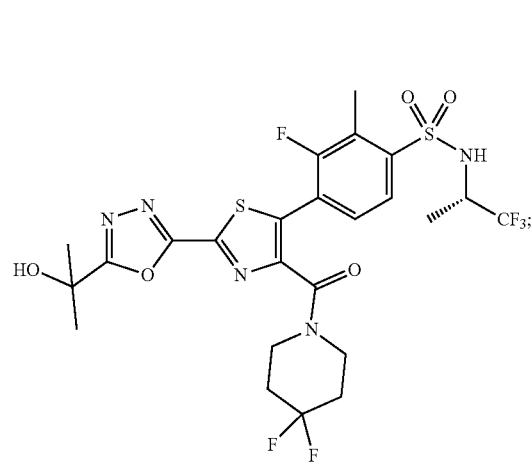
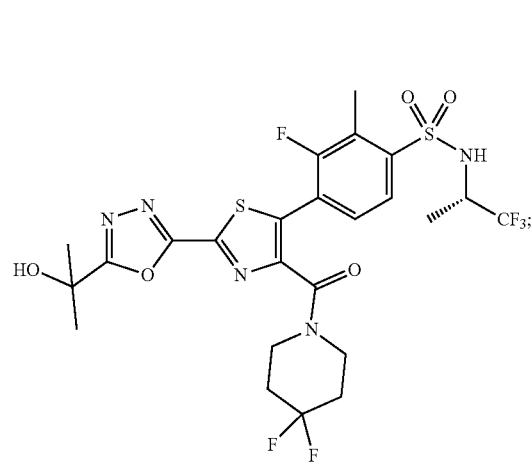

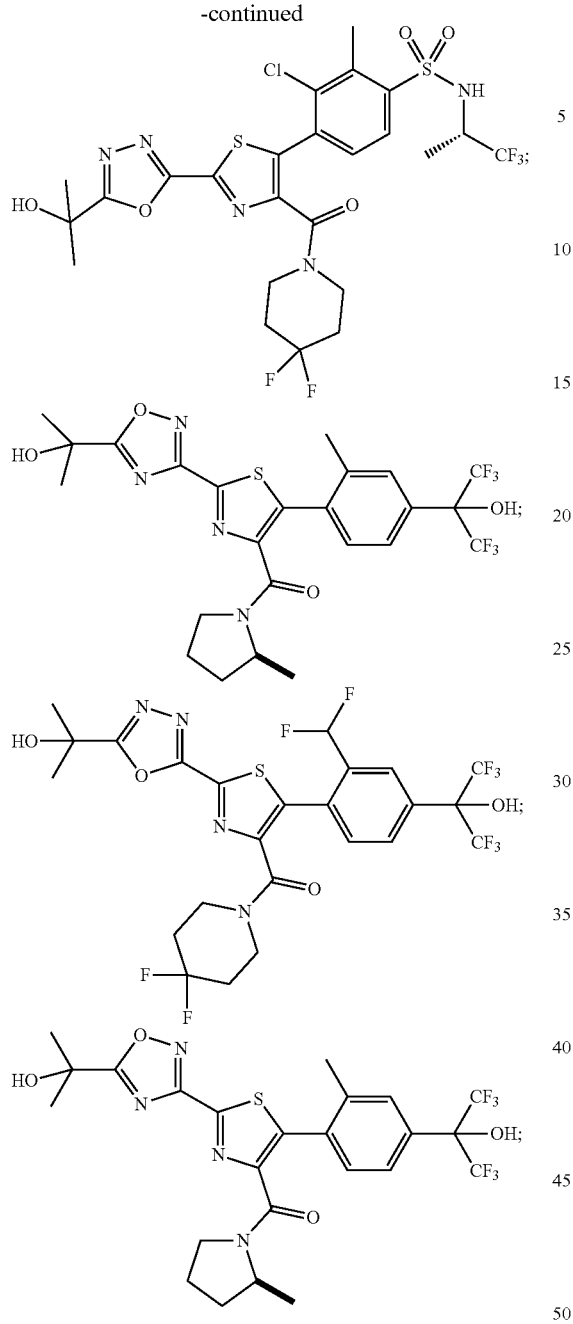
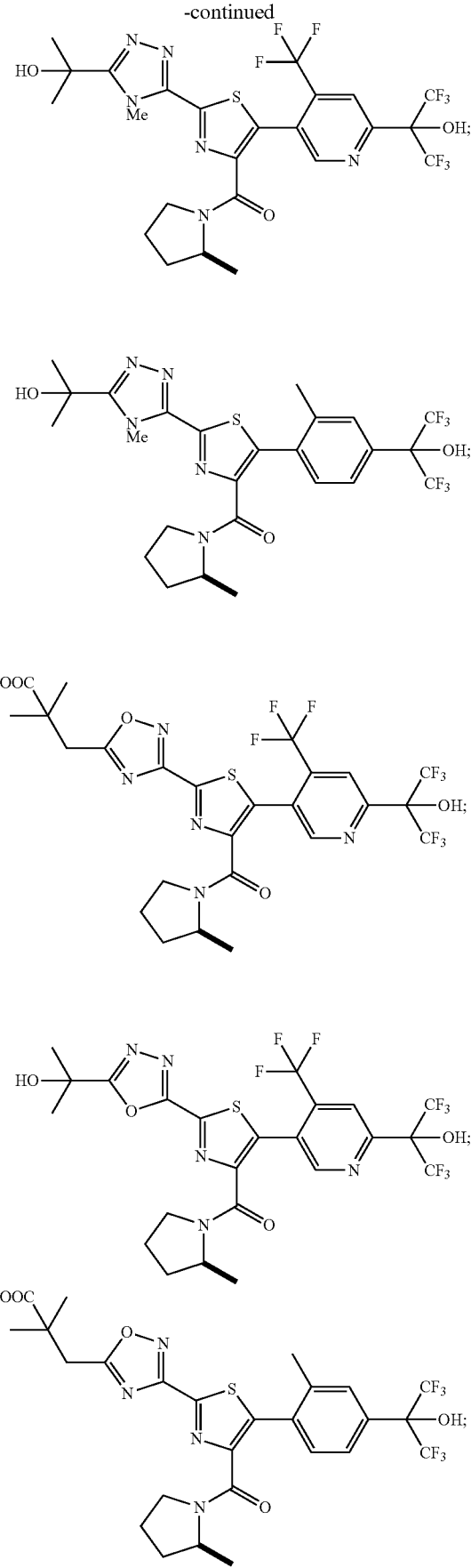
and pharmaceutically acceptable salts thereof.
7. The compound of claim 4 selected from the group consisting of:
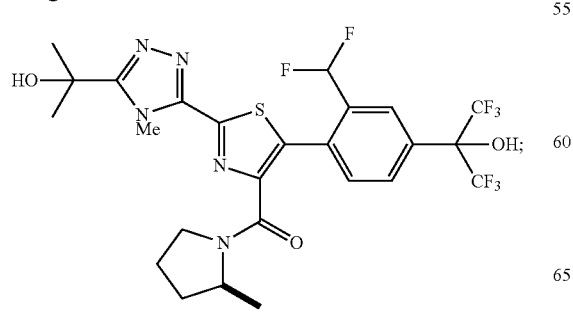

-continued

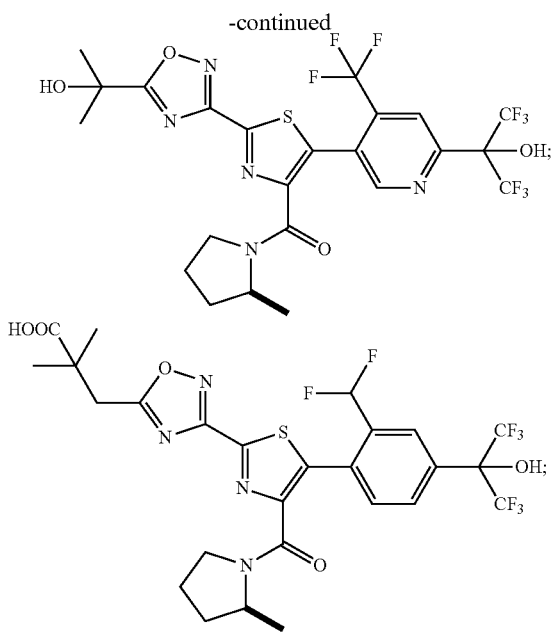

and pharmaceutically acceptable salts thereof.

8. A pharmaceutical composition, comprising a compound of claim 1 and a pharmaceutically acceptable carrier.

9. A pharmaceutical composition made by mixing a compound of claim 1 and a pharmaceutically acceptable carrier.

10. A process for making a pharmaceutical composition comprising mixing a compound of claim 1 and a pharmaceutically acceptable carrier.

11. A method for treating or ameliorating a RORγt mediated inflammatory syndrome, disorder or disease comprising administering to a subject in need thereof an effective amount of a compound of claim 1.

12. The method of claim 11, wherein the disease is selected from the group consisting of: rheumatoid arthritis, psoriasis, chronic obstructive pulmonary disorder, psoriatic arthritis, ankylosing spondylitis, Crohn's disease, neutrophilic asthma, steroid resistant asthma, multiple sclerosis, systemic lupus erythematosus, and ulcerative colitis.

13. The method of claim 11, wherein the disease is psoriasis.

14. The method of claim 11, wherein the disease is rheumatoid arthritis.

15. The method of claim 11, wherein the disease is ulcerative colitis.

16. The method of claim 11, wherein the disease is Crohn's disease.

17. The method of claim 11, wherein the disease is multiple sclerosis.

18. The method of claim 11, wherein the disease is neutrophilic asthma.

19. The method of claim 11, wherein the disease is steroid resistant asthma.

20. The method of claim 11, wherein the disease is psoriatic arthritis.

21. The method of claim 11, wherein the disease is ankylosing spondylitis.

22. The method of claim 11, wherein the disease is systemic lupus erythematosus.

23. The method of claim 11, wherein the disease is chronic obstructive pulmonary disorder.

24. A method of treating or ameliorating a syndrome, disorder or disease, in a subject in need thereof comprising administering to the subject an effective amount of a compound of claim 1 or composition or medicament thereof in a combination therapy with one or more anti-inflammatory agents, or immunosuppressive agents, wherein said syndrome, disorder or disease is selected from the group consisting of: rheumatoid arthritis, and psoriasis.

* * * * *

```
                        SEQUENCE LISTING

<160> NUMBER OF SEQ ID NOS: 4

<210> SEQ ID NO 1
<211> LENGTH: 3054
<212> TYPE: DNA
<213> ORGANISM: Homo sapiens

<400> SEQUENCE: 1
agagagctag gtgcagagct tcaggctgag gcgctgctga gagggcctcg ccccgcctct     60
gccgccagct gcaccccact cctggaccac cccctgctga gaaggacagg gagccaaggc    120
cggcagagcc aaggctcagt catgagaaca caaattgaag tgatcccttg caaaatctgt    180
ggggacaagt cgtctgggat ccactacggg gttatcacct gtgaggggtg caagggcttc    240
ttccgccgga gccagcgctg taacgcggcc tactcctgca cccgtcagca gaactgcccc    300
atcgaccgca ccagccgaaa ccgatgccag cactgccgcc tgcagaaatg cctggcgctg    360
ggcatgtccc gagatgctgt caagttcggc cgcatgtcca agaagcagag ggacagcctg    420
catgcagaag tgcagaaaca gctgcagcag cggcaacagc agcaacagga accagtggtc    480
aagacccctc cagcagggc ccaaggagca gataccctca cctacacctt ggggctccca    540
gacgggcagc tgccctggg ctcctcgcct gacctgcctg aggcttctgc ctgtcccct    600 ggcctcctga aagcctcagg ctctgggccc tcatattcca acaacttggc caaggcaggg    660
ctcaatgggg cctcatgcca ccttgaatac agccctgagc ggggcaaggc tgagggcaga    720
gagagcttct atagcacagg cagccagctg acccctgacc gatgtggact tcgttttgag    780
gaacacaggc atcctgggct tggggaactg ggacagggcc cagacagcta cggcagcccc    840
agtttccgca gcacaccgga ggcaccctat gcctccctga cagagataga gcacctggtg    900
cagagcgtct gcaagtccta cagggagaca tgccagctgc ggctggagga cctgctgcgg    960
cagcgctcca acatcttctc ccgggaggaa gtgactggct accagaggaa gtccatgtgg   1020
gagatgtggg aacggtgtgc ccaccacctc accgaggcca ttcagtacgt ggtggagttc   1080 gccaagagg tctcaggctt tatggagctc tgccagaatg accagattgt gcttctcaaa   1140
gcaggagcaa tggaagtggt gctggttagg atgtgccggg cctacaatgc tgacaaccgc   1200
acggtctttt ttgaaggcaa atacggtggc atggagctgt tccgagcctt gggctgcagc   1260
gagctcatca gctccatctt tgacttctcc cactccctaa gtgccttgca cttttccgag   1320
gatgagattg ccctctacac agcccttgtt ctcatcaatg cccatcggcc agggctccaa   1380
gagaaaagga aagtagaaca gctgcagtac aatctggagc tggccttttca tcatcatctc   1440 tgcaagactc atcgccaaag catcctggca aagctgccac ccaagggaa gcttcggagc   1500 ctgtgtagcc agcatgtgga aaggctgcag atcttccagc acctccaccc catcgtggtc   1560
caagccgctt tccctccact ctacaaggag ctcttcagca ctgaaaccga gtcacctgtg   1620
gggctgtcca agtgacctgg aagagggact ccttgcctct ccctatggcc tgctggccca   1680
cctccctgga ccccgttcca ccctcacccct tttccttttcc catgaaccct ggagggtggt   1740
ccccaccagc tctttggaag tgagcagatg ctgcggctgg ctttctgtca gcaggccggc   1800
ctggcagtgg gacaatcgcc agagggtggg gctggcagaa caccatctcc agcctcagct   1860
ttgacctgtc tcatttccca tattccttca cacccagctt ctggaaggca tggggtggct   1920
```

```
gggatttaag gacttctggg ggaccaagac atcctcaaga aaacaggggc atccagggct    1980
ccctggatga atagaatgca attcattcag aagctcagaa gctaagaata agcctttgaa    2040
atacctcatt gcatttccct ttgggcttcg gcttggggag atggatcaag ctcagagact    2100
ggcagtgaga gcccagaagg acctgtataa aatgaatctg gagctttaca ttttctgcct    2160
ctgccttcct cccagctcag caaggaagta tttgggcacc ctacccttta cctggggtct    2220
aaccaaaaat ggatgggatg aggatgagag gctggagata attgttttat ggatttggg    2280 tgtgggacta gggtacaatg aaggccaaga gcatctcaga catagagtta aaactcaaac    2340
ctcttatgtg cactttaaag atagacttta ggggctggca caaatctgat cagagacaca    2400
tatccataca caggtgaaac acatacagac tcaacagcaa tcatgcagtt ccagagacac    2460
atgaacctga cacaatctct cttatccttg aggccacagc ttggaggagc ctagaggcct    2520
caggggaaag tcccaatcct gagggaccct cccaaacatt tccatggtgc tccagtccac    2580
tgatcttggg tctggggtga tccaaatacc accccagctc cagctgtctt ctaccactag    2640
aagacccaag agaagcagaa gtcgctcgca ctggtcagtc ggaaggcaag atcagatcct    2700
ggaggacttt cctggcctgc ccgccagccc tgctcttgtt gtggagaagg aagcagatgt    2760
gatcacatca ccccgtcatt gggcaccgct gactccagca tggaggacac cagggagcag    2820
ggcctgggcc tgtttcccca gctgtgatct tgcccgaaac ctctcttggc ttcataaaca    2880
gctgtgaacc ctcccctgag ggattaacag caatgatggg cagtcgtgga gttgggggg    2940 ttgggggtgg gattgtgtcc tctaagggga cgggttcatc tgagtaaaca taaaccccaa    3000
cttgtgccat tctttataaa atgatttta aaggcaaaaa aaaaaaaaaa aaaa           3054

<210> SEQ ID NO 2
<211> LENGTH: 786
<212> TYPE: DNA
<213> ORGANISM: Homo sapiens

<400> SEQUENCE: 2
agcacaccgg aggcaccta tgcctccctg acagagatag agcacctggt gcagagcgtc      60
tgcaagtcct acagggagac atgccagctg cggctggagg acctgctgcg gcagcgctcc    120
aacatcttct cccgggagga agtgactggc taccagagga agtccatgtg ggagatgtgg    180
gaacggtgtg cccaccacct caccgaggcc attcagtacg tggtggagtt cgccaagagg    240
ctctcaggct ttatggagct ctgccagaat gaccagattg tgcttctcaa agcaggagca    300
atggaagtgg tgctggttag gatgtgccgg gcctacaatg ctgacaaccg cacggtcttt    360
tttgaaggca aatacggtgg catggagctg ttccgagcct tgggctgcag cgagctcatc    420
agctccatct ttgacttctc ccactcccta agtgccttgc acttttccga ggatgagatt    480
gccctctaca cagcccttgt tctcatcaat gcccatcggc cagggctcca agagaaaagg    540
aaagtagaac agctgcagta caatctggag ctggccttc atcatcatct ctgcaagact    600
catcgccaaa gcatcctggc aaagctgcca cccaagggga gcttcggag cctgtgtagc    660 cagcatgtgg aaaggctgca gatcttccag cacctccacc ccatcgtggt ccaagccgct    720
ttccctccac tctacaagga gctcttcagc actgaaaccg agtcacctgt ggggctgtcc    780
aagtga                                                                786

<210> SEQ ID NO 3
<211> LENGTH: 7
<212> TYPE: PRT
```

```
<213> ORGANISM: Artificial Sequence
<220> FEATURE:
<223> OTHER INFORMATION: TurboTEV protease cleavage site

<400> SEQUENCE: 3

Glu Asn Leu Tyr Phe Gln Gly
1               5

<210> SEQ ID NO 4
<211> LENGTH: 283
<212> TYPE: PRT
<213> ORGANISM: Artificial Sequence
<220> FEATURE:
<223> OTHER INFORMATION: Construct used in the Thermofluor assay

<400> SEQUENCE: 4

Met Ala His His His His His His Ala Gly Gly Ala Glu Asn Leu Tyr
1               5                   10                  15

Phe Gln Gly Ala Met Asp Ser Thr Pro Glu Ala Pro Tyr Ala Ser Leu
                20                  25                  30

Thr Glu Ile Glu His Leu Val Gln Ser Val Cys Lys Ser Tyr Arg Glu
            35                  40                  45

Thr Cys Gln Leu Arg Leu Glu Asp Leu Leu Arg Gln Arg Ser Asn Ile
    50                  55                  60

Phe Ser Arg Glu Glu Val Thr Gly Tyr Gln Arg Lys Ser Met Trp Glu
65                  70                  75                  80

Met Trp Glu Arg Cys Ala His His Leu Thr Glu Ala Ile Gln Tyr Val
                85                  90                  95

Val Glu Phe Ala Lys Arg Leu Ser Gly Phe Met Glu Leu Cys Gln Asn
                100                 105                 110

Asp Gln Ile Val Leu Leu Lys Ala Gly Ala Met Glu Val Val Leu Val
            115                 120                 125

Arg Met Cys Arg Ala Tyr Asn Ala Asp Asn Arg Thr Val Phe Phe Glu
    130                 135                 140

Gly Lys Tyr Gly Gly Met Glu Leu Phe Arg Ala Leu Gly Cys Ser Glu
145                 150                 155                 160

Leu Ile Ser Ser Ile Phe Asp Phe Ser His Ser Leu Ser Ala Leu His
                165                 170                 175

Phe Ser Glu Asp Glu Ile Ala Leu Tyr Thr Ala Leu Val Leu Ile Asn
                180                 185                 190

Ala His Arg Pro Gly Leu Gln Glu Lys Arg Lys Val Glu Gln Leu Gln
            195                 200                 205

Tyr Asn Leu Glu Leu Ala Phe His His Leu Cys Lys Thr His Arg
    210                 215                 220

Gln Ser Ile Leu Ala Lys Leu Pro Pro Lys Gly Lys Leu Arg Ser Leu
225                 230                 235                 240

Cys Ser Gln His Val Glu Arg Leu Gln Ile Phe Gln His Leu His Pro
                245                 250                 255

Ile Val Val Gln Ala Ala Phe Pro Pro Leu Tyr Lys Glu Leu Phe Ser
                260                 265                 270

Thr Glu Thr Glu Ser Pro Val Gly Leu Ser Lys
            275                 280
```